US006235778B1

(12) United States Patent
Tomczuk et al.

(10) Patent No.: US 6,235,778 B1
(45) Date of Patent: May 22, 2001

(54) AMINOGUANIDINES AND ALKOXYGUANIDINES AS PROTEASE INHIBITORS

(75) Inventors: Bruce E. Tomczuk, Collegeville, PA (US); Richard M. Soll, Lawrenceville, NJ (US); Tianbao Lu, Exton, PA (US); Cynthia L. Fedde, Warrington, PA (US); Carl R. Illig, Phoenixville, PA (US); Thomas P. Markotan, Pottstown, PA (US); Thomas P. Stagnaro, St. David, PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 08/979,234

(22) Filed: Nov. 26, 1997

Related U.S. Application Data
(60) Provisional application No. 60/013,822, filed on Nov. 26, 1996.

(51) Int. Cl.[7] ............... A61K 31/255; A61K 31/535; A61K 31/495; A61K 31/47

(52) U.S. Cl. ............ 514/517; 514/238.2; 514/255.02; 514/307; 514/311; 514/327; 514/357; 514/426; 514/459; 514/467; 514/633; 514/518; 544/158; 544/384; 546/145; 546/172; 546/221; 546/332; 548/558; 548/561; 549/229; 549/426

(58) Field of Search .................. 558/48, 50; 514/517, 514/518, 238.2, 255.02, 307, 311, 327, 357, 426, 459, 467, 633; 544/158, 384; 546/145, 172, 221, 332; 548/558, 561; 549/426, 229; 564/229

(56) References Cited

U.S. PATENT DOCUMENTS

| 3,131,218 | 4/1964 | Spickett et al. ............ 260/564 |
| 3,271,448 | 9/1966 | Augstein et al. ............ 260/564 |
| 3,413,303 | 11/1968 | Mull ........................ 260/309.6 |
| 4,429,146 | * 1/1984 | Liu .......................... 560/21 |
| 5,466,811 | 11/1995 | Alexander ................. 546/283 |

FOREIGN PATENT DOCUMENTS

| 2164684 | 6/1996 | (CA) . |
| 1 518 222 | 6/1969 | (DE) . |
| 0 064 022 | 6/1994 | (EP) . |
| 0 761 251 | 3/1997 | (EP) . |
| WO 94/20467 | 9/1994 | (WO) . |
| WO 95/07291 | 3/1995 | (WO) . |
| WO 96/11668 | 4/1996 | (WO) . |
| WO 96/32143 | 10/1996 | (WO) . |
| WO 96/38136 | 12/1996 | (WO) . |
| WO 97/11693 | 4/1997 | (WO) . |
| WO 97/22589 | 6/1997 | (WO) . |
| WO 97/36580 | 10/1997 | (WO) . |

OTHER PUBLICATIONS

Dialog file 351, Acession No. 66–19056F, Derwent WPI English language abstract for DE 1 518 222.

Ripka, W.C. and G.P. Vlasuk, "Chapter 8. Antithrombotics/Serine Proteases," In: *Annual Reports in Medicinal Chemistry*, Bristol, J.A., ed., Academic Press, Inc., New York, NY, pp. 71–89 (Sep. 1997).

Saulnier, M.G. et al., "An Efficient Method for the Synthesis of Guanidino Prodrugs," *Bioorg. & Med. Chem. Letters* 4(16): 1985–1990 (1994).

Tapparelli, C. et al., "Synthetic low–molecular weight thrombin inhibitors: molecular design and pharmacological profile," *Tips* 14: 366–376 (1993).

(List continued on next page.)

*Primary Examiner*—Peter O'Sullivan
(74) *Attorney, Agent, or Firm*—Sterne, Kessler, Goldstein & Fox P.L.L.C.

(57) ABSTRACT

Aminoguanidine and alkoxyguanidine compounds, including compounds of the formula:

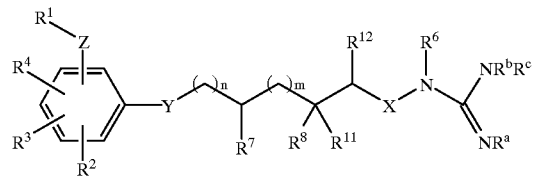

I wherein X is O or $NR^9$ and $R^1$ 14 $R^4$, $R^6$–$R^9$, $R^{11}$, $R^{12}$, $R^a$, $R^b$, $R^c$, Y, Z, n and m are set forth in the specification, as well as hydrates, solvates or pharmaceutically acceptable salts thereof, that inhibit proteolytic enzymes such as thrombin are described. Also described are methods for preparing the compounds of Formula I. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

42 Claims, No Drawings

OTHER PUBLICATIONS

Kimball, S.D., "Challanges in the development of orally bioavailable thrombin active site inhibitors," *Blood Coagulation and Fibrinolysis* 6:511–519 (Sep. 1995).

Lefkovits, J. and E.J. Topol, "Direct Thrombin Inhibitors in Cardiovascular Medicine," *Circulation* 90(3) : 1522–1536 (1994).

Ozawa, H. et al., "Pharmacological Studies of Aminoguanidines. I. Hypotensive and Some General Pharmacological Actions of Benzyl– and Benzylidene–hydrazino–3,4,5,6–tetrahydropyrimidines," *Yakugaku Zasshi* 95(8) : 966–974 (1975).

Harker, L.A., "Strategies for inhibiting the effects of thrombin," *Blood Coagulation and Fibrinolysis* 5(*Suppl. 1*):S47–S58 (1994).

Jeong, J.–H. et al., "Cyclic Guanidino–Sugars with Low $pK_a$ as Transition–State Analog Inhibitors of Glycosidases: Neutral Instead of Charged Species Are the Active Forms," *J. Amer. Chem. Soc.* 118(18):4227–4234 (May 1996).

Kim, K.S. et al., "Preparation of Argatroban Analog Thrombin Inhibitors with Reduced Basic Guanidine Moiety, And Studies of Their Cell Permeability and Antithrombotic Activities," *Med Chem. Res.* 6(6):377–383 (Oct. 1996).

Augstein, J. et al., "Aryloxyalkylaminoguanidines. Their Synthesis and Biological Properties," *J. Med. Chem.* 10(8):391–400 (1967).

Claeson, G., "Synthetic peptides and peptidomimetics as substrates and inhibitors of thrombin and other proteases in the blood coagulation system,"*Blood Coagulation and Fibrinolysis* 5: 411–436 (1994).

Coughlin, S.R., "Molecular Mechanisms of Thrombin Signaling," *Semin. in Hematology* 31(4): 270–277, (1994).

* cited by examiner

AMINOGUANIDINES AND ALKOXYGUANIDINES AS PROTEASE INHIBITORS

This application claims benefit under 35 U.S.C. § 119(e) of U.S. Provisional Application No. 60/031,822, filed Nov. 26, 1996, the contents of which are fully incorporated by reference herein.

BACKGROUND OF THE INVENTION

1. Field of the Invention

The present invention relates to novel compounds that function as enzyme inhibitors, and particularly to a new class of non-peptidic inhibitors of proteolytic enzymes.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons (Tapparelli et al., *Trends in Pharmacological Sciences* 14:366–376 (1993); Lefkovits and Topol, *Circulation* 90(3):1522–1536 (1994); Harker, *Blood Coagulation and Fibrinolysis* 5 (Suppl 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47–S58 (1994)).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

Ozawa, H. et al., *Yakugaku Zasshi*, 95(8):966–74 (1975) describe a number of benzyl- and benzylidine aminoguanidine and amidinohydrazone compounds. For example, the following salts are described:

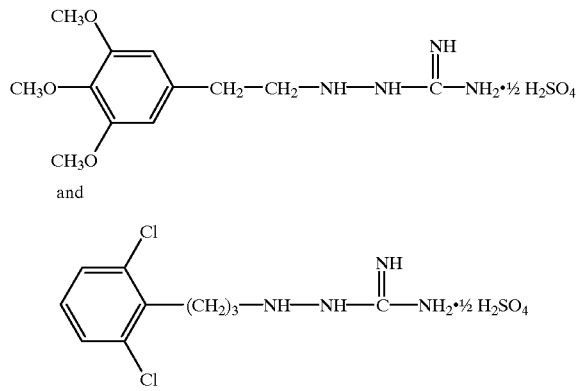

The compounds were tested for their effect on blood pressure in rats.

Augstein, J. et al.," *J Med. Chem.*, 10(3):391–400 (1967) discloses a series of aryloxyalkylamino-guanidines of the formula:

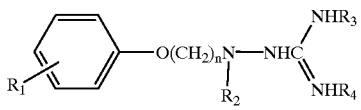

In some compounds $R_1$ is methoxy, while $R_2$ is hydrogen and $R_3$ and $R_4$ are either hydrogen or methyl. Several such aminoguanidines containing chloro and methyl substituents in the aromatic ring were shown to possess adrenergic neuron blocking properties and to inhibit dopamine β-oxidase in vitro. The synthesis and testing of aminoguanidines containing one or more methoxy substituents in the aromatic ring is also disclosed.

SUMMARY OF THE INVENTION

The present invention is directed to novel compounds having Formula I (below). Also provided are processes for preparing compounds of Formula L The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

DETAILED DESCRIPTION OF THE PREFERRED EMBODIMENTS

Compounds of the present invention include compounds of Formula I:

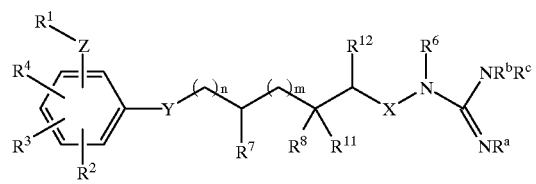

or a solvant, hydrate or pharmaceutically acceptable salt thereof; wherein;

$R^1$ is one of alkyl, cycloalkyl, alkenyl, alkynyl, aryl, aralkyl or heteroaryl, any of which may be optionally substituted;

Z is one of —$NR^{10}SO_2$—, —$SO_2NR^{10}$—, —$NR^{10}C(R^yR^z)$—, —$C(R^yR^z)NR^{10}$—, —$OSO_2$—, —$SO_2O$—, —$OC(R^yR^z)$—, —$C(R^yR^z)O$—, —$NR^{10}CO$— or —$CONR^{10}$—;

$R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^2$, $R^3$ and $R^4$ are each independently one of hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^2$ and $R^3$ may also be taken together to form one of —CH=CH—CH=CH— or —$(CH_2)_q$—, where q is from 2 to 6, and $R^4$ is defined as above;

$R^x$, in each instance, is independently one of hydrogen, alkyl or cycloalkyl wherein said alkyl or cycloalkyl groups may optionally have one or more unsaturations;

Y is one of —O—, —$NR^{10}$—, —S—, —$CHR^{10}$— or a covalent bond;

X is oxygen or $NR^9$;

$R^9$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^6$ is one of hydrogen, alkyl, aralkyl, aryl, hydroxyalkyl, aminoalkyl, monoalkylamino($C_{2-10}$)alkyl, dialkylamino($C_{2-10}$)alkyl or carboxyalkyl, or alternatively, $R^6$ and $R^{12}$ taken together to form —$(CH_2)_w$—, where w is 1–5;

$R^7$ is one of hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di-alkylamino, provided that n is other than zero when $R^7$ is hydroxy, alkoxy, aralkoxy, aryloxy, heteroaryloxy, or mono- or di-alkylamino;

$R^8$, $R^{11}$ and $R^{12}$ are each independently one of hydrogen, alkyl, aralkyl, aryl, hydroxyalkyl, aminoalkyl, monoalkylaminoalkyl, dialkylaminoalkyl or carboxyalkyl;

or $R^7$ and $R^8$ are taken together to form —$(CH_2)_y$—, where y is zero (a bond), 1 or 2, while $R^{11}$ and $R^{12}$ are defined as above; or $R^7$ and $R^{12}$ are taken together to form —$(CH_2)_q$—, where q is zero (a bond), or 1 to 8, while $R^5$ and $R^{11}$ are defined as above; or $R_8$ and $R^{11}$ are taken together to form —(CH$_2$)$_r$—, where r is 2–8, while R$^7$ and R$^{12}$ are defined as above;

R$^{10}$, in each instance, is independently one of hydrogen, alkyl, aralkyl, aryl, hydroxy(C$_{2-10}$)alkyl, amino(C$_{2-10}$)alkyl, monoalkylamino(C$_{2-10}$)alkyl, dialkylamino(C$_{2-10}$)alkyl or carboxyalkyl;

R$^a$, R$^b$ and R$^c$ are independently hydrogen, alkyl, hydroxy, alkoxy, aryloxy, aralkoxy, alkoxycarbonyloxy, cyano or —CO$_2$R$^w$;

R$^w$ is alkyl, cycloalkyl, phenyl, benzyl,

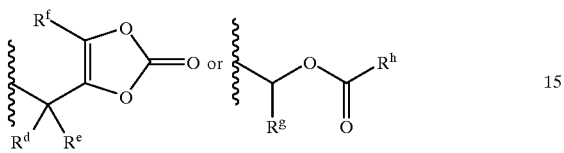

where R$^d$ and R$^e$ are independently hydrogen, C$_{1-6}$ alkyl, C$_{2-6}$ alkenyl or phenyl, R$^f$ is hydrogen, C$_{1-6}$ alkyl, C$_{2-6}$ alkenyl or phenyl, R$^g$ is hydrogen, C$_{,1-6}$ alkyl, C$_{2-6}$ alkenyl or phenyl, and R$^h$ is aralkyl or C$_{1-6}$ alkyl;

n is from zero to 8; and m is from zero to 4.

A preferred group of compounds falling within the scope of the present invention include compounds of Formula I wherein:

R$^1$ is one of C$_{6-10}$ aryl, pyridinyl, thiophenyl (i.e., thiophene), quinazolinyl, quinolinyl or tetrahydroquinolinyl, any of which is optionally substituted by one or two of hydroxy, nitro, trifluoromethyl, halogen, C$_{1-6}$ alkyl, C$_{6-10}$ aryl, C$_{1-6}$ alkoxy, C$_{6-10}$ ar(C$_{1-6}$)alkoxy, C$_{1-6}$ aminoalkyl, C$_{1-6}$ aminoalkoxy, amino, mono(C$_{1-4}$)alkylamino, di(C$_{1-4}$)alkylamino, C$_{2-6}$ alkoxycarbonylamino, C$_{2-6}$ alkoxycarbonyl, carboxy, C$_{1-6}$ hydroxyalkyl, C$_{2-6}$ hydroxyalkoxy, (C$_{1-6}$)alkoxy(C$_{2-6}$)alkoxy, mono- and di- C$_{1-4}$ alkylamino(C$_{2-6}$)alkoxy, C$_{2-10}$ mono(carboxyalkyl)amino, di(C$_{2-10}$ carboxyalkyl)amino, C$_{6-14}$ ar(C$_{1-6}$)alkoxycarbonyl, C$_{2-6}$ alkynylcarbonyl, C$_{1-6}$ alkylsulfonyl, C$_{2-6}$ alkenylsulfonyl, C$_{2-6}$ alkynylsulfonyl, C$_{6-10}$ arylsulfonyl, C$_{6-10}$ ar(C$_{1-6}$)alkylsulfonyl, C$_{1-6}$ alkylsulfinyl, C$_{1-6}$ alkylsulfonamido, C$_{6-10}$ arylsulfonamido, C$_{6-10}$ ar(C$_{1-6}$) alkylsulfonamido, amidino, guanidino, C$_{1-6}$ alkyliminoamino, formyliminoamino, C$_{2-6}$ carboxyalkoxy, C$_{2-6}$ carboxyalkyl, carboxyalkylamino, cyano, trifluoromethoxy, perfluoroethoxy and R$^{13}$R$^{14}$NSO$_2$—;

R$^{13}$ and R$^{14}$ are independently selected from the group consisting of hydrogen, alkyl, cycloalkyl, alkenyl, alkynyl, aryl, aralkyl, heterocycle, heterocycloalkyl, carboxyalkyl, alkoxycarbonylalkyl, cyano(C$_{2-10}$)alkyl, hydroxy(C$_{2-10}$)alkyl, alkoxy(C$_{2-10}$)alkyl, mono- and di-alkylamino(C$_{2-10}$)alkyl, or R$^{13}$ and R$^{14}$ can be taken together with the nitrogen atom to which they are attached to form a three to seven membered ring, optionally containing one or more heteroatoms in addition to said nitrogen, such as oxygen, sulfur, or nitrogen (NR$^{15}$), said ring being preferably saturated, and said ring having one or two optional substituents selected from the group consisting of hydroxy, acyloxy, alkoxy, aryloxy, amino, mono- and di-alkylamino, acylamino, alkyl, cycloalkyl, alkenyl, alkynyl, aryl, aralkyl, heterocycle, heterocycloalkyl, carboxyalkyl, alkoxycarbonylalkyl, cyano(C$_{2-10}$)alkyl, hydroxy (C$_{2-10}$)alkyl, alkoxy(C$_{2-10}$)alkyl, mono- and di-alkylamino(C$_{2-10}$)alkyl, carboxy, alkoxycarbonyl, carboxamido, formyl, alkanoyl, aroyl, aralkanoyl, sulfonyl, alkylsulfonyl, alkoxysulfonyl, sulfonamido, phosphonyl, phosphoramido, and phosphinyl, and wherein R$^{15}$ is selected from the group consisting of hydrogen, alkyl, cycloalkyl, alkenyl, alkynyl, aryl, aralkyl, heterocycle, heterocycloalkyl, carboxyalkyl, alkoxycarbonylalkyl, cyano(C$_{2-10}$)alkyl, hydroxy (C$_{2-10}$)alkyl, alkoxy(C$_{2-10}$)alkyl, mono- and di-alkylamino(C$_{2-10}$)alkyl, carboxy, alkoxycarbonyl, carboxamido, formyl, alkanoyl, aroyl, aralkanoyl, sulfonyl, alkylsulfonyl, alkoxysulfonyl, sulfonamido, phosphonyl, phosphoramido, and phosphinyl;

Z is one of —SO$_2$O—, —SO$_2$NR$^{10}$—, —C(R$^y$R$^z$)O— or —OC(R$^y$R$^z$)—, where R$^y$ and R$^z$ are each hydrogen;

R$^2$, R$^3$ and R$^4$ are independently one of hydrogen, C$_{1-4}$ alkyl, C$_{3-8}$ cycloalkyl, phenyl, benzyl, trifluoromethyl, halogen, hydroxy(C$_{1-4}$)alkyl, cyano, nitro, carboxamido, carboxy, C$_{1-4}$ alkoxycarbonyl, C$_{1-4}$ alkoxymethyl or C$_{1-4}$ alkoxy; or alternatively, R$^2$ and R$^3$, when present on adjacent carbon atoms, may also be taken together to form one of —CH=CH—CH=CH— or —CH$_2$)$_q$—, where q is from 2 to 6, and R$^4$ is as defined above;

Y is one of —O—, —S—, —NR$^{10}$—, or a covalent bond;

R$^a$, R$^b$ and R$^c$ are each one of hydrogen, C$_{1-4}$ alkyl, hydroxy, C$_{1-4}$ alkoxy, phenoxy, C$_{1-4}$ alkyloxycarbonyl, benzyloxycarbonyl, cyano,

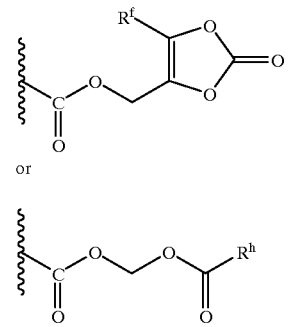

where
R$^h$ is benzyl, methyl, ethyl, isopropyl, sec-butyl or t-butyl, and where R$^f$ is hydrogen a or C$_{1-6}$ alkyl;

R$^6$ is one of hydrogen, C$_{1-6}$ alkyl, C$_{6-10}$ ar(C$_{1-6}$)alkyl, C$_{6-10}$ aryl, C$_{2-10}$ hydroxyalkyl, C$_{2-10}$ aminoalkyl, mono (C$_{1-4}$)alkylamino(C$_{2-8}$)alkyl, di(C$_{1-4}$)alkylamino(C$_{2-8}$) alkyl or C$_{2-10}$ carboxyalkyl;

R$^7$, R$^8$, R$^{11}$ and R$^{12}$ are independently one of hydrogen, C$_{1-6}$ alkyl, C$_{2-10}$ carboxyalkyl or C$_{2-10}$ hydroxyalkyl, or R$^7$ and R$^8$ are taken together to form —(CH$_2$)$_y$— where y is zero, 1 or 2, while R$^{11}$ and R$^{12}$ are defined as above; or R$^7$ and R$^{12}$ are taken together to form —(CH$_2$)$_q$—, where q is zero (a bond), or 1, 2 or 3, while R$^8$ and R$^{11}$ are defined as above; or R$^8$ and R$^{11}$ are taken together to form —(CH$_2$)$_r$—, where r is 2, 3, or 4, while R$^7$ and R$^{12}$ are defined as above;

R$^9$ is hydrogen, or C$_{1-10}$ alkyl, optionally substituted with amino, mono(C$_{1-4}$)alkylamino, C$_{1-6}$ alkoxy, hydroxy, carboxy, phenyl, C$_{1-4}$ alkyloxycarbonyl, C$_{6-10}$ ar(C$_{1-4}$) alkoxycarbonyl, C$_{1-6}$ acylamino, cyano or trifluoromethyl;

7

$R^{10}$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxyalkyl;

n is from zero to 8; and m is from zero to 4.

In this preferred embodiment, $R^1$ can be one of $C_{6-10}$ aryl, pyridinyl, thiophenyl (i.e., thiophene), quinazolinyl, quinolinyl or tetrahydroquinolinyl, any of which is optionally substituted by one or two of hydroxy, nitro trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$) alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, $C_{2-10}$ mono(carboxyalkyl)amino, bis($C_{2-10}$ carboxyalkyl)amino, $C_{6-14}$ ar($C_{1-6}$)alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, triflluromethoxy, and perfluoroethoxy.

An especially preferred group of compounds include compounds of Formula I wherein:

$R^1$ is one of phenyl, naphthyl, pyridyl, thiophenyl, quinolinyl or isoquinolinyl, optionally substituted by one or two of chloro, methoxy, methyl, trifluoromethyl, cyano, nitro, amino or dimethylamino;

Z is one of —$SO_2O$—, —$SO_2NR^{10}$—, —$CH_2O$— or —$OCH_2$—;

$R^2$ and $R^3$ are hydrogen or $C_{1-4}$ alkyl, or $R^2$ and $R^3$ may also be taken together to form —CH=CH—CH=CH—;

$R^4$ is one of hydrogen, methyl, methoxy or trifluoromethyl;

Y is one of O, $NR^{10}$ or a covalent bond;

$R^a$, $R^b$ and $R^c$ are hydrogen, hydroxy,

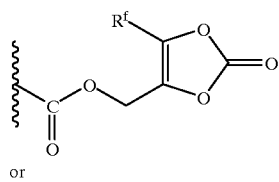

or

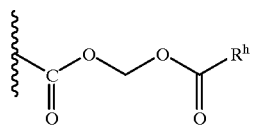

where $R^h$ is benzyl or t-butyl, and where $R^f$ is hydrogen or methyl;

$R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl;

$R^7$, $R^8$, $R^{11}$ and $R^{12}$ are independently one of hydrogen, $C_{1-6}$ alkyl, $C_{2-10}$ hydroxyalkyl or $C_{2-10}$ carboxyalkyl, or $R^7$ and $R^8$ are taken together to form —$(CH_2)_y$— where y is zero, 1 or 2, while $R^{11}$ and $R^{12}$ are defined as above; or $R^7$ and $R^{12}$ are taken together to form —$(CH_2)_q$—, where q is zero (a bond), or 1, 2 or 3, while $R^8$ and $R^{11}$ are defined as above; or $R^8$ and $R^{11}$ are taken together to form —$(CH_2)_r$—, where r is 2, 3 or 4, while $R^7$ and $R^{12}$ are defined as above;

8

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino ($C_{2-8}$)alkyl;

n is from zero to 4; and m is zero, 1, 2 or 3.

Another especially preferred group of compounds include compounds of Formula I wherein:

$R^1$ is phenyl, substituted by one of alkylsulfonyl, arylsulfonyl and $R^{13}R^{14}NSO_2$—, where $R^{13}$ and $R^{14}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$)alkyl, pyridyl, pyridyl($C_{1-4}$)alkyl, carboxy($C_{1-6}$)alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($C_{2-6}$)alkyl, mono- and di-($C_{1-4}$) alkylamino($C_{2-6}$)alkyl, or $R^{13}$ and $R^{14}$ can be taken together with the nitrogen atom to which they are attached to form a heterocyclic ring selected from the group consisting of N-morpholinosulfonyl, N-piperazinylsulfonyl (optionally N' substituted with $C_{1-6}$ alkyl, $C_{1-6}$ hydroxyalkyl, $C_{6-10}$ aryl, $C_{6-10}$ aryl ($C_{1-6}$)alkyl, $C_{1-6}$ alkylsulfonyl, $C_{6-10}$ arylsulfonyl, $C_{1-6}$ alkylcarbonyl, morpholino or $C_{6-10}$ arylcarbonyl), N-pyrrolylsulfonyl, N-piperidinylsulfonyl, N-pyrrolidinylsulfonyl, N-dihydropyridylsulfonyl, N-indolysufonyl, wherein said heterocyclic ring can be optionally substituted with one or two of hydroxy, $C_{1-8}$ alkanoyloxy, $C_{1-6}$ alkoxy, $C_{6-10}$ aryloxy, amino, mono- and di- $C_{1-6}$ alkylamino, $C_{1-8}$ alkanoylamino, $C_{1-4}$ alkyl, $C_{3-7}$ cycloalkyl, $C_{6-10}$ aryl, $C_{6-10}$ ar($C_{1-4}$)alkyl, heterocycle, heterocycloalkyl, carboxy($C_{1-6}$)alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($C_{2-6}$)alkyl, mono- and di-($C_{1-4}$) alkylamino($C_{2-6}$)alkyl, carboxy, $C_{1-6}$ alkoxycarbonyl, carboxamido, formyl, $C_{1-6}$ alkanoyl, $C_{6-10}$ aroyl, $C_{6-10}$ ar($C_{1-4}$)alkanoyl, sulfonyl, $C_{1-6}$ alkylsulfonyl, $C_{1-6}$ alkoxysulfonyl, sulfonamido, Z is one of —$SO_2$—, —$SO_2NR^{10}$—, —$CH_2O$— or —$OCH_2$—;

$R^2$ and $R^3$ are hydrogen or $C_{1-4}$ alkyl, or $R^2$ and $R^3$ may also be taken together to form —CH=CH—CH=CH—;

$R^4$ is one of hydrogen, methyl, methoxy or trifluoromethyl;

Y is one of O, $NR^{10}$ or a covalent bond;

$R^a$, $R^b$ and $R^c$ are hydrogen, hydroxy,

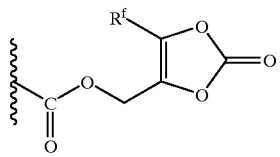

or

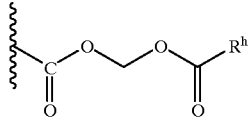

where $R^h$ is benzyl or t-butyl, and where $R^f$ is hydrogen or methyl;

$R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl;

$R^7$, $R^8$, $R^{11}$ and $R^{12}$ are independently one of hydrogen, $C_{1-6}$ alkyl, $C_{2-10}$ hydroxyalkyl or $C_{2-10}$ carboxyalkyl, or $R^7$ and $R^8$ are taken together to form —$(CH_2)_y$— where y is zero, 1 or 2, while $R^{11}$ and $R^{12}$ are defined ar above; or $R^7$ and $R^{12}$ are taken together to form —$(CH_2)_q$—, where q is zero (a bond), or 1, 2 or 3, while $R^8$ and $R^{11}$ are defined as above; or $R^8$ and $R^{11}$ are taken together to form —$(CH_2)_r$—, where r is 2, 3 or 4, while $R^7$ and $R^{12}$ are defined above;

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino ($C_{2-8}$)alkyl;

n is from zero to 4; and m is zero, 1 or 2 or 3.

The moiety —Z—$R^1$ of Formula I is attached to the benzene ring in a position ortho-, meta- or para- to Y, with the meta-position being preferred.

Preferred compounds of the present invention are those of Formula I wherein Y is one of divalent oxygen (—O—), —$NR^{10}$— or a covalent bond, most preferably —O— and Z is one of —$SO_2NR^{10}$—, —$SO_2$— or —$CH_2$—, most preferably —$SO_2O$—.

Preferred compounds of the present invention are those of Formula I wherein $R^1$ is one of $C_{1-12}$ alkyl, especially $C_{3-8}$ alkyl, $C_{4-7}$ cycloalkyl, $C_{2-8}$ alkenyl, $C_{2-8}$ alkynyl or $C_{6-14}$ aryl, especially $C_{6-10}$ aryl, any of which is optionally substituted. Substituents that can be optionally present on the $R^1$ moieties include one or more, preferably one or two, of hydroxy, nitro, trifluoromethyl, halogen, alkoxy, aralkoxy, aminoalkoxy, aminoalkyl, hydroxyalkyl, hydroxyalkoxy, alkoxyalkoxy, mono- and di-alkylaminoalkoxy, cyano, aryl, amino, monoalkylamino, dialkylamino, carboxy, carboxyalkyl, carboxyalkoxy, mono(hydroxyalkyl)amino, bis(hydroxyalkyl)amino, mono(carboxyalkyl)amino, bis (carboxyalkyl)amino, alkoxycarbonylamino, alkoxycarbonyl, aralkoxycarbonyl, alkenylcarbonyl, alkynylcarbonyl, alkylsulfonyl, alkenylsulfonyl, alkynylsulfonyl, arylsulfonyl, aralkylsulfonyl, alkylsulfinyl, alkylsulfonamido, arylsulfonamido, aralkylsulfonamido, amidino, guanidino, alkyliminoamino, formyliminoamino, trifluoromethoxy, perfluoroethoxy or an aminosulfonyl group $R^{13}R^{14}NSO_2$—, where $R^{13}$ and $R^{14}$ are as defined above. A further substituent on aryl, cycloalkyl, alkenyl, alkynyl and aralkyl moieties of $R^1$ includes one or more, preferably one or two, alkyl moieties.

Preferred values of optional substituents on $R^1$ include hydroxy, nitro, trifluoromethyl, halogen, $C_{1-6}$ alkyl, $C_{1-6}$ alkoxy, $C_{1-6}$ aminoalkyl, $C_{6-10}$ aryl, $C_{6-10}$ ar($C_{1-6}$)alkoxy, biphenyl($C_{1-6}$)alkoxy $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-10}$ mono(carboxyalkyl)amino, bis($C_{2-10}$ carboxyalkyl)amino, $C_{6-4}$ ar($C_{1-6}$)alkoxycarbonyl, $C_{2-6}$ alkynylcarbonyl, $C_{1-6}$ alkylsulfonyl, $C_{6-10}$ arylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, carboxyalkylamino, cyano, trifluoromethoxy, and perfluoroethoxy.

Additional preferred values of optional substituents on $R^1$ include $C_{1-6}$ alkylsulfonyl, $C_{6-10}$ arylsulfonyl, $C_{6-10}$ ar($C_{1-6}$) alkylsulfonyl, $C_{6-10}$ arylsulfonamido, $C_{6-10}$ ar($C_{1-6}$) alkylsulfonamido, N-morpholinosulfonyl, and $R^{13}R^{14}NSO_2$—, where $R^{13}$ and cycloalkyl, $C_{2-6}$ alkenyl, $C_{2-6}$ alkynyl, $C_{6-10}$ aryl, $C_{6-10}$ ar($C_{1-4}$)alkyl, pyridyl, pyridyl ($C_{1-4}$)alkyl, carboxy($C_{1-6}$)alkyl, $C_{1-4}$ alkoxycarbonyl($C_{1-4}$) alkyl, cyano($C_{2-6}$)alkyl, hydroxy($C_{2-6}$)alkyl, $C_{1-4}$ alkoxy ($C_{2-6}$)alkyl, mono- and di-($C_{1-4}$)alkylamino($C_{2-6}$)alkyl, or $R^{13}$ and $R^{14}$ can be taken together with the nitrogen atom to which they are attached to form a heterocyclic ring selected from the group consisting of N-morpholinosulfonyl, N-piperazinylsulfonyl (optionally N' substituted with $C_{1-6}$ alkyl, $C_{1-6}$ hydroxyalkyl, $C_{6-10}$ aryl, $C_{6-10}$ aryl($C_{1-6}$)alkyl, $C_{1-6}$ alkylsulfonyl, $C_{6-10}$ arylsulfonyl, $C_{1-6}$ alkylcarbonyl, morpholino or $C_{6-10}$ arylcarbonyl), N-pyrrolylsulfonyl, N-piperidinylsulfonyl, N-pyrrolidinylsulfonyl, N-dihydropyridylsulfonyl, N-indolylsufonyl, wherein said heterocyclic ring can be optionally substituted with one or two of hydroxy, $C_{1-8}$ alkanoyloxy, $C_{1-6}$ alkoxy, $C_{6-10}$ aryloxy, amino, mono- and di- $C_{1-6}$ alkylamino, $C_{1-8}$ alkanoylamino, $C_{1-4}$ alkyl, $C_{3-7}$ cycloalkyl, $C_{6-10}$ aryl, $C_{6-10}$ ar($C_{1-4}$)alkyl, heterocycle, heterocycloalkyl, carboxy($C_{1-6}$) alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, mono- or di-($C_{1-4}$)alkylamino($C_{2-6}$)alkyl, carboxy, $C_{1-6}$ alkoxycarbonyl, carboxamido, formyl, $C_{1-6}$ alkanoyl, $C_{6-10}$ aroyl, $C_{6-10}$ ar($C_{1-4}$)alkanoyl, sulfonyl, $C_{1-6}$ alkylsulfonyl, $C_{1-6}$ alkoxysulfonyl, sulfonamido, phosphonyl, phosphoramido, or phosphinyl.

An additional preferred group of compounds are those compounds of Formula I wherein $R^1$ is heteroaryl or substituted heteroaryl. Preferred $R^1$ heteroaryl groups include pyridyl, pyrazolyl, thiophenyl, chromenyl, benzoxazolyl, benzthiadiazolyl, quinazolinyl, quinolinyl, isoquinolinyl and tetrahydroquinolinyl, with thiophenyl, quinazolinyl quinolinyl and tetrahydroquinolinyl being more preferred and thiophenyl, isoquinolinyl and quinolinyl especially preferred. Preferred compounds when $R^1$ is substituted heteroaryl include those compounds having one of the heteroaryl groups mentioned as preferred that have one or more, preferably one or two, substituents that are listed in the preceding paragraph. Preferred substituents when $R^1$ is substituted heteroaryl include one or more substituents, preferably 1 to 3 substituents, independently selected from halogen, $C_{1-6}$ alkyl, $C_{1-6}$ alkoxy, amidino, guanidino, carboxyalkoxy, carboxyalkylamino, amino, mono($C_{1-6}$) alkylamino and/or di($C_{1-6}$)alkylamino.

Useful values of $R^1$ include phenyl, chlorophenyl, iodophenyl, dichlorophenyl, bromophenyl, trifluoromethylphenyl, methylsulfonylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, cyclopentyl, 2-propylbutyl, 5-chloro-2-methoxyphenyl, 2-cyanophenyl, 2-(N-hydroxy) aminophenyl, 2-(4-biphenylmethoxy)phenyl, 2-(3-biphenylmethoxy)phenyl, benzyl, 3-(6-(2,3-dihydro-1,1-dioxobenzo[b]thiophene)phenyl, 2-(phenylsulfonyl)phenyl, 2,4-bis(methylsulfonyl)phenyl, and 2-chloro-4-methylsulfonylphenyl. Additional useful values include 8-quinolinyl, 5-methyl-8-quinolinyl, 4-benzo-2,1,3-thiadiazolyl, 5-chloro-2-thiophenyl, 5-chloro-1,3-dimethyl-4-pyrazolyl, pyridyl, isoquinolinyl, and tetrahydroquinolinyl.

Useful values of $R^1$, when $R^1$ is phenyl substituted by $R^{13}R^{14}NSO_2$— include 2-(N-methylphenethylaminosulfonyl)phenyl, bis(2-methoxyethyl)aminosulfonylphenyl, 2-N-methyl-(3,4-dimethoxyphenyl)ethylaminosulfonylphenyl, N-methyl-N- ethoxycarbonylmethyl)aminosulfonylphenyl, 2-(N-methyl-N-(2-(2-pyridyl)ethyl)aminosulfonyl)phenyl, 2-(N-propyl-N-(2-(2-pyridyl)ethyl)aminosulfonyl)phenyl, 2-(N-ethyl-N-(4-pyridylmethyl)aminosulfonyl)phenyl, 2-(N-methyl-N-(4-methoxyphenyl)aminosulfonyl)phenyl, 2-(N-methyl-N-(4-methoxycarbonylphenyl)aminosulfonyl)phenyl, 2-(N-(2-cyanoethyl)-N-(3-pyridylmethyl)aminosulfonyl)phenyl, 2-(N,N-bis-(2-cyanoethyl)aminosulfonyl)phenyl, 2-(N-(2-ethoxycarbonylethyl)-N-benzylaminosulfonyl)phenyl, 2-(N-methyl-N-(2-(4-pyridyl)ethyl)aminosulfonyl)phenyl, 2-(N-(ethoxycarbonylmethyl)-N-(2-pyridylmethyl)aminosulfonyl)phenyl, 2-(N,N-,bis(ethoxycarbonylmethyl)aminosulfonyl)phenyl, 2-(N,N-bis(carboxymethyl)aminosulfonyl)phenyl, 2-(N-methyl-N-(4-carboxyphenyl)aminosulfonyl)phenyl, 2-(N-(2-carboxyethyl)-N-benzylaminosulfonyl)phenyl, 2-(N-(2-cyanoethyl)-N-(2-furanylmethyl)aminosulfonyl)phenyl, 2-(N-ethyl-N-(1-benzyl-3-pyrrolidinyl)aminosulfonyl)phenyl, 2-(N-benzyl-N-(2-(N,N-dimethylamino)ethyl)aminosulfonyl)phenyl, 2-(N-methyl-N-(1-methyl-4-piperidinyl)aminosulfonyl) phenyl, 2-(N-methyl-N-(3-pyridylmethyl)aminosulfonyl) phenyl, 2-(N-ethyl-N-(2-(N,N-dimethylamino)ethyl) aminosulfonyl)phenyl, 2-(2-(4-morpholinyl) ethylaminosulfonyl)phenyl, 2-(N-methyl-N-(2-(N,N-dimethylamino)ethyl)aminosulfonyl)phenyl, N-ethyl-3,4-(methylenedioxy)anilinosulfonylphenyl, 2-(N-methyl-N-(3-(N,N-dimethylamino)propyl)aminosulfonyl)phenyl, and 2-(4-pyridylmethyl-aminosulfonyl)phenyl.

Further useful values of $R^1$, when $R^1$ is phenyl substituted by $R^{13}R^{14}NSO_2$— include 2-morpholinylsulfonylphenyl, 2-(acetylpiperazinylsulfonyl)phenyl, 2-(4-ethyloxycarbonyl)piperidinylsulfonyl, 2-(4-carboxyl)piperidinylsulfonylphenyl, 3-ethoxycarbonyl-1-piperidinosulfonyl)phenyl, 3-carboxypiperidinosulfonyl) phenyl, 2-methoxycarbonyl-1-pyrrolidionsulfonyl)phenyl, 2-carboxy-1-pyrrolidionsulfonyl)phenyl, -2-(4-methylsulfonylpiperazin-1-ylsulfonyl)phenyl, 2-(4-(2-pyrimidinyl)piperazin-1-ylsulfonyl)phenyl, 2-(4-ethylpiperazin-1-ylsulfonyl)phenyl, 2-(4-(piperidin-1-yl) piperidin-1-ylsulfonyl)phenyl, 2-(4-(ethoxycarbonylmethyl) piperazin-1-ylsulfonyl)phenyl, 2-(4-(carboxymethyl) piperazin-1-ylsulfonyl)phenyl, 2-(4-(2-pyridyl)piperazinyl-sulfonyl)phenyl, 2-(4-phenylpiperazinylsulfonyl)phenyl, 2-(4-benzylpiperazinylsulfonyl)phenyl, 2-(4-(2-methoxyphenyl)piperazinylsulfonyl)phenyl, 2-(4-methylpiperazinylsulfonyl)phenyl, -2-(4-(pyrrolidin-1-yl) piperidin-1-ylsulfonyl)phenyl, and 2-(4-ethoxycarbonyl-1-piperazinylsulfonyl)phenyl.

The groups $R^2$, $R^3$ and $R^4$ in Formula I substitute for any remaining hydrogen atoms on the benzene ring after allowing for attachment of the moiety —Z—$R^1$. Preferred compound are those where $R^2$, $R^3$ and $R^4$ are independently hydrogen, $C_{1-4}$ alkyl, $C_{4-7}$ cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamide, carboxy, alkoxycarbonyl, carboxymethyl alkoxycarbonylmethyl, or cycloalkyloxycarbonyl.

Alternatively, $R^2$ and $R^3$, when attached to adjacent carbon atoms on the benzene ring, are one of —CH=CH—CH=CH— or —(CH_2)_q—, where q is from 2 to 6, thereby forming a fused ring. Preferred values of $R^2$ together with $R^3$ include —CH=CH—CH=CH—, —CH_2—CH_2—CH_2— and —CH_2—CH_2—CH_2—CH_2—. When $R^2$ and $R^3$ together form a fused ring, $R^4$ is preferably hdrogen.

Useful values of $R^2$, $R^3$ and $R^4$ include hydrogen, methyl, ethyl, chloro, bromo, trifluoromethyl, hydroxymethyl, methoxy, ethoxy, carboxamide, nitro, phenyl, cyclopropyl, hydroxy, isopropyl, methoxycarbonyl, ethoxycarbonyl and benzyl. Useful values of $R^2$, $R^3$ and $R^4$ also include $R^2$ and $R^3$ together forming —CH=CH—CH=CH— or —CH_2—CH_2—CH_2— and $R^4$ being hydrogen.

Preferred compounds are those of Formula I, where $R^6$ is hydrogen or $C_{1-6}$ alkyl.

Preferred compounds are those of Formula I, where $R^7$, $R^8$, $R^{11}$ and $R^{12}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl. Useful values of $R^7$, $R^8$, $R^{11}$ and $R^{12}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. Additional preferred compounds are those wherein $R^7$ and $R^8$ are taken together to form —(CH_2)_y— where y is most preferably 2. Another group of preferred compounds are those where $R^8$ and $R^{11}$ are taken together to form —(CH_2)_r— where r is most preferably 2.

Preferred compounds are those of Formula I, wherein $R^9$ is hydrogen or $C_{1-6}$ alkyl, optionally substituted by one, two or three, preferably one, of amino, monoalkylamino, dialkylamino, alkoxy,hydroxy, alkoxycarbonyl, aryloxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

Suitable values of $R^9$ include hydrogen, methyl, ethyl, propyl, n-butyl, benzyl, phenethyl, 2-hydroxyethyl, 3-hydroxypropyl, 4-hydroxybutyl, carboxymethyl and carboxyethyl.

Preferred values of $R^{10}$ in Formula I include hydrogen, $C_{1-6}$ alkyl, $C_{6-10}$ ar($C_{1-6}$)alkyl, $C_{6-10}$ aryl, $C_{2-10}$ hydroxy-alkyl $C_{2-10}$ aminoalkyl, $C_{2-7}$ carboxyalkyl, mono($C_{1-4}$ alkyl) amino($C_{1-8}$)alkyl, and di($C_{1-4}$ alkyl)amino ($C_{1-8}$)alkyl. Suitable values of $R^{10}$ include methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino) ethyl.

Preferred values of $R^a$, $R^b$ and $R^c$ in Formula I are hydrogen, hydroxy, $C_{1-6}$ alkyl, $C_{1-6}$ alkoxy, cyano or —$CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of

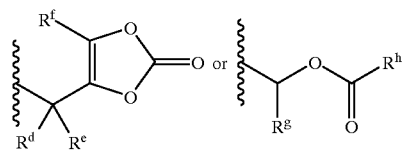

where $R^d$–$R^h$ are defined as above. When $R^a$, $R^b$ and $R^c$ are —$CO_2R^w$, where $R^w$ is one of one of the moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

Preferred values of n in Formula I include from zero to 6, more preferably from zero to 4, and most preferably zero, 1 or 2. Preferred values of m include from zero to 4, more preferably zero, 1, 2 or 3.

Compounds having the following formulae (Formula IIA and Formula IIB) have been discovered to have exceptional potency as inhibitors of serine proteases:

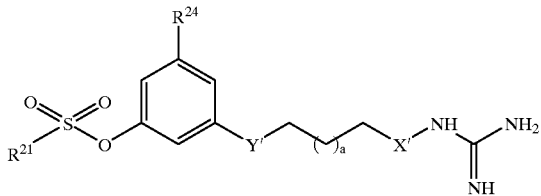

(IIA)

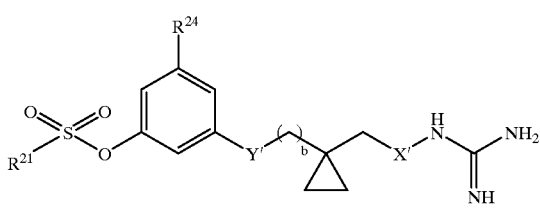

(IIB)

or a solvate, hydrate, pharmaceutically acceptable salt or prodrug thereof, wherein:

$R^{21}$ is one of phenyl, naphthyl, thiophenyl, quinolinyl or isoquinolinyl, optionally substituted by one or two substituents independently selected from the group consisting of halogen, $C_{1-4}$ alkyl, $C_{1-4}$ alkoxy, methoxy, trifluoromethyl, cyano, nitro, amino or dimethylamino; and when $R^{21}$ is phenyl, said phenyl can be optionally ortho- substituted by $C_{1-6}$ alkylsulfonyl, $C_{6-10}$ arylsulfonyl, $C_{6-10}$ $ar(C_{1-6})$alkylsulfonyl, $C_{6-10}$ arylsulfonamido, $C_{6-10}$ $ar(C_{1-6})$alkylsulfonamido, N-morpholinosulfonyl, or $R^{22}R^{23}NSO_2$—, where $R^{22}$ and $R^{23}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ $ar(C_{1-4})$ alkyl, pyridyl, pyridyl($C_{1-4}$)alkyl, carboxy($C_{1-6}$)alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, mono- and di-($C_{1-4}$)alkylamino($C_{2-6}$)alkyl, or $R^{22}$ and $R^{23}$ can be taken together with the nitrogen atom to which they are attached to form a heterocyclic ring selected from the group consisting of N-morpholinosulfonyl, N-piperazinylsulfonyl (optionally N' substituted with $C_{1-6}$ alkyl, $C_{1-6}$ hydroxyalkyl, $C_{6-10}$ aryl, $C_{6-10}$ aryl ($C_{1-6}$) alkyl, $C_{1-6}$ alkylsulfonyl, $C_{6-10}$ arylsulfonyl, $C_{1-6}$ alkylcarbonyl, morpholino or $C_{6-10}$ arylcarbonyl), N-pyrrolylsulfonyl, N-piperidinylsulfonyl, N-pyrrolidinylsulfonyl, N-dihydropyridylsulfonyl, N-indolylsufonyl, wherein said heterocyclic ring can be optionally substituted with one or two of hydroxy, $C_{1-8}$ alkanoyloxy, $C_{1-6}$ alkoxy, $C_{6-10}$ aryloxy, amino, mono- and di- $C_{1-6}$ alkylamino, $C_{1-8}$ alkanoylamino, $C_{1-4}$ alkyl, $C_{3-7}$ cycloalkyl, $C_{6-10}$ aryl, $C_{6-10}$ $ar(C_{1-4})$alkyl, heterocycle, hetercycloalkyl, carboxy($C_{1-6}$)alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($C_{2-6}$)alkyl, mono- and di-($C_{1-4}$) alkylamino($C_{2-6}$)alkyl, carboxy, $C_{1-6}$ alkoxycarbonyl, carboxamido, formyl, $C_{1-6}$ alkanoyl, $C_{6-10}$ aroyl, $C_{6-10}$ $ar(C_{1-4})$alkanoyl, sulfonyl, $C_{1-6}$ alkylsulfonyl, $C_{1-6}$ alkoxysulfonyl, sulfonamido, phosphonyl, phosphoramido, or phosphinyl;

$R^{24}$ is hydrogen or $C_{1-4}$ alkyl;

Y' is one of O, $NR^{10}$, where $R^{10}$ is defined as above, or a covalent bond;

a and b are 0, 1 or 2, preferably 1;

X' is O or $NR^{29}$; and $R^{29}$ is hydrogen or $C_{1-4}$ alkyl.

Preferred and suitable values of $R^{21}$ are the same as those described above for $R^1$; Y' is preferably O; a is preferably one; and X' is preferably O or NH.

Specific compounds within the scope of the invention include the following:

3-[3-(2-chlorophenylsulfonyloxy)-5-methylphenoxy] propoxyguanidine;

3-[3-(2-methoxyphenylsulfonyloxy)-5-methylphenoxy] propoxyguanidine;

3-[5-methyl-3-(quinolinyl-8-sulfonyloxy)phenoxy] propoxyguanidine hydrochloride;

3-[3-(5-chloro-2-methoxyphenylsulfonyloxy)-5-methylphenoxy]propoxyguanidine hydrochloride;

3-[3-(5-chlorothiophenyl-2-sulfonyloxy)-5-methylphenoxy] propoxyguanidine hydrochloride;

3-[3-(2-cyanophenylsulfonyloxy)-5-methylphenoxy] propoxyguanidine hydrochloride;

3-[3-(5-isoquinolinylsulfonyloxy)-5-methylphenoxy] propoxyguanidine hydrochloride;

3-[5-methyl-3-[2-(methylsulfonyl)phenylsulfonyloxy] phenoxy]propoxyguanidine hydrochloride 3-[5-methyl-3-(1,2,3,4-tetrahydroquinolinyl-8-sulfonyloxy) phenoxy]propoxyguanidine acetate;

3-[5-hydroxymethyl-3-(quinolinyl-8-sulfonyloxy)phenoxy] propoxyguanidineacetic acid salt;

1-[[5-methyl-3-(2-methylsulfonylphenylsulfonyloxy) phenoxy]methyl]cyclopropylmethoxy guanidine hydrochloride;

1-[[5-methyl-3-(2-cyanophenylsulfonyloxy)phenoxy] methyl]cyclopropylmethoxyguanidine acetate;

1-[[5-methyl-3-(quinolinyl-8-sulfonyloxy)phenoxy]methyl] cyclopropylmethoxyguanidine acetate;

3-[5-methyl-3-(2-morpholinylsulfonylphenylsulfonyloxy) phenoxy]propoxyguanidine hydrochloride;

3-[5-methyl-3-(2-(acetylpiperazinylsulfonyl) phenylsulfonyloxy)phenoxy]propoxyguanidine hydrochloride;

3-[5-methyl-3-(2-(N-methylphenethylaminosulfonyl) phenylsulfonyloxy)phenoxy]propoxy guanidine hydrochloride;

3-[5-methoxy-3-(2-methylsulfonylphenylsulfonyloxy) phenoxy]propoxyguanidine hydrochloride;

3-[5-ethyl-3-(2-methylsulfonylphenylsulfonyloxy)phenoxy] propoxyguanidine hydrochloride;

3-[5-methyl-3-(2-(phenylsulfonyl)phenylsulfonyloxy) phenoxy]propoxyguanidine hydrochloride;

3-[5-methyl-3-(2-(4-ethyloxycarbonyl) piperidinylsulfonylphenylsulfonyloxy)phenoxy]propoxy guanidine hydrochloride;

2-[5-methyl-3-(2-(methylsulfonyl)phenylsulfonyloxy) phenoxy]ethoxyguanidine;

2-hydroxy-3-[5-methyl-3-(2-methylsulfonyl) phenylsulfonyloxyphenoxy]propoxyguanidine;

3-[3-(2,4-bis(methylsulfonyl)phenylsulfonyloxy)-5-methylphenoxy]propoxyguanidine hydrochloride;

3-[5-methyl-3-(3-methylsulfonyl) phenylsulfonyloxyphenoxy]propoxyguanidine hydrochloride;

3-[3-((2-chloro-4-methylsulfonyl)phenylsulfonyloxy)-5-methylphenoxy]propoxyguanidine hydrochloride;

3-(6-(2,3-dihydro-1,1-dioxobenzo[b]thiophene) phenylsulfonyloxy)-5-methylphenoxypropoxy]guanidine trifluoroacetate;

3-[5-methyl-3-(2-(4-carboxyl) piperidinylsulfonylphenylsulfonyloxy)phenoxy] propoxyguanidine;

3-[5-methyl-3-(3-methylquinolinyl-8-sulfonyloxy) phenoxy]propoxyguanidine diacetate;

3-[5-methyl-3-[2-(N-hydroxy)aminophenylsulfonyloxy] phenoxy]propoxyguanidine hydrochloride;

3-[5-methyl-3-[2-aminophenylsulfonyloxy]phenoxy] propoxyguanidine hydrochloride;

3-[3-(2-(4-biphenylmethoxy)phenylsulfonyloxy)-5-methylphenoxy]propoxyguanidine;

3-[3-(2-(3-biphenylmethoxy)phenylsulfonyloxy)-5-methylphenoxy]propoxyguanidine hydrochloride;

1-[(3-benzyloxy-5-methylphenoxy)methyl]-1,1-cyclopropylethoxyguanidine;

3-[5-methyl-3-bis(2-methoxyethyl) aminosulfonylphenylsulfonyloxy)phenoxy] propoxyguanidine hydrochloride;

3-[5-methyl-3-(N-ethyl-3,4-(methylenedioxy) anilinosulfonylphenylsulfonyloxy)phenoxy] propoxyguanidine hydrochloride;

3-[5-methyl-3-(2-N-methyl-(3,4-dimethoxyphenyl) ethylaminosulfonylphenylsulfonyloxy)phenoxy] propoxyguanidine hydrochloride;

3-[5-methyl-3-((3-ethoxycarbonyl-1-piperidinosulfonyl) phenylsulfonyloxy)phenoxy]propoxyguanidine hydrochloride 3-[5-methyl-3-((3-carboxypiperidinosulfonyl) phenylsulfonyloxy)phenoxy]propoxyguanidine hydrochloride;

3-[5-methyl-3-((2-methoxycarbonyl1-pyrrolidinosulfonyl) phenylsulfonyloxy)phenoxy]propoxyguanidine hydrochloride;

3-[5-methyl-3-((2-carboxy-1-pyrrolidinosulfonyl) phenylsulfonyloxy)phenoxy]propoxyguanidine hydrochloride;

3-[5-methyl-3-(N-methyl-N-ethoxyarbonylmethyl) aminosulfonylphenylsulfonyloxy)phenoxy] propoxyguanidine hydrochloride;

3-[5-methyl-3-(N-methyl-N-ethoxyarbonylmethyl) aminosulfonylphenylsulfonyloxy)phenoxy] propoxyguanidine hydrochloride;

3-[5-methyl-3-(2-(4-methylsulfonylpiperazin-1-ylsulfonyl) phenylsulfonyloxy)phenoxy]propoxyguanidine hydrochloride;

3-[5-methyl-3-(2-(4-(2-pyrimidinyl)piperazin-1-ylsulfonyl) phenylsulfonyloxy)phenoxy]propoxyguanidine hydrochloride;

3-[5-methyl-3-(2-(N-methyl-N-(2-(2-pyridyl)ethyl) aminosulfonyl)phenylsulfonyloxy)phenoxy] propoxyguanidine hydrochloride;

3-[5-methyl-3-(2-(N-propyl-N-(2-(2-pyridyl)ethyl) aminosulfonyl)phenylsulfonyloxy)phenoxy] propoxyguanidine dihydrochloride;

3-[5-methyl-3-(2-(N-ethyl-N-(4-pyridylmethyl) aminosulfonyl)phenylsulfonyloxy)phenoxy] propoxyguanidine dihydrochloride;

3-[5-methyl-3-(2-(N-methyl-N-(4-methoxyphenyl) aminosulfonyl)phenylsulfonyloxy)phenoxy] propoxyguanidine hydrochloride;

3-[5-methyl-3-(2-(4-ethylpiperazin-1-ylsulfonyl) phenylsulfonyloxy)phenoxy]propoxyguanidine dihydrochloride;

3-[5-methyl-3-(2-(N-methyl-N-(4-methoxycarbonylphenyl) aminosulfonyl)phenylsulfonyloxy)phenoxy] propoxyguanidine hydrochloride;

3-[5-methyl-3-(2-(N-(2-cyanoethyl)-N-(3-pyridylmethyl) aminosulfonyl)phenylsulfonyloxy)phenoxy] propoxyguanidine dihydrochloride;

3-[5-methyl-3-(2-(N,N-bis-(2-cyanoethyl)aminosulfonyl) phenylsulfonyloxy)phenoxy]propoxyguanidine hydrochloride;

3-[5-methyl-3-(2-(N-(2-ethoxycarbonylethyl)-N-benzylaminosulfonyl)phenylsulfonyloxy)phenoxy] propoxyguanidine hydrochloride;

3-[5-methyl-3-(2-(4-(piperidin-1-yl)piperidin-1-ylsulfonyl) phenylsulfonyloxy)phenoxy]propoxyguanidine hydrochloride;

3-[5-methyl-3-(2-(N-methyl-N-(2-(4-pyridyl)ethyl) aminosulfonyl)phenylsulfonyloxy)phenoxy] propoxyguanidine hydrochloride;

3-[5-methyl-3-(2-(N-(ethoxycarbonylmethyl)-N-(2-pyridylmethyl)aminosulfonyl)phenylsulfonyloxy) phenoxy]propoxyguanidine hydrochloride;

3-[5-methyl-3-(2-(N,N-bis(ethoxycarbonylmethyl) aminosulfonyl)phenylsulfonyloxy)phenoxy] propoxyguanidine hydrochloride;

3-[5-methyl-3-(2-(4-(ethoxycarbonylmethyl)piperazin-1-ylsulfonyl)phenylsulfonyloxy)phenoxy] propoxyguanidine dihydrochloride;

3-[5-methyl-3-(2-(N,N-bis(carboxymethyl)aminosulfonyl) phenylsulfonyloxy)phenoxy]propoxyguanidine;

3-[5-methyl-3-(2-(N-methyl-N-(4-carboxyphenyl) aminosulfonyl)phenylsulfonyloxy)phenoxy] propoxyguanidine;

3-[5-methyl-3-(2-(N-(2-carboxyethyl)-N-benzylaminosulfonyl)phenylsulfonyloxy)phenoxy] propoxyguanidine;

3-[5-methyl-3-(2-(4-(carboxymethyl)piperazin-1-ylsulfonyl)phenylsulfonyloxy)phenoxy] propoxyguanidine;

3-[5-methyl-3-(2-(4-(2-pyridyl)piperazinylsulfonyl) phenylsulfonyloxy)phenoxy]propoxyguanidine hydrochloride;

3-[5-methyl-3-(2-(4-phenylpiperazinylsulfonyl) phenylsulfonyloxy)phenoxy]propoxyguanidine hydrochloride;

3-[5-methyl-3-(2-(4-benzylpiperazinylsulfonyl) phenylsulfonyloxy)phenoxy]propoxyguanidine hydrochloride;

3-[5-methyl-3-(2-(4-(2-methoxyphenyl) piperazinylsulfonyl)phenylsulfonyloxy)phenoxy] propoxyguanidine hydrochloride;

3-[5-methyl-3-(2-(N-(2-cyanoethyl)-N-(2-furanylmethyl) aminosulfonyl)phenylsulfonyloxy)phenoxy] propoxyguanidine;

3-[5-methyl-3-(2-(4-methylpiperazinylsulfonyl) phenylsulfonyloxy)phenoxy]propoxyguanidine hydrochloride;

3-[5-methyl-3-(2-(N-ethyl-N-(1-benzyl-3-pyrrolidinyl) aminosulfonyl)phenylsulfonyloxy)phenoxy] propoxyguanidine dihydrochloride;

3-[5-methyl-3-(2-(N-benzyl-N-(2-(N,N-dimethylamino) ethyl)aminosulfonyl)phenylsulfonyloxy)phenoxy] propoxyguanidine dihydrochloride;

3-[5-methyl-3-(2-(N-methyl-N-(1-methyl-4-piperidinyl) aminosulfonyl)phenylsulfonyloxy)phenoxy] propoxyguanidine dihydrochloride;

3-[5-methyl-3-(2-(N-methyl-N-(3-pyridylmethyl) aminosulfonyl)phenylsulfonyloxy)phenoxy] propoxyguanidine dihydrochloride;

3-[5-methyl-3-(2-(N-ethyl-N-(2-(N,N-dimethylamino) ethyl)aminosulfonyl)phenylsulfonyloxy)phenoxy] propoxyguanidine dihydrochloride;

3-[5-methyl-3-(2-(2-(4-morpholinyl)ethylaminosulfonyl) phenylsulfonyloxy)phenoxy]propoxyguanidine dihydrochloride;

3-[5-methyl-3-(2-(N-methyl-N-(2-(N,N-dimethylamino) ethyl)amino sulfonyl)phenylsulfonyloxy)phenoxy] propoxyguanidine dihydrochloride;

3-[5-methyl-3-(2-(4-(pyrrolidin-1-yl)piperidin-1-ylsulfonyl)phenylsulfonyloxy)phenoxy]propoxyguanidine;
3-[5-methyl-3-(2-(4-ethoxycarbonyl-1-piperazinylsulfonyl)phenylsulfonyloxy)phenoxy]propoxyguanidine hydrochloride;
3-[5-methyl-3-(2-(N-methyl-N-(3-(N,N-dimethylamino)propyl)aminosulfonyl)phenylsulfonyloxy)phenoxy]propoxyguanidine;
3-[5-methyl-3-(2-(4-pyridylmethylaminosulfonyl)phenylsulfonyloxy)phenoxy]propoxyguanidine;
N-methyl-N-{3-[5-methyl-3-(2-(methylsulfonyl)phenylsulfonyloxy)phenoxy]propoxy}guanidine hydrochloride;
3-[3-methyl-5-(N-methyl-2-(methylsulfonyl)phenylsulfonylamino)phenoxy]propoxyguanidine hydrochloride;
3-[3-(2-chlorophenylsulfonyloxy)-5-methylphenoxy]-propylaminoguanidinediacetate;
[3-[5-methyl-3-(2-trifluoromethylphenylsulfonyloxy)phenoxy]-propylamino]guanidine hydrochloride;
[3-[3-(5-chlorothiophenyl-2-sulfonyloxy)-5-methylphenoxypropylaminoguanidine acetate;
[3-[3-(2-methoxyphenylsulfonyloxy)-5-methylphenoxy]-propylamino]guanidine diacetate;
[3-[3-(2-cyanophenylsulfonyloxy)-5-methylphenoxy]propylamino]guanidine acetate;

as well as pharmaceutically acceptable salts thereof, for example the hydrochloride and acetate salts thereof. Structures for these compounds are provided in the pages prior to the claims.

Alternative embodiments of the present invention include compounds of Formula I in which two "R" groups together form a saturated or unsaturated hydrocarbon bridge, thus forming an additional cyclic moiety in the resulting compounds. Alternative embodiments include compounds of Formula I wherein Z, $R^1$–$R^4$, Y, m and n are as defined above; and:

A. $R^7$ and $R^{12}$ are taken together to form —$(CH_2)_o$—, where o is 1, 2 or 3; $R^{11}$ is hydrogen, alkyl, aralkyl, aryl, hydroxyalkyl or carboxyalkyl; $R^8$ is hydrogen and $R^6$, $R^a$, $R^b$ and $R^c$ are defined as above; or B. $R^{11}$ is hydrogen, alkyl, aralkyl, aryl, hydroxyalkyl or carboxyalkyl; $R^7$ is hydrogen;
$R^8$ and $R^{12}$ are taken together to form —$(CH_2)$—$(CH_2)$—$(CH_2)_p$—, where p is 1,2 or 3; and $R^6$, $R^a$, $R^b$ and $R^c$ are defined as above; or C. $R^6$ and $R^b$ are taken together to form —$(CH_2)$—$(CH_2)_r$— or =CH—N=CH—NH—, where r is 1, 2 or 3; $R^a$ is hydrogen or hydroxy; $R^c$ is hydrogen, alkyl, hydroxy, alkoxy, aryloxy, aralkoxy, alkoxycarbamoyloxy, cyano or —$CO_2R^w$—, where $R^w$ is as defined above; $R^7$, $R^8$, $R^{11}$ and $R^{12}$ are each independently one of hydrogen, alkyl, aralkyl, aryl, hydroxyalkyl or carboxyalkyl, or $R^7$ and $R^8$ are taken together to form —$(CH_2)_y$—, where y is zero, 1 or 2; or D. $R^a$ and $R^c$ are taken together to form —$CH_2$—$(CH_2)_s$—, where s is 1 or 2; $R^6$ is hydrogen, alkyl, alkoxy, aryloxy, aralkoxy, alkoxycarbonyloxy, cyano or —$CO_2R^w$—, where $R^w$ is as defined above; and $R^7$, $R^8$, $R^{11}$ and $R^{12}$ are each independently one of hydrogen, alkyl, aralkyl, aryl, hydroxyalkyl or carboxyalkyl, or $R^7$ and $R^8$ are taken together to form —$(CH_2)_y$—, where y is zero, 1 or 2.

Thus, compounds having formulae III, IV, V and VI are contemplated:

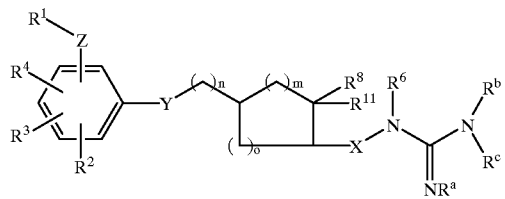

III

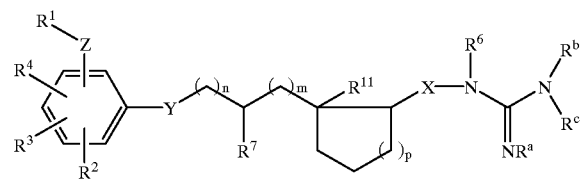

IV

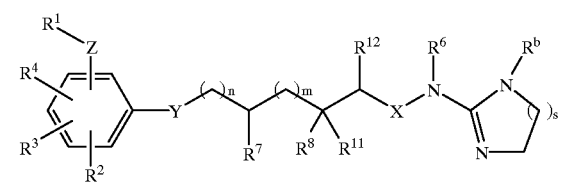

V

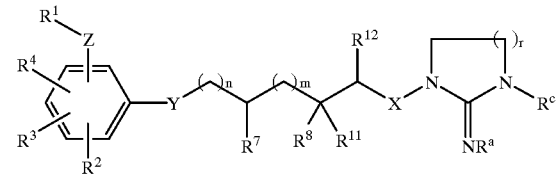

VI wherein $R^1$–$R^4$, Z, Y, $R^6$–$R^{12}$, $R^a$–$R^c$, n, m, o, p, r and s are defined as above. Preferred values for each of these variables are the same as described above for Formula I. Specific compounds within the scope of these formulae include:

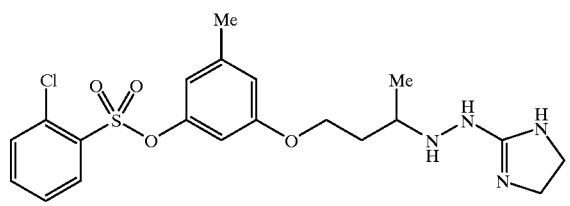

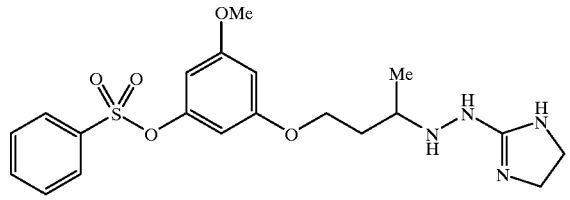

-continued

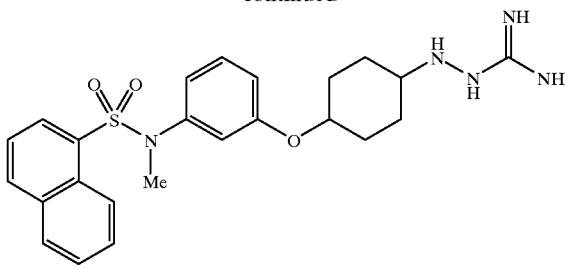

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112:309–323 (1985); Bodor, N., "Novel Approaches in Prodrug Design," *Drugs of the Future*, 6(3):165–182 (1981); and Bundgaard, H., "Design of Prodrugs: Bioreversible-Derivatives for Various Functional Groups and Chemical Entities," in *Design of Prodrugs* (H. Bundgaard, ed.), Elsevier, N.Y. (1985). Useful prodrugs are those where $R^a$, $R^b$ and/or $R^c$ are —$CO_2R^w$, where $R^w$ is defined above. See, U.S. Pat. No. 5,466,811 and Saulnier et al., *Bioorg. Med. Chem. Lett.* 4:1985–1990 (1994).

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocyclic" is used herein to mean a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or $C_1$ to $C_8$ alkyl, or together with the nitrogen to which they are bound, form a saturated or unsaturated 5-, 6-, or 7-membered ring.

Another aspect of the present invention is a process for preparing an aminoguanidine compound of Formula I, comprising reacting an aminoguanidine of the formula

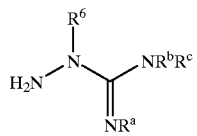

VII wherein $R^6$, $R^a$, $R^b$ and $R^c$ are defined as above, with a carbonyl-containing compound of the formula

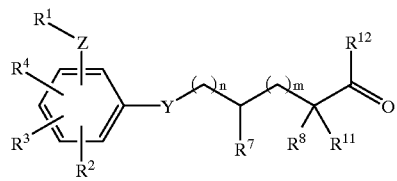

VIII wherein $R^1$–$R^4$, Z, Y, n, m, $R^7$, $R^8$, $R^{11}$ and $R^{12}$ are defined as above to form an amidinohydrazone, and thereafter selectively reducing the hydrazone carbon to nitrogen double bond of the amidinohydrazone.

The aminoguanidine is typically provided as a salt, preferably the nitrate salt. The first step proceeds at ambient temperature using alcohol as a solvent. An acid, such as 4N HCl in dioxane is added to the reaction mixture. The reaction is more fully described herein.

Another aspect of the present invention is a process for preparing a hydroxyguanidine compound of Formula I, comprising reacting an alkoxyamine compound of the formula

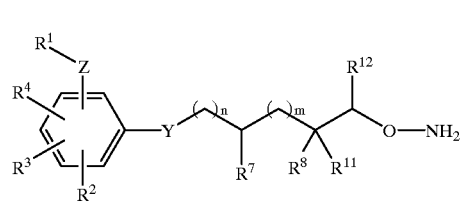

IX wherein $R^1$–$R^4$, Z, Y, n, m, $R^7$, $R^8$, $R^{11}$ and $R^{12}$ are defined as above with a guanidinylating reagent. Preferred guanidinylating reagents include: aminoiminosulfonic acid, optionally substituted 1H-pyrazole-1-carboxamidines, or N,N'-bis(tert-butoxycarbonyl) S-methyl isothiourea.

The invention is also directed to alkoxyamine intermediates that are useful for forming the protease inhibiting compounds of Formula I. These intermediates are represented by Formula IX:

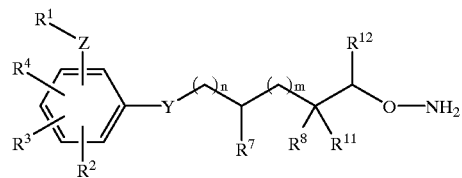

IX wherein $R^1$–$R^4$, Z, Y, n, m, $R^7$, $R^8$, $R^{11}$ and $R^{12}$ are defined as above for Formula I.

Schemes Ia, Ib, and Ic outline the synthetic steps to produce compounds of the present invention where $R^1$—Z is $R^1$—C($R^yR^z$)$_2$O— or $R^1$—SO$_2$O—. Scheme Ia illustrates but is not limited to the preparation of the compounds of Examples 1–8, 10–18, 21–22, 28–33, and 82–86.

Scheme Ia
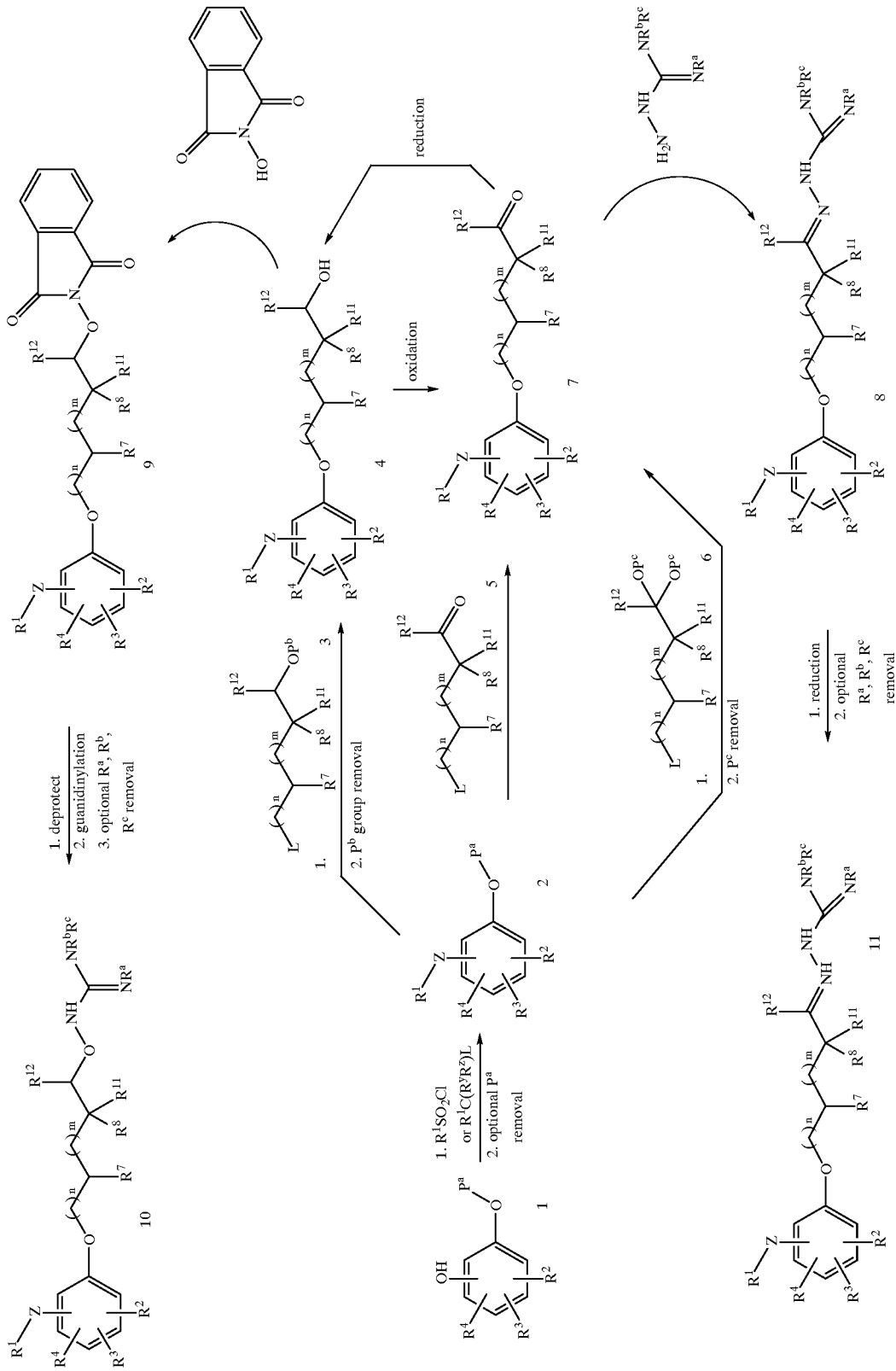

Phenols 1 (where $P^a$=H) are converted to monosulfonates 2 by treatment with appropriate sulfonyl chlorides. Preferred conditions include treating phenol 1 with a sulfonyl chloride in a biphasic system composed of an organic solvent, such as an ether, and an aqueous phase saturated with $NaHCO_3$. Alternatively, the reaction may be effected first by deprotonating 1 with one equivalent of a strong base, most preferably NaH, in a polar organic solvent, such as N,N-dimethylformamide or tetrahydrofuran, followed by treating the deprotonated phenol with the sulfonyl chloride. Still alternatively, phenol 1, in a typical organic solvent, such as dichloromethane, may be converted to 2 by treating the phenol with sulfonyl chloride in the presence of an amine base, such as 4-methylmorpholine.

Phenols 1 may be monoprotected ($P^a$ is a protecting group) with a variety of protecting groups known in the art, such as esters and benzyl ethers (Greene, T. W. and Wuts, P. G. M., *Protective Groups in Organic Synthesis*, 2nd edition, John Wiley and Sons, Inc. New York (1991)). Deprotection of the hydroxy groups is routinely accomplished using the reaction conditions well known in the art. For example, deprotection of benzyl ethers may be effected through catalytic hydrogenation using palladium on carbon as a catalyst in solvents such as ethanol or tetrahydrofuran. Deprotection of an acetate is accomplished by basic hydrolysis, most preferably with sodium hydroxide in aqueous tetrahydrofuran.

Phenols 2 are coupled to 3 (for L=OH) using a Mitsunobu coupling procedure (Mitsunobu, O., *Synthesis* 1 (1981)), where $P^b$ of 3 may be a suitable alcohol protecting group. Alternatively, suitable diols ($P^b$=H) may be used in the Mitsunobu reaction. Preferred coupling conditions include using a trialkylphosphine or triarylphosphine, such as triphenylphosphine or tri-n-butylphosphine, in a suitable solvent, such as tetrahydrofuran or dichloromethane, and an azodicarbonyl reagent, such as diethyl azodicarboxylate or 1,1'-(azodicarbonyl)dipiperidine. Typical $P^b$ (where $P^b$ is an alcohol protecting group) is well known in the art, such as esters and benzyl ethers (Greene, T. W. and Wuts, P. G. M., supra). Alternatively, where L is a reactive leaving group such as halide or sulfonate, phenol 2 may be treated with a base, such as sodium hydride, in a solvent, such as N,N-dimethylformamide, and then treated with 3. Removal of $P^b$ is routinely accomplished using the reaction conditions well known in the art. For example, deprotection of benzyl ethers may be effected through catalytic hydrogenation using palladium on carbon as a catalyst in solvents such as ethanol or tetrahydrofuran. Deprotection of an acetate is accomplished by basic hydrolysis, most preferably with sodium hydroxide in aqueous tetrahydrofuran.

Alternatively still, alcohol 4 can be obtained by reduction of the appropriate aldehyde or ketone 7 (obtained from 2 as described below) with a suitable reducing agent, such as sodium or lithium borohydride (Wallbridge, J. *Prog. Inorg. Chem* 11:99–231 (1970)).

Alcohol 4 is converted to 9 employing a Mitsunobu reaction with an N-hydroxycyclic imide derivative such as N-hydroxyphthalimide. Unveiling of the phthalimide protecting group is accomplished using standard conditions well known in the art (Greene, T. W. and Wuts, P. G. M., supra), for example, sodium borohydride in a mixture of an appropriate alcohol (e.g. ethanol or 2-propanol)/water followed by acidification. Alternatively, removal of the protecting group may be accomplished using hydrazine or methylamine.

Guanidinylation of the resulting alkoxyamine to 10 is achieved using standard reagents such as aminoiminosulfonic acid (Miller, A. E. and Bischoff, J. J. *Synthesis* 777 (1986)), or 1H-pyrazole-1-carboxamidine hydrochloride (Bernatowicz, M. S. et. al. *J Org. Chem* 57(8):2497 (1992)), or with substituted guanidinylating reagents such as N,N'-bis(tert-butoxycarbonyl)-S-methylisothiourea (Bergeron, R. J. and McManis, J. S. *J Org Chem.* 52:1700 (1987)) or N—$R^a$, N—$R^b$, N'—$R^c$-1H-pyrazole-1-carboxamidine, where $R^a$, $R^b$ and $R^c$ are defined as above for Formula I. Useful 1H-pyrazole-1-carboxamidines include N,N'-bis(tert-butoxycarbonyl)-1H-pyrazole-1-carboxamidine and N,N'-bis(benzyloxycarbonyl)-1H-pyrazole-1-carboxamidine (all of which can be prepared according to Bernatowicz, M. S. et. al., *Tetrahedron Letters* 34:3389 (1993)).

Conversion of alcohol 4 to the corresponding aldehyde or ketone 7 is accomplished using routine procedures for the oxidation of alcohols (see for example Carey, F. A, Sundberg, R. J. *Advanced Organic Chemistry, Part B: Reactions and Synthesis*, 3rd edition, Plenum Press, New York (1990)) such as the Swern oxidation (Mancuso, A. J. et al., *Journal of Organic Chemistry* 3329 (1976)) pyridinium chlorochromate (Corey, E. J. and Suggs, J. W. *Tetrahedron Letters* 2647 (1975)) pyridinium dichromate (Corey, E. J. and Schmidt, G. *Tetrahedron Letters* 399 (1979)), or sulfur trioxide pyridine complex/dimethylsulfoxide (*Tetrahedron Letters* 28:1603 (1987)).

Still alternatively, 2 may be coupled directly to 5 where L=OH or a reactive leaving group such as halide, alkyl sulfonate, or aryl sulfonate. In the case of L=OH, the Mitsunobu coupling procedure may be used. In cases where L is a reactive leaving group such as halide or sulfonate, phenol 2 may be treated with a base, such as sodium hydride, in a solvent, such as NAN-dimethylformamide, and then treated with 5.

Alternatively, phenol 2 may be converted to 7 by the Mitsunobu reaction using 6 wherein L=OH and $P^c$ is an aldehyde or ketone protecting group which is well known in the art (Greene, T. W. and Wuts, P. G. M., supra), for example, a dimethyl ketal or acetal, 1,3-dioxolane group, or 1,3-dioxane group. Alternatively, where L of 6 is a reactive leaving group such as halide or sulfonate, phenol 2 may be treated with a base, such as sodium hydride in a solvent such as N,N-dimethylformamide, and then treated with 6. $P^c$ may then be removed to afford 7 using standard conditions well known in the art, for example, p-toluenesulfonic acid in acetone (Greene, T. W. and Wuts, P. G. M., supra).

Compound 7 is then converted to amidinohydrazone 8 using standard conditions, for example, treatment with an aminoguanidine, such as aminoguanidine or 2-hydrazinoimidazoline, optionally in the presence of an acid such as nitric acid, hydrogen chloride, or hydrogen bromide, in an appropriate solvent, for example, ethanol or methanol, which, in addition, may contain other solvents such as dichloromethane or tetrahydrofuran. Conversion of 8 to 11 is accomplished under reducing conditions well known in the art, for example, lithium borohydride in an appropriate solvent such as tetrahydrofuran or methanol at various temperatures up to reflux. As an alternative method, catalytic hydrogenation with palladium on carbon catalyst can be employed.

When $R^a$, $R^b$ and/or $R^c$ are a protecting group, for example t-butyloxycarbonyl (Boc), these protecting groups can be optionally removed by treatment with acid, usually trifluoroacetic acid in a suitable solvent such as dichloromethane or water, or by HCl gas dissolved in a suitable solvent, such as 1,4-dioxane.

Scheme Ib

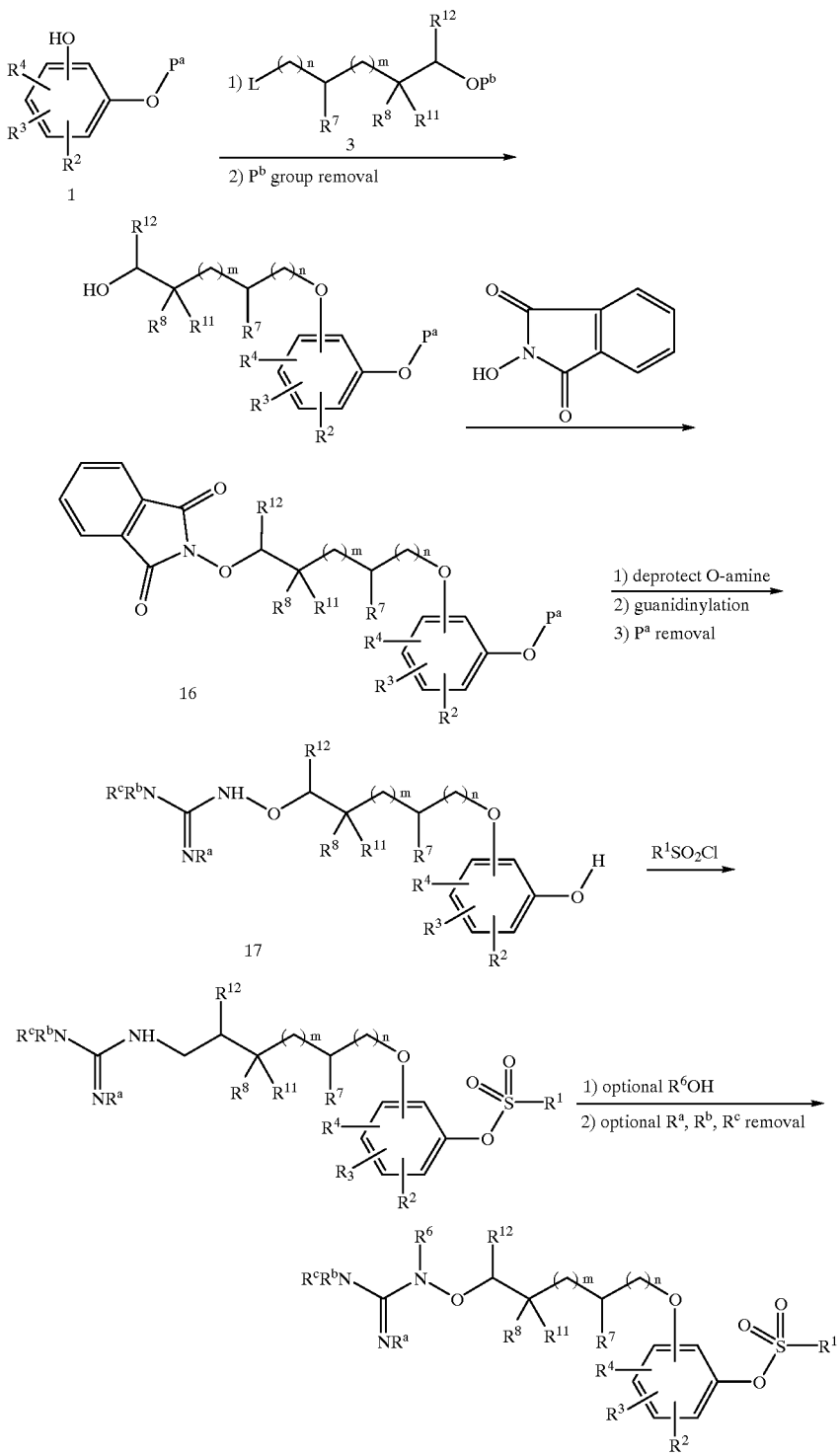

A variation of Scheme Ia (Scheme Ib) involves the use of monoprotected phenols in the synthesis of Examples 19–20, 23–26, and 80. Phenols 1 are monoprotected ($P^a$ is a protecting group) with a variety of protecting groups known in the art such as esters and benzyl ethers (Greene, T. W. & Wuts, P. G. M., supra). Monoprotected phenols 1 are coupled to 3 as described for Scheme Ia. Deprotection and another Mitsunobu coupling with an N-hydroxy imide derivative, such as N-hydroxyphthalimide, as described for Scheme Ia, gives the alkoxyphthalimides 16. The removal of the phthalimide group, as described for Scheme Ia, produces the alkoxyamine. The alkoxyamines are subsequently converted to the optionally protected alkoxyguanidines, using the standard guanidinylation reagents, such as aminoiminosulfonic acid (Miller, A. E. & Bischoff, J. J., supra) or 1H-pyrazole-1-carboxamidine hydrochloride (Bernatowicz, M. S. et. al., supra), or with substituted guanidinylating reagents such as N,N'-bis(tert-butoxycarbonyl)-S-methyl-isothiourea (Bergeron, R. J. & McManis, J. S., supra) or N—$R^a$, N—$R^b$, N'—$R^c$-1H-pyrazole-1-carboxamidine including N,N'-bis(tert-butoxycarbonyl)-1H-pyrazole-1-carboxamidine and N,N'-bis(benzyloxycarbonyl)-1H-pyrazole-1-carboxamidine (all of which can be prepared according to (Bernatowicz, M. S. et. al., supra) where $R^a$, $R^b$ and $R^c$ are as defined above. The phenolic protecting group, $P^a$, may be removed to give 17 and the resultant phenolic group reacted with sulfonyl chlorides. Optionally, the protected alkoxyguanidines may be alkylated on the unprotected nitrogen of the guanidine using a Mitsunobu coupling with an alcohol $R^6OH$ (e.g., methanol gives the N-methyl alkoxyguanidine derivative). Finally, the guanidine protecting groups, $R^a$, $R^b$, and $R^c$, may be removed as outlined for Scheme Ia.

Scheme Ic

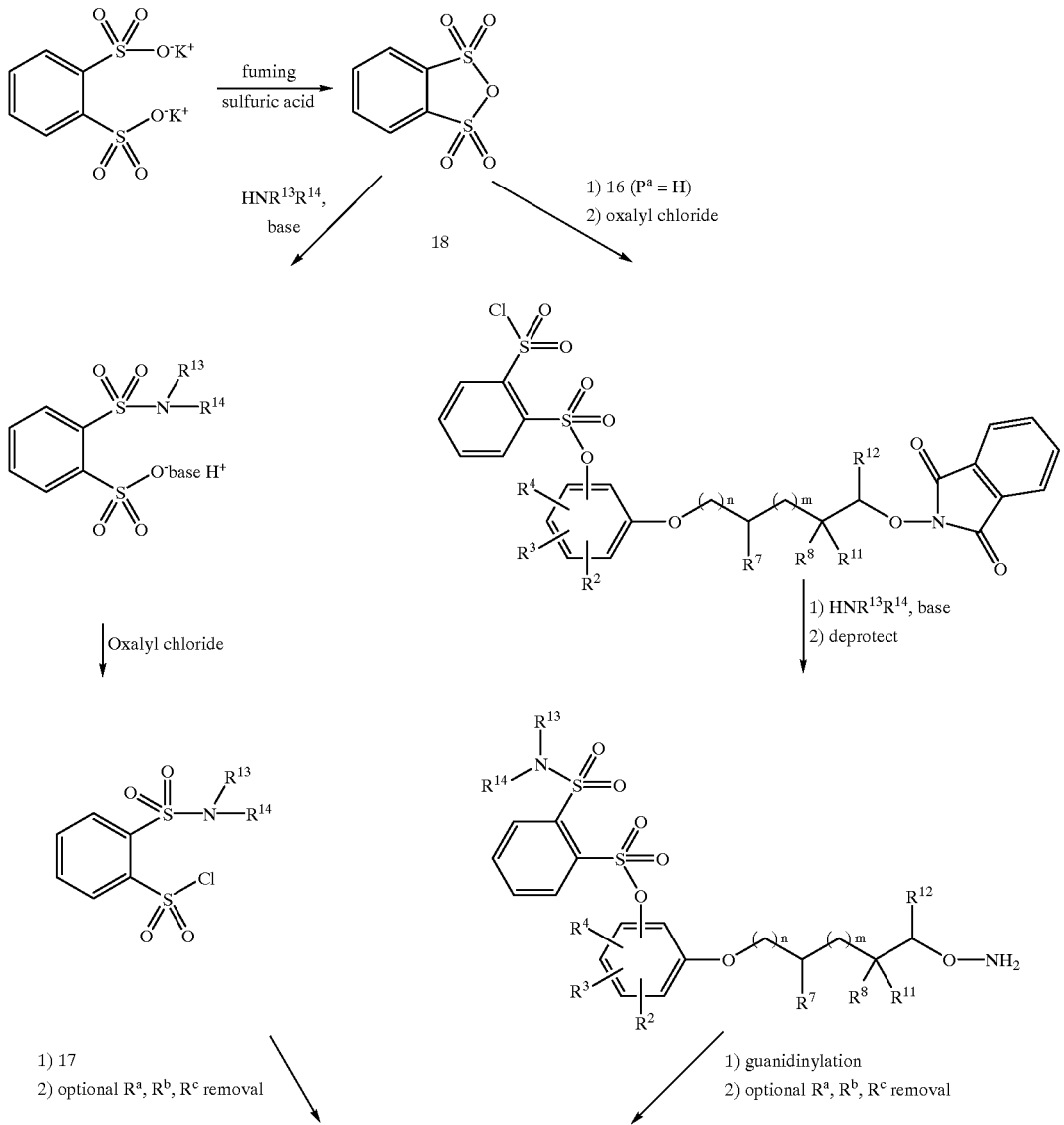

-continued

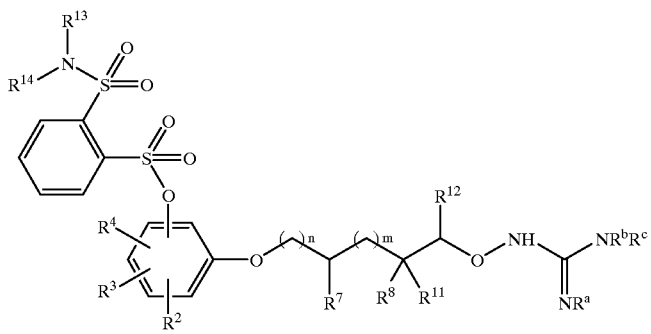

19

Scheme Ic outlines the synthesis of the 1,2-benzenedisulfo derivatives described in Examples 34–79. In particular, Examples 34–68 were synthesized by the reaction of 1,2-benzenedisulfonic anhydride 18 (Koeberg-Telder et al., *J Chem. Soc. Perkin II* 98 (1973)) with secondary amines, $R^{13}R^{14}NH$, in the presence of a base such as a tertiary amine where $R^{13}$ and $R^{14}$ are as defined above, provided that they are both other than hydrogen. The resultant monosulfonic acid salt is converted to the sulfonyl chloride in situ by reaction with 1 equivalent of oxalyl chloride. The resultant sulfonyl chloride is reacted in situ with the phenol 17. The optional guanidine protecting groups, $R^a$, $R^b$, and $R^c$, may be removed as outlined for Scheme Ia to give 19.

The Examples of 68–79 were alternatively synthesized by the reaction of the benzenedisulfonic anhydride 18 with the O-phthalimide 16 ($P^a$=H). The resultant monosulfonic acid salt is converted in situ to the sulfonyl chloride with 1 equivalent of oxalyl chloride. The resultant sulfonyl chloride is reacted with amines, especially primary and diamines, to produce sulfonamides. The O-amine is next deprotected and guanidinylated by the means outlined for Scheme Ia. Finally, the optional guanidine protecting groups, $R^a$, $R^b$, and $R^c$, may be removed as outlined for Scheme Ia to give 19.

Scheme IIa

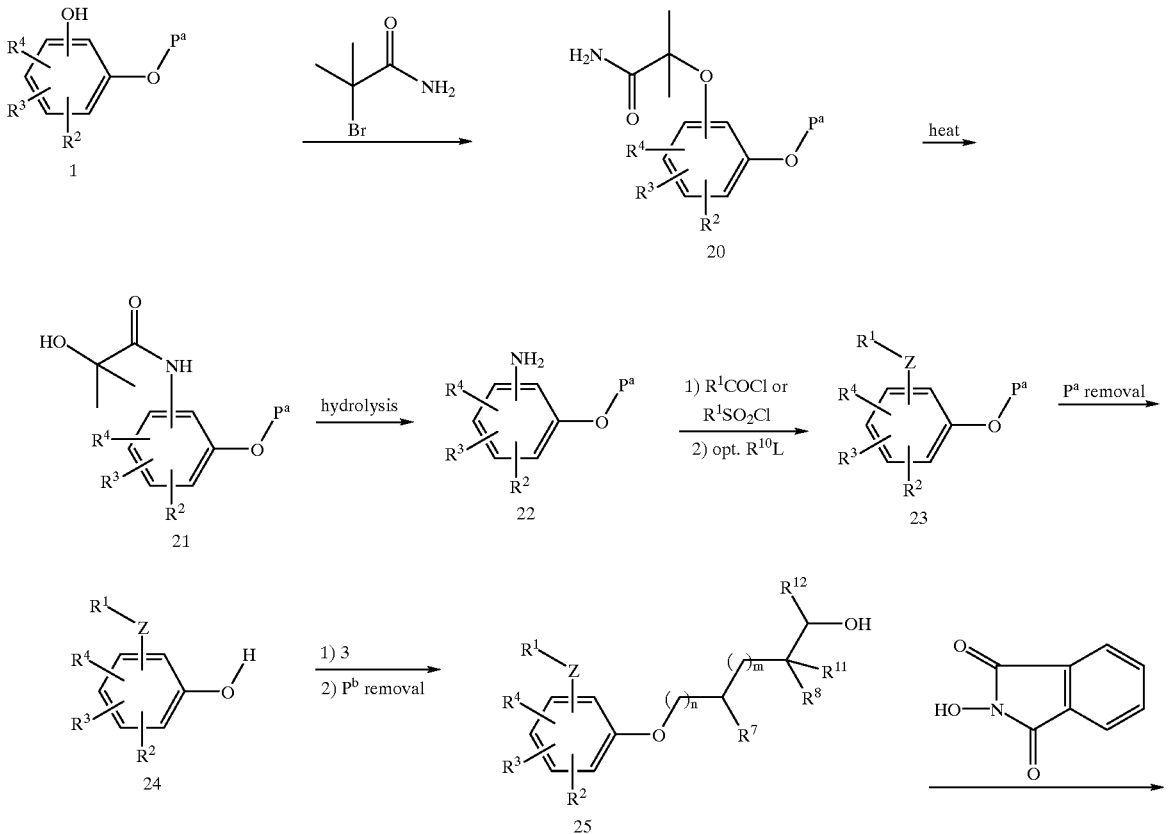

-continued

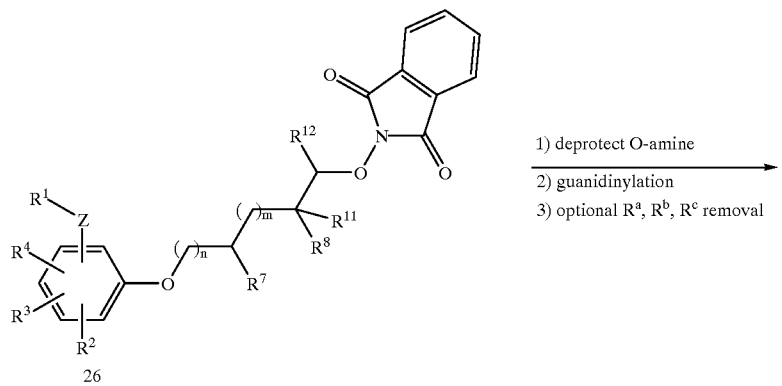

26

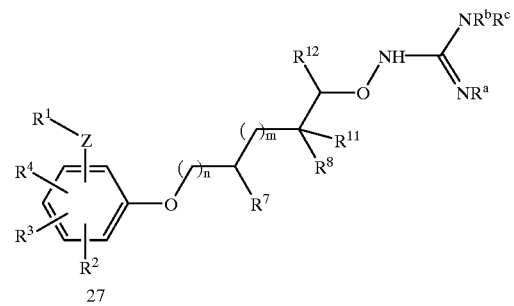

27

Schemes IIa and IIb outline the syntheses of primary and secondary sulfonamidophenoxy derivatives and carboxamido derivatives, where $R^1$—Z— is $R^1$—$SO_2NR^{10}$— or $R^1$—$CONR^{10}$—.

Scheme IIa outlines the synthesis of intermediate 1,3-aminophenols which are further converted to sulfonamidophenoxy derivatives where $R^1$—Z is $R^1$—$SO_2NR^{10}$— and $R^{10}$ is preferably an alkyl group, as exemplified by Example 81, or are alternatively converted to carboxamidophenoxy derivatives where $R^1$—Z is $R^1$—$CONR^{10}$—. Phenols 1 are reacted with 2-bromo-2-methyl propanamide in the presence of a base, such as sodium hydride, to give the aryloxyamides 20. The aryloxyamides 20 are treated with sodium hydride in a high boiling solvent, such as 1,3-dimethyl-3,4,5,6-tetrahydro-2(1H)-pyrimidinone, at an elevated temperature (e.g., 100° C. for 3 h) and undergo the Smiles rearrangement to the anilides 21 (Cotts & Southcott, J Chem. Soc. PTl 767 (1990)). The anilides 21 are hydrolyzed using strong base and elevated temperature (e.g., 10N sodium hydroxide at reflux) for extended times (e.g., 2 days) in order to provide the corresponding anilines 22. The anilines 22 are converted to sulfonamides 23 by the reaction with sulfonyl chlorides in the presence of a suitable base, such as a tertiary amine. The sulfonamides 23 are reacted with base (e.g., cesium carbonate) and $R^{10}L$ where L is a reactive leaving group, such as halide or sulfonate. Alternatively, the anilines 22 are converted to carboxamides by the reaction with acyl chlorides ($R^1COCl$) in the presence of a suitable base such as a tertiary amine. Still alternatively, the carboxamides may be produced by the reaction of anilines 22 with carboxylic acids ($R^1COOH$) by any of the known peptide coupling reagents, such as 1,3-dicyclohexylcarbodiimide or Castro's reagent (BOP) (Castro B., et al., Tetrahedron Lett. 1219 (1975)). The phenolic protecting group, $P^a$, is then removed and the resultant phenols 24 are coupled with 3 as described for Scheme Ia. After removal of the alcohol protecting group, $P^b$, the alcohol is coupled to N-hydroxy imides, such as N-hydroxyphthalimide, as described for Scheme Ia. The removal of the phthalimide group, as described for Scheme Ia, produces the alkoxyamine. The alkoxyamines are subsequently converted to the optionally protected alkoxyguanidines, using the standard guanidinylation reagents outlined for Scheme Ia. Finally, the guanidine protecting groups, $R^a$, $R^b$, and $R^c$, may be optionally removed as outlined for Scheme Ia to produce the target 27.

Scheme IIb

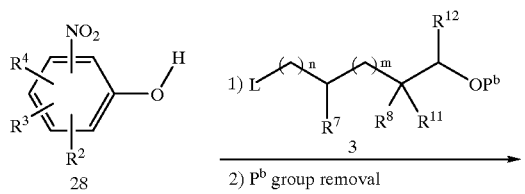

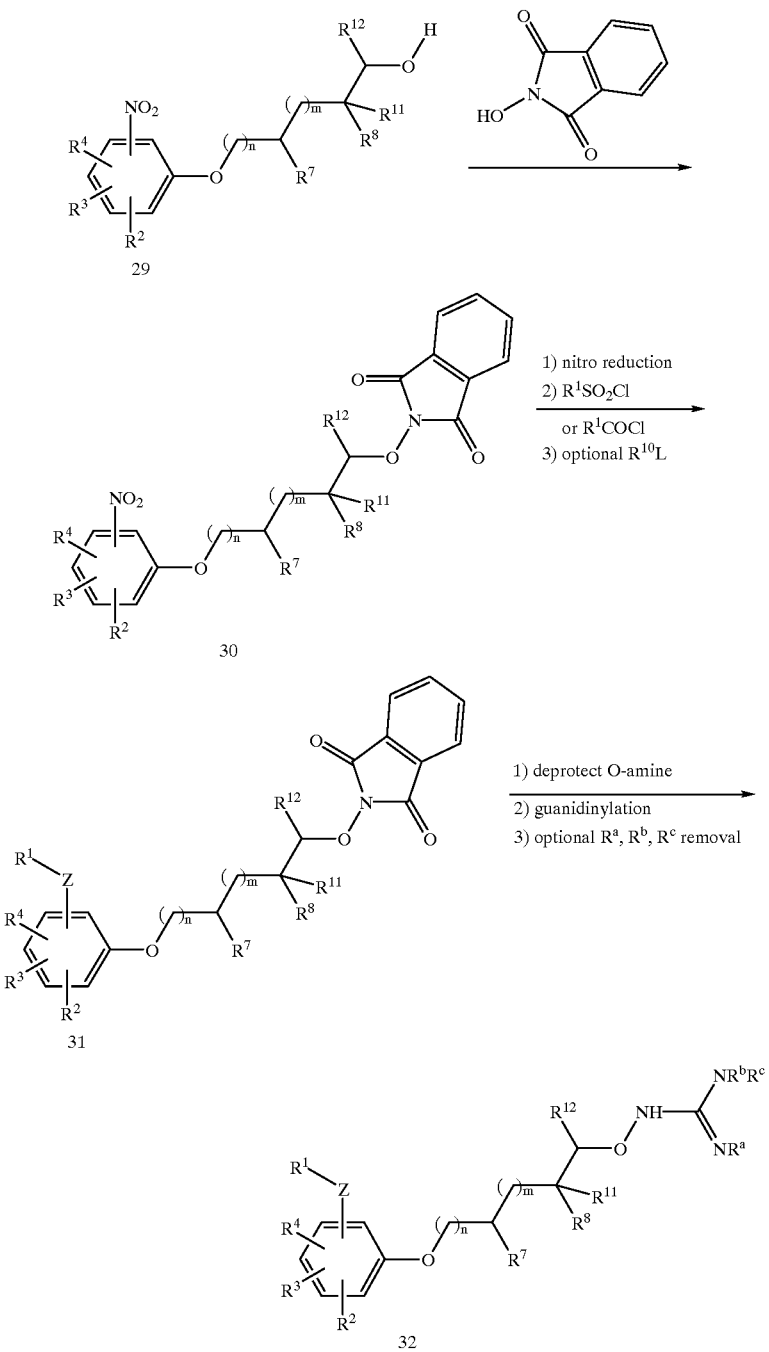

An alternative method to synthesize sulfonamides, especially unalkylated sulfonamides (where $R^{10}$=H) is shown in Scheme IIb. Nitrophenol 28 is coupled to 3 by standard techniques. Preferably, the reaction is effected by the Mitsunobu reaction (where L is OH). Alternatively, the nitrophenol is treated with a base, such as NaH, in a suitable solvent such as N,N-dimethylformamide or tetrahydrofuran, followed by the addition of 3 (where L is a reactive group, such as Cl, Br, I or sulfonate). After $P^b$ group removal, the alcohol 29 undergoes a Mitsunobu coupling with an N-hydroxy imide, such as N-hydroxyphthalimide, as described in Scheme Ia. The nitro group of 30 is thereafter reduced, for example, by catalytic reduction using palladium on carbon in a suitable solvent such as ethanol or tetrahydrofuran. The resulting product is treated with an appropriate sulfonyl chloride ($R^1SO_2Cl$) to provide the sulfonamide 31. At this point, the sulfonamide group may be optionally alkylated as described in Scheme IIa. Alternatively, the resulting product from nitro reduction is treated with an appropriate acyl chloride ($R^1COCl$) to provide the corresponding carboxamide 31. Still alternatively, the carboxamides 31 may be produced by the reaction of the product from nitro reduction with carboxylic acids ($R^1COOH$) by any of the known peptide coupling reagents, such as 1,3-dicyclohexylcarbodiimide or Castro's reagent (BOP). Removal of the O-amine protecting group and guanidinylation of the O-amine are accomplished by methods described in Scheme Ia. Finally, the O-guanidine protecting groups, $R^a$, $R^b$, and $R^c$, may be removed as outlined in Scheme Ia to give the target 32.

of acid such as p-toluenesulfonic acid, followed by reduction with sodium borohydride. Still alternatively, the imine may be reduced using catalytic hydrogenation using a cata- Scheme IIc

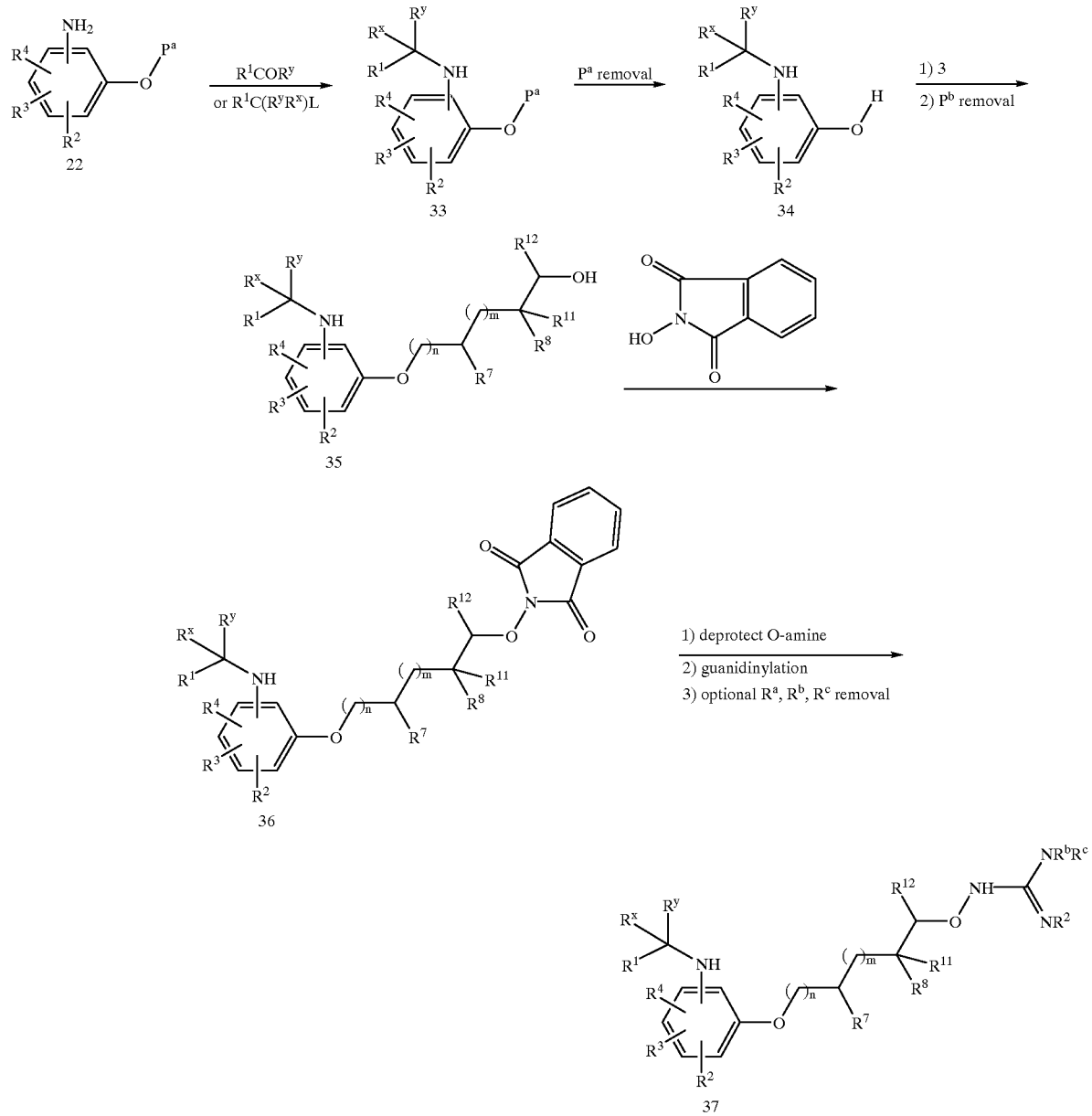

The compounds of the present invention where $R^1$—Z is $R^1$—CH($R^yR^z$)$NR^{10}$— can be synthesized by the steps outlined in Scheme IIc. Aniline 22 is converted to 33, where $R^x$ is H, by reductive amination with a suitable carbonyl component, $R^1COR^y$. The preferred reducing agent is tetramethylammonium triacetoxyborohydride. Alternatively, sodium triacetoxyborohydride or sodium cyanohydride may be used. Still alternatively, reductive amination may be carried out by forming an imine (Schiff base) between the amine and the carbonyl component using a catalytic amount lyst such as palladium on carbon in standard solvent such as ethanol. As an alternate to a reductive amination, aniline 22 may be reacted with $R^1(R^yR^x)L$, where L is a reactive leaving group, such as halide or sulfonate. The remaining conversion of 33 to 37, which comprises of pa removal, coupling to 3, $P^b$ removal and coupling to a N-hydroxy imide, deprotection of O-amine, guanidinylation and optional deprotection of the guanidine group, is similar to those steps detailed for the conversion of 23 to 27 in Scheme IIa.

Scheme III

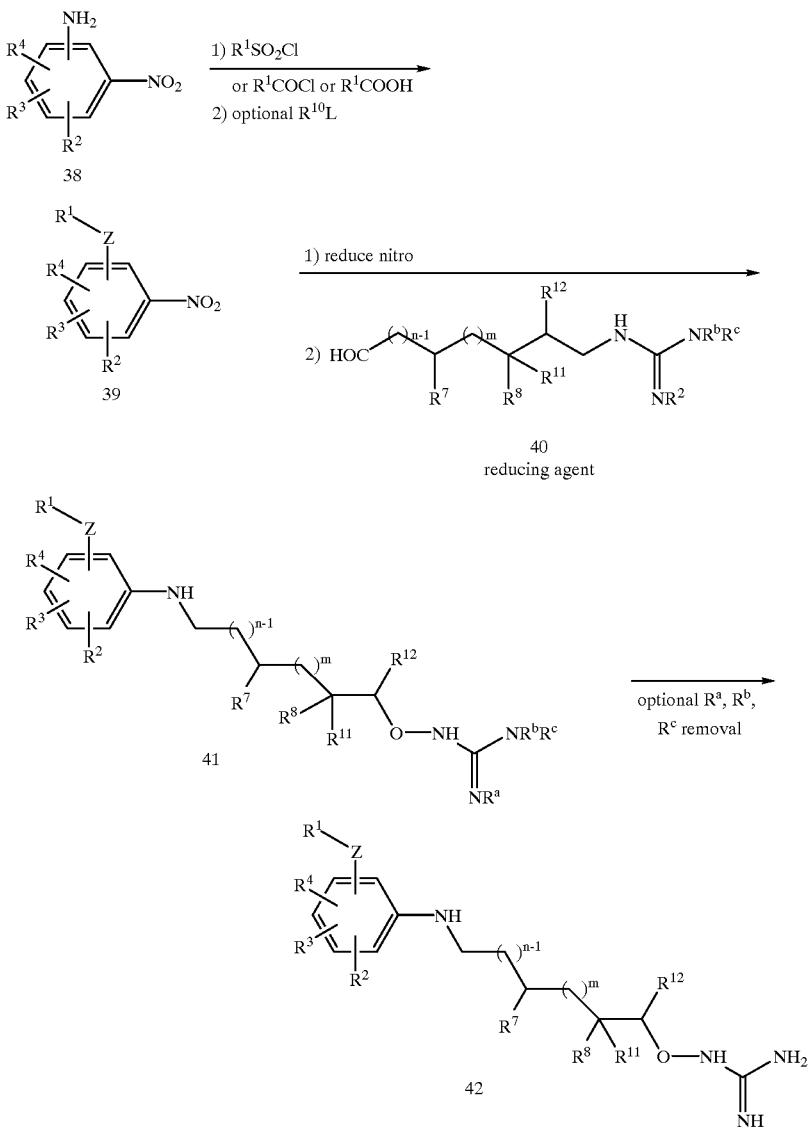

Additionally, compounds of the present invention where Y is $NR^{10}$ and $R^1$—Z is $R^1$—$S_2NR^{10}$— or $R^1$—$CONR^{10}$— can be prepared by Scheme III. Nitroaniline 38 is converted to a sulfonamide by treatment with an appropriate sulfonyl chloride $R^1SO_2Cl$ in the presence of a weak base, such as a tertiary amine. The resulting sulfonamide or carboxamide nitrogen can be alkylated with a suitable alkylating agent $R^{10}L$ as described in Scheme IIa to provide intermediate 39. Alternatively, 38 is treated with an appropriate acyl chloride ($R^1COCl$) to provide the corresponding carboxamide 39. Still alternatively, the carboxamides 39 may be produced by the reaction of 38 with carboxylic acids ($R^1COOH$) by any of the known peptide coupling reagents, such as 1,3-dicyclohexylcarbodiimide or Castro's reagent (BOP). After reduction of the nitro group, as described in Scheme IIb, the resulting aniline is coupled with aldehyde 40 preferably under reductive amination conditions to give 41. The preferred reducing agent is tetramethylammonium triacetoxyborohydride. Alternatively, sodium triacetoxyborohydride or sodium cyanohydride may be used. Still alternatively, reductive amination may be carried out by forming an imine (Schiff base) between the amine and the carbonyl component using a catalytic amount of acid such as p-toluenesulfonic acid, followed by reduction with sodium borohydride. Still alternatively, the imine may be reduced using catalytic hydrogenation using a catalyst such as palladium on carbon in standard solvent such as ethanol. Finally, the O-guanidine protecting groups, $R^a$, $R^b$, and $R^c$, of 41 may be removed as outlined in Scheme Ia to give 42.

Scheme IV

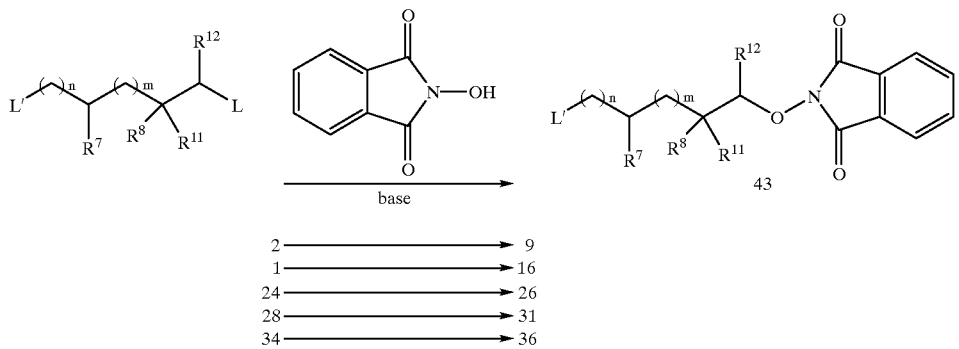

```
2  ———————→  9
1  ———————→ 16
24 ———————→ 26
28 ———————→ 31
34 ———————→ 36
```

As an alternative scheme to produce the O-phthalamide-containing intermediates 9, 16, 26, 31, and 36, the respective phenols 2, 1, 24, 28, and 34 may be reacted under basic conditions with reagent 43 which contains a leaving group L. This scheme is limited to producing compounds where $R^{12}$ is hydrogen. Reagent 43 is produced by reacting a compound having two leaving groups, L, and L' under basic conditions with N-hydroxyphthalimide (Khadilkar and Samant, *Indian J. Chem. Sec.* B 1137 (1993)).

Compounds wherein $R^a$ and $R^c$ together form a cyclic group, such as an imidazoline, can be synthesized by employing an imidazoline in place of the aminoguanidine in the above Schemes.

Compounds wherein $R^7$ and $R^{12}$ or $R^8$ and $R^{12}$ together form a methylene linkage can be synthesized by substituting a cyclic ketone having a reactive group L that is attached directly or indirectly to the carbocyclic ring. Examples of suitable reagents include 2-hydroxycyclopentanone, 3-hydroxycyclopentanone, 2-hydroxycyclohexanone and 3-hydroxycyclohexanone.

Compounds VI wherein $R^6$ and $R^b$ are taken together with the nitrogens to which they are attached to form a ring structure are prepared by substituting a heterocyclic amine 12 (below) for the aminoguanidine in the above Schemes.

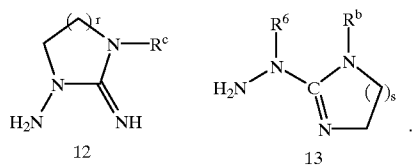

Compounds V wherein $R^9$ and $R^b$ are taken together with the nitrogen atoms to which they are attached to form an imidazoline moiety are prepared by substituting a 2-hydrazinoimidazoline 13 (above) for the aminoguanidines in the above Schemes.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA).

Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxy-propyl-methacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement. The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates,,for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

3-[3-(2-Chlorophenylsulfonyloxy)-5-methylphenoxy]propoxyguanidine a) 3-(2-Chlorophenylsulfonyloxy)-5-methylphenol Orcinol monohydrate (1.42 g, 10 mmol) and 2-chlorobenezenesulfonyl chloride (2.43 g, 11 mmol) were mixed in saturated $NaHCO_3$ (30 mL) and diethyl ether (30 mL). The biphasic mixture was stirred vigorously and extracted into ethyl acetate (3×50 mL). The organic phase was washed with brine (2×50 mL) and dried over $Na_2SO_4$. After removing the solvent in vacuo, the residue was purified by flash column chromatography (2% ethyl acetate in dichloromethane) to give the title compound as a pale-yellow liquid (2.15 g, 71%). $^1$H-NMR (300 MHz, $CDCl_3$) δ2.22 (s, 3H), 5.24 (s, 1H), 6.43 (s, 1H), 6.52 (s, 2H), 7.38 (m, 1H), 7.60 (m, 2H), and 7.96 (dd, 1H,J=3.9, 0.6 Hz).

b) 1-(2-Chlorophenylsulfonyloxy)-3-(3-benzyloxy)propoxy-5-methylbenzene

Diethyl azodicarboxylate (230 μL, 1.46 mmol) was added slowly to a solution of 3-(2-chlorophenylsulfonyloxy)-5-methylphenol (253 mg, 0.866 mmol), as prepared in the preceding step, 3-benzyloxypropanol (363 mg, 1.24 mmol), and triphenylphosphine (386 mg, (1.47 mmol) in dichloromethane (7 mL) at 0° C. The cold bath was removed, and the reaction mixture was stirred at ambient temperature for 3 h. The reaction mixture was quenched with water (10 mL) and extracted into diethyl ether (3×20 mL). The combined organic extracts were dried ($MgSO_4$) and the product purified by flash chromatography (2:1 to 100:0 dichloromethane/petroleum ether) to afford the title compound (328.5 mg, 85% yield) as a colorless oil. $^1$H-NMR (300 MHz, $CDCl_3$) δ7.95 (dd, 1H, J=7.9, 1.7 Hz), 7.52–7.62 (m, 2H), 7.28–7.38 (m, 6H), 6.58 (br s, 1H), 6.54 (br s, 1H), 6.48 (t, 1H, J=1.1 Hz), 4.51 (s, 2H), 3.95 (t, 3H, J=6.2 Hz), 3.62 (t, 2H, J=6.1 Hz), 2.24 (s, 3H), and 2.01 (pentet, 2H, J=6.2 Hz). Mass spectrum (MALDI-TOF, α-cyano-4-hydroxycinnamic acid matrix) calcd. for $C_{23}H_{23}ClO_5S$: 469.1 (M+Na). Found: 469.1.

c) 3-[3-(2-Chlorophenylsulfonyloxy)-5-methylphenoxy] propanol

A mixture of 1-(2-chlorophenylsulfonyloxy)-3-(3-benzyloxy)propoxy-5-methylbenzene (328.5 mg, 0.736 mmol), as prepared in the preceding step, 66 mg of 10% palladium on carbon, and 180 µL (0.72 mmol) of 4 N HCl/dioxane in 5 mL of tetrahydrofuran was hydrogenated (atmospheric pressure) at ambient temperature for 1 h. The reaction was hydrogenated through Celite 545 and then concentrated. Purification by flash chromatography using elutions of 2–10% diethyl ether/dichloromethane gave 217 mg (83% yield) of the title compound as an oil. $^1$H-NMR (300 MHz, CDCl$_3$) δ7.97 (dd, 1H, J=7.8, 1.4 Hz), 7.56–7.65 (m, 2H), 7.36–7.41 (m, 1H), 6.60 (br s, 1H), 6.54 (br s, 1H), 6.50 (t, 1H, J=2 Hz), 4.03 (t, 2H, J=4.7 Hz), 3.92 (s, 1H), 3.82 (q, 2H, J=6.7 Hz), 2.24 (s, 3H), and 1.99 (pentet, 2H, J=6 Hz).

d) N-[3-[3-(2-Chlorophenylsulfonyloxy)-5-methylphenoxy] propoxy]phthalimide

Diethyl azodicarboxylate (4.0 mL, 0.024 mol) was added dropwise to a solution of 3-[3-(2-chlorophenylsulfonyloxy)-5-methylphenoxy]propanol (8.5 g, 0.024 mol), as prepared in the preceding step, triphenylphosphine (6.26 g, 0.024 mol), and N-hydroxyphthalimide (4.01 g, 0.024 mol) in anhydrous tetrahydrofuran (240 mL). The solution was allowed to stir at ambient temperature overnight. The tetrahydrofuran was evaporated, and the residue was purified by silica gel chromatography. Elution was carried out using a gradient of 50% dichloromethane in hexane to 100% dichloromethane. The appropriate fractions were combined, evaporated to dryness, and placed under high vacuum to give 6.5 g (54% yield) of an oil. Mass spectrum (MALDI-TOF, α-cyano-4-hydroxycinnamic acid matrix) calcd. for C$_{24}$H$_{20}$ClNO$_7$S: 524.1 (M+Na). Found: 524.2.

e) 3-[3-(2-Chlorophenylsulfonyloxy)-5-methylphenoxy] propoxyamine

A suspension of N-[3-(2-chlorophenylsulfonyloxy)-5-methylphenoxy]propoxy]phthalimide 6.5 g, 0.013 mol), as prepared in the preceding step, in 2-propanol/water (6:1; 690 mL) was treated with sodium borohydride (2.46 g, 0.065 mol). The reaction mixture was stirred at ambient temperature for 2 days. The reaction mixture was quenched with 2N hydrochloric acid, and the mixture was warmed at 50° C. for 2 hours. The reaction mixture was cooled in an ice:water bath and adjusted to pH 8.0 with 2 N sodium hydroxide. The 2-propanol was evaporated on a rotary evaporator, and the residual aqueous solution was extracted with ethyl acetate (3×75 mL). The combined ethyl acetate extracts were washed with brine, dried over anhydrous sodium sulfate, and evaporated to dryness. The material was purified by silica gel chromatography by elution with a gradient of 50% dichloromethane/hexane to 100% dichloromethane, followed by 90% dichloromethane/10% acetonitrile. The appropriate fractions were combined and evaporated to an oil, which crystallized under high vacuum to give 4.1 g (85% yield) of the title compound. $^1$H-NMR (300 MHz, CDCl$_3$) δ7.97 (dd, J=7.9, 1.5 Hz, 1H), 7.55–7.65 (m, 2H), 7.37 (td, J=7.8, 1.6 Hz, 1H), 6.59 (br s, 1H), 6.53 (m, 1H), 6.49 (t, J=2.2 Hz, 1H), 5.39 (br d, 2H), 3.92 (t, J=6.3 Hz, 2H), 3.79 (t, J=6.2 Hz, 2H), 2.24 (s, 3H), and 2.00 (pentet, J=6.2 Hz, 2H). Mass spectrum (MALDI-TOF, α-cyano-4-hydroxycinnamic acid matrix) calcd. for C$_{16}$H$_{18}$ClNO$_5$S: 372.1 (M+H). Found: 371.5.

f) 3-[3-(2-Chlorophenylsulfonyloxy)-5-methylphenoxy] propoxyguanidine

A solution of 3-[3-(2-chlorophenylsulfonyloxy)-5-methylphenoxy]propoxyamine (0.43 g, 0.0012 mol), as prepared in the preceding step, in anhydrous N,N-dimethylformamide (15 mL) was treated with 1H-pyrazole-1-carboxamidine hydrochloride (0.34 g, 0.0034 mol). The reaction mixture was stirred overnight at ambient temperature. An additional 100 mg of 1H-pyrazole-1-carboxamidine hydrochloride was added, and the reaction mixture was stirred at ambient temperature overnight. The reaction mixture was evaporated to dryness under high vacuum. The residue was treated with acetonitrile, and the resulting crystalline material was collected by filtration and discarded. The filtrate was evaporated to dryness and partitioned between ether and water. The aqueous layer was washed with ether (4×25 mL). The aqueous layer was separated and basified with 2N sodium hydroxide, and the resultant aqueous layer was extracted with ethyl acetate (4×50 mL). The combined ethyl acetate extracts were washed with brine, dried, and evaporated to give 0.46 g of the title compound as an oil. $^1$H-NMR (300 MHz, CDCl$_3$) δ7.94 (d, J=7.6 Hz, 1H), 7.54–7.62 (m, 2H), 7.34–7.40 (m, 1H), 6.57 (br s, 1H), 6.48 (m, 2H), 5.75 (br m, 2H), 3.96 (t, J=6.2 Hz, 4H), 2.21 (s, 3H), and 2.05 (pentet, J=6.2 Hz, 2H). Mass spectrum (MALDI-TOF, α-cyano-4-hydroxycinnamic acid matrix) calcd. for C$_{17}$H$_{20}$ClN$_3$O$_5$S: 4.14.1 (M+H). Found: 4.14.2

EXAMPLE 2

3-[3-(2-Methoxyphenylsulfonyloxy)-5-methylphenoxy]propoxyguanidine a) 3-(5-Chloro-2-methoxyphenylsulfonyloxy)-5-methylphenol Saturated aqueous NaHCO$_3$ (70 mL) was added to a solution of 5-chloro-2-methoxynenzensulfonyl chloride (3.83 g, (15.9 mmol and orcinol monohydrate (3.39 g, 23.9 mmol) in di-n-butyl ether (53 mL) and tetrahydrofuran (17 mL). The biphasic solution was mixed vigorously at 50° C. for 7 h then at ambient temperature overnight. The reaction mixture was combined with that from a previous reaction (which used 4.53 g 18.8 mmol of 5-chloro-2-methoxybenzenesulfonyl chloride), the layers were separated, and the aqueous layer was extracted with ethyl acetate (2×100 mL). The combined organic extracts were washed with brine (250 mL), dried over Na$_2$SO$_4$, filtered, and evaporated to give 18.25 g of a clear brown oil. The product was purified by flash column chromatography (1% to 4% ethyl acetate in dichloromethane) to give the title compound (9.86 g, 86%) as a pale yellow oil which crystallized upon standing. $^1$H-NMR (300 MHz, CDCl$_3$) (7.81 (d, 1H, J=2.6 Hz), 7.55 (dd, 1H, J=8.9, 2.6 Hz), 7.02 (d, 1H, J=8.9 Hz), 6.53 (m, 2H), 6.41 (t, 1H, J=2.2 Hz), 3.99 (s, 3H), 2.24 (s, 3H). Mass spectrum (MALDI-TOF, α-cyano-4-hydroxycinnamic acid matrix) calcd. for C$_{14}$H$_{13}$ClO$_5$S: 351.0 (M+Na). Found: 351.1.

b) 3-(2-Methoxyphenylsulfonyloxy)-5-methylphenol

4-Methylmorpholine (3.2 mL, 29.1 mmol) was added to a mixture of 3-(5-chloro-2-methoxyphenylsulfonyloxy)-5-methylphenol (8.82 g, 26.8 mmol, prepared in the preceding step) and 10% palladium on carbon(2.23 g) in deoxygenated methanol (15 mL). The mixture was stirred at ambient temperature under hydrogen (balloon) for 3 h, then filtered through Celite (drafomaceous earth) with methanol. Solvent was removed in vacuo and crude product was purified by flash column chromatography (CH$_2$Cl$_2$ to 5% ethyl acetate in dichloromethane) to give the title compound (4.97 g, 63%) as a colorless syrup. $^1$H-NMR (300 MHz, DMSO-d$_6$) (9.71 (s, 1H), 7.76 (ddd, 1H, J=8.4, 7.4, 1.7 Hz), 7.69 (dd, 1H, J=7.9, 1.7 Hz), 7.38 (d, 1H, J=8.4 Hz), 7.09 (dt, 1H, J=7.9, 1.0 Hz), 6.48 (br s, 1H), 6.33 (br s, 1H), 6.26 (t, 1H, J=2.2 Hz), 4.00 (s, 3H), 2.15 (s, 3H). Mass spectrum (MALDI-TOF, α-cyano-4-hydroxycinnamic acid matrix) calcd. for $C_{14}H_{14}O_5S$: 317.0 (M+Na). Found: 316.9.

c) 3-[3-(2-Methoxyphenylsulfonyloxy)-5-methylphenoxy]propanol

Tri-n-butylphosphine (8.4 mL, 34 mmol) was added dropwise over 5 min to 3-(2-methoxyphenylsulfonyloxy)-5-methylphenol (4.97 g, 16.9 mmol, prepared in the preceding step), 1,3-propanediol (12 mL, 170 mmol) and 1,1'-(azodicarbonyl)dipiperidine (8.54 g, 33.8 mmol) in anhydrous tetrahydrofuran (75 mL) at 0° C. under a nitrogen atmosphere. Dichloromethane (75 mL) was added mid-way through the tri-n-butylphosphine addition to aid stirring. The slurry was stirred at ambient temperature for 1 h, then the mixture was cooled to 0° C. and additional 1,1'-(azodicarbonyl)dipiperidine (4.27 g, 16.9 mmol) and tri-n-butylphosphine (4.2 mL, 16.9 mmol) were added. The reaction was stirred overnight at ambient temperature. Diethyl ether (200 mL) was added and the mixture was filtered. The filtrate was concentrated in vacuo, and the residue was purified by flash column chromatography (25% ethyl acetate in hexane to 60% ethyl acetate in hexane, then 2% acetone in dichloromethane to 7% acetone in dichloromethane in two separate chromatographic separations) to give the title compound (3.79 g, 64%) as a gold oil. $^1$H-NMR (300 MHz, $CDCl_3$) δ7.82 (dd, 1H, J=7.9, 1.7 Hz), 7.61 (ddd, 1H, J=8.4, 7.5, 1.8 Hz), 7.08 (d, 1H, J=8.4 Hz), 7.01 (ddd, 1H, J=7.9, 7.5, 1 Hz), 6.58 (br s, 1H), 6,51 (br s, 1H), 6.46 (t, 1H, J=2.1 Hz), 4.02 (s, 3H), 4.00 (t, 2H, J=6.0 Hz), 3.81 (dt, 2H, J=5.7, 5.3 Hz), 2.24 (s, 3H), 1.98 (pentet, 2H, J=6.0 Hz), 1.72 (t, 1H, J=5.0 Hz). Mass spectrum (MALDI-TOF, (α-cyano-4-hydroxycinnamic acid matrix) calcd. for $C_{17}H_{20}O_6S$: 375.1 (M+Na). Found: 375.1.

d) N-[3-[3-(2-Methoxyphenylsulfonyloxy)-5-methylphenoxy]propoxy]phthalimide

Diethyl azodicarboxylate (67 (L, 0.40 mmol) was added dropwise over 5.5 min to 3-[3-(2-methoxyphenylsulfonyloxy)-5-methylphenoxy]propanol (118 mg, 0.33 mmol, prepared in the preceding step), triphenylphosphine (106 mg, 0.40 mmol), and N-hydroxyphthalimide (55 mg, 0.33 mmol) in anhydrous tetrahydrofuran (3 mL) at 0° C. under a nitrogen atmosphere. The solution was stirred at 0° C. for an additional 20 min then at ambient temperature overnight. The reaction mixture was concentrated, and the residue was purified by flash column chromatography (dichloromethane) to give the title compound (116 mg, 69%) as a colorless resin. $^1$H-NMR (300 MHz, $CDCl_3$) (7.88–7.73 (m, 5H), 7.61 (ddd, 1H, J=8.4, 7.4, 1.7 Hz), 7.10 (d, 1H, J=8.4 Hz), 7.01 (dt, 1H, J=7.7, 0.9 Hz), 6.60 (br s, 1H), 6.56, (br s, 1H), 6.42 (t, 1H, J=2.2 Hz), 4.36 (t, 2H, J=6.2 Hz), 4.09 (t, 2H, J=6.2 Hz), 4.04 (s, 3H), 2.25 (s, 3H), 2.18 (pentet, 2H, J=6.2 Hz). Mass spectrum (MALDI-TOF, α-cyano-4-hydroxycinnamic acid matrix) calcd. for $C_{25}H_{23}NO_8S$: 520.1 (M+Na). Found: 520.2.

e) 3-[3-(2-Methoxyphenylsulfonyloxy)-5-methylphenoxy]propoxyamine

A mixture of sodium borohydride (45 mg, 1.1 mmol) and N-[3-[3-(2-methoxyphenylsulfonyloxy)-5-methylphenoxy]propoxy]phthalimide (113 mg, 0.23 numol, prepared in the preceding step) in 2-propanol (12 mL) and water (2 mL) was stirred overnight at ambient temperature. The reaction mixture was adjusted to pH 1 aqueous HCl (3.5 mL, 2N), and the solution was stirred at 50° C. for 2 h. The solution was cooled to 0° C. and adjusted to pH 12 with 2N NaOH. The solution was stirred at ambient temperature for 2 h, then 2-propanol was removed by rotary evaporation. The resulting mixture was extracted with ethyl acetate (2×30 mL). The combined organic extracts were washed with brine (40 mL), dried over $Na_2SO_4$, filtered, and evaporated to give the title compound (79 mg, 95%) as a colorless oil. $^1$H-NMR (300 MHz, $CDCl_3$) (7.82 (dd, 1H, J=7.9,1.7 Hz), 7.61 (ddd, 1H, J=8.4, 7.5, 1.8 Hz), 7.08 (dd, 1H, J=8.4, 0.8 Hz), 7.00 (ddd, 1H, J=8, 7.5, 1 Hz), 6.58 (br s, 1H), 6.50 (br s, 1H), 6.45 (t, 1H, J=2.1 Hz), 5.38 (br s, 2H), 4.02 (s, 3H), 3.92 (t, 2H, J=6.3 Hz), 3.79 (t, 2H, J=6.2 Hz), 2.23 (s, 3H), 2.00 (pentet, 2H, J=6.2 Hz). Mass spectrum (MALDI-TOF, α-cyano-4-hydroxycinnamic acid matrix) calcd. for $C_{17}H_{21}NO_6S$: 390.1 (M+Na). Found: 390.1.

f) 3-[3-(2-Methoxyphenylsulfonyloxy)-5-methylphenoxy]propoxyguanidine

A solution of 3-[3-(2-methoxyphenylsulfonyloxy)-5-methylphenoxy]propoxyamine (74 mg, 0.20 mmol, prepared in the preceding step) and 1H-pyrazole-1-carboxamidine hydrochloride (60 mg, 0.41 mmol) in anhydrous N,N-dimethylformamide (2 mL) was stirred at ambient temperature overnight. Additional 1H-pyrazole-1-carboxamidine hydrochloride (30 mg, 0.20 mmol) was added, and the reaction was stirred at ambient temperature for 3 days. N,N-Dimethylformamide was removed in vacuo, then the residue was treated with acetonitrile. The mixture was filtered to remove excess 1H-pyrazole-1-carboxamidine hydrochloride, and the filtrate was concentrated in vacuo. The residual oil was partitioned between diethyl ether (10 mL) and water (10 mL). The aqueous layer was washed with diethyl ether (2×10 mL), adjusted to pH 8 with 2N NaOH, and extracted with ethyl acetate (2×10 mL). The ethyl acetate extracts were washed with pH 7 buffer (2×15 mL) and brine (15 mL), dried over $Na_2SO_4$, filtered, and evaporated to give the title compound (64 mg, 78%) as a colorless oil. $^1$H-NMR (300 MHz, DMSO-$d_6$) δ7.76 (ddd, 1H, J=8.4, 7.4, 1.8 Hz), 7.69 (dd, 1H, J=7.9, 1.6 Hz), 7.37 (d, 1H, J=7.7 Hz), 7.09 (dt, 1H, J=7.9, 1.0 Hz), 6.69 (s, 1H), 6.47 (s, 1H), 6.33 (t, 1H, J=2.1 Hz), 4.00 (s, 3H), 3.92 (t, 2H, J=6.5 Hz), 3.70 (t, 2H, J=6.1 Hz), 2.20 (s, 3H), 1.88 (pentet, 2H, J=6.3 Hz). Mass spectrum (MALDI-TOF, α-cyano-4-hydroxycinnamic acid matrix) calcd. for $C_{18}H_{23}N_3O_6S$: 410.1 (M+H), 432.1 (M+Na). Found: 410.1, 432.6.

EXAMPLE 3

3-[5-Methyl-3-(quinolinyl-8-sulfonyloxy)phenoxy]propoxyguanidine hydrochloride a) -Methyl-3-(quinolinyl-8-sulfonyloxy)phenol A mixture of orcinol monohydrate (4.0 g, 28 mmol) and 8-quinolinesulfonyl chloride (6.1 g, 26.7 mmol) in diethyl ether (120 mL) and saturated sodium bicarbonate (120 mL) was vigorously stirred at ambient temperature for 4 days. The reaction mixture was extracted into ethyl acetate, dried (MgSO$_4$), and concentrated. Crystallization from diethyl ether/ethyl acetate/hexane gave 4.48 g (50%) of the title compound as a tan powder. $^1$H-NMR (300 MHz, DMSO-d$_6$) δ9.62 (br s, 1H), 9.23 (dd, 1H, J=4, 2 Hz), 8.63 (dd, 1H, J=8, 2 Hz), 8.45 (dd, 1H, J=8, 2 Hz), 8.36 (1H, J=8, 2 Hz), 7.74–7.83 (m, 2H), 6.44 (br s, 1H), 6.29 (br s, 1H), 6.10 (t, 1H, J=2 Hz), 2.09 (s, 3H). Mass spectrum (MALDI-TOF, α-cyano-4-hydroxycinnamic acid matrix) calcd. for $C_{16}H_{13}NO_4S$: 316.1 (M+H), 338.0 (M+Na). Found 316.0, 338.1.

b) 3-[5-Methyl-3-(quinolinyl-8-sulfonyloxy)phenoxy]propanol

To 5-methyl-3-(quinolinyl-8-sulfonyloxy)phenol (3.0 g, 9.0 mmol), as prepared in the preceding step 1,3-propanediol (4 mL, 55.2 mmol), and 1,1'-(azodicarbonyl)dipiperidine (3.42 g, 13.6 mmol) at 0° C. in tetrahydrofuran (60 mL) was added slowly tri-n-butylphosphine (3.36 mL, 13.5 mmol). The cold bath was removed, and the reaction mixture was stirred at ambient temperature overnight. The TLC analysis showed starting material. To the reaction mixture was added sequentially 1,1'-(azodicarbonyl) dipiperidine (1.9 g) and tri-n-butylphosphine (1.7 mL). The reaction mixture was stirred at ambient temperature for 2 h. The reaction mixture was then diluted with diethyl ether and the resulting suspension filtered. The filtrate was concentrated and purified directly by flash chromatography using elutions of dichloromethane/ethyl acetate (3:1 then 2:3) to give 3.19 g (95% yield) of the title compound as an oil. $^1$H-NMR (300 MHz, CDCl$_3$) δ9.27 (dd, 1H, J=4, 2 Hz), 8.41 (dd, 1H, J=7, 2 Hz), 8.31 (dd, 1H, J=8, 2 Hz), 8.14 (dd, 1H, J=7, 2 Hz), 7.61–7.65 (m, 2), 6.54 (br s, 1H), 6.49 (br s, 1H), 6.42 (t, 1H, J=2 Hz), 3.92 (t, 2H, J=6 Hz), 3.77 (t, 2H), 2.17 (s, 3H). Mass spectrum (MALDI-TOF, α-cyano-4-hydroxycinnamic acid matrix) calcd. for $C_{19}H_{19}NO_5S$: 374.1 (M+H), 3.96.1 (M+Na). Found: 374.0, 396.2.

c) N-[3-[5-Methyl-3-(quinolinyl-8-sulfonyloxy)phenoxy]propoxy]phthalimide

Diethyl azodicarboxylate (136 μL, 0.81 mmol) was added dropwise over 7 min to 3-[5-methyl-3-(quinolinyl-8-sulfonyloxy)phenoxy]propanol (252 mg, 0.68 mmol, prepared in the preceding step), N-hydroxyphthalimide (11 mg, 0.68 mmol), and triphenylphosphine (213 mg, 0.81 mmol) in anhydrous tetrahydrofuran (6 mL) at 0° C. under a nitrogen atmosphere. The solution was stirred at 0° C. for 1 h then at ambient temperature for 3 days. Solvent was removed in vacuo, and the crude product was purified by flash column chromatography (100% dichloromethane to 1% acetone in dichloromethane) to give the title compound (332 mg, 92%) as a colorless foam. $^1$H-NMR (300 MHz, CDCl$_3$) δ9.28 (dd, 1H, J=4.2, 1.8 Hz), 8.43 (dd, 1H, J=7.4, 1.4 Hz), 8.30 (dd, 1H, J=8.4, 1.7 Hz), 8.14 (dd, 1H, J=8.3, 1.3 Hz), 7.85–7.75 (m, 4H), 7.63 (d, 1H, J=8.3 Hz), 7.61 (dd, 1H, J=8.2, 3.2 Hz), 6.56 (br s, 1H), 6.53 (br s, 1H), 6.36 (br s, 1H), 4.31 (t, 2H, J=6.2 Hz), 3.98 (t, 2H, J=6.2 Hz), 2.19 (s, 3H), 2.11 (pentet, 2H, J=6.2 Hz). Mass spectrum (MALDI-TOF, α-cyano-4-hydroxycinnamic acid matrix) calcd. for $C_{27}H_{22}N_2O_7S$: 519.1 (M+H), 541.1 (M+Na). Found: 518.7, 540.8.

d) 3-[5-Methyl-3-(quinolinyl-8-sulfonyloxy)phenoxy]propoxyamine

Sodium borohydride (107 mg, 2.8 mmol) was added to N-[3-[5-methyl-3-(quinolinyl-8-sulfonyloxy)phenoxy]propoxy]phthalimide (292 mg, 0.56 mmol, prepared in the preceding step) in 2-propanol (10 mL), tetrahydrofuran (1.7 mL) and water (1.7 mL). Hydrogen gas was evolved for 40 min. The mixture was stirred overnight at ambient temperature. Aqueous HCl (8.4 mL, 2N) was added dropwise (hydrogen was evolved), and the solution was heated at 50° C. for 2 h. The solution was cooled to 0° C. and adjusted to pH 10 with 2N NaOH. Organic solvent was removed in vacuo, and the residual mixture was extracted with ethyl acetate (2×30 mL). The combined organic extracts were washed with brine (50 mL), dried over Na$_2$SO$_4$, filtered, and evaporated to give a pale gold oil. Crude product was purified by flash column chromatography (60:40 to 80:20 ethyl acetate/hexane) to give the title compound (166 mg, 76%). $^1$H-NMR (300 MHz, CDCl$_3$) (9.27 (dd, 1H, J=4.3, 1.2 Hz), 8.42 (dd, 1H, J=7.4, 1.5 Hz), 8.30 (dd, 1H, J=8.3, 1.8 Hz), 8.14 (dd, 1H, J=8.2, 1.5 Hz), 7.63 (d, 1H, J=8.2 Hz), 7.61 (dd, 1H, J=8.3, 3.5 Hz), 6.53 (br s, 1H), 6.47 (br s, 1H), 6.41 (t, 1H, J=2 Hz), 5.37 (br s, 2H), 3.83 (t, 2 H, J=6.3 Hz), 3.75 (t, 2 H, J=6.2 Hz), 2.17 (s, 3 H), 1.94 (pentet, 2H, J=6.2 Hz). Mass spectrum (MALDI-TOF, α-cyano-4-hydroxycinnamic acid matrix) calcd. for $C_{19}H_{20}N_2O_5S$: 389.1 (M+H), 411.1 (M+Na). Found: 388.7, 410.9.

e) 3-[5-Methyl-3-(quinolinyl-8-sulfonyloxy)phenoxy]propoxyguanidine hydrochloride A solution of 3-[5-methyl-3-(quinolinyl-8-sulfonyloxy)phenoxy]propoxyamine (162 mg, 0.42 mmol, prepared in the preceding step) and 1H-pyrazole-1-carboxamidine hydrochloride (184 mg, 1.25 mmol) in anhydrous N,N-dimethylformamide (2.0 mL) was stirred at ambient hydrochloride (61.4 mg, 0.42 mmol) was added, and stirring was continued overnight. N,N-Dimethylformamide was removed in vacuo, then acetonitrile (5 mL) was added, and the solution was cooled to 0° C. to crystallize excess 1H-pyrazole-1-carboxamidine hydrochloride. The mixture was filtered and the filtrate was concentrated in vacuo to give a pale gold-brown oil. Crude product was dissolved in water (15 mL) and extracted with diethyl ether (2×15 mL). The aqueous layer was neutralized (pH 7) with 2N NaOH and extracted with ethyl acetate (2×15 mL). The combined ethyl acetate extracts were washed with pH 7 buffer (2×15 mL) and brine (15 mL), dried over Na$_2$SO$_4$, filtered, and evaporated to give the free base of the title compound (147 mg, 82%) as a colorless oil.

The title compound was made by adding a solution of the free base, 3-[5-methyl-3-(quinolinyl-8-sulfonyloxy)phenoxy]propoxyguanidine, (143 mg, 0.33 mmol, prepared above) in ethanol (1 mL) to ethanolic HCl (1.06 mL, 1.1 M, 1.2 mmol) in anhydrous diethyl ether (100 mL). Filtration under nitrogen gave the title compound (120 mg, 77%) as a hygroscopic yellow solid. $^1$H-NMR (300 MHz, DMSO-d$_6$) δ9.23 (dd, 1H, J=4.2, 1.8 Hz), 8.64 (dd, 1H, J=8.4, 1.8 Hz), 8.47 (dd, 1H, J=8.3, 1.4 Hz), 8.38 (dd, 1H, J=7.4, 1.4 Hz), 7.81 (dd, 1H, J=8, 4.2 Hz), 7.80 (d, 1H, J=8 Hz), 6.66 (br s, 1H), 6.40 (br s, 1H), 6.34 (t, 1H, J=2.2 Hz), 3.87 (q, 4H, J=6 Hz), 2.14 (s, 3H), 1.95 (pentet, 2H, J=6 Hz). Mass spectrum (MALDI-TOF, α-cyano-4-hydroxycinnamic acid matrix) calcd. for $C_{20}H_{22}N_4O_5S$: 431.1 (M+H). Found: 430.9.

EXAMPLE 4

3-[3-(5-Chloro-2-methoxyphenylsulfonyloxy)-5-methylphenoxy]propoxyguanidine hydrochloride a) 3-[3-(5-Chloro-2-methoxyphenylsulfonyloxy)-5-methylphenoxy]propanol Tri-n-butylphosphine (7.6 mL) 30.4 mmol) was added dropwise over 20 min to 3-(5-chloro-2-methoxyphenylsulfonyloxy)-5-methylphenol (5.00 g, 15.2 mmol, prepared in step a of Example 2), 1,3-propanediol (3.3 mL, 45.6 mmol) and 1,1'-(azodicarbonyl)dipiperidine (7.68 g, 30.4 mmol) in anhydrous tetrahydrofuran (80 mL) at 0° C. under a nitrogen atmosphere. Dichloromethane (150 mL) was added mid-way through the tri-n-butylphosphine addition to aid stirring. The slurry was stirred for an additional 5 min at 0° C. then at ambient temperature for 3 h. Diethyl ether (400 mL) was added, and the mixture was stirred for 10 min then filtered. The filtrate was concentrated and the product was purified by flash column chromatography (25% to 60% ethyl acetate in hexane) to give the title compound (4.07 g, 69%) as a gold oil. $^1$H-NMR (300 MHz, CDCl$_3$) (7.82 (d, 1H, J=2.8 Hz), 7.56 (dd, 1H, J=8.9, 2.6 Hz), 7.03 (d, 1H, J=8.9 Hz), 6.62 (br s, 1H), 6.52 (br s, 1H), 6.47 (t, 1H, J=2.3 Hz), 4.03 (t, 2H, J=6 Hz), 4.01 (s, 3H), 3.85–3.80 (m, 2H), 2.26 (s, 3H), 2.00 (pentet, 2H, J=6 Hz), 1.64 (t, 1H, J=5 Hz). Mass spectrum (MALDI-TOF, α-cyano-4-hydroxycinnamic acid matrix) calcd. for $C_{17}H_{19}ClO_6S$: 409.0 (M+Na). Found: 409.0.

b) N-[3-[3-(5-Chloro-2-methoxyphenylsulfonyloxy)-5-methylphenoxy]propoxy]phthalimide Diethyl azodicarboxylate (0.16 mL, 0.95 mmol) was added dropwise over 6 min to 3-[3-(5-chloro-2-methoxyphenylsulfonyloxy)-5-methylphenoxy]propanol (0.31 g, 0.79 mmol, prepared in the preceding step), triphenylphosphine (0.25 g, 0.93 mmol) and N-hydroxyphthalimide (0.13 g, 0.80 mmol) in anhydrous tetrahydrofuran (7.9 mL) at 0° C. under a nitrogen atmosphere. The solution was stirred 0° C. for an adddional 15 min then at ambient temperature overnight. The reaction mixture was concentrated, and the crude product was purified by flash column chromatography (1% acetone in dichloromethane) to give the title compound (0.417 g, 99%) as a colorless foam. $^1$H-NMR (300 MHz, CDCl$_3$) δ7.88–7.75 (m, 5H), 7.56 (dd, 1H, J=8.9, 2.7 Hz), 7.05 (d, 1H, J=8.9 Hz), 6.64 (br s, 1H), 6.57 (br s, 1H), 6.43 (t, 1H, J=2 Hz), 4.37 (t, 2H, J=6.1 Hz), 4.12 (t, 2H, J=6.2 Hz), 4.03 (s, 3H), 2.28 (s, 3H), 2.19 (pentet, 2H, J=6.1 Hz). Mass spectrum (MALDI-TOF, gentisic acid matrix) calcd. for $C_{25}H_{22}ClNO_8S$: 554.1 (M+Na). Found: 553.7.

c) 3-[3-(5-Chloro-2-methoxyphenylsulfonyloxy)-5-methylphenoxy]propoxyamine

Sodium borohydride (145 mg, 3.84 mmol) was added to a solution of N-[3-[3-(5-chloro-2-methoxyphenylsulfonyloxy)-5-methylphenoxy]propoxy] phthalimide (407 mg, 0.76 mmol, prepared in the preceding step) in 2-propanol (25 mL), tetrahydrofuran (5 mL), and water (4 mL). Hydrogen was evolved for 20 min. The mixture was stirred overnight at ambient temperature. Aqueous HCl (11.4 mL, 2N, 22.8 mmol) was added dropwise; hydrogen was evolved. The solution was stirred at 50° C. for 2 h, cooled to 0° C., and adjusted to pH 10 with 2N NaOH. Organic solvent was removed by rotary evaporation at ambient temperature, and the resulting mixture was extracted with ethyl acetate (2×30 mL). The combined organic extracts were washed with brine (50 mL), dried over Na$_2$SO$_4$, filtered, and evaporated to give 365 mg of a colorless oil. Crude product was purified by flash column chromatography (50% ethyl acetate in hexane to 100% ethyl acetate) to give the title compound (265 mg, 86%) as a colorless oil. $^1$H-NMR (300 MHz, CDCl$_3$) (7.82 (d, 1H, J=2.6 Hz), 7.56 (dd, 1H, J=8.9, 2.6 Hz), 7.03 (d, 1H, J=8.9 Hz), 6.60 (br s, 1H), 6.51 (br s, 1H), 6.46 (t, 1H, J=2.2 Hz), 5.39 (br s, 2H), 4.01 (s, 3H), 3.95 (t, 2H, J=6.3 Hz), 3.80 (t, 2H, J=6.2 Hz), 2.26 (s, 3H), 2.02 (pentet, 2H, J=6.2). Mass spectrum (MALDI-TOF, α-cyano-4-hydroxycinnamic acid matrix) calcd. for $C_{17}H_{20}ClNO_6S$: 402.1 (M+H), 424.1 (M+Na). Found: 401.6, 423.9.

d) 3-[3-(5-Chloro-2-methoxyphenylsulfonyloxy)-5-methylphenoxy]propoxyguanidine hydrochloride A mixture of 3-[3-(5-chloro-2-methoxyphenylsulfonyloxy)-5-methylphenoxy] propoxyamine (265 mg, 0.66 mmol, prepared in the preceding step) and 1H-pyrazole-1-carboxamidine hydrochloride (196 mg, 1.33 mmol) in anhydrous N,N-dimethylformamide (3 mL) was stirred at ambient temperature for 2.5 h. Additional 1H-pyrazole-1-carboxamidine hydrochloride (97 mg, 0.66 mmol) was added and the reaction was stirred at ambient temperature for 3 days. N,N-Dimethylformamide was removed in vacuo, then acetonitrile (1 mL) was added to precipitate excess 1H-pyrazole-1-carboxamidine hydrochloride. The mixture was filtered and the filtrate was concentrated in vacuo. The residual oil was partitioned between diethyl ether (20 mL) and water (20 mL). The aqueous layer was washed with diethyl ether (2×20 mL). The aqueous layer was neutralized (pH 7) with 2N NaOH and extracted with ethyl acetate (2×30 mL). The ethyl acetate extracts were washed with pH 7 buffer (2×20 mL) and brine (30 mL), dried over Na$_2$SO$_4$, filtered, and evaporated to give the free base of the title compound (281 mg, 96%) as a colorless oil. Mass spectrum (MALDI-TOF, α-cyano-4-hydroxycinnamic acid matrix) calcd. for $C_{18}H_{22}ClN_3O_6S$: 444.1 (M+H), 466.1 (M+Na). Found 444.6, 466.7.

The hydrochloride salt of the title compound was made by adding a solution of the free base, 3-[3-(5-chloro-2-methoxyphenylsulfonyloxy)-5-methylphenoxy] propoxyguanidine, (261 mg, 0.59 mmol) in 2-propanol (6 mL) to diethyl ether (100 mL) containing HCl in ethanol (1.1 mL of a 1.1 M solution, 1.2 mmol). Solvent was removed in vacuo to give the title compound (285 mg) as a colorless oil. $^1$H-NMR(300 MHz, DMSO-d6) (7.86 (dd, 1H, J=9.0, 2.7 Hz), 7.65 (d, 1H, J=2.7 Hz), 7.44 (d, 1H, J=9.0 Hz), 6.74 (br s, 1H), 6.49 (br s, 1H), 6.43 (br s, 1H), 4.01 (s, 3H), 4.00 (t, 2H, J=6.4 Hz), 3.91 (t, 2H, J=6.3 Hz), 2.23 (s, 3H), 2.02 (pentet, 2H, J=6.3 Hz). Mass spectrum (MALDI-TOF, α-cyano-4-hydroxycinnamic acid matrix) calcd. for $C_{18}H_{22}ClN_3O_6S$: 444.1 (M+H). Found 443.5.

EXAMPLE 5

3-[3-(5-Chlorothiophenyl-2-sulfonyloxy)-5-methylphenoxy]propoxyguanidine hydrochloride a) 3-(5-Chlorothiophenyl-2-sulfonyloxy)-5-methylphenol A mixture of orcinol monohydrate (5.0 g, 35.2 mmol), and 5-chlorothiopene-2-sulfonyl chloride (7.64 g, 35.2 mmol) in 50 mL of saturated sodium bicarbonate, 50 mL of diethyl ether, and 15 mL of tetrahydrofuran was stirred at 60° C. for 2 h and then at 40° C. overnight. The reaction mixture was extracted into diethyl ether, dried (MgSO$_4$), and passed through a thick pad of silica gel (ca. 500 mL) using elutions of dichloromethane and then 3% diethyl ether/dichloromethane to provide 5.49 g (51%) of the title compound as a pale orange oil. $^1$H-NMR (300 MHz, CDCl$_3$) δ7.40 (d, 1H, J=4 Hz), 6.94 (d, 1H, J=4 Hz), 6.59 (br s, 1H), 6.49 (br s, 1H), 6.40 (t, 1H, J=2 Hz), 5.38 (s, 1H), 2.26 (s, 3H). Mass spectrum (MALDI-TOF gentisic acid matrix) calcd. for $C_{11}H_9ClO_4S_2$: 327.0 (M+Na). Found: 327.0.

b) 3-[3-(5-Chlorothiophenyl-2-sulfonyloxy)-5-methylphenoxy]propanol

Tri-n-butylphosphine (6.1 mL, 24 mmol) was added dropwise over 5 min to 3-(5-chlorothiophenyl-2-sulfonyloxy)-5-methylphenol (3.49 g, 11.5 mmol, prepared in the preceding step), 1,3-propanediol (2.2 mL, 30 mmol) and 1,1'-(azodicarbonyl)dipiperidine 6.16 g, 24 mmol) in anhydrous THF (45 mL) at 0° C. under a nitrogen atmosphere. Dichloromethane (70 mL) and additional tetrahydrofuran (10 mL) were added mid-way through the tri-n-butylphosphine addition to aid stirring. The slurry was stirred at ambient temperature for 2.5 h, then diethyl ether (300 mL) was added and the mixture was filtered. The filtrate was concentrated, and the residue was purified by flash column chromatography (25% to 40% ethyl acetate in hexane) to give the title compound (3.11 g, 75%) as a gold oil. $^1$H-NMR (300 MHz, CDCl$_3$) (7.41 (d, 1H, J=4.1 Hz), 6.95 (d, 1H, J=4.1 Hz), 6.66 (br s, 1H), 6.50 (br s, 1H), 6.45 (t, 1H, J 2.2 Hz), 4.04 (t, 1H, J=6.0 Hz), 3.83 (t, 2H, J=6.0 Hz), 2.28 (s, 3H), 2.01 (pentet, 2H, J=6.0 Hz). Mass spectrum (MALDI-TOF, gentisic acid matrix) calcd. for $C_{14}H_{15}ClO_5S_2$: 385.0 (M+Na). Found: 385.1.

c) N-[3-[3-(5-Chlorothiophenyl-2-sulfonyloxy)-5-methylphenoxy]propoxy]phthalimide Diethyl azodicarboxylate (115 μL, 0.68 mmol) was added dropwise over 8.5 min to 3-[3-(5-chlorothiophenyl-2-sulfonyloxy)-5-methylphenoxy]propanol (207 mg, 0.57 mmol, prepared in the preceding step), triphenylphoshpine (180 mg, 0.68 mmol), and N-hydroxyphthalimide (93 mg, 0.57 mmol) in anhydrous tetrahydrofuran (5.1 mL) at 0° C. under a nitrogen atmosphere. The solution was stirred at 0° C. for additional 30 min. The reaction mixture was concentrated and the residue purified by flash column chromatography (dichloromethane) to give the title compound (272 mg, 94%) as a colorless resin. $^1$H-NMR (300 MHz, CDCl$_3$) δ7.86–7.75 (m, 4H), 7.42 (d, 1H, J=4.1 Hz), 6.96 (d, 1H, J=4.1 Hz), 6.69 (br s, 1H), 6.52 (br s, 1H), 6.44 (br s, 1H), 4.39 (t, 2H, J=6.1 Hz), 4.16 (t, 2H, J=6.1 Hz), 2.29 (s, 3H), 2.21 (pentet, 2H, J=6.1 Hz). Mass spectrum (MALDI-TOF, α-cyano-4-hydroxycinnamic acid matrix) calcd. for C$_{22}$H$_{18}$ClN$_7$S$_2$: 530.0 (M+Na). Found: 529.5.

d) 3-[3-(5-Chlorothiophenyl-2-sulfonyloxy)-5-methylphenoxy]propoxyamine

Sodium borohydride (85 mg, 2.2 mmol) was added to a solution of N-[3-[3-(5-chlorothiophenyl-2-sulfonyloxy)-5-methylphenoxy]propoxy]phthalimide (227 mg, 0.45 mmol, prepared in the preceding step) in 2-propanol (23.3 mL), tetrahydrofuran (5.8 mL), and water (3.9 mL). Hydrogen gas was evolved. The mixture was stirred overnight at ambient temperature. The reaction mixture was carefully acidified with aqueous HCl (6.6 mL, 2N), and the solution was stirred at 50° C. for 2 h. The solution was cooled to 0° C. and neutralized (pH 7) with 2N NaOH. Organic solvent was removed by rotary evaporation, and the resulting mixture was extracted with ethyl acetate (2×15 mL). The combined organic extracts were washed with brine (15 mL), dried over Na$_2$SO$_4$, filtered, and evaporated. The residue was purified by flash column chromatography (25% ethyl acetate in hexane) to give the title compound (141 mg, 84%) as a colorless oil. $^1$H-NMR (300 MHz, CDCl$_3$) δ7.40 (d, 1H, J=4.0 Hz), 6.95 (d, 1H, J=4.0 Hz), 6.65 (br s, 1H), 6.48 (br s, 1H), 6.43 (t, 1H, J=2.2 Hz), 5.39 (br s, 2H), 3.96 (t, 2H, J=6.3 Hz), 3.81 (t, 2H, J=6.1 Hz), 2.28 (s, 3H), 2.03 (pentet, 2H, J=6.2 Hz). Mass spectrum (MALDI-TOF, α-cyano-4-hydroxycinnamic acid matrix) calcd. for C$_{14}$H$_{16}$ClNO$_5$S$_2$: 378.0 (M+H), 400.0 (M+Na). Found: 377.6, 399.5.

e) 3-[3-(5-Chlorothiophenyl-2-sulfonyloxy)-5-methylphenoxy]propoxyguanidine hydrochloride A solution of 3-[3-(5-chlorothiophenyl-2-sulfonyloxy)-5-methylphenoxy]propoxyamine (129 mg, 0.34 mmol, prepared in the preceding step) and 1H-pyrazole-1-carboxamidine hydrochloride (103 mg, 0.70 mmol) in anhydrous N,N-dimethylformamide (1.5 mL) was stirred at ambient temperature overnight. Additional 1H-pyrazole-1-carboxamidine hydrochloride (103 mg, 0.70 mmol) was added, and the reaction was again stirred at ambient temperature overnight. N,N-Dimethylformamide was removed in vacuo, and the residue was treated with acetonitrile (3 mL). The mixture was filtered to remove excess 1H-pyrazole-1-carboxamidine hydrochloride, and the filtrate was concentrated. The residual oil was partitioned between diethyl ether (15 mL) and water (10 mL). The aqueous layer was washed with diethyl ether (2×15 mL), basified (pH 8) with 2N NaOH, and extracted with ethyl acetate (2×20 mL). The ethyl acetate extracts were washed with pH 7 buffer (2×25 mL) and brine (25 mL), dried over Na$_2$SO$_4$, filtered, and evaporated to give the free base of the title compound (129 mg, 90%) as a colorless oil.

The hydrochloride salt of the title compound was made by adding a solution of the free base, 3-[3-(5-chlorothiophenyl-2-sulfonyloxy)-5-methylphenoxy]propoxyguanidine, (114 mg, 0.27 mmol, prepared above) in a minimum volume of tetrahydrofuran to anhydrous diethyl ether (100 mL) containing HCl in ethanol (0.75 mL, 1.1 M, 0.82 mmol). Solvent was removed in vacuo to give 130 mg of the title compound as a pale yellow oil. $^1$H-NMR (300 MHz, DMSO-d$_6$) δ7.76 (d, 2H, J=4.2 Hz), 7.41 (d, 2H, J=4.2 Hz), 6.80 (br s, 1H), 6.55 (br s, 1H), 6.49 (t, 1H, J=2.2 Hz), 4.02 (t, 2H, J=6.3 Hz), 3.92 (t, 2H, J=6.3 Hz), 2.26 (s, 3H), 2.03 (pentet, 2H, J=6.3 Hz). Mass spectrum (MALDI-TOF, α-cyano-4-hydroxycinnamic acid matrix) calcd. for C$_{15}$H$_{18}$ClN$_3$O$_5$S$_2$: 420.0 (M+H). Found: 419.9.

EXAMPLE 6

3-[3-(2-Cyanophenylsulfonyloxy)-5-methylphenoxy] propoxyguanidine hydrochloride a) 3-(2-Cyanophenylsulfonyloxy)-5-methylphenol Orcinol monohydrate (1.42 g, 10.0 mmol) and 2-cyanobenzenesulfonyl chloride 2.02 g, 10.0 mmol) were mixed in saturated NaHCO$_3$ (30 mL) and diethyl ether 30 mL). The biphasic mixture was stirred vigorously at room temperature overnight. The reaction mixture was diluted with water (50 mL) and extracted into ethyl acetate (3×50 mL). The organic phase was washed with brine (2×50 mL) and dried over Na$_2$SO$_4$. After removing the solvent in vacuo, the residue was purified by flash column chromatography (dichloromethane to 5% ethyl acetate in dichloromethane) to give the title compound as a white solid (1.65 g, 57%). $^1$H-NMR (300 MHz, CDCl$_3$) δ8.07 (m, 1H), 7.94 (m, 1H), 7.75–7.80 (m, 2H), 6.57 (s, 1H), 6.53 (s, 1H), 6.49 (s, 1H), 5,69 (br s, 1H), 2.22 (s, 3H).

b) 3-[3-(2-Cyanophenylsulfonyloxy)-5-methylphenoxy] propanol

To a solution of 3-(2-cyanophenylsulfonyloxy)-5-methylphenol (580 mg, 2.0 mmol), as prepared in preceding step, tri-n-butylphosphine (607 mg, 3.0 mmol), and 1,3-propanediol (760 mg, 10 mmol) in tetrahydrofuran (20 mL) was added 1,1'-(azodicarbonyl)dipiperidine (757 mg, 3.0 mmol). The mixture was stirred at room temperature overnight. Hexane (30 mL) was added to the mixture, and the precipitates were removed by filtration. The filtrate was evaporated in vacuo, and the residue was purified by flash column chromatography (10% ethyl acetate in dichloromethane) to give the title compound as a colorless oil (560 mg, 80%). $^1$H-NMR (300 MHz, CDCl$_3$) δ8.11 (m, 1H), 7.94 (m, 1H), 7.77–7.82 (m, 2H), 6.65 (s, 1H, 6.59 (s, 1H), 6.57 (s, 1H), 4.05 (t, J=6.0 Hz, 2H), 3.82 (t, J=6.0 Hz, 2H), 2.26 (s, 3H), 2.00 (m, 2H), 1.76 (br s, 1H).

c) N-[3-[3-(2-Cyanophenylsulfonyloxy)-5-methylphenoxy] propoxy]phthalimide

To a solution of 3-[3-(2-cyanophenylsulfonyloxy)-5-methylphenoxy]propanol (1.04 g, 3.0 mmol), as prepared in the preceding step, triphenylphosphine (1.05 g, 4.0 mmol), and N-hydroxyphthalimide (490 mg, 3.0 mmol) at 0° C. in tetrahydrofuran (20 mL) was added diethyl azodicarboxylate (700 mg, 4.0 mmol). The reaction mixture was stirred overnight. Water (50 mL) was added, the reaction mixture was extracted into ethyl acetate (3×50 mL). The ethyl acetate solution was washed with brine (2×50 mL) and dried over Na$_2$SO$_4$. After removing the solvent, the residue was purified by flash column chromatography (2:1 dichloromethane/hexane to dichloromethane) to give the title compound as a colorless foam (1.12 g, 76%). $^1$H-NMR (300 MHz, CDCl$_3$) δ8.09 (m, 1H), 7.97 (m, 1H), 7.84 (m, 2H), 7.78 (m, 4H), 6.67 (s, 1H), 6.60 (s, 1H), 6.50 (s, 1H), 4.37 (t, J=6.1 Hz, 2H), 4.13 (t, J=6.1 Hz, 2H), 2.27 (s, 3H), 2.19 (m, 2H).

d) 3-[3-(2-Cyanophenylsulfonyloxy)-5-methylphenoxy] propoxyamine

To a solution of N-[3-[3-(2-cyanophenylsulfonyloxy)-5-methylphenoxy]propoxy]phthalimide (600 mg, 1.2 mmol), as prepared in the preceding step, in 40 mL of ethanol/ tetrahydrofuran/water (2:1:1) was added sodium borohydride (230 mg, 6.0 mmol). The reaction mixture was stirred at ambient temperature overnight. The mixture was acidified (pH 1–2) and heated to 50° C. for 2 hours. After cooling to room temperature, the solution was adjusted to pH 8–9 with 2N NaOH. The mixture was extracted into ethyl acetate (3×50 mL), and the organic phase was washed with brine (50 mL) and dried over $Na_2SO_4$. After removing the solvent, the residue was purified by flash column chromatography (dichloromethane to 2% methanol in dichloromethane) to give the title compound as a colorless oil (370 mg, 85%). $^1$H-NMR (300 MHz, $CDCl_3$) δ8.06 (m, 1H), 7.93 (m, 1H), 7.76 (m, 2H), 6.61 (s, 1H), 6.53 (s, 2H), 5.36 (br s, 2H), 3.94 (t, J=6.3 Hz, 2H), 3.78 (t, J=6.2 Hz, 2H), 2.23 (s, 3H), 1.99 (m, 2H).

e) 3-[3-(2-Cyanophenylsulfonyloxy)-5-methylphenoxy] propoxyguanidine hydrochloride To a solution of 3-[3-(2-cyanophenylsulfonyloxy)-5-methylphenoxy]propoxyamine (362 mg, 1.0 mmol), as prepared in the preceding step, in N,N-dimethylformamide (10 mL) was added 1H-pyrazole-carboxamidine hydrochloride (590 mg, 4.0 mmol). The reaction mixture was stirred at ambient temperature for two days. N,N-Dimethylformamide was removed under high vacuum. Acetonitrile (10 mL) was added, the solid was removed by filtration, the filtrate was concentrated in vacuo, and the residue was dried under high vacuum. The residue was partitioned between water (30 mL plus 2 mL brine) and diethyl ether (20 mL). The water solution was extracted with diethyl ether (20 mL), and the combined diethyl ether extracts were extracted with acidic water (pH 5). The combined water solutions were adjusted to pH 8–9 by using 2N NaOH and extracted with ethyl acetate (3×50 mL). The ethyl acetate solution was washed with pH 7 buffer solution (2×30 mL) and brine (30 mL) and dried over $Na_2SO_4$. After removing the solvent, 0.6N HCl methanol (10 mL) was added, and the solution was concentrated to give the title compound as a colorless oil (340 mg, 77%). $^1$H-NMR (300 MHz, DMSO-$d_6$) δ8.30 (d, J=7.5 Hz, 1H), 8.09 (t, J=7.5 Hz, 1H), 8.04 (m, 2H), 7.72 (br s, 5H), 6.79 (s, 1H), 6.49 (s, 1H), 6.47 (s, 1H), 3.99 (t, J=6.2 Hz, 2H), 3.90 (t, J=6.3 Hz, 2H), 2.22 (s, 3H), 2.01 (m, 2H). Mass spectrum (MALDI-TOF, (α-cyano-4-hydroxycinnamic acid matrix) calcd. for $C_{18}H_{20}N_4O_5S$: 405.1 (M+H), 427.1 (M+Na). Found: 405.1, 427.0.

EXAMPLE 7

3-[3-(5-Isoquinolinylsulfonyloxy)-5-methylphenoxy] propoxyguanidine hydrochloride a) 5-Isoquinolinesulfonyl chloride A mixture of 5-isoquinolinesulfonic acid (4.18 g, 20 mmol), and phosphorus pentachloride (6.24 g, 30 mmol) in phosphorus oxychloride (20 mL) was heated at 120 ° C. for two days. The reaction mixture was cooled to room temperature and diluted with dry chloroform (60 mL). The white precipitate was collected, washed with dry chloroform, and dried under high vacuum to give the title compound as a white solid (4.40 g, 83%) which was used for next step without further purification. $^1$H-NMR (300 MHz, $CDCl_3$) δ9.95 (s, 1H), 9.16 (d, J=6.8 Hz, 1H), 8.74 (d, J=6.8 Hz, 1H), 8.52 (t, J=7.0 Hz, 2H), 7.99 (t, J=7.3 Hz, 1H).

b) 3-(5-Isoquinolinylsulfonyloxy)-5-methylphenol

Orcinol monohydrate (1.42 g, 10.0 mmol) and 5-isoquinolinesulfonyl chloride (2.64 g, 10.0 mmol), as prepared in the preceding step, were mixed in saturated $NaHCO_3$ (30 mL) and diethyl ether (30 mL). The biphasic mixture was stirred vigorously at room temperature overnight. The reaction mixture was diluted with water (50 mL) and extracted into ethyl acetate (3×50 mL). The organic phase was washed with brine (2×50 mL) and dried over $Na_2SO_4$. After removing the solvent in vacuo, the residue was triturated with ether/hexane to give the title compound as a pale yellow solid (1.15 g, 37%). $^1$H-NMR (300 MHz, $CDCl_3$) δ9.67 (s, 1H), 9.60 (s, 1H), 8.86 (d, J=6.1 Hz, 1H), 8.63 (d, J=8.2 Hz, 1H), 8.37 (t, J=6.1 Hz, 2H), 7.86 (t, J=7.8 Hz, 1H), 6.46 (s, 1H), 6.23 (s, 1H), 5.97 (3, 1H), 2.08 (s, 3H).

c) 3-[3-(5-Isoquinolinylsulfonyloxy)-5-methylphenoxy] propanol

To a solution of 3-(5-isoquinolinylsulfonyloxy)-5-methylphenol (630 mg, 2.0 mmol), as prepared in the preceding step, tri-n-butylphosphine (607 mg, 3.0 mmol), and 1,3-propanediol (760 mg, 10 mmol) in tetrahydrofuran (20 mL) was added 1,1'-(azodicarbonyl)dipiperidine (757 mg, 3.0 mmol). The mixture was stirred at room temperature overnight. Hexane (30 mL) was added to the mixture, and the precipitates were removed by filtration. The filtrate was evaporated in vacuo, the residue was purified by flash column chromatography (4:1 ethyl acetate/$CH_2Cl_2$) to give the title compound as a colorless oil (620 mg, 82%). $^1$H-NMR (300 MHz, $CDCl_3$) δ9.41 (s, 1H), 8.80 (d, J=6.1 Hz, 1H), 8.54 (d, J=6.1 Hz, 1H), 8.33 (d, J=7.2 Hz, 1H), 8.29 (d, J=7.6 Hz, 1H), 7.67 (t, J=7.7 Hz, 1H), 6.56 (s, 1H), 6.29 (s, 1H), 6.24 (s, 1H), 3.89 (t, J=6.1 Hz, 2H), 3.75 (t, J=6.0 Hz, 2H), 2.16 (s, 3H), 2.05 (m, 2H), 1.90 (br s, 1H).

d) N-[3-[3-(5-Isoquinolinylsulfonyloxy)-5-methylphenoxy] propoxy]phthalimide

To a solution of 3-[3-(5-isoquinolinylsulfonyloxy)-5-methylphenoxy]propanol (560 mg, 1.5 mmol), as prepared in the preceding step, triphenylphosphine (520 mg, 2.0 mmol), and N-hydroxyphthalimide (245 mg, 1.5 mmol) in tetrahydrofuran (15 mL) at 0° C. was added diethyl azodicarboxylate (350 mg, 2.0 mmol). The reaction mixture was stirred at room temperature overnight. Water (50 mL) was added, and the reaction mixture was extracted into ethyl acetate (3×50 mL). The ethyl acetate solution was washed with brine (2×50 mL) and dried over $Na_2SO_4$. After removing the solvent, the residue was purified by flash column chromatography (4:1 dichloromethane/ethyl acetate) to give the title compound as a colorless foam (580 mg, 75%). $^1$H-NMR (300 MHz, $CDCl_3$) δ9.42 (s, 1H), 8.81 (d, J=6.1 Hz, 1H), 8.56 (d, J=6.1 Hz, 1H), 8.34 (d, J=7.1 Hz, 1H), 8.31 (d, J=7.2 Hz, 1H), 7.84 (m, 2H), 7.77 (m, 2H), 7.68 (t, J=7.7 Hz, 1H), 6.59 (s, 1H), 6.33 (s, 1H), 6.21 (s, 1H), 4.31 (t, J=6.1 Hz, 2H), 4.00 (t, J=6.1 Hz, 2H), 2.17 (s, 3H), 2.11 (m, 2H).

e) 3-[3-(5-Isoquinolinylsulfonyloxy)-5-methylphenoxy] propoxyamine

To a solution of N-[3-[3-(5-isoquinolinylsulfonyloxy)-5-methylphenoxy]propoxy]phthalimide (570 mg, 1.1 mmol), as prepared in the preceding step, in ethanol (20 mL), tetrahydrofuran (10 mL), and water (10 mL) was added sodium borohydride (230 mg, 6.0 mmol). The reaction mixture was stirred at ambient temperature overnight. The mixture was acidified (pH 1–2) with 2 N HCl and heated at 50° C. for 2 hours. After cooling to room temperature, 2 N NaOH was added to adjust the pH to 8–9. The mixture was extracted with ethyl acetate (3×50 mL). The combined organic extracts were washed with brine (50 mL) and dried over $Na_2SO_4$. After removing the solvent, the residue was purified by flash column chromatography (ethyl acetate) to give the title compound as a colorless oil (110 mg, 26%). $^1$H-NMR (300 MHz, $CDCl_3$) δ9.42 (s, 1H), 8.81 (d, J=6.1 Hz, 1H), 8.54 (d, J=6.1 Hz, 1H), 8.33 (m, 2H), 7.67 (t, J=7.8 Hz, 1H), 6.55 (s, 1H), 6.28 (s, 1H), 6.23 (s, 1H), 3.81 (t, J=6.3 Hz, 2H), 3.74 (t, J=6.1 Hz, 2H), 2.15 (s, 3H), 1.94 (m, 2H). Mass spectrum (MALDI-TOF, α-cyano-4-hydroxycinnamic acid matrix) calcd. for $C_{19}H_{20}N_2O_5S$: 389.1 (M+H), 411.1 (M+Na). Found: 389.3, 411.1.

f) 3-[3-(5-Isoquinolinylsulfonyloxy)-5-methylphenoxy] propoxyguanidine hydrochloride To a solution of 3-[3-(5-isoquinolinylsulfonyloxy)-5-methylphenoxy]propoxyamine (100 mg, 0.25 mmol), as prepared in the preceding step, in N,N-dimethylformamide (4 mL) was added 1H-pyrazole-carboxamidine hydrochloride (150 mg, 1.0 mmol). The reaction mixture was stirred at ambient temperature for two days. N,N-Dimethylformamide was removed under high vacuum. Acetonitrile (5 mL) was added and the solid was removed by filtration. The filtrate was concentrated in vacuo and the residue was dried under high vacuum. The residue was partitioned between water (20 mL plus 2 mL brine) and diethyl ether (10 mL). The water solution was extracted with diethyl ether (10 mL). The combined diethyl ether extracts were extracted with pH 5 water. The combined water solution was basified (pH 8–9) by using 2 N NaOH and extracted with ethyl acetate (3×30 mL). The ethyl acetate solution was washed with pH 7 buffer solution (2×20 mL) and brine (20 mL) then dried over $Na_2SO_4$. After removing the solvent, 0.6 N HCl methanol (3 mL) was added, and the solution was concentrated to give the title compound as colorless foam (95 mg, 81%). $^1$H-NMR (300 MHz, DMSO-$d_6$) δ11.16 (br s, 1H), 9.75 (s, 1H), 8.89 (d, J=6.3 Hz, 1H), 8.73 (d, J=8.3 Hz, 1H), 8.46 (m, 4H), 7.93 (t, J=7.9 Hz, 1H), 7.72 (br s, 4H), 6.71 (s, 1H), 6.33 (s, 1H), 6.27 (s, 1H), 3.88 (m, 4H), 2.13 (s, 3H), 1.94 (m, 2H). Mass spectrum (MALDI-TOF, α-cyano-4-hydroxycinnamic acid matrix) calcd. for $C_{20}H_{22}N_4O_5S$: 431.1 (M+H), 453.1 (M+Na). Found: 431.2, 453.3.

EXAMPLE 8

3-[5-Methyl-3-[2-(methylsulfonyl) phenylsulfonyloxy]phenoxy]propoxyguanidine hydrochloride a) 5-Methyl-3-[2-(methylsulfonyl)phenylsulfonyloxy] phenol A mixture of orcinol monohydrate (1.68 g, 12 mmol) and 2-methylsulfonylbenzenesulfonyl chloride (3.0 g, 11.8 mmol) in saturated $NaHCO_3$ (25 mL) and dichloromethane (25 mL) was stirred vigorously at room temperature for one week. The reaction mixture was diluted with 50 mL of water and extracted into dichloromethane (3×50 mL). The organic phase was washed with brine (2×50 mL) and dried over $Na_2SO_4$. After removing the solvent in vacuo, the residue was treated with dichloromethane and ether to initiate crystallization. The mixture was filtered to provide 1.05 g (26% yield) of a white solid. $^1$H-NMR (300 MHz, CDCl$_3$) δ2.22 (s, 3H), 3.45 (s, 3H), 5.20 (s, 1H), 6.51 (t, 1H), 6.54 (s, H), 6.61 (s, 1H), 7.74 (td, 1H, J=7.7, 1.4 Hz), 7.87 (td, 1H, J=7.7, 1.3 Hz), 8.12 (dd, 1H, J=7.8, 0.7 Hz), and 8.44 (dd, 1H, J=7.8, 0.5 Hz).

b) 3-[5-Methyl-3-[2-(methylsulfonyl)phenylsulfonyloxy] phenoxy]propanol

Diethyl azodicarboxylate (0.46 mL, 2.9 mmol) was added slowly to a solution of 1.0 g (2.9 mmol) of 5-methyl-3-[2-(methylsulfonyl)phenylsulfonyloxy]phenol, as prepared in the preceding step, 0.21 mL (2.9 mmol) of 1,3-propanediol, and 760 mg (2.9 mmol) of triphenylphosphine in tetrahydrofuran (25 mL). The reaction mixture was stirred at ambient temperature overnight. The reaction mixture was evaporated to dryness. The residue was triturated with hexane under sonication and decanted (4 times). The residue was dissolved in dichloromethane and diluted with hexane to produce a crystalline material, which was discarded. The filtrate was diluted with hexane to give an oil and the solvent was decanted. The oil was dissolved in a minimum of methanol and diluted with water to initiate crystallization. The solid was collected by filtration to afford the title compound 1.16 g (quantitative yield). $^1$H-NMR (300 MHz, CDCl$_3$) δ8.45 (dd, 1H, J=7.8, 1.3 Hz), 8.12 (dd, 1H, J=7.8, 1.2 Hz), 7.88 (td, 1H, J=7.7, 1.3 Hz), 7.74 (td, 1H, J=7.7, 1.3 Hz), 6.61–6.56 (m, 3H), 4.00 (t, 2H, J=6Hz), 3.81 (t, 3H, J=5.9 Hz), 3.45 (s, 3H), 2.24 (s, 3H), and 1.97 (pentet, 2H, J=6.2 Hz). Mass spectrum (MALDI-TOF, α-cyano-4-hydroxycinnamic acid matrix) calcd. for $C_{17}H_{20}O_7S_2$: 423.1 (M+Na). Found: 423.1.

c) N-[3-[5-Methyl-3-[2-(methylsulfonyl) phenylsulfonyloxy]phenoxy]propoxy]phthalimide The diethyl azodicarboxylate (3.5 mL, 0.022 mol) was added dropwise to a solution of 3-[5-methyl-3-[2-(methylsulfonyl)phenylsulfonyloxy]phenoxy]propanol (7.4 g, 0.018 mol), as prepared in the preceding step, triphenylphosphine (5.82 g, 0.018 mol), and N-hydroxyphthalimide (3.11 g, 0.018 mol) in anhydrous tetrahydrofuran (120 mL). The solution was allowed to stir at ambient temperature over a weekend. The tetrahydrofuran was evaporated. The residue was dissolved in acetonitrile (minimum) and diluted with hexane to produce a crystalline product which was collected by filtration and discarded. The filtrate was evaporated to dryness and purified by silica gel chromatography using dichloromethane as an elution solvent. The appropriate fractions were combined, evaporated to dryness, and placed under high vacuum to give 7.3 g (74% yield) of a colorless foam. $^1$H-NMR (300 MHz, CDCl$_3$) δ8.45 (dd, 1H, J=7.8, 1.3 Hz), 8.12 (dd, 1H, J=7.8, 1.2 Hz), 7.82–7.91 (m, 3H), 7.73–7.79 (m, 3H), 6.61–6.63 (m, 2H), 6.55 (t, 1H, J=2.1 Hz), 4.36 (t, 2H, J=6.2 Hz), 4.10 (m, 2H), 3.45 (s, 3H), 2.24 (s, 3H), 2.13–2.23 (pentet, 2H, J=6.2 Hz). Mass spectrum (MALDI-TOF, α-cyano-4-hydroxycinnamic acid matrix) calcd. for $C_{25}H_{23}NO_9S_2$: 568.1 (M+Na). Found: 568.0.

d) 3-[5-Methyl-3-[2-(methylsulfonyl)phenylsulfonyloxy] phenoxypropoxyamine

A solution of N-[3-[5-methyl-3-[2-(methylsulfonyl) phenylsulfonyloxy]phenoxy]propoxy]phthalimide (7.22 g, 0.013 mol), as prepared in the preceding step, in isopropanol:tetrahydrofuran:water (5:1:1; 700 mL) was treated with sodium borohydride (2.5 g, 0.066 mol). The reaction mixture was allowed to stir at ambient temperature overnight. The reaction mixture was quenched with 2N hydrochloric acid and the mixture was warmed at 50° C. for 2.5 hours. The reaction mixture was cooled in an ice:water bath and adjusted to pH 8.0 with 2N sodium hydroxide. The isopropanol was evaporated on a rotary evaporator and the residual aqueous solution was extracted with ethyl acetate (3×75 mL). The combined ethyl acetate extracts were washed with brine, dried over anhydrous sodium sulfate, and evaporated to dryness. The material was purified by silica gel chromatography by elution with 60% ethyl acetate/hexane, followed by 75% ethyl acetate/hexane. The appropriate fractions were combined and evaporated to 2.8 g (52% yield) of a white solid. $^1$H-NMR (300 MHz, CDCl$_3$) δ8.45 (dd, J=7.9, 1.2 Hz, 1H), 8.11 (dd, J=7.8, 1.3 Hz, 1H), 7.87 (td, J=7.7, 1.3 Hz, 1H), 7.74 (td, J=7.8, 1.3 Hz, 1H), 6.56–6.60 (m, 3H), 5.39 (m, 2H), 3.92 (t, J=6.3 Hz, 2H), 3.79 (t, J=6.1 Hz, 2H), 3.45 (s, 3H), 2.23 (s, 3H), and 1.99 (pentet, J=6.2 Hz, 2H). Mass spectrum (MALDI-TOF, α-cyano-4-hydroxycinnamic acid matrix) calcd. for $C_{17}H_{21}NO_7S_2$: 438.1 (M+Na). Found: 438.2.

e) 3-[5-Methyl-3-[2-(methylsulfonyl)phenylsulfonyloxy]phenoxy]propoxyguanidine hydrochloride A solution of 3-[5-methyl-3-[2-(methylsulfonyl)phenylsulfonyloxy]phenoxy]propoxyamine (2.75 g, 0.0066 mol), as prepared in the preceding step, in anhydrous N,N-dimethylformamide (100 mL) was treated with 1H-pyrazole-1-carboxamidine hydrochloride (2.93 g, 0.02 mol). The reaction mixture was allowed to stir overnight at ambient temperature. The reaction mixture was evaporated to dryness under high vacuum. The residue was treated with acetonitrile and the resulting crystalline material was collected by filtration and discarded. The filtrate was evaporated to dryness and applied to a silica gel column. The column was eluted with 5% methanol in acetonitrile, which resulted in mixed product fractions. These fractions were combined and evaporated to dryness. The residue was dissolved in water and the solution was adjusted to pH 3–4 with methanolic HCl. This solution was washed with ether and ethyl acetate. The aqueous solution was treated with solid sodium chloride and extracted with ethyl acetate and dichloromethane. Both the ethyl acetate and the dichloromethane extracts were separately washed with brine and dried ($Na_2SO_4$). The organic extracts were combined and evaporated to dryness. The residue was triturated with both hexane and ether under sonication and decanted. The residue was placed under high vacuum with sonication for 2 h to give 2.67 g (82% yield) of a white powder. $^1$H-NMR (300 MHz, $CDCl_3$) δ8.42 (dd, J=7.8, 1.3 Hz, 1H), 8.10 (dd, J=7.8, 1.3 Hz, 1H), 7.90 (td, J=7.7, 1.3 Hz, 1H), 7.77 (td, J=7.7, 1.3 Hz, 1H), 7.27 (broad), 6.57 (m, 2H), 6.52 (br t, 1H), 4.04 (t, J=6.1 Hz, 2H), 3.94 (t, J=5.6 Hz, 2H), 3.43 (s, 3H), 2.21 (s, 3H), and 2.06 (pentet, J=5.6 Hz, 2H). Mass spectrum (MALDI-TOF, α-cyano-4-hydroxycinnamic acid matrix) calcd. for $C_{18}H_{23}N_3O_7S_2$: 458.1 (M+H). Found: 457.9. HPLC (C18, 5μ, 4.6×100 mm, Gradient: 5→100% B in 15 min; A=0.1% $TFA/H_2O$; B=0.1% $TFA/CH_3CN$, 20 μL inj, 15 min run time, Det: 215 nm, FR:1 mL/min) 98% @8.74 min.

EXAMPLE 9

3-[-5-Methyl-3-(1,2,3,4-tetrahydroquinolinyl-8-sulfonyloxy)phenoxy]propoxyguanidine acetate A solution of 3-[5-methyl-3-(quinolinyl-8-sulfonyloxy)phenoxy]propoxyguanidine hydrochloride (0.317 g, 0.68 mmol), as prepared in Example 3, in methanol (32 mL) was evacuated, flushed with nitrogen, then treated with 10% palladium on carbon (115 mg). The reaction was then placed under a hydrogen-filled balloon. After 8 hours, a 52 mg-portion of 10% palladium on carbon was added and the reaction was again placed under a hydrogen-filled balloon. After stirring overnight, the reaction mixture was filtered through Celite and the filtrate was evaporated to dryness. The residue was triturated with hexane twice. The residue was taken up in a minimum amount of acetonitrile, filtered through a PTFE filter (0.45μ), and evaporated to dryness. The residue was purified on a Waters Sep-Pak silica gel column (5 g silica) by elution with a mixture of 40% dichloromethane:methanol:acetic acid (400/100/10) in dichloromethane. The appropriate fractions were combined and evaporated to dryness. The residue was triturated with hexane twice and then placed under high vacuum. The residue was treated with 50% aqueous acetonitrile and lyophilized overnight to give the title compound as a hydroscopic solid (0.248 g, 74% yield). $^1$H-NMR (300 MHz, $CDCl_3$) δ7.28 (d, J=8.0 Hz, 1H), 7.08 (d, J=7.1 Hz, 1H), 6.54 (s, 1H), 6.36–6.45 (m, 3H), 6.01 (broad s, 1H), 4.04 (m, 2H), 3.91 (m, 2H), 3.67 (m, 2H), 2.75(t, J=6.1 Hz, 2H), 2.18 (s, 3H), 2.03 (m, 2H), 1.87 (pentet, J=5.4 Hz, 2H). Mass spectrum (MALDI-TOF, α-cyano-4-hydroxycinnamic acid matrix) calcd. for $C_{20}H_{26}N_4O_5S$: 435.2 (M+H). Found: 434.9. HPLC (C18, 5μ, 4.6×100 mm, Gradient: 5→100% B in 15 min; A=0.1% $TFA/H_2O$; B=0.1% $TFA/CH_3CN$, 20 μL inj, 15 min run time, Det: 215 nm, FR: 1 mL/min) 98.8% @10.0 min.

EXAMPLE 10

3-[5-Hydroxymethyl-3-(quinolinyl-8-sulfonyloxy)phenoxy]propoxyguanidine acetic acid salt a) 5-Methoxycarbonyl-3-(quinolinyl-8-sulfonyloxy)phenol A mixture of methyl 1,3-dihydroxybenzoate (2.56 g, 0.015 mol) and 8-quinolinesulfonyl chloride (3.46 g, 0.015 mol) in dichloromethane (100 mL) and saturated sodium bicarbonate (100 mL) was stirred at room temperature for 5 days. The reaction mixture was diluted with water and dichloromethane. The dichloromethane was separated and the aqueous layer was extracted with dichloromethane (2×25 mL). The dichloromethane extracts were combined, washed with water and brine, dried over sodium sulfate and evaporated to dryness. The residue was treated with methanol and filtered to remove insoluble material. The filtrate was evaporated to dryness to give the title compound as a pale yellow foam (4.34 g, 80% yield) which was used without further purification.

b) 3-[5-Methoxycarbonyl-3-(quinolinyl-8-sulfonyloxy)phenoxy]propanol

A mixture of 5-methoxycarbonyl-3-(quinolinyl-8-sulfonyloxy)phenol (4.34 g, 0.012 mol), as prepared in the preceding step, 3-bromo-1-propanol, and cesium carbonate (3.91 g, 0.012 mol) in acetonitrile (40 mL) was warmed at 50° C. overnight. The reaction mixture was diluted with ethyl acetate (2×25 mL). The ethyl acetate layers were combined, washed with brine, dried, and evaporated to dryness. The residue was purified on a silica gel column (80 g) by elution with 10–20% ethyl acetate in dichloromethane. The appropriate fractions were collected, evaporated to dryness, and placed under high vacuum to give the title compound as a white solid (2.83 g, 57% yield). $^1$H-NMR (300 MHz, $CDCl_3$) δ9.25 (dd, 1H, J=4.2, 1.8 Hz), 8.43 (dd, 1H, J=7.4, 1.4 Hz), 8.31 (dd, 1H, J=8.4, 1.7 Hz), 8.16 (dd, 1H, J=8.2, 1.4 Hz), 7.60–7.66 (m, 2H), 7.41 (m, 1H), 7.30 (m, 1H), 6.91 (t, 1H, J=2.3 Hz), 4.03 (t, 2H, J=6.0 Hz), 3.83 (s, 3H), 3.80 (t, 2H, J=6.0 Hz), 1.98 (pentet, 2H, J=6.0 Hz). Mass spectrum (MALDI-TOF, α-cyano-4-hydroxycinnamic acid matrix) calcd. for $C_{20}H_{19}NO_7S$: 418.1 (M+H). Found:417.9.

c) N-[3-[5-Methoxycarbonyl-3-(quinolinyl-8-sulfonyloxy)phenoxy]propoxy]phthalimide A solution of 3-[5-methoxycarbonyl-3-(quinolinyl-8-sulfonyloxy)phenoxy]propanol (2.83 g, 0.0068 mol), as prepared in the preceding step, triphenylphosphine (2.1 g, 0.008 mol), and N-hydroxyphthalimide (1.11 g, 0.0068 mol) in anhydrous tetrahydrofuran (50 mL) was treated with diethyl azodicarboxylate (1.26 mL, 0.008 mol) dropwise. The reaction mixture was allowed to stir at ambient temperature overnight. The tetrahydrofuran was evaporated and the residue was treated with acetonitrile/hexane to produce a crystalline crop which was removed by filtration and discarded. The filtrate produced a granular crystalline material which was collected by filtration and discarded. The filtrate was evaporated to dryness and the residue was treated with ethyl acetate/hexane to produce the title compound as a crystalline material in two crops (3.53 g, 92% yield). $^1$H-NMR (300 MHz, $CDCl_3$) indicated 88% title compound and 12% triphenylphosphine oxide: δ9.28 (dd, 1H, J=4.2, 1.7 Hz), 8.43 (dd, 1H, J=7.4, 1.4 Hz), 8.31 (dd, 1H, J=8.4, 1.8 Hz), 8.16 (dd, 1H, J=8.2, 1.4 Hz), 7.75–7.88 (m, 4H), 7.60–7.71 (m, 2H), 7.43 (m, 1H), 7.33 (m, 1H), 6.88 (t, 1H, J=2.3 Hz), 4.35 (t, 2H, J=6.1 Hz), 4.13 (t, 2H, J=6.1), 3.84 (s, 3H), 2.18 (pentet, 2H, J=6.1 Hz). Mass spectrum (MALDI-TOF, α-cyano-4-hydroxycinnamic acid matrix) calcd. for $C_{28}H_{22}N_2O_9S$: 563.1 (M+H). Found: 563.1.

d) 3-[5-Hydroxymethyl-3-(quinolinyl-8-sulfonyloxy)phenoxy]propoxyamine

A suspension of N-[3-[5-methoxycarbonyl-3-(quinolinyl-8-sulfonyloxy)phenoxy]propoxy]phthalimide (3.52 g, 0.0063 mol), as prepared in the preceding step, in ethanol/tetrahydrofuran/water (48:48:24 mL each) was treated with sodium borohydride (1.2 g) and the reaction was stirred at ambient temperature overnight. The reaction mixture was quenched with 2N HCl and warmed at 50° C. for 2.5 h while maintaining a pH of 2.0. The solvents were evaporated and the concentrate was cooled in an ice bath, adjusted to pH=10 with 2N NaOH, and extracted with ethyl acetate (4×25 mL). The ethyl acetate extracts were combined, washed with brine, dried, and evaporated. The residue was dissolved in ethyl acetate and extracted with 10% citric acid (3×25 mL). The citric acid extracts were combined and washed with ethyl acetate (1×20 mL). The citric acid layer was adjusted to pH=10 with 2N NaOH and extracted with ethyl acetate (3×25 mL). The ethyl acetate extracts were combined, washed with brine, dried, and evaporated to dryness. The residue was placed under high vacuum overnight to give the title compound (1.2 g, 54% yield). Mass spectrum (MALDI-TOF, α-cyano-4-hydroxycinnamic acid matrix) calcd. for $Cl_{19}H_{20}N_2O_6S$: 405.1 (M+H). Found: 405.0, also 278.9 for triphenylphosphine oxide.

e) 3-[5-Hydroxymethyl-3-(quinolinyl-8-sulfonyloxy)phenoxy]propoxyguanidine acetic acid salt A solution of 3-[5-hydroxymethyl-3-(quinolinyl-8-sulfonyloxy)phenoxy]propoxyamine (1.2 g, 0.003 mol), as prepared in the preceding step, in N,N-dimethylformamide (25 mL) was treated with 1H-pyrazole-1-carboxamidine hydrochloride (1,3 g, 0.009 mol) and the reaction mixture was stirred at ambient temperature overnight. The N,N-dimethylformamide was evaporated under high vacuum. The residue was triturated with hot acetonitrile and filtered. The filtrate was evaporated to dryness. The residue was dissolved in water, acidified to pH 3–4 with methanolic HCl, and washed with diethyl ether. The aqueous layer was adjusted to pH 9–10 with 2N NaOH and extracted with ethyl acetate (3×25 mL). The ethyl acetate extracts were combined, washed with pH 7 buffer and brine, dried, and evaporated to dryness. The residue was redissolved in ethyl acetate and washed with pH 7 buffer and brine, dried, and evaporated. The residue was purified on a silica gel column (10 g) by elution with a 1:1 mixture of dichloromethane and a solution of dichloromethane/methanol/acetic acid (400/100/10), followed by a 1:3 mixture of the same composition. The appropriate fractions were combined and evaporated. The residue was treated with acetonitrile and water and lyophilized overnight to give the title compound (0.8 g, 60% yield). $^1$H-NMR (300 MHz, CDCl$_3$/DMSO-d$_6$) δ9.25 (dd, 1H, J=4.2, 1.8 Hz), 8.38 (td, 2H, J=7.5, 1.4 Hz), 8.20 (dd, 1H, J=8.3, 1.4 Hz), 7.62–7.68 (m, 2H), 6.79 (s, 1H), 6.64 (s, 1H), 6.41 (t, 1H, J=2.3 Hz), 4.45 (s, 2H), 3.88 (m, 4H), 1.93–2.02 (m, 5H). Mass spectrum (MALDI-TOF, α-cyano-4-hydroxycinnamic acid matrix) calcd. for $C_{20}H_{22}N_4O_6S$: 447.1 (M+H). Found: 447.0. HPLC (C18, 5μ, 4.6×100 mm, Gradient: 5→100% B in 15 min; A=0.1% TFA/H$_2$O; B=0.1% TFA/CH$_3$CN, 20 μL inj, 15 min run time, Det: 215 nm, FR:1 mL/min) 95.8% @11.5 min.

EXAMPLE 11

{1-[[5-Methyl-3-(2-methylsulfonylphenylsulfonyloxy)phenoxy]methyl]cyclopropylmethoxy}guanidine hydrochloride a) 1,1-Dihydroxymethylcyclopropane To a solution of BH$_3$.THF (1.0 M, 100 mL, 100 mmol) was added ethyl 1,1-cyclopropanedicarboxylate (9.3 mL, 50 mmol) at room temperature dropwise. The mixture was stirred at 50° C. overnight, quenched with methanol (100 mL) carefully at 0° C. and stirred at room temperature for 1 h. The reaction mixture was concentrated in vacuo. The residue was co-evaporated with methanol several times (4×50 mL) to give the title compound as colorless oil (5.3 g) which was directly used in the next step without further purification.

b) [1-[5-Methyl-3-(2-methylsulfonylphenylsulfonyloxy)phenoxy]methyl]cyclopropylmethanol To a solution of 3-(2-methylsulfonylphenylsulfonyloxy)-5-methylphenol (6.85 g, 20.0 mmol), as prepared in step a of Example 8, tri-N-butylphosphine (6.1 g, 30 mmol) and 1,1-dihydroxylmethylcyclopropane (5.1 g, 50 mmol), as prepared in the preceding step, in tetrahydrofuran (200 mL) was added 1,1'-(azodicarbonyl)dipiperidine (7.6 g, 30 mmol). The mixture was stirred at room temperature overnight, hexane (300 mL) was added to the mixture and the precipitates were removed by filtration. The filtrate was evaporated in vacuo, the residue was purified by flash column chromatography (1:1 to 2:1 ethyl acetate/hexane) and by crystallization from ethyl acetate/hexane (1:5) to give the title compound as white solid (4.9 g, 57%). $^1$H-NMR (300 MHz, CDCl$_3$) δ8.45 (d, J=7.8 Hz, 1H), 8.13 (d, J=7.9 Hz, 1H), 7.88 (t, J=7.7 Hz, 1H), 7.75 (t, J=7.7 Hz, 1H), 6.77 (br s, 3H), 3.82 (s, 2H), 3.59 (d, J=5.5 Hz, 2H), 3.45 (s, 3H), 2.23 (s, 3H), 0.61 (s, 4H).

c) N-{1-[[5-Methyl-3-(2-methylsulfonylphenylsulfonyloxy)phenoxy]methyl]cyclopropylmethoxy}phthalimide To a solution of [1-[5-methyl-3-(2-methylsulfonylphenylsulfonyloxy)phenoxy]methyl]cyclopropylmethanol (4.7 g, 11.0 mmol), as prepared in the preceding step, triphenylphosphine (3.4 g, 13.0 mmol), N-hydroxyphthalimide (2.1 g, 13.0 mmol) in tetrahydrofuran (80 mL) was added diethyl azodicarboxylate (2.3 g, 13.0 mmol) at 0° C. The reaction mixture was stirred at ambient temperature overnight. The reaction mixture was concentrated in vacuo and ethyl acetate (100 mL) was added to the residue. The solid was collected, washed with ethyl acetate and dried in high vacuum to give the title compound as white solid (5.5 g, 87%). $^1$H-NMR (300 MHz, CDCl$_3$) δ8.37 (d, J=7.8 Hz, 1H), 8.15 (d, J=7.8 Hz, 1H), 8.10 (t, J=7.7 Hz, 1H), 7.97 (t, J=7.7 Hz, 1H), 7.86 (s, 4H), 6.77 (s, 1H), 6.54 (s, 1H), 6.51 (s, 1H), 4.11 (s, 2H), 3.97 (s, 2H), 3.48 (s, 3H), 2.22 (s, 3H), 0.61–0.66 (m, 4H).

d) N-{1-[[5-Methyl-3-(2-methylsulfonylphenylsulfonyloxy)phenoxy]methyl]cyclopropylmethoxy}amine To a solution of N-{1-[[5-methyl-3-(2-methylsulfonylphenylsulfonyloxy)phenoxy]methyl]cyclopropylmethoxy}phthalimide (5.4 g, 9.5 mmol), as prepared in the preceding step, in ethanol (100 mL)/tetrahydrofuran (100 mL)/water (50 mL) was added sodium borohydride (1.15 g, 30.0 mmol). The reaction mixture was stirred at ambient temperature overnight. 2N HCl was added to adjust the pH to 1–2, the mixture was heated to 50° C. for 2 hours. The reaction mixture was concentrated to about 100 mL, water (50 mL) was added and the mixture was neutralized to pH 8–9 with 2N NaOH. The mixture was extracted into ethyl acetate (3×100 mL) and the organic phase was washed with brine (2×100 mL) and then dried over $Na_2SO_4$. After removing the solvent, the residue was purified by flash column chromatography (4:1 ethyl acetate/hexane) to give the title compound as a white solid (3.6 g, 86%). $^1$H-NMR (300 MHz, $CDCl_3$) δ8.45 (d, J=7.8 Hz, 1H), 8.13 (d, J=7.8 Hz, 1H), 7.88 (t, J=7.7 Hz, 1H), 7.74 (t, J=7.7 Hz, 1H), 6.61 (s, 1H), 6.58 (s, 2H), 5.44 (br s, 2H),3.76 (s, 2H), 3,63 (s 2H), 3.45 (s, 3H), 2.23 (s, 3H), 0.57–0.65 (m, 4H).

e) {1-[[5-Methyl-3-(2-methylsulfonylphenylsulfonyloxy) phenoxy]methyl]cyclopropylmethoxy}guanidine hydrochloride To a solution of N-{1-[[5-methyl-3-(2-methylsulfonylphenylsulfonyloxy)phenoxy]methyl] cyclopropylmethoxy}amine (3.5 g, 8.0 mmol), as prepared in the preceding step, in N,N-dimethylformamide (30 mL) was added 1H-pyrazole-carboxamidine hydrochloride (3.7 g, 25.0 mmol). The reaction mixture was stirred at ambient temperature overnight. N,N-Dimethylformamide was removed under high vacuum. Acetonitrile (50 mL) was added and the solid was removed by filtration. The filtrate was concentrated in vacuo and the residue was dried under high vacuum. The residue was partitioned between water (100 mL plus 5 mL brine) and diethyl ether (50 mL). The water solution was extracted with diethyl ether (50 mL). The combined diethyl ether solution was extracted with pH 5 water (30 mL). The combined water solution was adjusted to pH 8–9 by using 2N NaOH and extracted into ethyl acetate (3×100 mL). The ethyl acetate solution was washed with pH 7 buffer solution (5×60 mL) and brine (50 mL) and dried over $Na_2SO_4$. After removing the solvent, 0.6N HCl methanol (50 mL) was added and the solution was concentrated. The residual oil was crystallized from methanol/ethyl acetate (1:50) to give the title compound as white solid (3.6 g, 86%). $^1$H-NMR (300 MHz, DMSO-$d_6$) δ11.07 (br s, 1H), 8.37 (d, J=7.8 Hz, 1H), 8.09–8.14 (m, 2H), 7.97 (t, J=7.7 Hz, 1H), 7.65 (br s, 4H), 6.76 (s, 1H), 6.52 (s, 1H), 6.51 (s, 1H), 3.86 (s, 2H), 3.78 (s, 2H), 3.48 (s, 3H), 2.21 (s, 3H), 0.69 (m, 2H), 0.62 (m, 2H). Mass spectrum (MALDI-TOF, α-cyano-4-hydroxycinnamic acid matrix) calcd. for $C_{20}H_{25}N_3O_7S_2$: 484.1 (M+H), 506.1 (M+Na). Found: 484.0, 506.0.

EXAMPLE 12

{1-[[5-Methyl-3-(2-cyanophenylsulfonyloxy) phenoxy]methyl]cyclopropylmethoxy}guanidine acetate a) 1-[[3-(2-Cyanophenylsulfonyloxy)-5-methylphenoxy] methyl]cyclopropylmethanol The title compound was prepared in 62% yield from 3-(2-cyanophenylsulfonyloxy)-5-methylphenol, as prepared in step a of Example 6, in a manner analogous to step b of Example 11. $^1$H-NMR (300 MHz, $CDCl_3$) δ8.09 (m, 1H), 7.80 (m, 2H), 6.66 (s, 1H), 6.60 (s, 1H), 3.86 (s, 2H), 3.60 (s, 2H), 2.26 (s, 3H), 1.85 (br, s 1H), 0.62 (s, 4H).

b) {1-[[3-(2-Cyanophenylsulfonyloxy)-5-methylphenoxy] ethyl]yclopropoxy}pthalimide The title compound was prepared in 94% yield from 1-[[3-(2-cyanophenylsulfonyloxy)-5-methylphenoxy] methyl]cyclopropylmethanol, as prepared in the preceding step, in a manner analogous to step c of Example 11. $^1$H-NMR (300 MHz, $CDCl_3$) (8.10 (m 1H), 7.95 (m, 1H), 7.78 (m, 6H), 6.70 (s, 1H), 6.60 (s, 1H), 6.52 (s, 1H), 4.18 (s, 2H), 4.01 (s, 2H), 2.28 (s, 3H), 0.70 (m, 4H).

c) {1-[[3-(2-Cyanophenylsulfonyloxy)-5-methylphenoxy] methyl]cyclopropylmethoxy}amine The title compound was prepared in 60% yield from N-{1-[[3-(2-cyanophenylsulfonyloxy)-5-methylphenoxy] methyl]cyclopropoxy}phthalimide, as prepared in the preceding step, in a manner analogous to step d of Example 11. $^1$H-NMR (300 MHz, $CDCl_3$) (8.11 (m, 1H), 7.97 (m, 1H), 7.79 (m, 2H), 6.66 (s, 1H), 6.58 (s, 1H), 6.56 (s, 1H), 5.30 (br s, 2H), 3.80 (s, 2H), 3.64 (s, 2H), 2.26 (s, 3H), 0.63 (m, 4H).

d) {1-[[5-Methyl-3-(2-cyanophenylsulfonyloxy)phenoxy] methyl]cyclopropylmethoxy}guanidine acetate The title compound was prepared in 79% yield from {1-[[3-(2-cyanophenylsulfonyloxy)-5-methylphenoxy] methyl]cyclopropylmethoxy}amine, as prepared in the preceding step, in a manner analogous to step e of Example 11. Flash column chromatography (100:10:1 dichloromethane:methanol:acetic acid gave the title compound as an acetic acid salt. $^1$H-NMR (300 MHz, DMSO-$d_6$) δ8.29 (d, J=7.0 Hz, 1H), 8.02 (d, J=7.2 Hz, 1H), 7.98 (m, 2H), 6.77 (s, 1H), 6.47 (s, 1H), 6.42 (s, 1H), 5.02 (br,s 4H), 3.80 (s, 2H), 3.56 (s, 2H), 2.21 (s, 3H), 1.89 (s, 3H), 0.55 (s, 2H), 0.52 (s, 2H). Mass spectrum (MALDI-TOF, α-cyano-4-hydroxycinnamic acid matrix) calcd. for $C_{20}H_{22}N_4O_5S$: 431.1 (M+H), 453.1 (M+Na). Found: 430.9, 452.8.

EXAMPLE 13

{[[5-Methyl-3-(quinolinyl-8-sulfonyloxy)phenoxy] methyl]cyclopropylmethoxy}guanidine acetate a) 1-[[5-Methyl-3-(quinolinyl-8-sulfonyloxy)phenoxy] methyl]cyclopropylmethanol The title compound was prepared in 73% yield from 5-methyl-3-(quinolinyl-8-sulfonyloxy)phenol, as prepared in step a of Example 3, in a manner analogous to step b of Example 11. $^1$H-NMR (300 MHz, $CDCl_3$) (9.26 (d, J=4.2 Hz, 1H), 8.42 (d, J=7.4 Hz, 1H), 8.30 (d, J=7.4 Hz, 1H),8.14 (d, J=7.3 Hz, 1H), 7.64 (s, 1H), 7.61 (t, J=4.2 H, 1H), 6.55 (s, 1H), 6.46 (s, 2H), 3.73 (s, 2H), 3.55 (s, 2H), 2.16 (s, 3H), 1.66 (br s, 1H), 0.58 (m, 4H).

b) N-{1-[[5-Methyl-3-(quinolinyl-8-sulfonyloxy)phenoxy] methyl]cyclopropoxy}phthalimide The title compound was prepared in 89% yield from 1-[[5-methyl-3-(quinolinyl-8-sulfonyloxy)phenoxy]methyl] cyclopropylmethanol, as prepared in the preceding step, in a manner analogous to step c of Example 11. $^1$H-NMR (300 MHz, $CDCl_3$) δ9.29 (d, J=4.3 Hz, 1H), 8.43 (d, J=7.4 Hz, 1H), 8.30 (d, J=7.4 Hz, 1H), 8.14 (d, J=7.2 Hz, 1H), 7.82 (m, 2H), 7.75 (m, 2H), 7.62 (m, 2H), 6.59 (s, 1H), 6.50 (s, 1H), 6.42 (s, 1H), 4.13 (s, 2H), 3.88 (s, 2H), 2.18 (s, 3H), 0.64 (s, 4H).

c) {1-[[5-Methyl-3-(quinolinyl-8-sulfonyloxy)phenoxy] methyl]cyclopropylmethoxy}amine The title compound was prepared in 79% yield from N-{1-[[5-methyl-3-(quinolinyl-8-sulfonyloxy)phenoxy] methyl]cyclopropoxy}phthalimide, as prepared in the preceding step, in a manner analogous to step d of Example 11. $^1$H-NMR (300 MHz, $CDCl_3$) δ9.23 (d, J=4.2 Hz, 1H), 8.63 (d, J=7.4 Hz, 1H), 8.46 (d, J=7.3 Hz, 1H), 8.38 (d, J=7.3 Hz, 1H), 7.78 (m 2H), 6.64 (s, 1H), 6.38 (s, 1H), 6.27 (s, 1H), 5.93 (br s, 2H), 3.59 (s, 2H), 3.42 (s, 2H), 2.12 (s, 3H), 0.47 (m, 4H).

d) {1-[[5-Methyl-3-(quinolinyl-8-sulfonyloxy)phenoxy] methyl]cyclopropylmethoxy}guanidine acetate The title compound was prepared in 83% yield from {1-[[5-methyl-3-(quinolinyl-8-sulfonyloxy)phenoxy] methyl]cyclopropylmethoxy}amine, as prepared in the preceding step, in a manner analogous to step d of Example 11. Flash column chromatography (100:10:1) dichloromethane:methanol:acetic acid) gave the title compound as the acetic acid salt. $^1$H-NMR (300 MHz, DMSO-$d_6$) δ9.23 (d, J=4.3 Hz, 1H), 8.63 (d, J=8.3 Hz, 1H), 8.45 (d, J=8.3 Hz, 1H), 8.38 (d, J=7.4 Hz, 1H), 7.78 (m, 2H), 6.64 (s, 1H), 6.38 (s, 1H), 6.27 (s, 1H), 5.25 (br s, 4H), 3.65 (s, 2H), 3.53 (s, 2H), 2.12 (s, 3H), 1.89 (s, 3H), 0.55 (br s, 2H), 0.44 (br s, 2H). Mass spectrum (MALDI-TOF, α-cyano-4-hydroxycinnamic acid matrix) calcd. for $C_{22}H_{24}N_4O_5S$: 457.2 (M+H), 479.1 (M+Na). Found: 457.2, 479.0.

EXAMPLE 14

{3-[5-Methyl-3-(2-morpholinylsulfonylphenylsulfonyloxy)phenoxy]propoxy}guanidine hydrochloride a) 1-(Morpholinylsulfonyl)-2-nitrobenzene To a solution of morpholine (1.91 g, 22 mmol and triethylamine (2.2 g, 22 mmol) in dichloromethane (100 mL) at 0° C. was added 2-nitrobenzenesulfonyl chloride (4.42 g, 20 mmol). The mixture was stirred for 4 h and then additional dichloromethane (100 mL) was added. The dichloromethane solution was washed with saturated $NaHCO_3$ (2×50 mL), 10% HCl (2×50 mL) and brine (50 mL) and dried over $Na_2SO_4$. Evaporating the solvent in vacuo gave the title compound as a yellow solid (5.3 g, 97%). $^1$H-NMR (300 MHz, $CDCl_3$) δ7.97 (d, J=7.3 Hz, 1H), 7.62–7.77 (m, 3H), 3.75 (t, J=4.7 Hz, 4H), 3.30 (t, J=4.8 Hz, 4H).

b) 2-(Morpholinylsulfonyl)aniline

A mixture of 1-(morpholinylsulfonyl)-2-nitrobenzene (5.18 g, 19 mmol); as prepared in the preceding step, and 10% palladium on carbon (520 mg) in ethanol (80 mL) and tetrahydrofuran (80 mL) was stirred under hydrogen (balloon) for 5 h. The catalyst was removed by filtration through Celite. The filtrate was concentrated to give the title compound as a yellow solid (4.50 g, 98%) which was directly used for the next step without further purification.

c) 2-(Morpholinylsulfonyl)phenylsulfonyl chloride

The title compound was prepared in 47% yield from 2-(morpholinylsulfonyl)aniline, as prepared in the preceding step, in a manner analogous to step a of Example 19. $^1$H-NMR (300 MHz, $CDCl_3$) δ8.43 (d, J=7.4 Hz, 1H), 8.24 (d, J=7.4 Hz, 1H), 7.88 (m, 2H), 3.74 (t, J=4.7 Hz, 4H), 3.36 (t, J=4.7 Hz, 4H).

d) 5-Methyl-3-[2-(morpholinylsulfonyl)phenylsulfonyloxy]phenol

The title compound was prepared in 60% yield from 2-(morpholinylsulfonyl)phenylsulfonyl chloride, as prepared in the preceding step, in a manner analogous to step a of Example 1. $^1$H-NMR (300 MHz, $CDCl_3$) (8.25 (d, J=7.8 Hz, 1H), 8.21 (d, J=7.8 Hz, 1H), 7.80 (t, J=6.3 Hz, 1H), 7.70 (t, J=6.4 Hz, 1H), 6.60 (s, 1H), 6.49 (s, 1H), 3.73 t, J=4.7 Hz, 4H), 3.36 (t, J=4.7 Hz, 4H), 2.24 (s, 3H).

e) 3-{5-Methyl-3-[(2-morpholinylsulfonyl)phenylsulfonyloxy]phenoxy}propanol

The title compound was prepared in 83% yield from 5-methyl-3-[2-(morpholinylsulfonyl)phenylsulfonyloxy]phenol, as prepared in the preceding step, in a manner analogous to step b of Example 10. $^1$H-NMR (300 MHz, $CDCl_3$) δ8.25 (d, J=7.8 Hz, 1H), 8.21 (d, J=7.8 Hz, 1H), 7.81 (t, J=7.7 Hz, 1H), 7.70 (t, J=7.6 Hz, 1H), 6.60 (s, 2H), 6.56 (s, 1H), 4.36 (t, J=6.7 Hz, 2H), 4.11 (t, J=7.0 Hz, 2H), 3.75 (t, J=4.7 Hz, 4H), 3.35 (t, J=4.7 Hz, 4H), 2.24 (s, 3H) 2.05 (t, J=7.0 Hz, 2H).

f) N-{3-[5-Methyl-[3-(2-morpholinylsulfonyl)phenylsulfonyloxy]phenoxy]propoxy}phthalimide The title compound was prepared in 83% yield from 3-}5-methyl-3-[(2-morpholinylsulfonyl)phenylsulfonyloxy]phenoxy}propanol, as prepared in the preceding step, in a manner analogous to step d of Example 1. $^1$H-NMR (300 MHz, $CDCl_3$) δ8.28 (d, J=7.8 Hz, 1H), 8.21 (d, J=7.8 Hz, 1H), 7.68–7.86 (m, 6H), 6.63 (s, 1H), 6.59 (s, 1H), 6.51 (s, 1H), 4.36 (t, J=6.7 Hz, 2H), 4.11 (t, J=7.0 Hz, 2H), 3.72 (t, J=4.7 Hz, 4H), 3.36 (t, J=4.7 Hz, 4H), 2.25 (s, 3H), 2.18 (t, J=6.4 Hz, 2H).

g) 3-[5-Methyl-[3-(2-morpholinylsulfonyl)phenylsulfonyloxy]phenoxy]propoxyamine

The title compound was prepared in 95% yield from N-{3-[5-methyl-[3-(2-morpholinylsulfonyl)phenylsulfonyloxy]phenoxy]propoxy}phthalimide, as prepared in the preceding step, in a manner analogous to step e of Example 1. $^1$H-NMR (300 MHz, $CDCl_3$) (8.26 (d, J=7.9 Hz, 1H), 8.20 (d, J=7.8 Hz, 1H), 7.81 (t, J=7.7 Hz, 1H), 7.70 (t, J=7.7 Hz, 1H), 6.59 (s, 1H), 6.57 (s, 1H), 6.54 (s, 1H), 3.93 (t, J=6.3 Hz, 2H), 3.79 (t, J=6.2 Hz, 2H), 3.73 (t, J=4.7 Hz, 4H), 3.36 (t, J=4.7 Hz, 4H), 2.25 (s, 3H), 2.00 (t, J=6.3 Hz, 2H).

h) {3-[5-Methyl-3-(2-morpholinylsulfonylphenylsulfonyloxy)phenoxy]propoxy}guanidine hydrochloride The title compound was prepared in 95% yield from 3-[5-methyl-[3-(2-morpholinylsulfonyl)phenylsulfonyloxy]phenoxy]propoxyamine, as prepared in the preceding step, in a manner analogous to step f of Example 1. $^1$H-NMR (300 MHz, DMSO-$d_6$) δ8.21 (t, J=8.0 Hz, 2H), 8.04 (t, J=7.8 Hz, 1H), 7.92 (t, J=7.8 Hz, 1H), 7.71 (br s, 4H), 6.75 (s, 1H), 6.53 (s, 1H), 6.49 (s, 1H), 3.99 (t, J=6.3 Hz, 2H), 3.90 (t, J=6.4 Hz, 2H), 3.62 (t, J=4.7 Hz, 4H), 3.25 (t, J=4.7 Hz, 4H), 2.22 (s, 3H), 2.02 (t, J=6.3 Hz, 2H). Mass spectrum (MALDI-TOF, α-cyano-4-hydroxycinnamic acid matrix) calcd. for $C_{21}H_{28}N_4O_8S_2$: 529.1 (M+H), 551.1 (M+Na). Found: 528.9, 550.8.

EXAMPLE 15

{3-[5-Methyl-3-(2-(acetylpiperazinykulfonyl)phenylsulfonyloxy)phenoxy]propoxy}guanidine hydrochloride a) 1-(Acetylpiperazinylsulfonyl)-2-nitrobenzene The title compound was prepared in 87% yield from acetylpiperazine in a manner analogous to step a of Eg. 14. $^1$H-NMR (300 MHz, $CDCl_3$) δ7.99 (d, J=6.8 Hz, 1H), 7.74 (m, 2H), 7.64 (d, J=6.8 Hz, 1H), 3.70 (t, J=5.1 Hz, 2H), 3.57 (t, J=5.0 Hz, 2H), 3.35 (t, J=5.0 Hz, 2H), 3.27 (t, J=5.21 Hz, 2H), 2.10 (s, 3H).

b) 2-(Acetylpiperazinylsulfonyl)aniline

The title compound was prepared in 80% yield from 1-(acetylpiperazinylsulfonyl)-2-nitrobenzene, as prepared in the preceding step, in a manner analogous to step b of Example 14. This compound was directly used for next step without further purification.

c) 2-(Acetylpiperazinylsulfonyl)phenylsulfonyl chloride

The title compound was prepared in 46% yield from 2-(acetylpiperazinylsulfonyl)aniline, as prepared in the preceding step, in a manner analogous to step a of Example 19. $^1$H-NMR (300 MHz, $CDCl_3$) δ8.42 (d, J=7.2 Hz, 1H), 8.27 (d, J=7.3 Hz, 1H), 7.89 (m, 2H), 3.27–3.68 (m, 8H), 2.10 (s, 3H).

d) 5-Methyl-3-[2-(acetylpepiperazinylsulfonyl)phenylsulfonyloxy]phenol

The title compound was prepared in 44% yield from 2-(acetylpiperazinylsulfonyl)phenylsulfonyl chloride, as prepared in the preceding step, in a manner analogous to step a of Eg.1. $^1$H-NMR (300 MHz, $CDCl_3$) δ8.26 (d, J=7.8 Hz, 1H), 8.17 (d, J=7.8 Hz, 1), 7.81 (t, J=7.7 Hz, 1H), 7.70 (t, J=7.6 Hz, 1H), 7.16 (s, 1H), 6.55 (s, 1H), 6.51 (s, 1H), 6.45 (s, 1H), 3.68 (t, J=4.8 Hz, 2H), 3.55 (m, 2H), 3.46 (m, 2H), 3.29 (t, J=4.9 Hz, 2H), 2.21 (s, 3H), 2.09 (s, 3H).

e) 3-{5-Methyl-3-[2-(acetylpiperazinylsulfonyl)phenylsulfonyloxy]phenoxy}propanol The title compound was prepared in 76% yield from 5-methyl-3-[2-(acetylpepiperazinylsulfonyl)

phenylsulfonyloxy]phenol, as prepared in the preceding step, in a manner analogous to step b of Example 10. $^1$H-NMR (300 MHz, CDCl$_3$) δ8.29 (d, J=7.8 Hz, 1H), 8.19 (d, J=7.8 Hz, 1H), 7.82 (t, J=7.7 Hz, 1H), 7.71 (t, J=7.7 Hz, 1H), 6.61 (s, 1H), 6.56 (s, 1H), 6.53 (s, 1H), 4.00 (t, J=6.0 Hz, 2H), 3.78 (m, 2H), 3.65 (m, 2H), 3.62 (m, 2H), 3.54 (m, 2H), 3.30 (m, 2H), 2.24 (s, 3H), 2.08 (s, 3H), 1.97 (t, J=6.0 Hz, 2H).

f) N-{3-[5-Methyl-3-[2-(acetylpiperazinylsulfonyl) phenylsulfonyloxy]phenoxy]propoxy}phthalimide The title compound was prepared in 89% yield from 3-{5-methyl-3-[2-(acetylpiperazinylsulfonyl) phenylsulfonyloxy]phenoxy}propanol, as prepared in the preceding step, in a manner analogous to step d of Example 1. $^1$H-NMR (300 MHz, CDCl$_3$) δ8.31 (d, J=7.8 Hz, 1H), 8.18 (d, J=7.8 Hz, 1H), 7.44–7.86 (m, 6H), 6.63 (s, 1H), 6.57 (s, 1H), 6.49 (s, 1H), 4.36 (d, J=6.1 Hz, 2H), 4.10 (t, J=6.0 Hz, 2H), 3.67 (m 2H), 3.54 (m, 2H), 3.48 (m, 2H), 3.28 (m, 2H), 2.25 (s, 3H), 2.18 (t, J=6.1 Hz, 2H), 2.08 (s, 3H).

g) 3-[5-Methyl-3-2-(acetylpiperazinylsulfonyl) phenylsulfonyloxy]phenoxy]propoxyamine The title compound was prepared in 73% yield from N-{3-[5-Methyl-3-[2-(acetylpiperazinylsulfonyl) phenylsulfonyloxy]phenoxy]propoxy}phthalimide, as prepared in the preceding step, in a manner analogous to step e of Example 1. $^1$H-NMR (300 MHz, CDCl$_3$) δ8.29 (d, J=7.9 Hz, 1H), 8.18 (d, J=7.8 Hz, 1H), 7.82 (t, J=7.8 Hz, 1H), 7.70 (t, J=7.8 Hz, 1H), 6.60 (s, 1H), 6.54 (s, 1H), 6.52 (s, 1H), 3.92 (t, J=6.3 Hz, 2H), 3.79 (t, J=6.2 Hz, 2H), 3.67 (t, J=5.5 Hz, 2H), 3.55 (t, J=6.0 Hz, 2H), 3.48 (t, J=5.8 Hz, 2H), 3.30 (t, J=5.6 Hz, 2H), 2.24 (s, 3H), 2.08 (s, 3H), 2.00 (t, J=6.2 Hz, 2H).

h) {3-[5-Methyl-3-[2-(acetylpiperazinylsulfonyl) phenylsulfonyloxy]phenoxy]propoxy}guanidine hydrochloride The title compound was prepared in 84% yield from 3-[5-methyl-3-[2-(acetylpiperazinylsulfonyl) phenylsulfonyloxy]phenoxy]propoxyamine, as prepared in the preceding step, in a manner analogous to step f of Example 1. $^1$H-NMR (300 MHz, DMSO-d$_6$)δ11.11 (br s, 1H), 8.19 (t, J=7.9 Hz, 2H), 8.03 (t, J=7.7 Hz, 1H), 7.91 (t, J=7.7 Hz 1H), 7.71 (br s, 4H), 6.75 (s, 1H), 6.53 (s, 1H), 6.49 (s, 1H), 3.99 (t, J=6.2 Hz, 2H), 3.90 (t, J=6.3 Hz, 2H), 3.50 (m, 4H), 3.32 (m, 2H), 3.24 (m, 2H), 2.22 (s, 3H), 2.04 (t, J=6.2 Hz, 2H), 1.99 (s, 3H). Mass spectrum (MALDI-TOF, α-cyano-4-hydroxycinnamic acid matrix) calcd. for C$_{23}$H$_{31}$N$_5$O$_8$S$_2$: 570.2 (M+H), 592.2 (M+Na). Found: 570.2, 592.2.

EXAMPLE 16

{3-[5-Methyl-3-(2-(N-methylphenethylaminosulfonyl)phenylsulfonyloxy) phenoxy]propoxy}guanidine hydrochloride a) 1-(N-Methylphenethylaminosulfonyl)-2-nitrobenzene The title compound was prepared in 94% yield from N-methylphenethylamine in a manner analogous to step a of Example 14. $^1$H-NMR (300 MHz, CDCl$_3$) δ7.93 (d, J=7.7 Hz, 1H), 7.56–7.68 (m, 3H), 7.18–7.31 (m, 5H), 3.47 (t, J=7.8 Hz, 2H), 2.92 (s, 3H), 2.90 (t, J=7.6 Hz, 2H).

b) 2-(N-Methylphenethylaminosulfonyl)aniline

The title compound was prepared in 95% yield from 1-(N-methylphenethylaminosulfonyl)-2-nitrobenzene, as prepared in the preceding step, in a manner analogous to step b of Example 14. This compound was directly used for next step with further purification.

c) 2-(N-Methylphenethylaminosulfonyl)phenylsulfonyl chloride

The title compound was prepared in 40% yield from 2-(N-methylphenethylaminosulfonyl)aniline, as prepared in the preceding step, in a manner analogous to step a of Example 19. $^1$H-NMR (300 MHz, CDCl$_3$) δ7.93 (d, J=7.7 Hz, 1H), 8.10 (d, J=7.6 Hz, 1H), 7.7 (t, J=7.6 Hz, 2H), 7.18–7.31 (m, 5H), 3.50 (t, J=7.8 Hz, 2H), 2.94 (s, 3H), 2.90 (t, J=7.6 Hz, 2H).

d) 5-Methyl-3-[2-(N-methylphenethylaminosulfonyl) phenylsulfonyloxy]phenol

The title compound was prepared in 24% yield from 2-(N-methylphenethylaminosulfonyl)phenylsulfonyl chloride, as prepared in the preceding step, in a manner analogous to step a of Eg. 1. $^1$H-NMR (300 MHz, CDCl$_3$) δ8.18 (d, J=7.8 Hz, 1H), 8.12 (d, J=7.8 Hz, 1H), 7.73 (t, J=7.7 Hz, 1H), 7.63 (t, J=7.7 Hz, 1H), 7.17–7.29 (m, 5H), 6.59 (s, 1H), 6.53 (s, 1H), 6.49 (s, 1H), 3.56 (t, J=7.8 Hz, 2H), 2.96 (s, 3H), 2.92 (t, J=7.7 Hz, 2H), 2.22 (s, 3H).

e) 3-{5-Methyl-3-[2-(N-methylphenethylaminosulfonyl) phenylsulfonyloxy]phenoxy}propanol The title compound was prepared in 73% yield from 5-methyl-3-[2-(N-methylphenethylaminosulfonyl) phenylsulfonyloxy]phenol, as prepared in the preceding step, in a manner analogous to step b of Example 10. $^1$H-NMR (300 MHz, CDCl$_3$) δ8.20 (d, J=7.9 Hz, 1H), 8.13 (d, J=7.8 Hz, 1H), 7.74 (t, J=7.7 Hz, 1H), 7.63 (t, J=7.7 Hz, 1H), 7.17–7.29 (m, 5H), 6.59 (s, 1H), 6.57 (s, 1H), 6.53 (s, 1H), 3.99 (t, J=6.0 Hz, 2H), 3.80 (t, J=5.9 Hz, 2H), 3.55 (t, J=7.8 Hz, 2H), 2.97 (s, 3H), 2.92 (t, J=7.7 Hz, 2H), 2.22 (s, 3H), 1.96 (t, J=6.0 Hz, 2H).

f) N-{3-[5-Methyl-3-[2-N-methylphenethylaminosulfonyl) phenylsulfonyloxy]phenoxy]propoxy}phthalimide The title compound was prepared in 63% yield from 3-{5-methyl-3-[2-(N-methylphenethylaminosulfonyl) phenylsulfonyloxy]phenoxy}propanol, as prepared in the preceding step, in a manner analogous to step d of Example 1. $^1$H-NMR (300 MHz, CDCl$_3$) δ8.22 (d, J=7.8 Hz, 1H), 8.13 (d, J=7.8 Hz, 1H), 7.83 (m, 2H), 7.74 (m, 3H), 7.63 (t, J=7.7 Hz, 1H), 7.17–7.29 (m, 5H), 6.62 (s, 1H), 6.59 (s, 1H), 6.52 (s, 1H), 4.35 (t, J=6.0 Hz, 2H), 4.08 (t, J=6.1 Hz, 2H), 3.57 (t, J=7.8 Hz, 2H), 2.97 (s, 3H), 2.92 (t, J=7.7 Hz, 2H), 2.24 (s, 3H), 2.17 (t, J=6.0 Hz, 2H).

g) 3-[5-Methyl-[3-(2-N-methylphenethylaminosulfonyl) phenylsulfonyloxy]phenoxy]propoxyamine The title compound was prepared in 90% yield from N-{3-[5-methyl-3-[2-(N-methylphenethylaminosulfonyl) phenylsulfonyloxy]phenoxy]propoxy}phthalimide, as as prepared in the preceding step, in a manner analogous to step e of Example 1. $^1$H-NMR (300 MHz, CDCl$_3$) δ8.21 (d, J=7.9 Hz, 1H), 8.13 (d, J=7.9 Hz, 1H), 7.74 (t, J=7.8 Hz, 2H), 7.62 (t, J=7.7 Hz, 1H), 7.17–7.29 (m, 5H), 6.58 (s, 2H), 6.55 (s, 1H), 3.91 (t, J=6.2 Hz, 2H), 3.80 (t, J=6.1 Hz, 2H), 3.57 (t, J=7.8 Hz, 2H), 2.97 (s, 3H), 2.92 (t, J=7.7 Hz, 2H), 2.23 (s, 3H), 1.99 (t, J=6.2 Hz, 2H).

h) {3-[5-Methyl-3-(2-(N-methylphenethylaminosulfonyl) phenylsulfonyloxy)phenoxy]propoxy}guanidine hydrochloride The title compound was prepared in 84% yield from 3-[5-methyl-3-[2-(N-methylphenethylaminosulfonyl) phenylsulfonyloxy]phenoxy]propoxyamine, as prepared in the preceding step, in a manner analogous to step f of Example 1. $^1$H-NMR (300 MHz, DMSO-d$_6$) δ11.01 (br s, 1H), 8.14 (d, J=7.9 Hz, 1H), 8.07 (d, J=7.9 Hz, 1H), 7.97 (t, J=7.8 Hz, 2H), 7.86 (t, J=7.7 Hz, 1H), 7.63 (br s, 4H), 7.17–7.29 (m, 5H), 6.74 (s, 1H), 6.54 (s, 1H), 6.51 (s, 1H), 3.98 (t, J=6.2 Hz, 2H), 3.90 (t, J=6.1 Hz, 2H), 3.53 (t, J=7.8 Hz, 2H), 2.94 (s, 3H), 2.87 (t, J=7.7 Hz, 2H), 2.21 (s, 3H), 2.01 (t, J=6.2 Hz, 2H). Mass spectrum (MALDI-TOF, α-cyano-4-hydroxycinnamic acid matrix) calcd. for $C_{23}H_{31}N_5O_8S_2$: 577.2 (M+H), 599.2 (M+Na). Found: 577.1, 599.0.

EXAMPLE 17

{3-[5-Methoxy-3-(2-methylsulfonylphenylsulfonyloxy)phenoxy]propoxy}guanidine hydrochloride a) 5-Methoxy-3-[2-(methylsulfonyl)phenylsulfonyloxy]phenol The title compound was prepared in 80% yield from 2-methylsulfonylbenzenesulfonyl chloride and 5-methoxyresorcinol in a manner analogous to step a of Example 1. $^1$H-NMR (300 MHz, CDCl$_3$) δ8.42 (d, J=7.8 Hz, 1H), 8.13 (d, J=7.8 Hz, 1H), 7.88 (t, J=7.8 Hz, 1H), 7.75 (t, J=7.7 Hz, 1H), 6.36 (s, 1H), 6.31 (s, 1H), 6.28 (s, 1H), 3.68 (s, 3H), 3.45 (s, 3H).

b) 3-{5-Methoxy-3-[2-(methylsulfonyl)phenylsulfonyloxy]phenoxy}propanol

The title compound was prepared in 72% yield from 5-methoxy-3-[2-(methylsulfonyl)phenylsulfonyloxy]phenol, as prepared in the preceding step, in a manner analogous to step a of Example 10. $^1$H-NMR (300 MHz, CDCl$_3$) δ8.44 (d, J=7.8 Hz, 1H), 8.14 (d, J=7.8 Hz, 1H), 7.88 (t, J=7.7 Hz, 1H), 7.75 (t, J=7.7 Hz, 1H), 6.40 (s, 1H), 6.38 (s, 1H), 6.33 (s, 1H), 4.13 (t, J=6.3 Hz, 2H), 3.99 (t, J=6.0 Hz, 2H), 3.69 (s, 3H), 3.45 (s, 3H), 1.97 (t, J=6.0 Hz, 2H), 1.67 (br s, 1H).

c) N-{3-[5-Methoxy-3-[2-(methylsulfonyl)phenylsulfonyloxy]phenoxy]propoxy}phthalimide The title compound was prepared in 88% yield from 3-{5-methoxy-3-[2-(methylsulfonyl)phenylsulfonyloxy]phenoxy}propanol, as prepared in the preceding step, in a manner analogous to step d of Example 1. $^1$H-NMR (300 MHz, CDCl$_3$) δ8.45 (d, J=7.8 Hz, 1H), 8.14 (d, J=7.8 Hz, 1H), 7.74–7.89 (m, 6H), 6.37 (s, 3H), 4.46 (t, J=6.2 Hz, 2H), 4.10 (t, J=6.1 Hz, 2H), 3.69 (s, 3H), 3.45 (s, 3H), 2.18 (t, J=6.1 Hz, 2H).

d) 3-[5-Methoxy-3-[2-(methylsulfonyl)phenylsulfonyloxy]phenoxy]propoxyamine

The title compound was prepared in 79% yield from N-{3-[5-methoxy-3-[2-(methylsulfonyl)phenylsulfonyloxy]phenoxy]propoxy}phthalimide, as prepared in the preceding step, in a manner analogous to step e of Example 1. $^1$H-NMR (300 MHz, CDCl$_3$) δ8.45 (d, J=7.8 Hz, 1H), 8.13 (d, J=7.8 Hz, 1H), 7.88 (t, J=7.7 Hz, 1H), 7.75 (t, J=7.7 Hz, 1H), 6.38 (s, 1H), 6.36 (s, 1H), 6.32 (s, 1H), 5.40 (br s, 2H), 3.92 (t, J=6.3 Hz, 2H), 3.78 (t, J=6.1 Hz, 2H), 3.69 (s, 3H), 3.45 (s, 3H), 1.99 (t, J=6.2 Hz, 2H).

e) {3-[5-Methoxy-3-(2-methylsulfonylphenylsulfonyloxy)phenoxy]propoxy}guanidine hydrochloride The title compound was prepared in 71% yield from 3-[5-methoxy-3-[2-(methylsulfonyl)phenylsulfonyloxy]phenoxy]propoxyamine, as prepared in the preceding step, in a manner analogous to step f of Example 1. $^1$H-NMR (300 MHz, DMSO-d$_6$) δ11.14 (br s, 1H), 8.37 (d, J=7.8 Hz, 1H), 8.13 (m, 2H), 7.97 (t, J=7.7 Hz, 1H), 7.71 (br,s 4H), 6.48 (s, 1H), 6.31 (s, 1H), 6.26 (s, 1H), 3.99 (t, J=6.2 Hz, 2H), 3.90 (t, J=6.3 Hz, 2H), 3.66 (s, 3H), 3.47 (s, 3H), 2.01 (t, J=6.2 Hz, 2H). Mass spectrum (MALDI-TOF, α-cyano-4-hydroxycinnamic acid matrix) calcd. for $C_{18}H_{23}N_3O_8S_2$: 474.1 (M+H), 496.1 (M+Na). Found: 474.0, 496.0.

EXAMPLE 18

{3-[5-Ethyl-3-(2-methylsulfonylphenylsulfonyloxy)phenoxy]propoxy}guanidine hydrochloride a) 5-Ethyl-3-[2-(methylsulfonyl)phenylsulfonyloxy]phenol The title compound was prepared in 89% yield from 2-methylsulfonylbenzenesulfonyl chloride and 5-ethylresorcinol in a manner analogous to step a of Eg. 1. $^1$H-NMR (300 MHz, CDCl$_3$) δ8.43 (d, J=7.8 Hz, 1H), 8.09 (d, J=7.8 Hz, 1H), 7.87 (t, J=7.8 Hz, 1H), 7.73 (t, J=7.7 Hz, 1H), 6.56 (s, 2H), 6.52 (s, 1H), 5.59 (br s, 1H), 3.45 (s, 3H), 2.49 (q, J=7.6 Hz, 2H), 1.09 (t, J=7.6 Hz, 3H).

b) 3-{5-Ethyl-3-[2-(methylsulfonyl)phenylsulfonyloxy]phenoxy}propanol

The title compound was prepared in 82% yield from 5-ethyl-3-[2-(methylsulfonyl)phenylsulfonyloxy]phenol, as prepared in the preceding step, in a manner analogous to step b of Example 10. $^1$H-NMR (300 MHz, CDCl$_3$) δ8.45 (d, J=7.8 Hz, 1H), 8.10 (d, J=7.8 Hz, 1H), 7.88 (t, J=7.7 Hz, 1H), 7.73 (t, J=7.8 Hz, 1H), 6.62 (s, 1H), 6.61 (s, 1H), 6.57 (s, 1H), 4.01 (t, J=6.0 Hz, 2H), 3.82 (t, J=6.0 Hz, 2H), 3.45 (s, 3H), 2.51 (q, J=7.6 Hz, 2H), 1.09 (t, J=7.6 Hz, 3H).

c) N-{3-[5-Ethyl-3-[2-(methylsulfonyl)phenylsulfonyloxy]phenoxy]propoxy}phthalimide The title compound was prepared in 97% yield from 3-{5-ethyl-3-[(2-methyl-sulfonyl)phenylsulfonyloxy]phenoxy}propanol, as prepared in the preceding step, in a manner analogous to step d of Eg. 1. $^1$H-NMR (300 MHz, CDCl$_3$) δ8.45 (d, J=7.8 Hz, 1H), 8.10 (d, J=7.8 Hz, 1H), 7.74–7.90 (m, 6H), 6.65 (s, 1H), 6.57 (s, 2H), 4.37 (t, J=6.2 Hz, 2H), 4.12 (t, J=6.1 Hz, 2H), 3.46 (s, 3H), 2.51 (q, J=7.6 Hz, 2H), 1.10 (t, J=7.6 Hz, 3H).

g) 3-[5-Ethyl-3-[2-(methylsulfonyl)phenylsulfonyloxy]phenoxy]propoxyamine

The title compound was prepared in 78% yield from N-{3-[5-ethyl-3-[2-(methylsulfonyl)phenylsulfonyloxy]phenoxy]propoxy}phthalimide, as prepared in the preceding step, in a manner analogous to step e of Example 1. $^1$H-NMR (300 MHz, CDCl$_3$) δ8.45 (d, J=7.8 Hz, 1H), 8.09 (d, J=7.8 Hz, 1H), 7.87 (t, J=7.7 Hz, 1H), 7.73 (t, J=7.7 Hz, 1H), 6.61 (s, 1H), 6.59 (s, 1H), 6.56 (s, 1H), 3.93 (t, J=6.2 Hz, 2H), 3.81 (t, J=6.1 Hz, 2H), 3.45 (s, 3H), 2.50 (q, J=7.6 Hz, 2H), 1.09 (t, J=7.6 Hz, 3H).

h) {3-[5-Ethyl-3-(2-methylsulfonylphenylsulfonyloxy)phenoxy]propoxy}guanidine hydrochloride The title compound was prepared in 82% yield from 3-[5-ethyl-3-[2-(methylsulfonyl)phenylsulfonyloxy]phenoxy]propoxyamine, as prepared in the preceding step, in a manner analogous to step f of Example 1. $^1$H-NMR (300 MHz, DMS0-d$_6$) δ11.17 (br s, 1H), 8.37 (d, J=7.8 Hz, 1H), 8.08 (m, 2H), 7.95 (t, J=7.6 Hz, 1H), 7.73 (br s, 4H), 6.77 (s, 1H), 6.54 (s, 1H), 6.48 (s, 1H), 4.00 (t, J=6.2 Hz, 2H), 3.91 (t, J=6.3 Hz, 2H), 3.47 (s, 3H), 2.50 (q, J=7.6 Hz, 2H), 1.02 (t, J=7.6 Hz, 3H). Mass spectrum (MALDI-TOF, α-cyano-4-hydroxycinnamic acid matrix) calcd. for $C_{19}H_{25}N_3O_7S_2$: 472.1 (M+H), 494.1 (M+Na), 510.1 (M+K). Found: 472.0, 493.9, 509.9.

EXAMPLE 19

{3-[5-Methyl-3-(2-(phenylsulfonyl)phenylsulfonyloxy)phenoxy]propoxy}guanidine hydrochloride a) 2-(Phenylsulfonyl)benzenesulfonyl chloride To a solution of 2-(phenylsulfonyl)aniline (2.33 g, (10 mmol) in 30% aqueous hydrochloric acid (4 mL) was added 40% aqueous sodium nitrite (4 mL) at 0–5° C. After 15 minute, to the diazo solution were added 30% aqueous hydrochloric acid (10 mL), cooper sulfate (50 mg) and 40% aqueous sodium bisulfite (10 mL) at 5–10° C. The mixture was stirred for 30 minutes and additional water (30 mL) was added. The mixture was extracted into dichloromethane (3× 40 mL) and the dichloromethane solution was washed with brine (40 mL) and dried over $Na_2SO_4$. After removing the solvent in vacuo, the residue was purified by flash column chromatography (dichloromethane) to give the title compound as a white solid (2.1 g, 66%). $^1$H-NMR (300 MHz, $CDCl_3$) δ8.62 (d, J=7.8 Hz, 1H), 8.34 (d, J=7.9 Hz, 1H), 7.85–7.98 (m, 4H), 7.48–7.63 (m, 3H).

b) N,N'-(Bis-tert-butyloxycarbonyl)-{3-[5-methyl-3-(2-(phenylsulfonyl)phenylsulfonyloxy)phenoxy]propoxy}guanidine To a solution of (N,N'-bis-tert-butyloxycarbonyl)-{3-[(3-hydroxy-5-methyl)phenoxy)propoxy}guanidine (88 mg, 0.2 mmol), as prepared in step f of Example 20, and triethylamine (0.2 mL) in dichloromethane (10 mL) was added 2-(phenylsulfonyl)benzenesulfonyl chloride (64 mg, 0.2 mmol), as prepared in the preceding step. The mixture was stirred at ambient temperature for 2 h. Additional dichloromethane (50 mL) was added. The dichloromethane solution was washed with 10% citric acid (2×30 mL) and brine (30 mL) and dried over $Na_2SO_4$. After removing the solvent, the residue was purified on a Waters Sep-Pak (10 g silica, dichloromethane) to give the title compound as a colorless foam (109 mg, 75%). $^1$H-NMR (300 MHz, $CDCl_3$) δ9.08 (s, 1H), 8.64 (d, J=7.9 Hz, 1H), 8.07 (d, J=7.8 Hz, 1H), 7.97 (d, J=7.9 Hz, 2H), 7.89 (t, J=7.8 Hz, 1H), 7.71 (t, J=7.8 Hz, 2H), 7.56 (d, J=7.2 Hz, 1H), 7.49 (t, J=7.1 Hz, 2H), 6.59 (s, 1H), 6.57 (s, 1H), 6.53 (s, 1H), 3.19 (t, J=6.2 Hz, 2H), 3.94 (t, J=6.2 Hz, 2H), 2.91 (s, 3H), 2.23 (s, 3H), 2.11 (t, J=6.2 Hz, 2H), 1.49 (s, 18H).

c) {3-[5-Methyl-3-(2-(phenylsulfonyl)phenylsulfonyloxy)phenoxy]propoxy}guanidine hydrochloride To a solution of N,N'-(bis-tert-butyloxycarbonyl)-{3-[5-methyl-3-(2-phenylsulfonylphenylsulfonyloxy)phenoxy]propoxy}guanidine (108 mg, 0.15 mmol), as prepared in the preceding step, in dichloromethane (5 mL) was added trifluoroacetic acid (2 mL). The mixture was stirred at ambient temperature for 3 h and then the solvent was evaporated in vacuo. The residue was dissolved in dichloromethane (50 mL), washed with 2 N $K_2CO_3$ (2×30 mL) and dried over $Na_2SO_4$. After the solvent was evaporated, the residue was converted to the HCl salt with methanolic HCl and purified on a Waters Sep-Pak (5 g silica, 10% methanol in dichloromethane) to give the title compound as a colorless foam (78 mg, 93%). $^1$H-NMR (300 MHz, DMSO-$d_6$) δ11.05 (br s, 1H), 8.62 (d, J=7.9 Hz, 1H), 8.13 (m, 2H), 7.98 (d, J=8.1 Hz, 1H), 7.93 (m, 2H), 7.69 (d, J=7.6 Hz, 1H), 7.60 (t, J=7.8 Hz, 2H), 7.20 (br s, 4H), 6.74 (s, 1H), 6.47 (s, 1H), 6.45 (s, 1H), 3.98 (t, J=6.3 Hz, 2H), 3.88 (t, J=6.3 Hz, 2H), 2.91 (s, 3H), 2.21 (s, 3H), 2.00 (t, J=6.3 Hz, 2H). Mass spectrum (MALDI-TOF, α-cyano-4-hydroxycinnamic acid matrix) calcd. for $C_{23}H_{25}N_3O_7S_2$: 520.1 (M+H), 542.1 (M+Na). Found: 520.3, 542.2.

EXAMPLE 20

{3-[5-Methyl-3-(2-(4-ethyloxycarbonyl)piperidinylsulfonylphenylsulfonyloxy)phenoxy]propoxy}guanidine hydrochloride a) 3-Benzyloxy-5-methylphenol Orcinol monohydrate (7.10 g, 50 mmol) in N,N-dimethylformamide (20 mL) was added dropwise to a mixture of NaH (95%, 24 g, 100 mmol) in N,N-dimethylformamide (60 mL) and the mixture was stirred at room temperature for 20 min. Benzyl bromide (8.55 g, 50 mmol) in N,N-dimethylformamide (20 mL) was added dropwise to the mixture and stirred at room temperature for 2 hours. Water (100 mL) was added slowly to the reaction mixture. The reaction mixture was extracted with ethyl acetate (3×100 mL) and then the organic phase was washed with brine (2×50 mL) and dried over $Na_2SO_4$. After the solvent was evaporated, the residue was purified by flash column chromatography (silica gel, 3:1 hexane:ethyl acetate) to give the title compound as a yellow oil (5.20 g, 48%). $^1$H-NMR (300 MHz, $CDCl_3$) δ7.39 (m, 5H), 6.40 (s, 1H), 6.29 (t, J=5.3 Hz, 1H), ), 6.26 (s, 1H), 5.25 (s, 1H), 4.99 (s, 2H), 2.26 (s, 3H).

b) 3-[(3-Benzyloxy-5-methyl)phenoxy]propanol

3-Benzyloxy-5-methylphenol (5.20 g, 24 mmol), as prepared in the preceding step, was stirred with 3-bromopropanol (3.6 g, 26 mmol) and $Cs_2CO_3$ (8.2 g, 25 mmol) in acetonitrile (80 mL) at 50° C. overnight. After cooling to room temperature, the solid was removed by filtration. The filtrate was concentrated in vacuo and the residue was purified by flash column chromatography (1:2 to 1:1 ethyl acetate:hexane) to give the title compound as a yellow oil (4.3 g, 66%). $^1$H-NMR (300 MHz, $CDCl_3$) δ7.38 (m, 5H), 6.41 (s, 1H), 6.36 (s, 2H), 5.01 (s, 2H), 4.07 (t, J=6.3 Hz, 2H), 3.83 (t, J=6.0 Hz, 2H), 2.29 (s, 3H), 2.05 (m, 2H).

c) N-{3-[(3-Benzyloxy-5-methyl)phenoxy]propoxy}phthalimide

To a solution of 3-[(3-benzyloxy-5-methyl)phenoxy]propanol (4.2 g, 15.0 mmol), as prepared in the preceding step, triphenylphosphine (4.5 g, 17.0 mmol) and N-hydroxyphthalimide (2.8 g, 17.0 mmol) in tetrahydrofuran (100 mL) was added diethyl azodicarboxylate (3.0 g, 17.0 mmol) at 0° C. The reaction mixture was stirred at ambient temperature overnight. The reaction mixture was concentrated in vacuo and ethyl acetate (100 mL) was added to the residue. The solid was removed by filtration and the filtrate was concentrated in vacuo. The residue was purified by flash column chromatography (dichloromethane) to give the title compound as a pale yellow oil (5.0 g, 89%). $^1$H-NMR (300 MHz, $CDCl_3$) δ7.82 (d, J=8.2 Hz, 2H), 7.74 (d, J=8.3 Hz, 2H), 7.38 (m, 5H), 6.41 (s, 1H), 6.39 (s, 1H), 6.38 (s, 1H), 5.02 (s, 2H), 4.40 (t, J=6.3 Hz, 2H), 4.19 (t, J=6.1 Hz, 2H), 2.29 (s, 3H), 2.23 (t, J=6.2 Hz, 2H).

d) {3-[(3-Benzyloxy-5-methyl)phenoxy]propoxy}amine

N-{3-[(3-Benzyloxy-5-methyl)phenoxy]propoxy}phthalimide (2.25 g, 6.0 mmol), as prepared in the preceding step, was stirred with 40% aqueous methylamine (4.8 mL, 60 mmol) in ethanol (60 mL) and tetrahydrofuran (20 mL) for 1 h. The reaction mixture was concentrated in vacuo to give a white solid. Flash column chromatography (20% ethyl acetate in dichloromethane) gave the title product as a colorless oil (1.40 g, 82%). $^1$H-NMR (300 MHz, $CDCl_3$) δ7.40 (m, 5H), 6.41 (s, 1H), 6.36 (s, 2H), 5.35 (br s, 2H), 5.00 (s, 2H), 4.00 (t, J=6.3 Hz, 2H), 3.83 (t, J=6.2 Hz, 2H), 2.29 (s, 3H), 2.04 (t, J=6.3 Hz, 2H).

e) (N,N'-Bis-tert-butyloxycarbonyl)-{3-[(benzyloxy-5-methyl)phenoxy]propoxy}guanidine To a solution of 3-[(3-benzyloxy-5-methyl)phenoxy]propoxyamine (1.75 g, 6.0 mmol), as prepared in the preceding step, in N,N-dimethylformamide (20 mL) was added (N,N'-bis-tert-butyloxycarbonyl)-1H-pyrazole-carboxamidine (2.2 g, 7.0 mmol). The mixture was stirred at ambient temperature overnight. The solvent was evaporated under high vacuum and the residue (3.8 g) was directly used in the next step without purification.

f) (N,N'-Bis-tert-butyloxycarbonyl)-{3-[(3-hydroxy-5-methyl)phenoxy)propoxy}guanidine A mixture of (N,N'-bis-tert-butyloxycarbonyl)-{3-[(benzyloxy-5-methyl)phenoxy]propoxy}guanidine (3.8 g), as prepared in the preceding step, and 10% palladium on carbon (400 mg) in ethanol (30 mL) and THF (30 mL) was stirred under hydrogen (balloon) overnight. The catalyst was removed by filtration through Celite and the filtrate was concentrated in vacuo. The residue was purified by flash column chromatography (3:1 ether:hexane) to give the title compound as a white foam (2.45 g, 93%). $^1$H-NMR (300 MHz, CDCl$_3$) δ9.09 (s, 1H), 7.74 (br s, 1H), 6.33 (s, 1H), 6.29 (s, 1H), 6.27 (s, 1H), 4.20 (t, J=5.9 Hz, 2H), 4.03 (t, J=6.1 Hz, 2H), 2.25 (s, 3H), 2.15 (pentet, J=5.9 Hz, 2H), 1.49 (s, 18H).

g) 1,2-Benzenedisulfonic anhydride

A mixture of 1,2-benzenedisulfonic acid dipotassium salt (20 g, 0.064 mol) in fuming sulfuric acid (100 mL) was heated at 70–75° C. overnight. The reaction mixture was slowly poured onto ice and the precipitate was quickly collected by filtration. The solid was treated with benzene (500 mL) and dried over anhydrous sodium sulfate. The solvent was filtered and evaporated to give the title compound as a crystalline solid (7.0 g, 50% yield), mp 182–3° C. $^1$H-NMR (300 MHz, CDCl$_3$) δ8.02–8.09 (m, 4H).

h) N,N'-(Bis-tert-butyloxycarbonyl)-{3-[5-methyl-3-(2-(4-ethyloxycarbonyl)piperidinylsulfonylphenylsulfonyloxy)phenoxy]propoxy}guanidine To a solution of 1,2-benzenedisulfonic anhydride (440 mg, 2.0 mmol), as prepared in preceding step, and N,N-diisopropylethylamine (360 μL, 2.0 mmol) in dichloromethane (20 mL) was added ethyl isonipecotate (315 mg, 2.0 mmol). After stirring the mixture for 4 h at ambient temperature, oxalyl chloride (160 μL, 2.0 mmol) and 5 drops of N,N-dimethylformamide were added. The mixture was stirred for another 4 h. (N,N'-Bis-tert-butyloxycarbonyl)-{3-[(3-hydroxy-5-methyl)phenoxy)propoxy}guanidine (700 mg, 1.6 mmol), as prepared in step f, and N,N-diisopropylethylamine (360 (L, 2.0 mmol) were added to the mixture. The mixture was stirred at ambient temperature overnight and then additional dichloromethane (100 mL) was added. The solution was washed with 10% citric acid (3×50 mL) and brine (50 mL), and dried over Na$_2$SO$_4$. After the solvent was evaporated in vacuo, the residue was purified by flash column chromatography (dichloromethane to 10% ethyl acetate in dichloromethane) to give the title compound as a colorless foam (1.04 g, 81%). $^1$H-NMR (300 MHz, CDCl$_3$) δ9.08 (s, 1H), 8.28 (d, J=7.9 Hz, 1H), 8.15 (d, J=7.8 Hz, 1H), 7.78 (t, J=7.7 Hz, 1H), 7.68 (t, J=7.8 Hz, 1H), 7.66 (t, J=7.7 Hz, 1H), 6.58 (s, 1H), 6.56 (s, 1H), 6.50 (s, 1H), 4.18 (t, J=6.2 Hz, 2H), 4.12 (q, J=7.1 Hz, 2H), 3.94 (t, J=6.2 Hz, 2H), 3.84 (m, 2H), 2.97 (t, J=10.3 Hz, 2H), 2.41 (m, 1H), 2.23 (s, 3H), 2.10 (t, J=6.2 Hz, 2H), 1.95 (m, 2H), 1.79 (m, 2H), 1.49 (s, 18H), 1.23 (t, J=7.1 Hz, 3H).

i) {3-[5-Methyl-3-(2-(4-ethyloxycarbonyl)piperidinylsulfonylphenylsulfonyloxy)phenoxy]propoxy}guanidine hydrochloride To a solution of N,N'-(bis-tert-butyloxycarbonyl)-{3-[5-methyl-3-(2-(4-ethyloxycarbonyl)piperidinyl sulfonylphenylsulfonyloxy)phenoxy]propoxy}guanidine (270 mg, 0.34 mmol), as prepared in the preceding step, in dichloromethane (10 mL) was added trifluoroacetic acid (4.0 mL). The mixture was stirred at ambient temperature for 3 h and the solvent was evaporated in vacuo. The residue was dissolved in dichloromethane (50 mL), washed with 2 N K$_2$CO$_3$ (2×30 mL) and dried over Na$_2$SO$_4$. After the solvent was evaporated, the residue was purified by flash column chromatography (10% methanol in dichloromethane) and converted to the HCl salt (1 eq. methanolic HCl and concentration) to give the title compound as a colorless foam (175 mg, 85%). $^1$H-NMR (300 MHz, DMSO-d$_6$) δ 8.20 (d, J=7.9 Hz, 1H), 8.15 (d, J=7.9 Hz, 1H), 8.01 (t, J=7.7 Hz, 1H), 7.88 (t, J=7.7 Hz, 1H), 6.73 (s, 1H), 6.51 (s, 1H), 6.41 (s, 1H), 6.25 (br s, 4H), 4.05 (q, J=7.1 Hz, 2H), 3.93 (t, J=6.4 Hz, 2H), 3.76 (m, 2H), 3.71 (t, J=6.1 Hz, 2H), 2.93 (t, J=10.2 Hz, 2H), 2.50 (m, 1H), 2.21 (s, 3H), 1.88 (m, 4H), 1.55 (m, 2H), 1.16 (t, J=7.1 Hz, 3H). Mass spectrum (MALDI-TOF, α-cyano-4-hydroxycinnamic acid matrix) calcd. for C$_{25}$H$_{34}$N$_4$O$_9$S$_2$: 599.2 (M+H), 621.2 (M+Na). Found: 599.2, 621.3.

EXAMPLE 21

2-[5-Methyl-3-(2-(methylsulfonyl)phenylsulfonyloxy)phenoxy]ethoxyguanidine a) 2-[5-Methyl-3-(2-(methylsulfonyl)phenylsulfonyloxy)phenoxy]ethoxytoluene A solution of 5-methyl-3-[2-(methylsulfonyl)phenylsulfonyloxy]phenol (505 mg, 1.47 mmol), as prepared in step a of Example 8, 2-benzyloxyethanol (209 μL, 1.47 mmol), 1,1'-(azodicarbonyl)dipiperidine (444 mg, 1.76 mmol) and anhydrous tetrahydrofuran (10 mL), was cooled to 0° C. under nitrogen. Neat tri-N-butylphosphine (0.44 mL, 1.77 mmol) was added over 3.5 minutes. The solution was stirred at 0° C. for 1 hour and then at ambient temperature overnight. Diethyl ether was added and the mixture was filtered. The solid was discarded and the filtrate was concentrated in vacuo. The product was purified by flash column chromatography through 40 g of silica gel using 0% to 0.5% diethyl ether in dichloromethane to give the title compound (495 mg, 71%) as a colorless solid. $^1$H-NMR (300 MHz, CDCl$_3$) δ8.44 (dd, 1H, J=7.9, 1.3 Hz), 8.10 (dd, 1H, J=7.9, 1.3 Hz), 7.85 (td, 1H, J=7.7, 1.4 Hz), 7.71 (td, 1H, J=7.7, 1.4 Hz), 7.28–7.37 (m, 5H), 6.58–6.63 (m, 3H), 4.60 (s, 2H), 4.02 (m, 1H), 3.76 (m, 1H), 3.45 (s, 3H), 2.23 (s, 3H). Mass spectrum (MALDI-TOF, α-cyano-4-hydroxycinnamic acid matrix) calcd. for C$_{23}$H$_{24}$O$_7$S$_2$: 499.1 (M+Na), Found: 498.7.

b) 2-[5-Methyl-3-(2-(methylsulfonyl)phenylsulfonyloxy)phenoxy]ethanol

A mixture of 2-[5-methyl-3-(2-(methylsulfonyl)phenylsulfonyloxy)phenoxy]ethoxytoluene (480 mg, 1.01 mmol), as prepared in the preceding step, 10% palladium on activated carbon (48.2 mg, ethanol (2 mL) and tetrahydrofuran (9 mL) was stirred at ambient temperature under hydrogen (balloon) for 45 minutes. The mixture was filtered through Celite and the filtrate was concentrated to give the title compound (404 mg, quantitative) as a colorless gum. $^1$H-NMR (300 MHz, CDCl$_3$) δ8.45 (dd, 1H, J=7.8, 1.4 Hz), 8.13 (dd, 1H, J=7.8, 1.4 Hz), 7.88 (td, 1H, J=7.7, 1.4 Hz), 7.75 (td, 1H, J=7.7, 1.4 Hz), 6.60–6.66 (m, 3H), 3.77–3.98 (m, 4H), 2.25 (s, 3H), 1.95 (t, 1H, J=6 Hz). Mass spectrum (MALDI-TOF, α-cyano-4-hydroxycinnamic acid matrix) calcd. for C$_{16}$H$_{18}$O$_7$S$_2$: 409.0 (M+Na). Found: 408.7.

c) 2-[5-Methyl-3-(2-(methylsulfonyl)phenylsulfonyloxy)phenoxy]ethoxyguanidine

The title compound was prepared from 2-[5-methyl-3-(2-(methylsulfonyl)phenylsulfonyloxy)phenoxy]ethanol (as prepared in the preceding step) in a manner analogous to steps c, d, and e of Example 10. Mass spectrum (MALDI-TOF α-cyano-4-hydroxycinnamic acid matrix) calcd. for C$_{17}$H$_{21}$N$_3$O$_7$S$_2$: 444.1 (M+H), 4.66 (M'Na). Found: 444.5, 466.3.

EXAMPLE 22

2-Hydroxy-3-[5-methyl-3-(2-methylsulfonyl)phenylsulfonyloxyphenoxy]propoxyguanidine a) 2-Benzyloxy-3 [5-methyl-3-(2-methylsulfonyl)phenylsulfonyloxyphenoxy]propanol A solution of 5-methyl-3-[2-(methylsulfonyl)phenylsulfonyloxy]phenol (2.00 g, 5.85 mmol), as prepared in step a of Example 8, 2-benzyloxy-1,3-propanediol (2.0 g, 11.0 mmol), and tri-N-butylphosphine (2.38 g, 9.44 mmol) in tetrahydrofuran (100 mL) at 0° C. was treated with dropwise addition of 1,1'-(azodicarbonyl)dipiperidine (2.38 g, 9.44 mmol) in tetrahydrofuran (20 mL). The reaction mixture was stirred to ambient temperature overnight. The reaction mixture was diluted with diethyl ether and filtered. The filtrate was concentrated and purified by flash chromatography using elutions of 5–10% diethyl ether/methylene chloride to give 1.11 g (38%) of the title compound as colorless oil. $^1$H-NMR (300 MHz, CDCl$_3$) δ8.45 (dd, 1H, J=7, 1 Hz), 8.12 (d, 1H, J=7, 1 Hz), 7.85 (td, 1H, J=7, 1 Hz), 7.72 (td, 1H, J=7, 1 Hz), 7.28–7.39 (m, 5H), 6.60–6.63 (m, 3H), 4.74 (d, 1H, J=12 Hz), 4.64 (d, 1H, J=12 Hz), 3.99 (m, 2H), 3.67–3.86 (m, 3H), 3.45 (s, 3H), 2.24 (s, 3H). Mass spectrum (MALDI-TOF, α-cyano-4-hydroxycinnamic acid matrix) calcd. for C$_{24}$H$_{26}$O$_8$S$_2$: 5.29 (M+Na). Found: 529.1 b) 2-Hydroxy-3-[5-methyl-3-(2-methylsulfonyl) phenylsulfonyloxyphenoxy]propanol

A mixture of 2-benzyloxy-3-[5-methyl-3-(2-methylsulfonyl)phenylsulfonyloxyphenoxy]propanol (627 mg, 1.24 mmol), as prepared in the preceding step, 10% palladium on activate carbon (97.9 mg) and deoxygenated ethanol (20 mL) was stirred at ambient temperature under hydrogen (balloon) for two hours. The mixture was filtered through Celite 545 and the filtrate was evaporated. The product was purified by flash column chromatography through 50 g of silica gel using 10% hexane in ethyl acetate to give the title compound (342 mg, 66%) as a colorless resin. $^1$H-NMR (300 MHz, CDCl$_3$) δ8.45 (dd, 1H, J=7.8, 1.4 Hz), 8.13 (dd, 1H, J=7.8, 1.4 Hz), 7.88 (td, 1H, J=7.7, 1.4 Hz), 7.75 (td, 1H, J=7.7, 1.4 Hz), 7.26 (br s, 2H), 6.65 (br s, 1H), 4.03 (complex m, 1H), 3.89–3.97 (m, 2H), 3.80 (dd, 1H, J=11.4, 3.9 Hz), 3.70 (dd, 1H, J=11.4, 5.5 Hz), 3.45 (s, 3H), 2.25 (s, 3H). Mass spectrum (MALDI-TOF, α-cyano-4-hydroxycinnamic acid matrix) calcd. for C$_{17}$H$_{20}$O$_8$S: 439.0 (M+Na) Found 438.8.

c) N-[2-Hydroxy-3-[5-methyl-3-(2-methylsulfonyl) phenylsulfonyloxyphenoxy]propoxy]phthalimide A solution of 2-hydroxy-3-[5-methyl-3-(2-methylsulfonyl)phenylsulfonyloxyphenoxy]propanol (461 mg, 1.11 mmol), as prepared in the preceding step), N-hydroxyphthalimide (186 mg, 1.14 mmol), 1,1'-(azodicarbonyl)dipiperidine (425 mg, 1.68 mmol) and anhydrous tetrahydrofuran (14.7 mL) was cooled to 0° C., and neat tri-N-butylphosphine (419 μL, 1.68 mmol) was added dropwise over 3 minutes. The reaction was stirred at 0° C. for 5 minutes and then at ambient temperature for 3 days. The product was purified by flash column chromatography through 75 g of silica gel using 60:40 ethyl acetate/hexane to give the title compound (209 mg, 33%) as a white foam. Mass spectrum (MALDI-TOF, α-cyano-4-hydroxycinnamic acid matrix) calcd. for C$_{25}$H$_{23}$NO$_{10}$S: 584.1 (M+Na), 600.0 (M+K). Found: 583.9, 599.8.

d) 2-Hydroxy-3-[5-methyl-3-(2-methylsulfonyl) phenylsulfonyloxyphenoxy]propoxyguanidine The title compound was prepared from N-[2-hydroxy-3-[5-methyl-3-(2-methylsulfonyl)phenylsulfonyloxyphenoxy] propoxy]phthalimide (as prepared in the preceding step) in a manner analogous to steps d and e of Example 68. Mass spectrum (MALDI-TOF, α-cyano-4-hydroxycinnamic acid matrix) calcd. for C$_{18}$H$_{23}$N$_3$O$_8$S$_2$: 474.1 (M+H), 496.1 (M+Na). Found: 473.9, 496.1.

EXAMPLE 23

3-[3-(2,4-Bis(methylsulfonyl)phenylsulfonyloxy)-5-methylphenoxy]propoxyguanidine hydrochloride a) 2,4-Bis(methylsulfonyl)benzenesulfonyl chloride The title compound was prepared in 24% yield from 2,4-bis(methylsulfonyl)aniline in a manner analogous to step a of Example 26. $^1$H-NMR (300 MHz, CDCl$_3$) δ8.91 (d, 1H, J=1.9 Hz), 8.60 (d, 1H, J=8.2 Hz), 8.47 (dd, 1H, J=8.2, 1.9 Hz), 3.46 (s, 3H), 3.21 (s, 3H).

b) 3-[3-(2,4-Bis(methylsulfonyl)phenylsulfonyloxy)-5-methylphenoxy]propoxyguanidine hydrochloride The title compound was prepared from 2,4-bis (methylsulfonyl)benzenesulfonyl chloride (as prepared in the preceding step) in a manner analogous to step b of Example 26 and then step g of Example 29. Mass spectrum (MALDI-TOF, α-cyano-4-hydroxycinnamic acid matrix) calcd. for C$_{19}$H$_{25}$N$_3$O$_9$S$_3$: 536.1 (M+H), 558.1 (M+Na). Found: 536.2, 558.2.

EXAMPLE 24

3-[5-Methyl-3-(3-methylsulfonyl) phenylsulfonyloxyphenoxy]propoxyguanidine hydrochloride a) 3-Methylsulfonylbenzenesulfonyl chloride The title compound was prepared in 64% yield from 3-methylsulfonylylaniline hydrochloride in a manner analogous to step a of Example 26. $^1$H-NMR (300 MHz, CDCl$_3$) δ8.62 (t, 1H, J=2 Hz), 8.35 (m, 1H), 8.32 (m, 1H), 7.90 (t, 1H, J=8 Hz), 3.16 (s, 3H).

b) 3-[5-Methyl-3-(3-methylsulfonyl) phenylsulfonyloxyphenoxy]propoxyguanidine hydrochloride The title compound was prepared from 3-methylsulfonylbenzenesulfonyl chloride (as prepared in the preceding step) in a manner analogous to step b of Example 26 and then step g of Example 29. Mass spectrum (MALDI-TOF, α-cyano-4-hydroxycinnamic acid matrix) calcd. for C$_{18}$H$_{23}$N$_3$O$_7$S$_2$: 458.1 (M+H). Found: 458.7.

EXAMPLE 25

3-[3-((2-Chloro-4-methylsulfonyl) phenylsulfonyloxy)-5-methylphenoxy] propoxyguanidine hydrochloride a) 2-Chloro-4-methylsulfonylbenzenesulfonyl chloride The title compound was prepared in 51% yield from 2-chloro-4-methylsulfonylaniline in a manner analogous to step a of Example 26. $^1$H-NMR (300 MHz, CDCl$_3$) δ8.37 (d, 1H, J=8.4 Hz), 8.22 (d, 1H, J=1.8 Hz), 8.06 (dd, 1H, J=8.4, 1.8 Hz), 3.15 (s, 3H).

b) 3-[3-((2-Chloro-4-methylsulfonyl)phenylsulfonyloxy)-5-methylphenoxy]propoxyguanidine hydrochloride The title compound was prepared from 2-chloro-4-methylsulfonylbenzenesulfonyl chloride (as prepared in the preceding step) in a manner analogous to step b of Example 26 and then step g of Example 29. Mass spectrum (MALDI-TOF, α-cyano-4-hydroxycinnamic acid matrix) calcd for C$_{18}$H$_{22}$ClN$_3$O$_7$S$_2$: 492.1 (M+H). Found: 492.2.

EXAMPLE 26

(3-(6-(2,3-Dihydro-1,1-dioxobenzo[b]thiophene) phenylsulfonyloxy)-5-methylphenoxy)propoxy] guanidine trifluoroacetate a) 1,1-Dioxobenzo[b]thiophene-6-sulfonyl chloride A mixture of 6-amino-1,1-dioxobenzo[b]thiophene (253 mg, 1.39 mmol) and 30% aqueous HCl (1.53 mL) was cooled to 0° C. in an open flask, and then 40% aqueous sodium nitrite (754 μL) was added dropwise over 2.25 minutes. The mixture was stirred at 0° C. for 15 minutes, and then 30% aqueous HCl (768 μL) and solid CuSO$_4$ (20.4 mg, 0.128 mmol) were added. To this mixture was added 40% aqueous NaHSO$_3$ (2.39 mL) dropwise over 6 minutes, and the reaction was stirred at 0° C. for 2.5 hours. The reaction was diluted with water (50 mL) and extracted with dichloromethane (2×50 mL). The combined organic layers were washed with brine (75 mL), dried over Na$_2$SO$_4$, filtered and evaporated. The product was purified by flash column chromatography through 20 g of silica gel using CH$_2$Cl$_2$ to give the title compound (171 mg, 46%) as a pale yellow solid. $^1$H-NMR (300 MHz, CDCl$_3$) δ8.35 (m, 1H), 8.26 (dd, 1H, J=8.0, 1.8 Hz), 7.65 (d, 1H, J=8.0 Hz), 7.34 (dd, 1H, J=7.0, 1.0 Hz), 7.02 (d, 1H, J=7.0 Hz).

b) N,N'-Bis-tert-butyloxycarbonyl-[(3-(6-(1,1-dioxobenzo[b]thiophene)phenylsulfonyloxy)-5-methylphenoxy)propoxy]guanidine A solution of (N,N'-bis-tert-butyloxycarbonyl)-[3-((3-hydroxy-5-methyl)phenoxy)propoxy]guanidine (60.0 mg, 0.137 mmol, as prepared in step f of Example 20), CH$_2$Cl$_2$ (660 μL), N,N-diisopropylethylamine (36 μL, 0.207 mmol), and 1,1-dioxobenzo[b]thiophene-6-sulfonyl chloride (36.1 mg, 0.136 mmol, as prepared in the preceding step) was stirred overnight at ambient temperature. The reaction mixture was concentrated in vacuo, and the residual gold oil was partitioned between dilute aqueous HCl (10 mL, pH 2) and diethyl ether (10 mL). The organic layer was washed with brine (10 mL), dried over Na$_2$SO$_4$, filtered and evaporated. The product was purified by column chromatography through 4.6 g of silica gel using 60:40 diethyl ether/hexane to give the title compound (78.7 mg, 86%) as a white semisolid. $^1$H-NMR (300 MHz, CDCl$_3$) δ8.13 (s, 1H), 8.05 (dd, 1H, J=7.9, 1.6 Hz), 7.57 (d, 1H, J=7.9 Hz), 7.34 (dd, 1H, J=7.0, 0.7 Hz), 6.95 (d, 1H, J=7.0 Hz), 6.64 (s, 1H), 6.46 (s, 1H), 6.30 (t, 1H, J=2.2 Hz), 4.18 (t, 2H, J=6.2 Hz), 3.96 (t, 2H, J=6.2 Hz), 2.27 (s, 3H), 2.11 pentet, 2H, J=6.2 Hz), 1.50 (s, 9H), 1.49 (s, 9H). Mass spectrum (MALDI-TOF, α-cyano-4-hydroxycinnamic acid matrix) calcd. for C$_{29}$H$_{37}$N$_3$O$_{11}$S$_2$: 468.1 (M-2 t-BOC+3H). Found: 468.2.

c) N,N'-Bis-tert-butyloxycarbonyl-[(3-(6-(2,3-dihydro-1,1-dioxobenzo[b]thiophene)phenylsulfonyloxy)-5-methylphenoxy)propoxy]guanidine A mixture of N,N'-bis-tert-butyloxycarbonyl-[(3-(6-(1,1-dioxobenzo[b]thiophene)-phenylsulfonyloxy)-5-methylphenoxy)propoxy]guanidine (8.0 mg, 0.012 mmol, as prepared in the preceding step), deoxygenated ethanol (600 μL), and 10% palladium on activated carbon (1.6 mg) was stirred at room temperature under hydrogen (balloon) for 1.5 hours. The mixture was filtered through Celite 545, and the filtrate was concentrated to give the title compound (6.9 mg, 86%) as a colorless oil. $^1$H-NMR (300 MHz, CDCl$_3$) δ9.09 (s, 1H), 8.21 (d, 1H, J=1.8 Hz), 8.04 (dd, 1H, J=8.1, 1.8 Hz), 7.71 (s, 1H), 7.58 (d, 1H, J=8.0 Hz), 6.63 (br s, 1H), 6.46 (br s, 1H), 6.30 (t, 1H, J=2.2 Hz), 4.18 (t, 2H, J=6.2 Hz), 3.96 (t, 2H, J=6.2 Hz), 3.48–3.69 (m, 4H), 2.27 (s, 3H), 2.11 (pentet, 2H, J=6.2 Hz), 1.50 (s, 9H), 1.49 (s, 9H).

d) (3-(6-(2,3-Dihydro-1,1-dioxobenzo[b]thiophene)phenylsulfonyloxy)-5-methylphenoxxy)propoxy]guanidinetrifluoroacetate A solution of N,N'-bis-tert-butyloxycarbonyl-[(3-(6-(2,3-dihydro-1,1-dioxobenzo[b]thiophene)phenylsulfonyloxy)-5-methylphenoxy)propoxy]guanidine (6.8 mg, 0.010 mmol, as prepared in the preceding step) dichloromethane (150 μL), water (10 μL), and trifluoroacetic acid (150 μL) was stirred at ambient temperature for 1.5 hours. The solution was concentrated in vacuo to give the title compound (8.0 mg, quantitative yield) as a light gold oil. $^1$H-NMR (300 MHz, CDCl$_3$) δ8.16 (dd, 1H, J=8.1, 1.5 Hz), 8.08 (br s, 1H), 7.65 (d, 1H, J=8.1 Hz), 6.65 (br s, 1H), 6.60 (br s, 1H), 6.24 (br s, 1H), 4.11 (t, 2H, J=5.5 Hz), 4.04 (t, 2H, J=5.5 Hz), 3.50–3.66 (m, 4H), 2.30 (s, 3H), 2.09 (pentet, 2H, J=5.5 Hz). Mass spectrum (MALDI-TOF, α-cyano-4-hydroxycinnamic acid matrix) calcd. for C$_{19}$H$_{23}$N$_3$O$_7$S$_2$: 470.1 (M+H), 492.1 (M+Na). Found: 470.1, 492.2.

EXAMPLE 27

{3-[5-Methyl-3-(2-(4-carboxyl)piperidinylsulfonylphenylsulfonyloxy)phenoxy]propoxy}guanidine To a solution of {3-[5-methyl-3-(2-(4-ethyloxycarbonyl)piperidinylsulfonylphenylsulfonyloxy)phenoxy]propoxy}guanidine hydrochloride (90 mg, 0.15 mmol), as prepared in step h of Example 20, in methanol (4.0 mL) was added 2N NaOH (0.2 mL, 0.4 mmol). The mixture was stirred at ambient temperature for 2 h. The ethyl acetate (3×20 mL). The ethyl acetate solution was washed with brine (20 mL) and dried over Na$_2$SO$_4$. After the solvent was evaporated, the residue was purified on a Waters Sep-Pak (10 g silica, 15% methanol in dichloromethane) to give the title compound as a white solid (50 mg, 58%). $^1$H-NMR (300 MHz, DMSO-d$_6$) δ8.15 (m, 2H), 8.01 (t, J=7.8 Hz, 1H), 7.88 (t, J=7.7 Hz, 1H), 6.72 (s, 1H), 6.53 (s, 1H), 6.40 (s, 1H), 5.33 (br s, 4H), 3.93 (t, J=6.4 Hz, 2H), 3.72 (t, J=6.2 Hz, 2H), 3.65 (m, 2H), 2.93 (t, J=10.0 Hz, 2H), 2.34 (m, 1H), 2.22 (s, 3H), 1.90 (t, J=6.2 Hz, 2H), 1.86 (m, 2H), 1.53 (m, 2H). Mass spectrum (MALDI-TOF, α-cyano-4-hydroxycinnamic acid matrix) calcd. for C$_{23}$H$_{30}$N$_4$O$_9$S$_2$: 571.2 (M+H), 593.1 (M+Na). Found: 571.2, 593.1.

EXAMPLE 28

3-[5-Methyl-3-(3-methylquinolinyl-8-sulfonyloxy)phenoxy]propoxyguanidine diacetate a) 3-Methyl-8-quinolinesulfonyl chloride The title compound was prepared according to the procedure of U.S. Pat. No. 5,332,822. To 9 mL (135 mmol) of chlorosulfonic acid at 0° C. was added slowly 3-methylquinoline (5.2 g, 36 mmol). The bath was removed and stirring was continued at 100° C. overnight. The reaction mixture was cooled to ambient temperature and then treated with 3.3 mL (45 mmol) of thionyl chloride. The reaction mixture was heated at 70° C. for 1 h, cooled to 0° C. and carefully quenched with ice (very vigorous reaction). The reaction mixture was diluted with 100 mL of water and extracted into dichloromethane (100 mL). The organic phase was washed with water, dried (MgSO$_4$) and concentrated. The residue was triturated with dichloromethane/diethyl ether to provide 1.58 g (18%) of the title compound as a tan solid. $^1$H-NMR (300 MHz, DMSO-d$_6$) δ9.17–9.29 (m, 2H), 8.32–8.38 (m, 2H), 7.96 (dd, 1H, J=7 Hz), and 2.51 (t, 3H, J=2 Hz).

b) 5-Methyl-3-(3-methylquinolinyl-8-sulfonyloxy)phenol

A mixture of orcinol monohydrate (2.8 g, 19.7 mmol) and 3-methyl-8-quinolinesulfonyl chloride (3.68 g, 15.2 mmol), as prepared by the preceding procedure, in diethyl ether (70 mL), tetrahydrofuran (20 mL), and saturated sodium bicarbonate (100 mL) was vigorously stirred at ambient temperature for 12 h. The reaction mixture was extracted into 15% tetrahydrofuran/85% dichloromethane, dried (MgSO$_4$), and purified by flash chromatography using elutions of dichloromethane/diethyl ether (95:5 to 92:8) to give 1.57 g (31% yield) of the title compound as a colorless solid. $^1$H-NMR (300 MHz, DMSO-d$_6$) δ9.62 (s, 1H), 9.09 (d, 1H, J=1.2 Hz), 8.38–8.34 (m, 2H), 8.27 (dd, 1H, J=7, 1 Hz), 7.72 (t, 1H, J=8 Hz), 6.43 (m, 1H), 6.29 (m, 1H), 6.09 (t, 1H, J=2

Hz), 2.58 (s, 3H), 2.09 (s, 3H). Mass spectrum (MALDI-TOF, α-cyano-4-hydroxycinnamic acid matrix) calcd. for $C_{17}H_{15}NO_4S$: 330.1 (M+H), 352.1 (M+Na). Found 329.8, 351.9.

c) 3-[5-Methyl-3-(3-methylquinolinyl-8-sulfonyloxy) phenoxy]propanol

A mixture of 5-methyl-3-(methylquinolinyl-8-sulfonyloxy)phenol (1.73 g, 5.26 mmol), as prepared in the preceding step, 3.2 mL (6.4 mmol) of 2 N NaOH, and 540 μL (5.79 mmol) of 3-bromopropanol in 20 mL of tetrahydrofuran was stirred at 50° C. overnight. The reaction mixture was diluted with water (70 mL), extracted into a 1:1 mixture of ethyl acetate/diethyl ether, dried ($MgSO_4$), and concentrated. The residue was crystallized from methanol/diethyl ether/hexane to give 1.50 g (74%) of the title compound as a colorless powder. $^1$H-NMR (300 MHz, DMSO-$d_6$) δ9.09 (d, 1H, J=2 Hz), 8.26–8.39 (m, 3H), 7.72 (t, 1H, J=7 Hz), 6.63 (s, 1H), 6.40 (s, 1H), 6.22 (s, 1H), 4.51 (t, 1H, J=5 Hz), 3.78 (t, 2H, J=7 Hz), 3.43 (q, 2H, J=6 Hz), 2.58 (s, 3H), 2.14 (s, 3H), 3.80 (pentet, 2H, J=7 Hz). Mass spectrum (MALDI-TOF, α-cyano-4-hydroxycinnamic acid matrix) calcd. for $C_{20}H_{21}NO_5S$: 388.1 (M+H), 410.1 (M+Na). Found: 388.0, 409.9.

d) N-[3-[5-Methyl-3-(3-methylquinolinyl-8-sulfonyloxy) phenoxy]propoxy]phthalimide Diethyl azodicarboxylate (830 μL, 5.3 mmol) was added slowly to 3-[5-methyl-3-(3-methylquinolinyl-8-sulfonyloxy)phenoxy]propanol (1.5 g, 3.88 mmol), as prepared in the preceding step, N-hydroxyphthalimide (710 mg, 4.36 mmol), and triphenylphosphine (1.3 g, 4.96 mmol) in anhydrous tetrahydrofuran (70 mL) at 0° C. under a nitrogen atmosphere. The solution was stirred at ambient temperature for 90 min. The reaction mixture was diluted with diethyl ether (200 mL), washed with water (2×150 mL), dried ($MgSO_4$), and concentrated. The residue was dissolved in dichloromethane and passed through a thick pad of silica gel (100:0 to 95:5 dichloromethane/diethyl ether) to give the title compound (2.0 g, 82%) as a colorless solid. $^1$H-NMR (300 MHz, DMSO-$d_6$) δ9.11 (s, 1H), 8.28–8.38 (m, 3H), 7.72 (t, 1H, J=8 Hz), 6.67 (s, 1H), 6.43 (s, 1H), 6.29 (s, 1H), 4.21 (t, 2H, J=7 Hz), 3.96 (t, 2H, J=7 Hz), 2.50 (s, 3H), 2.15 (s, 3H), 1,99 (pentet, 2H, J=6 Hz). Mass spectrum (MALDI-TOF, α-cyano-4-hydroxycinnamic acid matrix) calcd. for $C_{28}H_{24}N_2O_7S$: 533.1 (M+H), 555.1 (M+Na). Found 532.9, 554.9.

e) 3-[5-Methyl-3-(quinolinyl-8-sulfonyloxy)phenoxy] propoxyamine

Sodium borohydride (388 mg, 10.3 mmol) was added to N-[3-[5-methyl-3-(3-methylquinolinyl-8-sulfonyloxy) phenoxy]propoxy]phthalimide (2.0 g, 3.17 mmol), as prepared in the preceding step, in ethanol (30 mL), tetrahydrofuran (30 mL) and water (10 mL). Hydrogen gas was evolved for 40 min. The mixture was stirred overnight at ambient temperature. Aqueous HCl (10 mL, 2N) was added dropwise (hydrogen was evolved), and the solution was heated at 50° C. for 40 min. The reaction mixture was concentrated to ca. ⅓ volume. The reaction mixture was adjusted to pH 10 with 2N NaOH, diluted with water and extracted into dichloromethane. The organic extracts were washed with water, dried ($K_2CO_3$), and purified by flash chromatography (85:15 to 67:33 diethyl ether/dichloromethane) to give 1.14 g of the title compound as an oil. $^1$H-NMR (300 MHz, CDCl$_3$) δ9.11 (d, 1H, J=2 Hz), 8.33 (dd, 1H, J=7, 2 Hz), 8.04–8.07 (m, 2H), 7.56 (t, 2H, J=8 Hz), 6.53 (s, 1H), 6.46 (s, 1H), 6.41 (s, 1H), 3.84 (t, 2H, J=6 Hz), 3.75 (t, 2H, J=6 Hz), 2.61 (s, 3H, 2.17 (s, 3H), 1.95 (pentent, 2H, J=6 Hz). Mass spectrum (MALDI-TOF, α-cyano-4-hydroxycinnamic acid matrix) calcd. for $C_{20}H_{22}N_2O_5S$: 403.1 (M+H), 425.1 (M+Na). Found: 403.2, 425.1.

f) 3-[5-Methyl-3-(quinolinyl-8-sulfonyloxy)phenoxy] propoxyguanidine diacetate

A solution of 3-[5-methyl-3-(3-methylquinolinyl-8-sulfonyloxy)phenoxy]propoxyamine (1.1 g, 2.2 mmol), as prepared in the preceding step, and 1H-pyrazole-1-carboxamidine hydrochloride (970 mg, 6.62 mmol) in anhydrous N,N-dimethylformamide (5.0 mL) was stirred at ambient temperature under nitrogen for 18 h. The solvent was removed in vacuo and acetonitrile was added. The reaction mixture was stirred for 1 h at ambient temperature and the resulting pyrazole was removed by filtration. The filtrate was concentrated and the residue diluted with dichloromethane. The solution was treated with 2 mL of acetic acid and concentrated. The residue was purified by flash chromatography (93:6.3:0.7 to 89:9.5:1.5 to 78:19:3 dichloromethane/methanol/acetic acid) to give 860 mg (69% yield) of the title compound as a foam. $^1$H-NMR (300 MHz, DMSO-$d_6$) δ9.00 (d, 1H, J=2 Hz), 8.22–8.28 (m, 3H), 7.64 (m, 1H), 6.59 (s, 1H), 6.32–6.35 (m, 2H), 3.95 (t, 2H, J=6 Hz), 3.87 (t, 2H, J=6 Hz), 2.61 (s, 3H), 2.11 (s, 3H), 2.01 (pentet, 2H, J=6 Hz). Mass spectrum (MALDI-TOF, α-cyano-4-hydroxycinnamic acid matrix) calcd. for $C_{21}H_{24}N_4O_5S$: 445.2 (M+H), 467.1 (M+Na). Found 445:0, 466.9.

EXAMPLE 29

3-[5-Methyl-3-[2-(N-hydroxy) aminophenylsulfonyloxy]phenoxy] propoxyguanidine hydrochloride a) 2-(2-Nitrophenylsulfonyloxy)phenol A mixture of orcinol monohydrate (4.32 g, 30.2 mmol) and 2-nitrobenzenesulfonyl chloride (6.65 g, 30.0 mmol) in diethyl ether (100 mL) and saturated NaHCO$_3$ (100 mL) was stirred at ambient temperature for 36 h. The reaction mixture was diluted with water (100 mL) and extracted into 10% tetrahydrofuran/ethyl acetate, dried ($MgSO_4$), and concentrated. The residue was diluted with diethyl ether (150 mL) and the resulting disulfonated product (1.6 g) removed by filtration. The filtrate was concentrated and purified by flash chromatography (3:97 to 10:90 diethyl ether/dichloromethane) to give 5.67 g (61%) of the title compound as an oil. $^1$H-NMR (300 MHz, CDCl$_3$) δ7.99 (dd, 1H, J=7, 2 Hz), 7.79–7.86 (m, 2H), 7.65–7.73 (m, 1H), 6.60–6.61 (m, 1H), 6.58–6.59 (m, 1H), 6.50–6.51 (m, 1H), 5.32 (s, 1H), 2.25 (s, 3H).

b) 3-[3-(2-Nitrophenylsulfonyloxy)-5-methylphenoxy] propanol

A mixture of 2-(2-nitrophenylsulfonyloxy)phenol (2.0 g, 6.47 mmol), as prepared in the preceding step, 3-bromopropanol (700 μL, 7.5 mmol) and 2N NaOH (4 mL, 8 mmol) in tetrahydrofuran (20 mL) was heated at 60° C. for 6 h. The reaction mixture was acidified with 2N HCl, extracted into dichloromethane, dried ($MgSO_4$), concentrated, and purified by flash chromatography using elutions of 5–20% diethyl ether/dichloromethane to give 1.77 g (74%) of the title compound. $^1$H-NMR (300 MHz, CDCl$_3$) δ7.99 (d, 1H, J=7 Hz), 7.80–7.86 (m, 2H), 7.69–7.74 (m, 1H), 6.65 (s, 1H), 6.61 (s, 1H), 6.57 (t, 1H, J=2 Hz). 4.03 (t, 2H, J=6 Hz), 3.82 (t, 2H, J=6 Hz), 2.27 (s, 3H), 2.00 pentet, 2H, J=6 Hz).

c) N-[3-[3-(2-Nitrophenylsulfonyloxy)-5-methylphenoxy] propoxy]phthalimide

Diethyl azodicarboxylate (910 μL, 5.78 mmol) was slowly added to a solution of 3-[3-(2-nitrophenylsulfonyloxy)-5-methylphenoxy]propanol (1.77 g, 4.82 mmol), as prepared in the preceding step, triphenylphosphine (1.52 g, 5.80 mmol), and N-hydroxyphthalimide (864 mg, 530 mmol) in tetrahydrofuran (10 mL) at 0° C. The reaction mixture was stirred at room temperature overnight. The reaction mixture was concentrated and the product purified by flash chromatography (dichloromethane) to give 2.33 g (95%) of the title compound as an oil. $^1$H-NMR (300 MHz, $CDCl_3$) δ7.98 (dd, 1H, J=7, 1 Hz), 7.67–7.88 (m, 7H), 6.67 (s, 1H), 6.64 (m, 1H), 6.55 (t, 1H, J=2 Hz), 4.36 (t, 2H, J=6 Hz), 4.12 (t, 2H, J=6 Hz), 2.28 (s, 3H), 2.18 (pentet, 2H, J=6 Hz). Mass spectrum (MALDI-TOF, α-cyano-4-hydroxycinnamic acid) calcd. for $C_{24}H_{20}N_2O_9S$: 535.1 (M+Na). Found 535.0.

d) 3-[3-(2-Nitrophenylsulfonyloxy)-5-methylphenoxy]propoxyamine

A solution of N-[3-[3-(2-nitrophenylsulfonyloxy)-5-methylphenoxy]propoxy]-phthalimide (2.33 g, 4.55 mmol), as prepared in the preceding step, in tetrahydrofuran (30 mL) and ethanol (30 mL) was treated with sodium borohydride (524 mg, 13.9 mmol). The reaction mixture was stirred at room temperature overnight, quenched carefully with 2N HCl (14 mL) and heated at 50° C. for 90 min. The reaction mixture was then concentrated to ¼ volume, basified with 2N NaOH, diluted with water, and extracted into ethyl acetate. The organic phase was dried ($K_2CO_3$) and purified by flash chromatography (1:4 to 1:2 diethyl ether/dichloromethane to give 1.12 g (64%) of the title compound as a pale yellow oil. $^1$H-NMR (300 MHz, $CDCl_3$) δ7.98–8.01 (m, 1H), 7.79–7.87 (m, 2H), 7.66–7.74 (m, 1H), 6.64 (m, 1H), 6.60 (s, 1H), 6.57 (t, 1H, J=2 Hz), 3.96 (t, 2H, J=6 Hz), 3.80 (t, 2H, J=6 Hz), 2.27 (s, 3H), 2.02 (penet, 2H, J=6 Hz). Mass spectrum (MALDI-TOF, α-cyano-4-hydroxycinnamic acid) calcd. for $C_{16}H_{18}N_2O_7S$: 405.1 (M+Na). Found 405.2.

e) N,N'-(Bis-tert-butyloxycarbonyl)[3-[3-(2-nitrophenylsulfonyloxy)-5-methylphenoxy]propoxy]guanidine A solution of 3-[3-(2-nitrophenylsulfonyloxy)-5-methylphenoxy]propoxyamine (1.12 g, 2.93 mmol), as prepared in the previous step, in N,N-dimethylformamide (10 mL) was treated with bis(1,3-t-butyl)-2-methyl-2-thiopseudourea (894 mg, 3.08 mmol). The reaction mixture was stirred at 50° C. overnight, then at 65° C. for 24 h. Another 113 mg of bis(1,3-t-butyl)-2-methyl-2-thiopseudourea was added to the reaction. After stirring at 65° C. for 12 h, the reaction mixture was concentrated and the residue purified by flash chromatography using 3% diethyl ether/dichloromethane to give 833 mg (46%) of the title compound as oil. $^1$H-NMR (300 MHz, $CDCl_3$) δ9.09 (s, 1H), 7.97 (d, 1H), 7.80–7.86 (m, 2H), 7.66–7.74 (m, 2H), 6.64 (s, 1H), 6.61 (s, 1H), 6.52 (t, 1H, J=2 Hz), 4.18 (t, 2H, J=6 Hz), 3.97 (t, 2H, J=6Hz), 2.27 (s, 3H), 2.11 (pentet, 2H, J=6 Hz), 1.49 and 1.50 (two singlets, 18H). Mass spectrum (MALDI-TOF, α-cyano-4-hydroxycinnamic acid) calcd. for $C_{25}H_{36}N_4O_{11}S$: 447 (M−2 t-BOC+3H). Found: 447.

f) N,N'-(Bis-tert-butyloxycarbonyl)-[3-[3-(2-(N-hydroxy)aminophenyl-sulfonyloxy)-5-methylphenoxy]propoxy]guanidine A solution of N,N'-(bis-tert-butyloxycarbonyl)-[3-[3-(2-nitrophenylsulfonyloxy)-5-methylphenoxy]propoxy]guanidine (833 mg, 1.3 mmol), as prepare in the preceding step, in tetrahydrofuran (5 mL) containing 10% palladium on carbon (160 mg) was hydrogenated at atmospheric pressure for 3 h. The reaction mixture was filtered through Celite 545, concentrated, and resubmitted to hydrogenation with fresh catalyst (123 mg) in tetrahydrofuran (5 mL). The reaction still did not consume the starting material. The reaction mixture was concentrated and the product was purified by flash chromatography (5 to 10% diethyl ether/$CH_2Cl_2$) to give 574 mg (71% yield) of the title compound as a foam. $^1$H-NMR (300 MHz, $CDCl_3$) δ9.05 (s, 1H), 8.37 (s, 1H), 7.69 (s, 1H), 7.50–7.61 (m, 4H), 6.89 (t, 1H, J=7 Hz), 6.57 (s, 1H), 6.49 (s, 1H), 6.32 (s, 1H), 5.82 (s, 1H), 4.16 (t, 2H, J=6 Hz), 3.90 (t, 2H, J=6 Hz), 2.23 (s, 3H), 2.06 (pentet, 2H, J=6 Hz), 1.50 (s, 9H), 1.48 (s, 9H). g) 3-[5-Methyl-3-[2-(N-hydroxy)aminophenylsulfonyloxy]phenoxy]propoxyguanidine hydrochloride A solution of N,N'-(bis-tert-butyloxycarbonyl)-[3-[3-(2-(N-hydroxy)aminophenyl-sulfonyloxy)-5-methylphenoxy]propoxy]guanidine (85 mg, 0.14 mmol) in dichloromethane (1 mL) was treated with HCl (4N in dioxane). The reaction mixture was stirred at ambient temperature for 1 h. Additional HCl (300 μL) was added and stirring was continued for 1 h. Another 3 mL of 4N HCl was added. The reaction mixture was stirred for 2 h. The reaction mixture was concentrated and suspended in a mixture of diethyl ether/dichloromethane/hexane. The solvent was removed in vacuo and the concentration from diethyl ether/dichloromethane/hexane was repeated several times to give 74 mg of the title compound as an orange solid. $^1$H-NMR (300 MHz, $CD_3OD$) δ7.58 (td, 1H, J=7, 1 Hz), 7.40–7.50 (m, 2H), 6.80–6.85 (m, 1H), 6.65 (s, 1H), 6.44 (s, 1H), 6.42 (s, 2H), 3.95–4.15 (m, 4H), 2.19 (s, 3H), 2.05–2.17 (m, 2H). Mass spectrum (MALDI-TOF, α-cyano-4-hydroxycinnamic acid matrix) calcd. for $C_{17}H_{22}N_4O_6S$: 411.1 (M+H). Found: 411.0.

EXAMPLE 30

3-[5-Methyl-3-[2-aminophenylsulfonyloxy]phenoxy]propoxyguanidine hydrochloride

A solution of N,N'-(bis-tert-butyloxycarbonyl)-[3-[3-(2-(N-hydroxy)aminophenyl-sulfonyloxy)-5-methylphenoxy]propoxy]guanidine (289 mg), as prepared in step f of the preceding Example, in tetrahydrofuran (2 mL) containing 10% palladium on carbon was hydrogenated at atmospheric pressure for 20 h. The reaction mixture was filtered and concentrated. The residue was treated with HCl (1.5 mL; 4N in dioxane). After stirring for 4 h, the reaction mixture was concentrated from dichloromethane/methanol/diethyl ether/hexane to give 52 mg (26% yield) of impure title compound. Mass spectrum (MALDI-TOF, α-cyano-4-hydroxycinnamic acid matrix) calcd. for $C_{17}H_{22}N_4O_5S$: 395.1 (M+H). Found: 395.2.

EXAMPLE 31

3-[3-(2-(4-Biphenylmethoxy)phenylsulfonyloxy)-5-methylphenoxy]propoxyguanidine a) 4-(Bromomethyl)biphenyl A mixture of 4-phenyltoluene (4.83 g, 28.7 mmol), N-bromosuccinimide (5.64 g, 31.7 mmol), benzoyl peroxide (catalytic), and anhydrous carbon tetrachloride (35 mL) was refluxed for 24 hours. The mixture was cooled to room temperature and filtered to give a mixture (7.32 g) of 4-(dibromomethyl)biphenyl, 4-(bromomethyl)biphenyl, and 4-phenyltoluene (14:82:4 molar ratio by $^1$H-NMR). The product was used without further purification in the next step. $^1$H-NMR of the title compound (300 MHz, $CDCl_3$) δ7.56–7.60 (m, 4H), 7.33–7.48 (m, 5H), 4.55 (s, 2H). Partial $^1$H-NMR of 4-(dibromomethyl)biphenyl (300 MHz, $CDCl_3$) δ6.71 (s, 1H).

b) 1-(4-Biphenylmethoxy)-2-iodobenzene

A mixture of 2-iodophenol (6.35 g, 28.8 mmol), acetonitrile (150 mL), cesium carbonate (11.25 g, 3.45 mmol) and 4-(bromomethyl)biphenyl (7.26 g, mixture of 4-(dibromomethyl)biphenyl, 4-(bromomethyl)biphenyl and 4-phenyltoluene, 14:82:4 molar ratio, as prepared in the preceding step) was stirred at ambient temperature for 1 hour and then concentrated in vacuo. The residual solid was partitioned between water (200 mL) and ethyl acetate 250 mL). The organic layer was washed with aqueous NaOH (0.1N, 2×200 mL) and brine (200 mL), dried over $MgSO_4$, filtered and evaporated. The product was purified by flash column chromatography through 200 g of silica gel using 0% to 10% dichloromethane in hexane to give the title compound (8.38 g, 76% from 4-phenyltoluene) as a white solid. $^1$H-NMR (300 MHz, $CDCl_3$) δ7.81 (dd, 1H, J=7.8, 1.5 Hz), 7.56–7.64 (m, 6H), 7.26–7.47 (m, 4H), 6.89 (dd, 1H, J=8.2, 1.2 Hz), 6.74 (td, 1H, J=7.6, 1.2 Hz), 5.20 (s, 2H).

c) 2-(4-Biphenylmethoxy)benzenesulfonyl chloride

A solution 1-(4-biphenylmethoxy)-2-iodobenzene (6.04 g, 15.6 mmol, as prepared in the preceding step) in 40 mL of anhydrous THF was added over 45 minutes to a cooled (−78° C.) solution of N-butyllithium (0.89M in hexanes, 14.0 mL, 12.5 mmol) in 75 mL of anhydrous THF. Additional N-butyllithium (13 mL, 11.6 mmol) was added to drive the reaction to completion. The reaction was stirred at −78° C. for 3 hours, and then a cooled (0° C.) solution of $SO_2$ (18 g, 280 mmol) in 55 mL anhydrous tetrahydrofuran was added over 15 minutes. The solution was allowed to warm from −78° C. to 0° C. and then stirred at 0° C. for 30 minutes. Sulfuryl chloride (1.0M in dichloromethane, 72 mL, 72 mmol) was added to the cooled (0° C.) reaction mixture over 45 minutes. The solution was stirred at 0° C. for 45 minutes and then at ambient temperature overnight. The reaction was again cooled to 0° C. and sulfuryl chloride (1.0M in dichloromethane, 47 mL, 47 mmol) was added over 30 minutes. The solution was stirred at 0° C. for 30 minutes and then at ambient temperature for 1 hour. THF was removed by rotary evaporation, and the residual solution was poured into 1 liter of water and 600 mL of diethyl ether and separated. The organic layer was washed with water (2×1 L) and brine (600 mL), dried over $MgSO_4$, filtered, and evaporated. The product was chromatographed through 800 g of silica gel using 20% to 35% $CH_2Cl_2$ in hexane. The resulting solid was triturated with hexane and filtered to give the title compound (2.23 g, 40%) as a fluffy white solid. $^1$H-NMR (300 MHz, $CDCl_3$) δ8.16 (dd, 1H, J=8.0, 1.7 Hz), 7.74–7.84 (m, 7H), 7.48–7.63 (m, 3H), 7.33 (d, 1H, J=8.5 Hz), 7.27 (t, 1H, J=7.7 Hz), 5.56 (s, 2H).

d) [3-(2-(4-Biphenylmethoxy)phenylsulfonyloxy)-5-methylphenyl]acetate 2-(4-Biphenylmethoxy)enzenesulfonyl chloride (3.99 mg, 1.11 mmol, as prepared in the preceding step) was added to a solution of orcinol monoacetate (185 mg, 1.11 mmol), N,N-diisopropylethylamine (272 μL, 1.56 mmol) and dichloromethane (5.6 mL). After stirring overnight at ambient temperature, the solution was concentrated in vacuo. The residual oil was partitioned between ethyl acetate (45 mL) and dilute aqueous HCl (0.02N, 45 mL). The organic layer was washed with brine (45 mL), dried over $Na_2SO_4$, filtered and evaporated to give the title compound (534 mg, 98%) as a white solid. $^1$H-NMR (300 MHz, $CDCl_3$) δ7.89 (dd, 1H, J=7.9, 1.7 Hz), 7.57–7.64 (m, 7H), 7.32–7.47 (m, 3H), 7.15 (d, 1H, J=8.4 Hz), 7.05 (t, 1H, J=7.7 Hz), 6.79 (m, 1H), 6.75 (br s, 1H), 6.66 (m, 1H), 5.33 (s, 2H), 2.20 (s, 3H), 2.15 (s, 3H). Mass spectrum (MALDI-TOF, gentisic acid matrix) calcd. for $C_{28}H_{24}O_6S$: 511.1 (M+Na). Found: 511.0.

e) 3-(2-(4-Biphenylmethoxy)phenylsulfonyloxy)-5-methylphenol

A mixture of [3-(2-(4-biphenylmethoxy)phenylsulfonyloxy)-5-methylphenyl]acetate (503 mg, 1.03 mmol, as prepared in the preceding step), methanol (10 mL), tetrahydrofuran (5 mL) and aqueous NaOH (2N, 0.52 mL) was stirred at ambient temperature for 20 minutes and then concentrated in vacuo. The residue was partitioned between dilute aqueous HCl and ethyl acetate. The organic layer was washed with brine, dried over $Na_2SO_4$, filtered and evaporated to give the title compound (468 mg, quantitative yield) as a colorless foam. $^1$H-NMR (300 MHz, $CDCl_3$) δ7.90 (dd, 1H, J=7.9, 1.7 Hz), 7.57–7.63 (m, 7H), 7.33–7.47 (m, 3H), 7.16 (d, 1H, J=8.2 Hz), 7.05 (t, 1H, J=7.6 Hz), 6.49 (br s, 1H), 6.47 (br s, 1H), 6.30 (t, 1H, J=2.1 Hz), 5.35 (s, 2H), 2.15 (s, 3H). Mass spectrum (MALDI-TOF, gentisic acid matrix) calcd. for $C_{26}H_{22}O_5S$: 469.1 (M+Na). Found: 469.2 f) 3-[3-(2-(4-Biphenylmethoxy)phenylsulfonyloxy)-5-methylphenoxy]propoxyguanidine The title compound was prepared from 3-(2-(4-biphenylmethoxy)phenylsulfonyloxy)-5-methylphenol (as prepared in the preceding step) in a manner analogous to steps b, c, d and e of Example 10. Mass spectrum (MALDI-TOF, α-cyano-4-hydroxycinnamic acid matrix) calcd. for $C_{30}H_{31}N_3O_6S$: 562.2 (M+H). Found: 562.0.

EXAMPLE 32

3-[3-(2-(3-Biphenylmethoxy)phenylsulfonyloxy)-5-methylphenoxy]propoxyguanidine hydrochloride a) 3-(Bromomethyl)biphenyl The title compound was prepared as a mixture of 3-(dibromomethyl)biphenyl, 3-(bromomethyl)biphenyl and 3-phenyltoluene in a 22:69:9 molar ratio (7.77 g from 29.4 mmol of 3-phenyltoluene) in a manner analogous to step a of Example 31. The compound was used without purification in the next step. $^1$H-NMR of the title compound (300 MHz, $CDCl_3$) δ7.33–7.62 (m, 9H), 4.56 (s, 2H).

b) 1-(3-Biphenylmethoxy)-2-iodobenzene

The title compound was prepared in 68% yield (over two steps) in a manner analogous to step b of Example 31. $^1$H-NMR (300 MHz, $CDCl_3$) δ7.81 (dd, 1H, J=7.8, 1.6 Hz), 7.77 (br s, 1H), 7.26–7.65 (m, 9H), 6.90 (dd, 1H, J=8.2, 1.3 Hz), 6.74 (td, 1H, J=7.6, 1.3 Hz), 5.22 (s, 2H).

c) 2-(3-Biphenylmethoxy)benzenesulfonyl chloride

The title compound, a light yellow oil was prepared in 23% yield in a manner analogous to step of Example 31. $^1$H-NMR (300 MHz, $CDCl_3$) δ8.01 (dd, 1H, J=8.0, 1.7 Hz), 7.81 (br s, 1H), 7.33–7.68 (m, 9H), 7.17 (d, 1H, J=8.4 Hz), 7.11 (t, 1H, J=7.7 Hz), 5.42 (s, 2H).

d) [3-(2-(3-Biphenylmethoxy)phenylsulfonyloxy)-5-methylphenyl]acetate

The title compound was prepared in 71% yield from 2-(3-biphenylmethoxy)benzenesulfonyl chloride in a manner analogous to step d of Example 31. $^1$H-NMR (300 MHz, $CDCl_3$) δ7.89 (dd, 1H, J=7.9, 1.7 Hz), 7.81 (br s, 1H), 7.31–7.63 (m, 9H), 7.14 (d, 1H, J=8.4 Hz), 7.05 (t, 1H, J=7.6 Hz), 6.76 (br s, 1H), 6.72 (br s, 1H), 6.64 (t, 1H, J=2.2 Hz), 5.35 (s, 2H), 2.18 (s, 3H), 2.14 (s, 3H). Mass spectrum (MALDI-TOF, gentisic acid matrix) calcd. for $C_{28}H_{24}O_6S$: 511.1 (M+Na). Found: 510.9.

e) 3-(2-(3-Biphenylmethoxy)phenylsulfonyloxy)-5-methylphenol

The title compound was prepared in quantitative yield from [3-(2-(3-biphenylmethoxy)phenylsulfonyloxy)-5-methylphenyl]acetate in a manner analogous to step e of Example 31. $^1$H-NMR (300 MHz, $CDCl_3$) δ7.91 (dd, 1H, J=7.9, 1.7 Hz), 7.85 (br s, 1H), 7.32–7.63 (m, 9H), 7.16 (d, 1H, J=8.3 Hz), 7.05 (t, 1H, J=7.8 Hz), 6.48 (br,s 1H), 6.43 (br s, 1H), 6.25 (t, 1H, J=2.2 Hz), 5.36 (s, 2H), 2.11 (s, 3H). Mass spectrum (MALDI-TOF, α-cyano-4-hydroxycinnamic acid matrix) calcd. for $C_{26}H_{22}O_5S$: 469.1 (M+Na). Found: 469.1.

f) 3-[3-(2-(3-Biphenylmethoxy)phenylsulfonyloxy)-5-methylphenoxy]propoxyguanidine hydrochloride The title compound was prepared from 3-(2-(3-biphenylmethoxy) phenylsulfonyloxy)-5-methylphenol (as prepared in the preceding step) in a manner analogous to steps b, c, d and e of Example 10. Mass spectrum (MALDI-TOF, α-cyano-4-hydroxycinnamic acid matrix) calcd. for $C_{30}H_{31}N_3O_6S$: 562.2 (M+H), 584.2 (M+Na). Found 561.9, 584.0.

EXAMPLE 33

1-[(3-Benzyloxy-5-methylphenoxy)methyl]-1,1-cyclopropylethoxyguanidine a) 1-[(3-Benzyloxy-5-methylphenoxy)methyl]-1,1-cyclopropylethanol The title compound was prepared in 72% yield from 3-benzyloxy-5-methylphenol, as prepared in step a of Example 20, in a manner analogous to step b of Example 11. $^1$H-NMR (300 MHz, $CDCl_3$) δ7.34–7.44 (m, 5H), 6.43 (s, 1H), 6.37 (s, 1H), 6.36 (s, 1H), 5.02 (s, 2H), 3.89 (s, 2H), 3.63 (s, 2H), 2.29 (s, 3H), 0.63 (s, 4H).

b) N-{1-[(3-Benzyloxy-5-methylphenoxy)methyl]-1,1-cyclopropylethoxy}phthalimide

The title compound was prepared in 72% yield from 1-[(3-benzyloxy-5-methylphenoxy)methyl]-1,1-cyclopropylethanol, as prepared in the preceding step, in a manner analogous to step a of Example 11. $^1$H-NMR (300 MHz, $CDCl_3$) δ7.81 (m, 2H), 7.73 (m, 2H), 7.31–7.45 (m, 5H), 6.44 (s, 1H), 6.43 (s, 1H), 6.41 (s, 1H), 5.03 (s, 2H), 4.23 (s, 2H), 4.09 (s, 2H), 2.29 (s, 3H), 0.71 (m, 4H).

c) 1-[(3-Benzyloxy-5-methylphenoxy)methyl]-1,1-cyclopropylethoxyamine

A solution of N-{1-[(3-benzyloxy-5-methylphenoxy)methyl]-1,1-cyclopropylethoxy}phthalimide (419 mg, 0.945 mmol, as prepared in the preceding step), tetrahydrofuran (3.5 mL), ethanol (25 mL), and 40% aqueous methylamine (0.81 mL, 9.45 mmol) was stirred at ambient temperature for 1 hour and then concentrated in vacuo. After stirring the residue with 15 mL of 8:2 ethyl acetate/hexane, the mixture was filtered and the filtrate was concentrated. The product was purified by flash column chromatography (1:1 ethyl acetate/hexane) to give the title compound (271 mg, 92%) as a colorless liquid. $^1$H-NMR (300 MHz, $CDCl_3$) δ7.32–7.45 (m, 5H), 6.41 (br s, 1H), 6.39 (t, 1H, J=2.2 Hz), 6.37 (br s, 1H), 5.44 (br s, 1H), 5.02 (s, 2H), 3.84 (s, 2H), 3.69 (s, 2H), 2.29 (s, 3H), 0.64 (s, 4H). Mass spectrum (MALDI-TOF, α-cyano-4-hydroxycinnamic acid matrix) calcd. for $C_{19}H_{23}NO_3$: 314.2 (M+H), 336.2 (M+Na). Found 314.3, 336.3.

d) 1-[(3-Benzyloxy-5-methylphenoxy)methyl]-1,1-cyclopropylethoxyguanidine

A solution of 1-[(3-benzyloxy-5-methylphenoxy)methyl]-1,1-cyclopropylethoxyamine (245 mg, 0.782 mmol), as prepared in the preceding step, 1H-pyrazole-1-carboxamidine hydrochloride (228 mg, 1.56 mmol) and N,N-dimethylformamide (5 mL) was stirred overnight at ambient temperature. The reaction mixture was concentrated in vacuo, and the residual colorless oil was dissolved in acetonitrile (5 mL). The mixture was filtered, the collected solid was discarded, and the filtrate was concentrated. The crude product was partitioned between dilute aqueous HCl (15 mL, pH 2) and diethyl ether (10 mL). The aqueous layer was extracted again with diethyl ether (10 mL), and the ether layers were discarded. The aqueous layer was neutralized (pH 6–7) with 2N aqueous NaOH and extracted with ethyl acetate (2×25 mL). The combined ethyl acetate layers were washed with brine, dried over $Na_2SO_4$, filtered and evaporated. The product was purified by flash column chromatography (7% to 10% methanol in dichloromethane) to give the title compound (123 mg, 44%) as a white solid. $^1$H-NMR (300 MHz, $CD_3OD$) δ7.26–7.43 (m, 5H), 6.41 (br s, 1H), 6.35 (br s, 1H), 5.01 (s, 2H), 3.89 (s, 2H), 3.77 (s, 2H), 2.25 (s, 3H), 0.64 (s, 4H). Mass spectrum (MALDI-TOF, α-cyano-4-hydroxycinnamic acid matrix) calcd. for $C_{20}H_{25}N_3O_3$: 356.2 (M+H), 378.2 (M+Na). Found 356.1, 378.1.

EXAMPLE 34

{3-[5-Methyl-3-bis(2-methoxyethyl)aminosulfonylphenylsulfonyloxy)phenoxy]propoxy}guanidine hydrochloride a) N,N'-(Bis-tert-butyloxycarbonyl)-{3-[5-methyl-3-bis(2-methoxyethyl)aminosulfonylphenylsulfonyloxy)phenoxy]propoxyguanidine The title compound was prepared in 29% yield from bis(2-methoxyethyl)amine in a manner analogous to step h of Example 20. $^1$H-NMR (300 MHz, $CDCl_3$) δ9.05 (s, 1H), 8.28 (dd, J=4.9, 1.3 Hz, 1H), 8.10 (dd, J=7.9, 1.4 Hz, 1H), 7.58–7.76 (m, 3H), 6.51–6.57 (m, 3H), 4.15 (t, J=6.2 Hz, 2H), 3.91 (t, J=6.2 Hz, 2H), 3.65 (t, J=5.6 Hz, 2H), 3.50 (t, J=5.7 Hz, 2H), 3.24 (s, 3H), 2.22 (s, 3H), 2.07 (pentet, 2H, J=6 Hz), 1.47 (s, 18H).

b) {3-[5-Methyl-3-bis(2-methoxyethyl)aminosulfonylphenylsulfonyloxy)phenoxy]propoxy}guanidine hydrochloride The title compound was prepared in 87% yield from N,N'-(bis-tert-butyloxycarbonyl)-{3-[5-methyl-3-bis(2-methoxyethyl)aminosulfonyl phenylsulfonyloxy)phenoxy]propoxy}guanidine, as prepared in the preceding step, in a manner analogous to step i of Example 20. $^1$H-NMR (300 MHz, $CDCl_3$) δ8.24 (d, J=6.6 Hz, 1H), 8.18 (d, J=7.6 Hz, 1H), 7.69–7.79 (m, 2H), 6.64 (br s, 1H), 659 (br s, 2H), 4.08 (m, 2H), 4.00 (m, 2H), 3.65 (br s, 4H), 3.52 (br, s 4H), 3.27 (s, 6H), 2.25 (s, 3H), 2.09 (m, 2H). Mass spectrum (MALDI-TOF, α-cyano-4-hydroxycinnamic acid matrix) calcd. for $C_{23}H_{34}N_4O_9S_2$: 575.2 (M+H), 597.2 (M+Na). Found: 575.1, 597.3.

EXAMPLE 35

{3-[5-Methyl-3-(N-ethyl-3,4-(methylenedioxy)anilinosulfonylphenylsulfonyloxy)phenoxy]propoxy}guanidine hydrochloride a) N,N'-(Bis-tert-butyloxycarbonyl)-{3-[5-methyl-3-(N-ethyl-3,4-(methylenedioxy)anilinosulfonylphenylsulfonyloxy)phenoxy]propoxy}guanidine The title compound was prepared in 35% yield from N-ethyl-3,4-(methylenedioxy)aniline in a manner analogous to step h of Example 20. $^1$H-NMR (300 MHz, $CDCl_3$) δ9.07 (s, 1H), 8.09–8.14 (m, 1H), 7.83–7.88 (m, 1H), 7.71 (s, 1H), 7.52–7.61 (m, 2H), 6.71 (d, J=1.8 Hz, 1H), 6.56–6.66 (m, 5H), 5.95 (s, 2H), 4.12 (q, J=7.0 Hz, 4H), 3.94 (q, J=6.9 Hz, 4H), 2.26 (s, 3H), 2.09 (pentet, 2H, J=6 Hz), 1,49 (s, 18H), 1.16 (t, J=7.1 Hz, 3H).

b) {3-[5-Methyl-3-(N-ethyl-3,4-(methylenedioxy)anilinosulfonylphenylsulfonyloxy)phenoxy]propoxy}guanidine hydrochloride The title compound was prepared in 61% yield from N,N'-(bis-tert-butyloxycarbonyl)-{3-[5-methyl-3-(N-ethyl-3,4-(methylenedioxy)anilinosulfonylphenylsulfonyloxy)phenoxy]propoxy}guanidine, as prepared in the preceding step, in a manner analogous to step i of Example 20. $^1$H-NMR (300 MHz, $CDCl_3$) δ10.82 (s 1H), 8.13 (m, 1H), 7.87 (m, 1H), 7.61 (m, 2H), 6.56–6.69 (m, 6H), 5.95 (s, 2H), 3.85–4.07 (m, 6H), 2.23 (s, 3H), 2.08 (m, 2H), 1.14 (t, J=7.1 Hz, 3H). Mass spectrum (MALDI-TOF, α-cyano-4-hydroxycinnamic acid matrix) calcd. for $C_{26}H_{30}N_4O_9S_2$: 607.2 (M+H), 629.1 (M+Na). Found: 607.0, 629.1.

EXAMPLE 36

{3-[5-Methyl-3-(2-N-methyl-(3,4-dimethoxyphenyl)ethylaminosulfonylphenylsulfonyloxy)phenoxy]propoxy}guanidine hydrochloride a) N,N'-(Bis-tert-butyloxycarbonyl)-{3-[5-methyl-3-(2-N-methyl-(3,4-dimethoxyphenyl)ethylaminosulfonylphenylsulfonyloxy)phenoxy]propoxy}guanidine The title compound was prepared in 46% yield from N-methylhomoveratrylamine in a manner analogous to step h of Example 20.

b) {3-[5-Methyl-3-(2-N-methyl-(3,4-dimethoxyphenyl)ethylaminosulfonylphenylsulfonyloxy)phenoxy]propoxy}guanidine hydrochloride The title compound was prepared in 63% yield from N,N'-(bis-tert-butyloxycarbonyl)-{3-[5-methyl-3-(2-N-methyl-(3,4-dimethoxyphenyl)ethylaminosulfonylphenylsulfonyloxy)phenoxy]propoxy}guanidine, as prepared in the preceding step, in a manner analogous to step i of Example 20. $^1$H-NMR (300 MHz, CDCl$_3$) δ10.85 (s, 1H), 8.11 (m, 2H), 7.75 (t, J=7.0 Hz, 1H), 7.66 (t, J=7.5 Hz, 1H), 6.53–6.76 (m, 6H), 4.06 (t, J=5.4 Hz, 2H), 3.96 (t, J=5.5 Hz, 2H), 3.83 (s, 6H), 3.55 (t, J=7.5 Hz, 2H), 2.97 (s, 3H), 2.84 (t, J=7.0 Hz, 2H), 2.23 (s, 3H), 2.06 (m, 2H). Mass spectrum (MALDI-TOF, α-cyano-4-hydroxycinnamic acid matrix) calcd. for $C_{28}H_{36}N_4O_9S_2$: 637.2 (M+H), 659.2 (M+Na). Found: 637.3, 659.5.

EXAMPLE 37

{3-[5-Methyl-3-((3-ethoxycarbonyl-1-piperidinosulfonyl)phenylsulfonyloxy)phenoxy]propoxy}guanidine hydrochloride a) N,N'-(Bis-tert-butyloxycarbonyl)-{3-[5-methyl-3-((3-ethoxycarbonyl-1-piperidinosulfonyl)phenylsulfonyloxy)phenoxy]propoxy}guanidine The title compound was prepared in 51% yield from ethyl nipecotate in a manner analogous to step h of Example 20. Mass spectrum (MALDI-TOF, α-cyano-4-hydroxycinnamic acid matrix) calcd. for $C_{35}H_{50}N_4O_{13}S_2$: 599.3 (M -2 t-BOC+3H). Found: 599.5.

b) {3-[5-Methyl-3-((3-ethoxycarbonyl-1-piperidinosulfonyl)phenylsulfonyloxy) phenoxy]propoxy}guanidine hydrochloride The title compound was prepared in 63% yield from N,N'-(bis-tert-butyloxycarbonyl)-{3-[5-methyl-3-((3-ethoxycarbonyl-1-piperidinosulfonyl)phenylsulfonyloxy)phenoxy]propoxy}guanidine, as prepared in the preceding step, in a manner analogous to step i of Example 20. $^1$H-NMR (300 MHz, CDCl$_3$) δ10.84 (s, 1H), 8.22 (dd, J=7.9, 1.3 Hz, 1H), 8.15 (dd, J=7.9, 1.3 Hz, 1H), 7.80 (td, J=7.7, 1.3 Hz, 1H), 7.68 (td, J=7.7, 1.3 Hz, 1H), 6.57 (m, 1H), 6.51 (m, 2H), 4.03–4.12 (m, 4H), 3.90–3.97 (m, 3H), 3.75 (m, 1H), 2.97–3.05 (m, 1H), 2.83–2.90 (m, 1H), 2.57–2.66 (m, 1H), 2.22 (s, 3H), 2.02–2.14 (m, 3H), 1.48–1.79 (m, 3H), 1.21 (t, J=7.0 Hz, 3H). Mass spectrum (MALDI-TOF, α-cyano-4-hydroxycinnamic acid matrix) calcd. for $C_{25}H_{34}N_4O_9S_2$: 599.2 (M+H), 621.2 (M+Na). Found: 599.0, 620.9.

EXAMPLE 38

{3-[5-Methyl-3-((3-carboxypiperidinosulfonyl)phenylsulfonyloxy)phenoxy]propoxy}guanidine hydrochloride A solution of {3-[5-methyl-3-((3-ethoxycarbonyl-1-piperidinosulfonyl)phenylsulfonyloxy)phenoxy]propoxy}guanidine hydrochloride (0.056 g, 0.09 mmol), as prepared in the preceding step, in methanol (3 mL) and 0.25N NaOH (1.5 mL) was stirred at ambient temperature for 2 h. The methanol was evaporated. The concentrate was diluted with water, washed with dichloromethane and adjusted to pH 7 with 10% HCl. The aqueous layer was extracted with ethyl acetate (4×10 mL). The ethyl acetate extracts were combined, washed with brine, dried (Na$_2$SO$_4$), and evaporated to dryness to give the title compound as a white solid (0.035 g, 69% yield). $^1$H-NMR (300 MHz, CDCl$_3$/DMSO-d$_6$) δ8.07 (dd, J=7.9, 1.1 Hz, 1H), 8.00 (dd, J=7.9, 1.3 Hz, 1H), 7.81 (td, J=7.7, 1.4 Hz, 1H), 7.65 (td, J=7.7, 1.2 Hz, 1H), 6.79 (s, 1H), 6.60 (s, 1H), 6.30 (t, J=2.0 Hz, 1H), 3.92–4.02 (m, 5H), 3.73–3.84 (m, 1H), 2.94–3.04 (m, 2H), 2.40–2.47 (m, 1H), 2.33 (s, 3H), 1.85–2.16 (m, 4H), 1.51–1.73 (m, 2H). Mass spectrum (MALDI-TOF, α-cyano-4-hydroxycinnamic acid matrix) calcd. for $C_{23}H_{30}N_4O_9S_2$: 571.2 (M+H), 593.1 (M+Na). Found: 571.2, 593.3.

EXAMPLE 39

{3-[5-Methyl-3-((2-methoxycarbonyl1-pyrrolidinosulfonyl)phenylsulfonyloxy)phenoxy]propoxy}guanidine hydrochloride a) N,N'-(Bis-tert-butyloxycarbonyl)-{3-[5-methyl-3-((2-methoxycarbonyl-1-pyrrolidinosulfonyl)phenylsulfonyloxy)phenoxy]propoxy}guanidine The title compound was prepared in 35% yield from L-proline methyl ester hydrochloride in a manner analogous to step h of Example 20. $^1$H-NMR (300 MHz, CDCl$_3$) δ9.05 (s, 1), 8.36 (dd, J=7.9, 1.3 Hz, 1H), 8.11 (dd, J=7.9, 1.3 Hz, 1H), 7.76 (td, J=7.6, 1.3 Hz, 1H), 7.60–7.68 (m, 2H), 6.51–6.56 (m, 3H), 4.79 (dd, J=8.3, 2.8 Hz, 1H), 4.15 (t, J=6.2 Hz, 2H), 3.91 (td, J=6.2, 1.3 Hz, 2H), 3.62 (s, 3H), 2.2–2.30 (m, 4H), 1.91–2.17 (m, 7H), 1.47 (s, 18H), 1.24 (t, J=7.1 Hz, 2H).

b) {3-[5-Methyl-3-((2-methoxycarbonyl-1-pyrrolidinosulfonyl)phenylsulfonyloxy)phenoxy]propoxy}guanidine hydrochloride The title compound was prepared in 45% yield from N,N'-(bis-tert-butyloxycarbonyl)-{3-[5-methyl-3-((2-methoxycarbonyl-1-pyrrolidinosulfonyl)phenylsulfonyloxy)phenoxy]propoxy}guanidine, as prepared in the preceding step, in a manner analogous step i of Example 20. $^1$H-NMR (300 MHz, CDCl$_3$) δ8.35 (dd, J=7.9, 1.3 Hz, 1), 8.19 (dd, J=7.9, 1.3 Hz, 1H), 7.84 (td, J=7.7, 1.3 Hz, 1H), 7.71 (td, J=7.7, 1.3 Hz, 1H), 6.57–6.66 (m, 1H), 4.78 (dd, J=8.3, 2.6 Hz, 1H), 4.08 (t, J==5.8 Hz, 2H), 3.99 (t, J=5.8 Hz, 2H), 3.60–3.66 (m, 4H), 3.42 (m, 1H), 2.25 (s, 3H), 1.91–2.20 (m, 4H). Mass spectrum (MALDI-TOF, α-cyano-4-hydroxycinnamic acid matrix) calcd. for $C_{23}H_{30}N_4O_9S_2$: 571.2 (M+H), 593.1 (M+Na). Found: 571.0, 593.3.

EXAMPLE 40

{3-[5-Methyl-3-((2-carboxy-1-pyrrolidinosulfonyl)phenylsulfonyloxy)phenoxy]propoxy}guanidine hydrochloride A solution of {3-[5-methyl-3-((2-carboxy-1-pyrrolidinosulfonyl)phenylsulfonyloxy)phenoxy]propoxy}guanidine hydrochloride (0.037 g, 0.065 mmol), as prepared in the preceding step, in methanol (3 mL) and 0.25 NaOH (1.0 mL) was stirred at ambient temperature for 2 h. The methanol was evaporated. The concentrate was diluted with water, washed with dichloromethane, and adjusted to pH 7 with 10% HCl. The aqueous was extracted with ethyl acetate (4×10 mL). The ethyl acetate extracts were combined, washed with brine, dried, and evaporated to dryness to give the title compound as a white solid (0.015 g, 43% yield). $^1$H-NMR (300 MHz, CDCl$_3$/DMSO-d$_6$) δ8.41 (d, J=7.0 Hz, 1H), 8.05 (dd, J=7.8, 1.0 Hz, 1H), 7.79 (td, J=7.7, 1.2 Hz, 1H), 7.64 (t, 1H), 6.72 (s, 1H), 6.60 (s, 1H), 6.49 (s, 1H), 4.60 (dd, J=7.7, 2.9 Hz, 1H), 3.88–4.03 (m, 4H), 3.54–3.67 (m, 2H), 2.30 (s, 3H), 1.94–2.27 (m, 6H). Mass spectrum (MALDI-TOF, α-cyano-4-hydroxycinnamic acid matrix) calcd. for C$_{22}$H$_{28}$N$_4$O$_9$S$_2$: 557.1 (M+H), 579.1 (M+Na). Found: 557.0, 579.0.

EXAMPLE 41

{3-[5-Methyl-3-(N-methyl-N-ethoxycarbonylmethyl)aminosulfonylphenylsulfonyloxy)phenoxy]propoxy}guanidine hydrochloride a) N,N'-(Bis-tert-butyloxycarbonyl)-{3-[5-methyl-3-(N-methyl-N-ethoxycarbonylmethyl)aminosulfonylphenylsulfonyloxy)phenoxy]propoxy}guanidine The title compound was prepared in 67% yield from sarcosine ethyl ester hydrochloride in a manner analogous to step h of Example 20. $^1$H-NMR (300 MHz, CDCl$_3$) δ9.08 (s, 1H), 8.37 (dd, J 7.9, 1.3 Hz, 1H), 8.14 (dd, J=7.9, 1.3 Hz, 1H), 7.81 (dt, J=7.7, 1.4 Hz, 1H), 7.64–7.73 (m, 2H), 6.51–6.59 (m, 3H), 4.09–4.20 (m, 4H), 3.94 (t, J=6.2 Hz, 2H), 2.99 (s, 3H), 2.26 (s, 3H), 2.06–2.15 (m, 2H), 1.49 (s, 18H), 1.20–1.28 (m, 5H).

b) {3-[5-Methyl-3-(N-methyl-N-ethoxycarbonylmethyl)aminosulfonylphenylsulfonyloxy)phenoxy]propoxy}guanidine hydrochloride The title compound was prepared in 72% yield from N,N'-(Bis-tert-butyloxycarbonyl)-{3-[5-methyl-3-(N-methyl-N-ethoxycarbonylmethyl)aminosulfonylphenylsulfonyloxy)phenoxy]propoxy}guanidine, as prepared in the preceding step, in a manner analogous to step i of Example 20. $^1$H-NMR (300 MHz, CDCl$_3$) δ8.34 (dd, J=7.9, 1.3 Hz, 1H), 8.18 (dd, J=7.9, 1.3 Hz, 1H), 7.85 (td, J=7.7, 1.3 Hz, 1H), 7.71 (td, J=7.7, 1.3 Hz, 1H), 6.64 (s, 1H), 6.59 (s, 1H), 6.54 (t, J=2.0 Hz, 1H), 4.27 (s, 2H), 4.06–4.17 (m, 4H), 3.98 (t, J=5.7 Hz, 2H), 2.99 (s, 3H), 2.25 (s, 3H), 2.06–2.17 (m, 2H), 1.22 (t, J=7.2 Hz, 3H). Mass spectrum (MALDI-TOF, α-cyano-4-hydroxycinnamic acid matrix) calcd. for C$_{22}$H$_{30}$N$_4$O$_9$S$_2$: 559.2 (M+H), 581.1 (M+Na). Found: 559.2, 581.2.

EXAMPLE 42

{3-[5-Methyl-3-(N-methyl-N-ethoxycarbonylmethyl)aminosulfonylphenylsulfonyloxy)phenoxy]propoxy}guanidine hydrochloride A solution of {3-[5-methyl-3-(N-methyl-N-ethoxycarbonylmethyl)aminosulfonylphenylsulfonyloxy)phenoxy]propoxy}guanidine hydrochloride (0.076 g, 0.136 mmol), as prepared in the preceding step, in methanol (3 mL) and 0.25N NaOH (1.5 mL) was stirred at ambient temperature for 2 h. The methanol was evaporated. The concentrate was diluted with water, washed with dichloromethane, and adjusted to pH 7 with 10% HCl. The aqueous was extracted with ethyl acetate (4×10 mL). The ethyl acetate extracts were combined, washed with brine, dried, and evaporated to dryness to give the title compound as a white solid (0.055 g, 76% yield). $^1$H-NMR (300 MHz, DMSO-d$_6$) δ8.26 (dd, J=7.9, 1.3 Hz, 1H), 8.11 (dd, J=7.9, 1.3 Hz, 1H), 7.99 (td, J=7.7, 1.2 Hz, 1H), 7.85 (td, J=7.7, 1.2 Hz, 1H), 6.74 (m, 1 H), 6.47–6.56 (m, 2H), 4.13 (s, 2H), 3.97 (t, J=6.2 Hz, 2H), 3.89 (t, J=6.2 Hz, 2H), 3.34 (s, 3H), 2.22 (s, 3H), 1.96–2.02 (m, 2H). Mass spectrum (MALDI-TOF, α-cyano-4-hydroxycinnamic acid matrix) calcd. for C$_{20}$H$_{26}$N$_4$O$_9$S$_2$: 531.1 (M+H), 553.1 (M+Na). Found: 531.3, 553.3.

EXAMPLE 43

3-[5-Methyl-3-(2-(4-methylsulfonylpiperazin-1-ylsulfonyl)phenylsulfonyloxy)phenoxy]propoxy}guanidine hydrochloride a) N,N'-(Bis-tert-butyloxycarbonyl)-{3-[5-methyl-3-(2-(4-methylsulfonylpiperazin-1ylsulfonyl)phenylsulfonyloxy)phenoxy]propoxy}guanidine hydrochloride To a solution of 1,2-benzenedisulfonic anhydride (440 mg, 2.0 mmol), as prepared in step g of Example 20, and N,N-diisopropylethylamine (720 (L, 4.0 mmol) in dichloromethane (20 mL) was added (N-methylsulfonyl)piperazine hydrochloride (400 mg, 2.0 mmol). After stirring the mixture for 4 h at ambient temperature, oxalyl chloride (160 (L, 2.0 mmol) and 5 drops of N,N-dimethylformamide were added. The mixture was stirred for another 4 h. (N,N'-bis-tert-butyloxycarbonyl)-{3-[(3-hydroxy-5-methyl)phenoxy)propoxy}guanidine (560 mg, 1.4 mmol), as prepared in step f of Example 20, and N,N-diisopropylethylamine (360 (L, 2.0 mmol) were added to the mixture. The mixture was stirred at ambient temperature overnight. Additional dichloromethane (100 mL) was added and the solution was washed with 10% citric acid (3×50 mL), brine (50 mL), and dried over Na$_2$SO$_4$. After the solvent was evaporated n vacuo, the residue was purified by flash column chromatography (dichloromethane to 5% ethyl acetate in dichloromethane) to give the title compound as a colorless foam (1.0 g, 89%). $^1$H-NMR (300 MHz, CDCl$_3$) δ9.08 (s, 1H), 8.31 (d, J=7.9 Hz 1H), 8.18 (d, J=7.9Hz, 1H), 7.82 (t, J=7.8 Hz, 1H), 7.72 (t, J=7.7 Hz, 2H), 6.60 (s, 1H), 6.54 (s, 1H), 6.48 (s, 1H), 4.18 (t, J=6.1 Hz, 2H), 3.95 (t, J=6.2 Hz, 2H), 3.52 (m, 4), 3.31 (m, 4H), 2.78 (s, 3H), 2.24 (s, 3H), 2.11 (t, J=6.2 Hz, 2H), 1.49 (s, 18H).

b) 3-[5-Methyl-3-(2-(4-methylsulfonylpiperazin-1-ylsulfonyl)phenylsulfonyloxy)phenoxy]propoxy}guanidine hydrochloride To a solution of N,N'-(bis-tert-butyloxycarbonyl)-{3-[5-methyl-3-(2-(4-methylsulfonylpiperazin-1-ylsulfonyl)phenylsulfonyloxy)phenoxy]propoxy}guanidine (725 mg, 0.9 mmol), as prepared in the preceding step, in dichloromethane (20 mL) was added trifluoracetic acid (5 mL). The mixture was stirred at ambient temperature for 3 h, the solvent was evaporated in vacuo. The residue was dissolved in dichloromethane (100 mL), washed with 2N K$_2$CO$_3$ (2×50 mL) and dried over Na$_2$SO$_4$. After evaporated the solvent, the residue was converted to the HCl salt (1 eq. methanolic HCl and concentration) and purified by flash column chromatography (10% methanol in dichloromethane) to give the title compound as a colorless foam (530 mg, 91%). $^1$H-NMR (300 MHz, DMSO-d$_6$) δ10.97 (br s, 1H), 8.22 (d, J=7.9 Hz, 1H), 8.17 (d, J=7.9 Hz, 1H), 8.03 (t, J=7.7 Hz, 1H), 7.91 (t, J=7.7 Hz, 2H), 7.23 (br s, 4H), 6.75 (s, 1H), 6.52 (s, 1H), 6.49 (s, 1H), 3.98 (t, J=6.3 Hz, 2H), 3.88 (t, J=6.3 Hz, 2H), 3.42 (m, 4H), 3.20 (m, 4H), 2.91 (s, 3H), 2.22 (s, 3H), 2.00 (pentet, J=6.3 Hz, 2H). Mass spectrum (MALDI-TOF, α-cyano-4-hydroxycinnamic acid matrix) calcd. for C$_{22}$H$_{31}$N$_5$O$_9$S$_3$: 606.1 (M+H), 628.1 (M+Na). Found: 605.9, 628.1.

EXAMPLE 44

{3-[5-Methyl-3-(2-(4-(2-pyrimidinyl)piperazin-1-ylsulfonyl)phenylsulfonyloxy)phenoxy]propoxyguanidine hydrochloride a) N,N'-(Bis-tert-butyloxycarbonyl)-{3-[5-methyl-3-(2-(4-(2-pyrimidinyl)piperazin-1-ylsulfonyl)phenylsulfonyloxy)phenoxy]propoxyguanidine}hydrochloride To a solution of 1,2-benzenedisulfonic anhydride (110 mg, 0.5 mmol), as prepared in step g of Example 20, and N,N-diisopropylethylamine (90 (L, 0.5 mmol) in dichloromethane (10 mL) was added 2-(1-piperazinyl)pyrimidine (82 mg, 0.5 mmol). After stirring the mixture for 4 h at ambient temperature, oxalyl chloride (40 (L, 0.5 mmol) and 2 drops of N,N-dimethylformamide were added. The mixture was stirred for another 4 h. (N,N'-Bis-tert-butyloxycarbonyl)-{3-[(3 -hydroxy-5-methyl)phenoxy)propoxy}guanidine (180 mg, 0.4 mmol), as prepared in step f of Example 20, and N,N-diisopropylethylamine (180 (L, 1.0 mmol) were added to the mixture. The mixture was stirred at ambient temperature overnight. Additional dichloromethane (50 mL) was added, washed with 10% citric acid (3×20 mL) and brine (20 mL), and dried over $Na_2SO_4$. After the solvent was evaporated in vacuo, the residue was purified on a Waters Sep-Pak (5 g silica, 3:1 hexane:ethyl acetate) to give the title compound as a colorless foam (185 mg, 64%). $^1$H-NMR (300 MHz, $CDCl_3$) δ9.08 (s, 1H), 8.29 (d, J=4.8 Hz, 1H),8.17 (d, J=8.0 Hz, 1H), 7.81 (t, J=7.7 Hz, 1H), 7.70 (m, 2H), 6.59 (s, 1H), 6.57 (s, 1H), 6.52 (s, 1H), 6.49 (s, 1H), 4.18 (t, J=6.2 Hz, 2H), 3.93 (m, 6H), 3.43 (m, 4H), 2.24 (s, 3H), 2.10 (pentet, J=6.2 Hz, 2H), 1.49 (s, 18H).

b) 3-[5-Methyl-3-(2-(4-(2-pyrimidinyl)piperazin-1-ylsulfonyl)phenylsulfonyloxy)phenoxy]propoxyguanidine hydrochloride To a solution of N,N'-(bis-tert-butyloxycarbonyl)-{3-[5-methyl-3-(2-(4-(2-pyrimidinyl)piperazin-1-ylsulfonyl)phenyl sulfonyloxy)phenoxy]propoxy}guanidine (170 mg, 0.235 mmol), as prepared in the preceding step, in dichloromethane (6 mL) was added trifluoroacetic acid (3 mL). The mixture was stirred at ambient temperature for 2 h, the solvent was evaporated in vacuo. The residue was dissolved in dichloromethane (50 mL), washed with 2N $K_2CO_3$ (2×30 mL) and dried over $Na_2SO_4$. After evaporated the solvent, the residue was converted to the HCl salt by HCl methanol to give the title compound as a colorless foam (140 mg, 93%). $^1$H-NMR (300 MHz, DMSO-$d_6$) δ11.09 (s, 1H), 8.38 (d, J=5.0 Hz, 2H), 8.16–8.24 (m, 2H), 8.01 (t, J=7.7 Hz, 1H), 7.90 (t, J=7.7 Hz, 2H), 7.69 (br s, 4H), 6.74 (s, 1H), 6.68 (t, J=4.8 Hz, 1H), 6.54 (s, 1H), 6.51 (s, 1H), 3.99 (t, J=6.2 Hz, 2H), 3.90 (t, J=6.3 Hz, 2H), 3.83 (m, 4H), 3.36 (m, 4H), 2.22 (s, 3H), 2.01 (pentet, J=6.3 Hz, 2H). Mass spectrum (MALDI-TOF, α-cyano-4-hydroxycinnamic acid matrix) calcd. for $C_{25}H_{31}N_7O_7S_2$: 606.2 (M+H), 628.2 (M+Na). Found: 606.0, 627.9.

EXAMPLE 45

3-[5-Methyl-3-(2-(N-methyl-N-(2-(2-pyridyl)ethyl) aminosulfonyl)phenylsulfonyloxy)phenoxy] propoxyguanidine dihydrochloride a) N,N'-(Bis-tert-butyloxycarbonyl)-{3-[5-methyl-3-(2-(N-methyl-N-(2-(2-pyridyl)ethyl)aminosulfonyl) phenylsulfonyloxy)phenoxy]propoxy}guanidine The title compound was prepared in 67% yield from 2-(2-methylaminoethyl)pyridine in a manner analogous to step h of Example 20. $^1$H-NMR (300 MHz, $CDCl_3$) δ9.08 (s, 1H), 8.44 (d, J=4.9 Hz, 1H), 8.21 (d, J=7.9 Hz, 1H), 8.10 (d, J=7.9 Hz, 1H), 7.77 (d, J=7.7 Hz, 1H), 7.72 (d, J=7.7 Hz, 1H), 7.62 (t, J=7.8 Hz, 1H), 7.60 (t, J=7.6 Hz, 1H), 7.23 (d, J=7.8 Hz, 1H), 7.11 (m, 1H), 6.58 (s, 1H), 6.56 (s, 1H), 6.50 (s, 1H), 4.17 (t, J=6.2 Hz, 2H), 3.92 (t, J=6.1 Hz, 2H), 3.75 (t, J=7.4 Hz, 2H), 3.11 (t, J=7.5 Hz, 2H), 2.96 (s, 3H), 2.22 (s, 3H), 2.09 (pentet, J=6.2 Hz, 2H), 1.49 (s, 18H).

b) 3-[5-Methyl-3-(2-(N-methyl-N-(2-(2-pyridyl)ethyl) aminosulfonyl)phenylsulfonyloxy)phenoxy] propoxyguanidine dihydrochloride The title compound was prepared in 89% yield from N,N'-(bis-tert-butyloxycarbonyl)-{3-[5-methyl-3-(2-(N-methyl-N-(2-(2-pyridyl)ethyl)aminosulfonyl) phenylsulfonyloxy)phenoxy]propoxy}guanidine, as prepared in the preceding step, in a manner analogous to step i of Example 20. $^1$H-NMR (300 MHz, DMSO-$d_6$) δ11.14 (br s, 2H), 8.58 (d, J=4.5 Hz, 1H), 8.10 (d, J=7.8 Hz, 1H), 8.06 (d, J=7.8 Hz, 1H), 7.98 (t, J=7.7 Hz, 2H), 7.57 (t, J=7.6 Hz, 1H), 7.71 (br s, 4H), 7.56 (br s, 1H), 7.47 (m, 1H), 6.74 (s, 1H), 6.51 (s, 1H), 6.46 (s, 1H), 3.97 (t, J=6.2 Hz, 2H), 3.90 (t, J=6.2 Hz, 2H), 3.74 (t, J=7.3 Hz, 2H), 3.17 (t, J=7.1 Hz, 2H), 2.98 (s, 3H), 2.21 (s, 3H), 2.01 (pentet, J=6.2 Hz, 2H). Mass spectrum (MALDI-TOF, α-cyano-4-hydroxycinnamic acid matrix) calcd. for $C_{25}H_{31}N_5O_7S_2$: 578.2 (M+H), 600.2 (M+Na). Found: 578.2, 600.0.

EXAMPLE 46

3-[5-Methyl-3-(2-(N-propyl-N-(2-(2-pyridyl)ethyl) aminosulfonyl)phenylsulfonyloxy)phenoxy] propoxyguanidine dihydrochloride a) N,N'-(Bis-tert-butyloxycarbonyl)-{3-[5-methyl-3-(2-(N-propyl-N-(2-(2-pyridyl)ethyl)aminosulfonyl) phenylsulfonyloxy)phenoxy]propoxy}guanidine The title compound was prepared in 53% yield from 2-[2-(N-propylamino)ethyl]pyridine in a manner analogous to step h of Example 20. $^1$H-NMR (300 MHz, $CDCl_3$) δ9.08 (s, 1H), 8.43 (d, J=4.9 Hz, 1H), 8.22 (d, J=7.9 Hz, 1H), 8.07 (d, J=7.9 Hz, 1H), 7.75 (m, 3H), 7.61 (t, J=7.7 Hz, 1H), 7.32 (m, 2H), 7.20 (m, 2H), 6.56 (s, 2H), 6.51 (s, 1H), 4.17 (t, J=6.2 Hz, 2H), 3.92 (t, J=6.1 Hz, 2H), 3.82 (t, J=7.4 Hz, 2H), 3.39 (t, J=7.5 Hz, 2H), 3.15 (t, J=6.6 Hz, 2H), 2.15 (s, 3H), 2.09 (t, J=6.1 Hz, 2H), 1.61 (m, 2H), 1.49 (s, 18H), 0.84 (pentet, J=7.4 Hz, 3H).

b) 3-[5-Methyl-3-(2-(N-propyl-N-(2-(2-pyridyl)ethyl) aminosulfonyl)phenylsulfonyloxy)phenoxy] propoxyguanidine dihydrochloride The title compound was prepared in 89% yield from N,N'-(bis-tert-butyloxycarbonyl)-{3-[5-methyl-3-(2-(N-propyl-N-(2-(2-pyridyl)ethyl)aminosulfonyl) phenylsulfonyloxy)phenoxy]propoxy}guanidine, as prepared in the preceding step, in a manner analogous to step i of Example 20. $^1$H-NMR (300 MHz, DMSO-$d_6$) δ11.08 (br s, 2H), 8.43 (d, J=4.0 Hz, 1H), 8.11 (d, J=7.9 Hz, 1H), 8.09 (d, J=7.7 Hz, 1H), 7.95 (t, J=7.7 Hz, 1H), 7.84 (t, J=7.7 Hz, 1H), 7.68 (br s, 5H), 7.27 (m, 2H), 6.73 (s, 1H), 6.53 (s, 1H), 6.49 (s, 1H), 3.97 (t, J=6.2 Hz, 2H), 3.89 (t, J=6.3 Hz, 2H), 3.71 (t, J=7.8 Hz, 2H), 3.34 (t, J=7.5 Hz, 2H), 3.01 (t, J=7.6 Hz, 2H), 2.20 (s, 3H), 2.00 (pentet, J=6.2 Hz, 2H), 1.52 (m, 2H), 0.77 (t, J=7.4 Hz, 3H). Mass spectrum (MALDI-TOF, α-cyano-4-hydroxycinnamic acid matrix) calcd. for $C_{27}H_{35}N_5O_7S_2$: 606.2 (M+H), 628.2 (M+Na). Found: 606.2, 628.3.

EXAMPLE 47

3-[5-Methyl-3-(2(N-ethyl-N-(4-pyridylmethyl) aminosulfonyl)phenylsulfonyloxy)phenoxy] propoxyguanidine dihydrochloride a) N,N'-(Bis-tert-butyloxycarbonyl)-{3-[5-methyl-3-(2-(N-ethyl-N-(4-pyridylmethyl)aminosulfonyl) phenylsulfonyloxy)phenoxy]propoxy}guanidine The title compound was prepared in 48% yield from 4-(N-ethyl)aminomethylpyridine in a manner analogous to step h of Example 20. $^1$H-NMR (300 MHz, $CDCl_3$) δ9.08 (s, 1H), 8.56 (d, J=4.7 Hz, 2H), 8.37 (d, J=7.8 Hz, 1H), 8.16 (d, J=7.8 Hz, I1H), 7.77 (t, J=7.7 Hz, 1H), 7.68 (d, J=7.8 Hz, 2H), 7.28 (m, 2H), 6.58 (s, 2H), 6.53 (s, 1H), 4.70 (s, 2H), 4.17 (t, J=6.2 Hz, 2H), 3.93 (t, J=6.1 Hz, 2H), 3.32 (t, J=7.4 Hz, 2H), 2.23 (s, 3H), 2.09 (pentet, J=6.1 Hz, 2H), 1.49 (s, 18H), 0.94 (t, J=7.2 Hz, 3H).

b) {3-[5-Methyl-3-(2-(N-ethyl-N-(4-pyridylmethyl)aminosulfonyl)phenylsulfonyloxy)phenoxy]propoxy}guanidine dihydrochloride The title compound was prepared in 84% yield from N,N'-(Bis-tert-butyloxycarbonyl)-{3-[5-methyl-3-(2-(N-ethyl-N-(4-pyridylmethyl)aminosulfonyl)phenylsulfonyloxy)phenoxy]propoxy}guanidine, as prepared in the preceding step, in a manner analogous to step i of Example 20. $^{1}$H-NMR (300 MHz, DMSO-$d_6$) δ8.54 (d, J=4.5 Hz, 2H), 8.23 (d, J=7.9 Hz, 1H), 8.17 (d, J=7.8 Hz, 1H), 8.01 (t, J=7.7 Hz, 1H), 7.89 (t, J=7.7 Hz, 1H), 7.42 (br s, 4H), 7.34 (d, J=5.8 Hz, 2H), 6.74 (s, 1H), 6.54 (s, 1H), 6.50 (s, 1H), 4.67 (s, 2H), 3.97 (t, J=6.3 Hz, 2H), 3.87 (t, J=6.3 Hz, 2H), 3.36 (t, J=7.1 Hz, 2H), 2.21 (s, 3H), 2.00 (pentet, J=6.1 Hz, 2H), 0.92 (t, J=7.1 Hz, 3H). Mass spectrum (MALDI-TOF, α-cyano-4-hydroxycinnamic acid matrix) calcd. for $C_{25}H_{31}N_5O_7S_2$: 578.2 (M+H), 600.2 (M+Na), 616.1 (M+K). Found: 578.1, 599.9, 616.0.

EXAMPLE 48

3-[5-Methyl-3-(2-(N-methyl-N-(4-methoxyphenyl)aminosulfonyl)phenylsulfonyloxy)phenoxy]propoxyguanidine hydrochloride a) N,N'(Bis-tert-butyloxycarbonyl)-{3-[5-methyl-3-(2-(N-methyl-N-(4-methoxyphenyl)aminosulfonyl)phenylsulfonyloxy)phenoxy]propoxy}guanidine The title compound was prepared in 80% yield from N-methyl-p-anisidine in a manner analogous to step h of Example 20. $^{1}$H-NMR (300 MHz, CDCl$_3$) δ9.08 (s, 1H), 8.15 (d, J=7.6 Hz, 1H), 7,78 (d, J=7.6 Hz, 1H), 7.71 (br s, 1H), 7.57 (t, J=7.7 Hz, 2H), 7.11 (d, J=8.9 Hz, 2H), 6.77 (d, J=8.9 Hz, 2H), 6.61 (s, 1H), 6.58 (s, 2H), 4.18 (t, J=6.1 Hz, 2H), 3.94 (t, J=6.2 Hz, 2H), 3.77 (s, 3H), 3.44 (s, 3H), 2.23 (s, 3H), 2.09 (pentet, J=6.1 Hz, 2H), 1.49 (s, 18H).

b) 3-[5-Methyl-3-(2-(N-methyl-N-(4-methoxyphenyl)aminosulfonyl)phenylsulfonyloxy)phenoxy]propoxyguanidine hydrochloride The title compound was prepared in 92% yield from N,N'-(Bis-tert-butyloxycarbonyl)-{3-[5-methyl-3-(2-(N-methyl-N-(4-methoxyphenyl)aminosulfonyl)phenylsulfonyloxy)phenoxy]propoxy}guanidine, as prepared in the preceding step, in a manner analogous to step i of Example 20. $^{1}$H-NMR (300 MHz, DMSO-$d_6$) δ11.04 (s, 1H), 8.16 (d, J=6.7 Hz, 1H), 7.88 (m, 3H), 7.66 (br s, 4H), 7.16 (d, J=8.9 Hz, 2H), 6.88 (d, J=8.9 Hz, 2H), 6.673 (s, 1H), 6.48 (s, 2H), 3.97 (t, J=6.2 Hz, 2H), 3.90 (t, J=6.3 Hz, 2H), 3.72 (s, 3H), 3.35 (s, 3H), 2.19 (s, 3H), 2.01 (pentet, J=6.3 Hz, 2H). Mass spectrum (MALDI-TOF, α-cyano-4-hydroxycinnamic acid matrix) calcd. for $C_{25}H_{30}N_4O_8S_2$: 579.2 (M+H), 601.1 (M+Na), 617.1 (M+K). Found: 579.1, 601.3, 617.2.

EXAMPLE 49

3-[5-Methyl-3-(2-(4-ethylpiperazin-1-ylsulonyl)phenylsulfonyloxy)phenoxy]propoxyguanidine dihydrochloride a) N,N'(Bis-tert-butyloxycarbonyl)-{3-[5-methyl-3-(2-(4-ethylpiperazin-1-ylsulfonyl)phenylsulfonyloxy)phenoxy]propoxy}guanidine The title compound was prepared in 23% yield from N-ethylpiperazine in a manner analogous to step h of Example 20. $^{1}$H-NMR (300 MHz, CDCl$_3$) δ9.08 (s, 1H), 8.20 (t, J=8.2 Hz, 2H), 7.80 (t, J=7.8 Hz, 1H), 7.69 (m, 2H), 6.57 (s, 2H), 6.51 (s, 1H), 4.18 (t, J=6.2 Hz, 2H), 3.94 (t, J=6.2 Hz, 2H), 3.40 (t, J=4.8 Hz, 4H), 2.51 (t, J=4.8 Hz, 4H), 2.43 (q, J=7.2 Hz, 2H), 2.23 (s, 3H), 2.10 (pentet, J=6.2 Hz, 2H), 1.49 (s, 18H), 1.05 (t, J 7.2 Hz, 3H).

b) 3-[5-Methyl-3-(2-(4-ethylpiperazin-1-ylsulfonyl)phenylsulfonyloxy)phenoxy]propoxyguanidine dihydrochloride The title compound was prepared in 80% yield from N,N'-(Bis-tert-butyloxycarbonyl)-{3-[5-methyl-3-(2-(4-ethylpiperazin-1-ylsulfonyl)phenylsulfonyloxy)phenoxy]propoxy}guanidine, as prepared in the preceding step, in a manner analogous to step i of Example 20. $^{1}$H-NMR (300 MHz, DMSO-$d_6$) δ11.06 (br s, 1H), 10.89 (br s, 1H), 8.29 (d, J=7.9 Hz, 1H), 8.19 (d, J=7.9 Hz, 1H), 8.07 (t, J=7.8 Hz, 1H), 7.94 (t, J=7.7 Hz, 1H), 7.66 (br s, 4H), 6.76 (s, 1H), 6.51 (s, 1H), 6.48 (s, 1H), 3.99 (t, J=6.2 Hz, 2H), 3.90 (t, J=6.3 Hz, 2H), 3.52 (br s, 2H), 3.33 (br s, 4H), 3.26 (br s, 2H), 3.13 (br s, 2H), 2.22 (s, 3H), 2.02 (pentet, J=6.2 Hz, 2H), 1.21 (t, J=7.2 Hz, 3H). Mass spectrum (MALDI-TOF, α-cyano-4-hydroxycinnamic acid matrix) calcd. for $C_{23}H_{33}N_5O_7S_2$: 556.2 (M+H), 578.2 (M+Na), 594.1 (M+K). Found: 555.9, 577.9, 593.7.

EXAMPLE 50

3-[5-Methyl-3-(2-(N-methyl-N-(4-methoxycarbonylphenyl)aminosulfonyl)phenylsulfonyloxy)phenoxy]propoxyguanidine hydrochloride a) N,N-(Bis-tert-butyloxycarbonyl)-{3-[5-methyl-3-(2-(N-methyl-N-(4-methoxycarbonylphenyl)aminosulfonyl)phenylsulfonyloxy)phenoxy]propoxy}guanidine The title compound was prepared in 80% yield from methyl 4-methylaminobenzoate in a manner analogous to step h of Example 20. $^{1}$H-NMR (300 MHz, CDCl$_3$) δ9.11 (s, 1H), 8.14 (d, J=9.0Hz, 1H), 7.94 (d, J=8.8 Hz, 2H), 7.86 (d, J=9.1 Hz, 1H), 7.60 (m, 2H), 7.34 (d, J=8.8 Hz, 2H), 6.58 (s, 1H), 6.54 (s, 1H), 6.51 (s, 1H), 4.18 (t, J=6.1 Hz, 2H), 3.93 (t, J=6.1 Hz, 2H), 3.89 (s, 3H), 3.51 (s, 3H), 2.22 (s, 3H), 2.10 (pentet, J=6.0 Hz, 2H), 1.49 (s, 18H).

b) {3-[5-Methyl-3-(2-(N-methyl-N-(4-methoxycarbonylphenyl)aminosulfonyl)phenylsulfonyloxy)phenoxy]propoxy}guanidine hydrochloride The title compound was prepared in 92% yield from N,N'-(Bis-tert-butyloxycarbonyl)-{3-[5-methyl-3-(2-(N-methyl-N-(4-methoxycarbonylphenyl)aminosulfonyl)phenylsulfonyloxy)phenoxy]propoxy}guanidine, as prepared in the preceding step, in a manner analogous to step i of Example 20. $^{1}$H-NMR (300 MHz, DMSO-$d_6$) δ11.07 (br s, 1H), 8.17 (d, J=7.5 Hz, 1H), 7.88–7.99 (m, 5H), 7.67 (br s, 4H), 7.43 (d, J=7.7 Hz, 2H), 6.74 (s, 1H), 6.45 (s, 2H), 3.98 (t, J=6.2 Hz, 2H), 3.90 (t, J=6.3 Hz, 2H), 3.83 (s, 3H), 3.46 (s, 3H), 2.19 (s, 3H), 2.02 (pentet, J=6.2 Hz, 2H). Mass spectrum (MALDI-TOF, α-cyano-4-hydroxycinnamic acid matrix) calcd. for $C_{26}H_{30}N_4O_9S_2$: 607.2 (M+H), 629.1 (M+Na). Found: 606.9, 628.8.

EXAMPLE 51

3-[5-Methyl-3-(2-(N-(2-cyanoethyl)-N-(3-pyridylmethyl)aminosulfonyl)phenylsulfonyloxy)phenoxy]propoxyguanidine dihydrochloride a) N,N'-(Bis-tert-butyloxycarbonyl)-{3-[5-methyl-3-(2-(N-(2-cyanoethyl)-N-(3-pyridylmethyl)aminosulfonyl)phenylsulfonyloxy)phenoxy]propoxy}guanidine The title compound was prepared in 66% yield from 3-(3-pyridylmethylamino)propionitrile in a manner analogous to step h of Example 20. $^{1}$H-NMR (300 MHz, CDCl$_3$)

δ9.08 (s, 1H), 8.56 (br s, 1H), 8.50 (br s, 1H), 8.35 (d, J=7.7 Hz, 1H), 8.18 (d, J=7.8 Hz, 1H), 7.81 (t, J=7.7 Hz, 1H), 7.72 (m, 3H), 7.29 (t, J=7.7 Hz, 1H), 6.60 (s, 1H), 6.57 (s, 1H), 6.52 (s, 1H), 4.70 (s, 2H), 4.17 (t, J=6.2 Hz, 2H), 3.94 (t, J=6.2 Hz, 2H), 3.65 (t, J=7.0 Hz, 2H), 2.50 (t, J=7.0 Hz, 2H), 2.24 (s, 3H), 2.12 (pentet, J=6.3 Hz, 2H), 1.49 (s, 18H).

b) 3-[5-Methyl-3-(2-(N-(2-cyanoethyl)-N-(3-pyridylmethyl)aminosulfonyl)phenylsulfonyloxy)phenoxy]propoxyguanidine dihydrochloride The title compound was prepared in 91% yield from N,N'-(bis-tert-butyloxycarbonyl)-{3-[5-methyl-3-(2-(N-(2-cyanoethyl)-N-(3-pyridylmethyl)aminosulfonyl)phenylsulfonyloxy)phenoxy]propoxy}guanidine, as prepared in the preceding step, in a manner analogous to step i of Example 20. $^1$H-NMR (300 MHz, DMSO-d$_6$) δ11.09 (s, 1H), 8.70 (m, 2H), 8.27 (d, J=7.9 Hz, 1H), 8.15 (t, J=7.8 Hz, 2H), 8.01 (t, J=7.7 Hz, 1H), 7.91 (t, J=7.7 Hz, 1H), 7.75 (t, J=7.7 Hz, 1H), 7.68 (br s, 4H), 6.75 (s, 1H), 6.54 (s, 1H), 6.51 (s, 1H), 4.81 (s, 2H), 3.99 (t, J=6.2 Hz, 2H), 3.90 (t, J=6.3 Hz, 2H), 3.68 (t, J=6.7 Hz, 2H), 2.73 (t, J=6.6 Hz, 2H), 2.22 (s, 3H), 2.01 (pentet, J=6.3 Hz, 2H). Mass spectrum (MALDI-TOF, α-cyano-4-hydroxycinnamic acid matrix) calcd. for C$_{26}$H$_{30}$N$_6$O$_7$S$_2$: 603.2 (M+H), 625.1 (M+Na); Found: 603.0, 624.9.

EXAMPLE 52

3-[5-Methyl-3-(2-(N,N-bis-(2-cyanoethyl)aminosulfonyl)phenylsulfonyloxy)phenoxy]propoxyguanidine hydrochloride a) N,N'-(Bis-tert-butyloxycarbonyl)-N''-{3-[5-methyl-3-(2-(N,N-bis-(2-cyanoethyl)aminosulfonyl)phenylsulfonyloxy)phenoxy]propoxy}guanidine The title compound was prepared in 46% yield from 3,3'-iminodipropionitrile in a manner analogous to step h of Example 20. $^1$H-NMR (300 MHz, CDCl$_3$) δ9.08 (s, 1H), 8.39 (d, J=7.9 Hz, 1H), 8.19 (d, J=7.8 Hz, 1H), 7.88 (t, J=7.7 Hz, 1H), 7.76 (t, J=7.7 Hz, 1H), 7.70 (s, 1H), 6.60 (s, 1H), 6.55 (s, 1H), 6.49 (s, 1H), 4.17 (t, J=6.2 Hz, 2H), 3.94 (t, J=6.2 Hz, 2H), 3.78 (t, J=6.8 Hz, 4H), 2.73 (t, J=6.8 Hz, 4H), 2.24 (s, 3H), 2.10 (pentet, J=6.2 Hz, 2H), 1.49 (s, 18H).

b) 3-[5-Methyl-3-(2-(N,N-bis-(2-cyanoethyl)aminosulfonyl)phenylsulfonyloxy)phenoxy]propoxyguanidine hydrochloride The title compound was prepared in 85% yield from N,N'-(bis-tert-butyloxycarbonyl)-N''-{3-[5-methyl-3-(2-(N,N-bis-(2-cyanoethyl)aminosulfonyl)phenylsulfonyloxy)phenoxy]propoxy}guanidine, as prepared in the preceding step, in a manner analogous to step i of Example 20. $^1$H-NMR (300 MHz, DMSO-d$_6$) δ11.05 (br s, 1H), 8.25 (d, J=7.9 Hz, 1H), 8.14 (d, J=7.8 Hz, 1H), 8.01 (t, J=7.7 Hz, 1H), 7.90 (t, J=7.7 Hz, 1H), 7.66 (br s, 4H), 6.74 (s, 1H), 6.54 (s, 1H), 6.51 (s, 1H), 3.99 (t, J=6.2 Hz, 2H), 3.91 (t, J=6.3 Hz, 2H), 3.71 (t, J=6.8 Hz, 4H), 2.84 (t, J=6.8 Hz, 4H), 2.22 (s, 3H), 2.02 (pentet, J=6.2 Hz, 2H). Mass spectrum (MALDI-TOF, α-cyano-4-hydroxycinnamic acid matrix) calcd. for C$_{23}$H$_{28}$N$_6$O$_7$S$_2$: 565.2 (M+H), 587.1 (M+Na); Found: 565.2, 587.0.

EXAMPLE 53

3-[5-Methyl-3-(2-(N-(2-ethoxycarbonylethyl)-N-benzylaminosulfonyl)phenylsulfonyloxy)phenoxy]propoxyguanidine hydrochloride a) N,N'-(Bis-tert-butyloxycarbonyl)-{3-[5-methyl-3-(2-(N-(2-ethoxycarbonylethyl)-N-benzylaminosulfonyl)phenylsulfonyloxy)phenoxy]propoxy}guanidine The title compound was prepared in 74% yield from N-benzyl-3-aminopropionic acid ethyl ester in a manner analogous to step h of Example 20. $^1$H-NMR (300 MHz, CDCl$_3$) δ9.02 (s, 1H), 8.76 (s, 1H), 8.16 (t, J=8.1 Hz, 2H), 7.98 (t, J=7.7 Hz, 1H), 7.88 (t, J=7.8 Hz, 1H), 7.34 (m, 5H), 6.74 (s, 1H), 6.54 (s, 1H), 6.47 (s, 1H), 4.63 (s, 2H), 3.91 (m, 6H), 3.53 (t, J=7.2 Hz, 2H), 2.37 (t, J=7.3 Hz, 4H), 2.21 (s, 3H), 1.96 (pentet, J=6.2 Hz, 2H), 1.39 (s, 18H), 1.09 (t, J=7.1 Hz, 3H).

b) 3-[5-Methyl-3-(2-(N-(2-ethoxycarbonylethyl)-N-benzylaminosulfonyl)phenylsulfonyloxy)phenoxy]propoxyguanidine hydrochloride The title compound was prepared in 92% yield from N,N'-(bis-tert-butyloxycarbonyl)-{3-[5-methyl-3-(2-(N-(2-ethoxycarbonylethyl)-N-benzylaminosulfonyl)phenylsulfonyloxy)phenoxy]propoxy}guanidine, as prepared in the preceding step, in a manner analogous to step i of Example 20. $^1$H-NMR (300 MHz, DMSO-d$_6$) δ11.10 (br s, 1H, 8.18 (t, J=8.8 Hz, 2H), 7.99 (t, J=7.7 Hz, 1H), 7.89 (t, J=7.8 Hz, 1H), 7.69 (br s, 4H), 7.34 (m, 5H), 6.75 (s, 1H), 6.54 (s, 1H), 6.52 (s, 1H), 4.63 (s, 2H), 3.98 (t, J=6.2 Hz, 2H), 3.91 (q, J=7.0 Hz, 4H), 3.53 (t, J=7.3 Hz, 2H), 2.38 (t, J=7.3 Hz, 4H), 2.21 (s, 3H), 2.01 (pentet, J=6.2 Hz, 2H), 1.09 (t, J=7.1 Hz, 3H). Mass spectrum (MALDI-TOF, α-cyano-4-hydroxycinnamic acid matrix) calcd. for C$_{29}$H$_{36}$N$_4$O$_9$S$_2$: 649.2 (M+H), 671.2 (M+Na); Found: 649.0, 671.0.

EXAMPLE 54

3-[5-Methyl-3-(2-(4-(piperidin-1-yl)piperidin-1-ylsulfonyl)phenylsulfonyloxy)phenoxy]propoxyguanidine dihydrochloride a) N,N'-(Bis-tert-butyloxycarbonyl)-{3-[5-methyl-3-(2-(4-(piperidin-1-yl)piperidin-1-ylsulfonyl)phenylsulfonyloxy)phenoxy]propoxy}guanidine The title compound was prepared in 37% yield from 4-piperidinopiperidine in a manner analogous to step h of Example 20. $^1$H-NMR (300 MHz, CDCl$_3$) δ9.08 (s, 1H), 8.31 (d, J=7.9 Hz, 1H), 8.15 (d, J=7.9 Hz, 1H), 7.82 (t, J=7.7 Hz, 1H), 7.70 (m, 2H), 6.60 (s, 1H), 6.52 (s, 1H), 6.47 (s, 1H), 4.17 (t, J=6.2 Hz, 2H), 4.07 (m, 2H), 3.94 (t, J=6.2 Hz, 2H), 2.88 (m, 3H), 2.27 (m, 2H), 2.24 (s, 3H), 2.10 (pentet, J=6.2 Hz, 2H), 1.51–1.96 (m, 10H), 1.49 (s, 18H), 1.25 (m, 2H).

b) 3-[5-Methyl-3-(2-(4-(piperidinyl-yl)piperidin-1-ylsulfonyl)phenylsulfonyloxy)phenoxy]propoxyguanidine dihydrochloride The title compound was prepared in 88% yield from N,N'-(Bis-tert-butyloxycarbonyl)-{3-[5-methyl-3-(2-(4-(piperidin-1-yl)piperidin-1-ylsulfonyl)phenylsulfonyloxy)phenoxy]propoxy}guanidine, as prepared in the preceding step, in a manner analogous to step i of Example 20. $^1$H-NMR (300 MHz, DMSO-d$_6$) δ11.10 (br s, 1H), 10.29 (br s, 1H), 8.24 (d, J=7.9 Hz, 1H), 8.17 (d, J=7.9 Hz, 1H), 8.03 (t, J=7.7 Hz, 1H), 7.91 (t, J=7.7 Hz, 1H), 7.68 (br s, 4H), 6.75 (s, 1H), 6.52 (s, 1H), 6.48 (s, 1H), 3.98 (t, J=6.2 Hz, 4H), 3.90 (t, J=6.3 Hz, 2H), 3.35 (m, 5H), 2.88 (m, 4H), 2.22 (s, 3H), 2.16 (m, 2H), 2.02 (pentet, J=6.3 Hz, 2H), 1.67–1.79 (m, 6H). Mass spectrum (MALDI-TOF, α-cyano-4-hydroxycinnamic acid matrix) calcd. for C$_{27}$H$_{39}$N$_5$O$_7$S$_2$: 610.2 (M+H), 632.2 (M+Na), 648.2 (M+K); Found: 610.1, 632.0, 648.1.

EXAMPLE 55

{3-[5-Methyl-3-(2-(N-methyl-N-(2-(4-pyridyl)ethyl)aminosulfonyl)phenylsulfonyloxy)phenoxy]propoxy}guanidine dihydrochloride a) N,N'-(Bis-tert-butyloxycarbonyl)-{3-[5-methyl-3-(2-(N-methyl-N-(2-(4-pyridyl)ethyl)aminosulfonyl)phenylsulfonyloxy)phenoxy]propoxy}guanidine The title compound was prepared in 15% yield from 4-[(2-methylamino)ethyl]pyridine in a manner analogous to step h of Eg. 20. $^1$H-NMR (300 MHz, CDCl$_3$) δ9.08 (s, 1H), 8.55 (d, J=5.1 Hz, 2H), 8.24 (d, J=7.7 Hz, 1H), 8.12 (d, J=7.8 Hz, 1H), 7.69 (m, 3H), 7.30 (m, 2H), 6.58 (s, 1H), 6.54 (s, 1H), 6.48 (s, 1H), 4.18 (t, J=6.2 Hz, 2H), 3.92 (t, J=6.2 Hz, 2H), 3.65 (t, J=7.3 Hz, 2H), 3.05 (t, J=7.4 Hz, 2H), 2.90 (s, 3H), 2.23 (s, 3H), 2.08 (pentet, J=6.2 Hz, 2H), 1.49 (s, 18H).

b) {3-[5-Methyl-3-(2-(N-methyl-N-(2-(4-pyridyl)ethyl)aminosulfonyl)phenylsulfonyloxy)phenoxy]propoxy}guanidine dihydrochloride The title compound was prepared in 83% yield from N,N'-(bis-tert-butyloxycarbonyl)-{3-[5-methyl-3-(2-(N-methyl-N-(2-(4-pyridyl)ethyl)aminosulfonyl)phenylsulfonyloxy)phenoxy]propoxy}guanidine, as prepared in the preceding step, in a manner analogous to step i of Example 20. $^1$H-NMR (300 MHz, CDCl$_3$/CD$_3$OD) δ8.72 (br s, 2H), 8.15 (t, J=7.8 Hz, 2H), 7.65–7.95 (m, 3H), 7.74 (t, 7.4 Hz, 1H), 6.64 (s, 1H), 6.60 (s, 1H), 6.45 (s, 1H), 4.03 (br s, 2H), 3.94 (br s, 2H), 3.83 (br s, 2H), 3.39 (m, 2H), 2.98 (s, 3H), 2.27 (s, 3H), 2.07 (m, 2H). Mass spectrum (MALDI-TOF, α-cyano-4-hydroxycinnamic acid matrix) calcd. for C$_{25}$H$_{31}$N$_5$O$_7$S$_2$: 578.2 (M+H), 600.2 (M+Na); Found: 578.0, 599.9.

EXAMPLE 56

3-[5-Methyl-3-(2-(N-(ethoxycarbonylmethyl)-N-(2-pyridylmethyl)aminosulfonyl)phenylsulfonyloxy)phenoxy]propoxyguanidine dihydrochloride a) N,N'-(Bis-tert-butyloxycarbonyl)-{3-[5-methyl-3-(2-(N-(ethoxycarbonylmethyl)-N-(2-pyridylmethyl)aminosulfonyl)phenylsulfonyloxy)phenoxy]propoxy}guanidine The title compound was prepared in 38% yield from N-(pyridylmethyl)glycine ethyl ester in a manner analogous to step h of Example 20. $^1$H-NMR (300 MHz, CDCl$_3$), δ9.05 (s, 1H), 8.47 (d, J=4.0 Hz, 1H), 8.37 (d, J=7.8 Hz, 1H), 8.14 (d, J=7.9 Hz, 1H), 7.75 (t, J=7.7 Hz, 1H), 7.63 (m, 3H), 7.40 (t, J=7.9 Hz, 1H), 6.57 (s, 2H), 6.53 (s, 1H), 4.73 (s, 3H), 4.31 (s, 3H), 4.16 (t, J=6.2 Hz, 2H), 4.02 (q, J=7.1 Hz, 2H), 3.92 (t, J=6.1 Hz, 2H), 2.21 (s, 3H), 2.07 (pentet, J=6.2 Hz, 2H), 1.49 (s, 18H), 1.15 (t, J=7.1 Hz, 3H).

b) 3-[5-Methyl-3-(2-(N-(ethoxycarbonylmethyl)-N-(2-pyridylmethyl)aminosulfonyl)phenylsulfonyloxy)phenoxy]propoxyguanidine dihydrochloride The title compound was prepared in 90% yield from N,N'-(Bis-tert-butyloxycarbonyl)-{ 3-[5-methyl-3-(2-(N-(ethoxycarbonylmethyl)-N-(2-pyridylmethyl)aminosulfonyl)phenylsulfonyloxy)phenoxy]propoxy}guanidine, as prepared in the preceding step, in a manner analogous to step i of Example 20. $^1$H-NMR (300 MHz, DMSO-d$_6$) δ8.54 (d, J=4.4 Hz, 1H), 8.39 (d, J=7.8 Hz, 1H), 8.14 (d, J=7.8 Hz, 1H), 7.97 (t, J=7.7 Hz, 1H), 7.87 (t, J=7.8 Hz, 2H), 7.67 (br s, 4H), 7.43 (t, J=7.7 Hz, 2H), 6.75 (s, 1H), 6.53 (s, 1H), 6.50 (s, 1H), 4.76 (s, 3H), 4.36 (s, 3H), 3.97 (q, J=7.1 Hz, 2H), 3.90 (t, J=6.5 Hz, 4H), 2.22 (s, 3H), 2.02 (pentet, J=6.4 Hz, 2H), 1.06 (t, J=7.1 Hz, 3H). Mass spectrum (MALDI-TOF, α-cyano-4-hydroxycinnamic acid matrix) calcd. for C$_{27}$H$_{33}$N$_5$O$_9$S$_2$: 636.2 (M+H), 658.2 (M+Na); Found: 636.0, 658.0.

EXAMPLE 57

3-[5-Methyl-3-(2-(N,N-bis(ethoxycarbonylmethyl)aminosulfonyl)phenylsulfonyloxy)phenoxy]propoxyguanidine hydrochloride a) N,N'-(Bis-tert-butyloxycarbonyl)-{3-[5-methyl-3-(2-(N,N-bis(ethoxycarbonylmethyl)aminosulfonyl)phenylsulfonyloxy)phenoxy]propoxy}guanidine The title compound was prepared in 76% yield from diethyl iminodiacetate in a manner analogous to step h of Eg. 20. $^1$H-NMR (300 MHz, CDCl$_3$) δ9.07 (s, 1H), 8.35 (d, J=7.9 Hz, 1H), 8.15 (d, J=7.8 Hz, 1H), 7.79 (t, J=7.7 Hz, 1H), 7.69 (d, J=7.9 Hz, 1H), 7.66 (t, J 7.7 Hz, 1H), 6.57 (s, 2H), 6.52 (s, 1H), 4.35 (s, 4H), 4.18 (t, J 6.2 Hz, 2H), 4.12 (q, J=7.1 Hz, 4H), 3.94 (t, J=6.2 Hz, 2H), 2.23 (s, 3H), 2.10 (pentet, J 6.2 Hz, 2H), 1.49 (s, 18H), 1.21 (t, J=7.1 Hz, 6H).

b) 3-[5-Methyl-3-(2-(N,N-bis(ethoxycarbonylmethyl)aminosulfonyl)phenylsulfonyloxy)phenoxy]propoxyguanidine hydrochloride The title compound was prepared in 74% yield from N,N'-(bis-tert-butyloxycarbonyl)-{3-[5-methyl-3-(2-(N,N-bis(ethoxycarbonylmethyl)aminosulfonyl)phenylsulfonyloxy)phenoxy]prepared in the preceding step, in a manner analogous to step i of Example 20. $^1$H-NMR (300 MHz, DMSO-d$_6$) δ8.41 (d, J=7.9 Hz, 1H), 8.13 (d, J=7.8 Hz, 1H), 7.98 (t, J=7.7 Hz, 1H), 7.88 (d, J=7.8 Hz, 1H), 7.65 (br s, 4H), 6.75 (s, 1H), 6.52 (s, 1H), 6.49 (s, 1H), 4.30 (s, 4H), 4.99 (q, J=7.1 Hz, 6H), 3.91 (t, J=6.3 Hz, 2H), 2.22 (s, 3H), 2.02 (pentet, J=6.2 Hz, 2H), 1.10 (t, J=7.1 Hz, 6H). Mass spectrum (MALDI-TOF, α-cyano-4-hydroxycinnamic acid matrix) calcd. for C$_{25}$H$_{34}$N$_4$O$_{11}$S$_2$: 631.2 (M+H), 653.2 (M+Na); Found: 630.9, 653.1.

EXAMPLE 58

3-[5-Methyl-3-(2-(4-(ethoxycarbonylmethyl)piperaziny1-ylsulfonyl)phenylsulfonyloxy)phenoxy]propoxyguanidine dihydrochloride a) N,N'-(Bis-tert-butyloxycarbonyl)-{3-[5-methyl-3-(2-(4-ethoxycarbonylmethyl)piperazin-1-ylsulfonyl)phenylsulfonyloxy)phenoxy]propoxy}guanidine The title compound was prepared in 74% yield from 1-(ethoxycarbonylmethyl)piperazine in a manner analogous to step h of Example 20. $^1$H-NMR (300 MHz, CDCl$_3$) δ9.08 (s, 1H), 8.23 (d, J=7.9 Hz, 1H), 8.19 (d, J=7.9 Hz, 1H), 7.80 (t, J=7.7 Hz, 1H), 7.71 (s, 1H), 7.68 (t, J=7.8 Hz, 1H), 6.59 (s, 1H), 6.56 (s, 1H), 6.51 (s, 1H), 4.17 (m, 4H), 3.94 (t, J=6.2 Hz, 2H), 3.47 (t, J=4.6 Hz, 4H), 3.25 (s, 2H), 2.72 (m, 4H), 2.23 (s, 3H), 2.10 (pentet, J=6.2 Hz, 2H), 1.49 (s, 18H), 1.26 (t, J=7.2 Hz, 3H).

b) 3-[5-Methyl-3-(2-(4-(ethoxycarbonylmethyl)piperazin-1-ylsulfonyl)henylsulfonyloxy)phenoxy]propoxyguanidine dihydrochloride The title compound was prepared in 82% yield from N,N'-(bis-tert-butyloxycarbonyl)-3-[5-methyl-3-(2-(4-(ethoxycarbonylmethyl)piperazin-1-ylsulfonyl)phenylsulfonyloxy)phenoxy]propoxy}guanidine, as prepared in the preceding step, in a manner analogous to step i of Example 20. $^1$H-NMR (300 MHz, DMSO-d$_6$) δ11.15 (s, 1H), 8.27 (d, J=7.8 Hz, 1H), 8.18 (d, J=7.8 Hz, 1H), 8.07 (t, J=7.7 Hz, 1H), 7.94 (t, J=7.8 Hz, 1H), 7.71 (br s, 4H), 6.75 (s, 1), 6.51 (s, 1H), 6.47 (s, 1H), 4.18 (q, J=7.1 Hz , 2H), 3.98 (t, J=6.2 Hz, 2H), 3.90 (t, J=6.3 Hz, 2H), 3.56 (br s, 6H), 3.20 (br s, 4H), 2.22 (s, 3H), 2.02 (pentet, J=6.2 Hz, 2H), 1.22 (t, J=7.2 Hz, 3H). Mass spectrum (MALDI-TOF, α-cyano-4-hydroxycinnamic acid matrix) calcd. for C$_{25}$H$_{35}$N$_5$O$_9$S$_2$: 614.2 (M+H), 636.2 (M+Na), 652.2 (M+K). Found 614.1, 636.0, 652.1.

EXAMPLE 59

3-[5-Methyl-3-(2-M -bis(carboxymethyl)aminosulfonyl)phenylsulfonyl)phenoxy]propoxyguanidine The title compound was prepared in 87% yield from 3-[5-methyl-3-(2-(N,N-bis(ethoxycarbonylmethyl)

aminosulfonyl)phenylsulfonyloxy)phenoxy]propoxyguanidine hydrochloride, as prepared in step b of Example 57, in a manner analogous to Example 27. $^1$H-NMR (300 MHz, DMSO-$d_6$) δ8.29 (d, J=7.0 Hz, 1H), 8.10 (d, J=7.6 Hz, 1H), 7.97 (t, J=7.6 Hz, 1H), 7.84 (t, J=7.6 Hz, 1H), 7.63 (br s, 4H), 6.72 (s, 1H), 6.58 (s, 1H), 6.49 (s, 1H), 4.13 (s, 4H), 3.97 (t, J=6.3 Hz, 2H), 3.90 (t, J=6.3 Hz, 2H), 2.23 (s, 3H), 2.03 (pentet, J=6.2 Hz, 2H). Mass spectrum (MALDI-TOF, α-cyano-4-hydroxycinnamic acid matrix) calcd. for $C_{21}H_{26}N_4O_{11}S_2$: 575.1 (M+H), 597.1 (M+Na), 613.1 (M+K). Found: 575.1, 597.0, 613.1.

EXAMPLE 60

3-[5-Methyl-3-(2-(N-methyl-N-(4-carboxyphenyl)aminosulfonyl)phenylsulfonyloxy)phenoxy]propoxyguanidine The title compound was prepared in 84% yield from 3-[5-methyl-3-(2-(N-methyl-N-(4-methoxycarbonylphenyl)aminosulfonyl)phenylsulfonyloxy)phenoxy]propoxyguanidine hydrochloride, as prepared in step b of Example 50, in a manner analogous to Example 27. $^1$H-NMR (300 MHz, DMSO-$d_6$) δ8.17 (d, J=7.4 Hz, 1H), 7.97 (t, J=7.6 Hz, 1H), 7.90 (m, 4H), 7.61 (br s, 4H), 7.40 (d, J=7.7 Hz, 2H), 6.74 (s, 1H), 6.45 (s, 2H), 3.98 (t, J=6.2 Hz, 2H), 3.90 (t, J=6.3 Hz, 2H), 3.46 (s, 3H), 2.19 (s, 3H), 2.01 (pentet, J=6.2 Hz, 2H). Mass spectrum (MALDI-TOF, α-cyano-4-hydroxycinnamic acid matrix) calcd. for $C_{25}H_{28}N_4O_9S_2$: 593.1 (M+H), 615.1 (M+Na), 631.1 (M+K). Found: 593.1, 615.0, 630.9.

EXAMPLE 61

3-[5-Methyl-3-(2-(N-(2-carboxyethyl)-N-benzylaminosulfonyl)phenylsulfonyloxy)phenoxy]propoxyguanidine The title compound was prepared in 97% yield from 3-[5-methyl-3-(2-(N-(2-ethoxycarbonylethyl)-N-benzylaminosulfonyl)phenylsulfonyloxy)phenoxy]propoxyguanidine hydrochloride as prepared in step b of Example 53, in a manner analogous to Example 27. $^1$H-NMR (300 MHz, DMSO-$d_6$) δ8.19 (t, J=7.9 Hz, 2H), 7.99 (t, J=7.7 Hz, 1H), 7.88 (t, J=7.8 Hz, 1H), 7.56 (br s, 4H), 7.34 (m, 5H), 6.74 (s, 1H), 6.54 (s, 1H), 6.51 (s, 1H), 4.63 (s, 2H), 3.97 (t, J=6.2 Hz, 2H), 3.89 (t, J=6.1 Hz, 2H), 3.51 (t, J=7.4 Hz, 2H), 2.28 (t, J=7.5 Hz, 4H), 2.22 (s, 3H), 1.99 (pentet, J=6.1 Hz, 2H). Mass spectrum (MALDI-TOF, α-cyano-4-hydroxycinnamic acid matrix) calcd. for $C_{27}H_{32}N_4O_9S_2$: 621.2 (M+H), 643.2 (M+Na). Found: 621.0, 642.9.

EXAMPLE 62

{3-[5-Methyl-3-(2-(4-(carboxymethyl)piperazinN-1-ylsulfonyl)phenylsulfonyloxy)phenoxy]propoxylguanidine The title compound was prepared in 85% yield from {3-[5-methyl-3-(2-(4-(ethoxycarbonylmethyl)piperazin-1-ylsulfonyl)phenylsulfonyloxy)phenoxy]propoxy}guanidine dihydrochloride, as prepared in step b of Example 58, in a manner analogous to Example 27. $^1$H-NMR (300 MHz, DMSO-$d_6$) δ11.12 (s, 1H), 8.27 (d, J=7.9 Hz, 1H), 8.18 (d, J=7.9 Hz, 1H), 8.08 (t, J=7.7 Hz, 1H), 7.94 (t, J=7.7 Hz, 1H), 7.69 (br s, 4H), 6.76 (s, 1H), 6.51 (s, 1H), 6.47 (s, 1H), 3.99 (t, J=6.2 Hz, 2H), 3.90 (t, J=6.3 Hz, 2H), 3.43 (br s, 6H), 3.25 (br s, 4H), 2.22 (s, 3H), 2.02 (pentet, J=6.2 Hz, 2H). Mass spectrum (MALDI-TOF, α-cyano-4-hydroxycinnamic acid matrix) calcd. for $C_{23}H_{31}N_5O_9S_2$: 586.2 (M+H), 608.1 (M+Na). Found: 586.2, 608.0.

EXAMPLE 63

3-[5-methyl-3-(2-(4-(2-pyridyl)piperazinylsulfonyl)phenylsulfonyloxy)phenoxy]propoxyguanidine hydrochloride a) N,N'-Bis-(tert-butoxycarbonyl)-3-[5-methyl-3-(2-(4-(2-pyridyl)piperazinylsulfonyl)phenylsulfonyloxy)phenoxy]propoxyguanidine The title compound was prepared in 67% yield from 1-(2-pyridyl)piperazine, in a manner analogous to step h of Eg. 20. $^1$H NMR (300 MHz, CDCl$_3$) δ9.08 (s, 1H), 8.28 (dd, 1H, J=7.9, 1.3 Hz), 8.16 (m, 2H), 7.81 (td, 1H, J=7.7, 1.4 Hz), 7.68 (m, 2H), 7.48 (m, 1H), 6.61 (m, 4H), 6.51 (t, 1H, J=2.1 Hz), 4.18 (m, 2H), 3.94 (t, 2H, J=6.2 Hz), 3.63 (m, 4H), 3.48 (m, 4H), 2.23 (s, 3H), 2.10 (m, 2H), 1.49 (s, 18H).

b) 3-[5-methyl-3-(2-(4-(2-pyridyl)piperazinylsulfonyl)phenylsulfonyloxy)phenoxy]propoxyguanidine hydrochloride The title compound was prepared in quantitative yield from N,N'-bis-(tert-butoxycarbonyl)-3-[5-methyl-3-(2-(4-(2-pyridyl)piperazinylsulfonyl)phenylsulfonyloxy)phenoxy]propoxyguanidine, as prepared in the previous step, in a manner analogous to step i of Example 20 (without chromatographic purification). $^1$H NMR (300 MHz, CDCl$_3$/CD$_3$OD) δ8.33 (d, 1H, J=6.9 Hz), 8.20 (dd, 1H, J=7.8, 1.1 Hz), 8.11 (dd, 1H, J=6.0, 1.5 Hz), 7.90 (m, 2H), 7.78 (m, 1H), 7.06 (d, 1H, J=8.9 Hz), 6.93 (t, 1H, J=6.6 Hz), 6.63 (m, 2H), 6.50 (t, 1H, J=2.1 Hz), 4.06 (t, 2H, J=6.0 Hz), 4.01 (t, 2H, J=5.9 Hz), 3.89 (m, 4H), 3.60 (m, 4H), 2.28 (s, 3H), 2.10 (pentet, 2H, J=5.9 Hz). Mass spectrum (MALDI-TOF, α-cyano-4-hydroxycinnamic acid matrix) calcd. for $C_{26}H_{32}N_6O_7S_2$: 605.2 (M+H), 627.2 (M+Na). Found: 605.0, 627.1.

EXAMPLE 64

3-[5-methyl-3-(2-(4-phenylpiperazinylsulfonyl)phenylsulfonyloxy)phenoxy]propoxyguanidine hydrochloride a) N,N Bis-(tert-butoxycarbonyl)-3-[5-methyl-3-(2-(4-phenylpiperazinylsulfonyl)phenylsulfonyloxy)phenoxy]propoxyguanidine The title compound was prepared in 40% yield from 1-phenylpiperazine, in a manner analogous to step h of Example 20. $^1$H NMR (300 MHz, CDCl$_3$) δ9.08 (s, 1H), 8.28 (dd, 1H, J=7.9, 1.3 Hz), 8.19 (dd, 1H, J=7.9, 1.4 Hz), 7.81 (td, 1H, J=7.7, 1.4 Hz), 7.69 (m, 2H), 7.27 (m, 4H), 6.89 (m, 3H), 6.58 (br s, 2H), 6.52 (t, 1H, J=2.1 Hz), 4.18 (t, 2H, J=6.2Hz), 3.94 (t, 2H, J=6.2 Hz), 3.43 (m, 4H), 3.24 (m, 4H), 2.24 (s, 3H), 2.10 (m, 2H), 1.49 (s, 18H).

b) 3-[5-methyl-3-(2-(4-phenylpiperazinylsulfonyl)phenylsulfonyloxy)phenoxy]propoxyguanidine hydrochloride The title compound was prepared in quantitative yield from N,N'-bis-(tert-butoxycarbonyl)-3-[5-methyl-3-(2-(4-phenylpiperazinylsulfonyl)phenylsulfonyloxy)phenoxy]propoxyguanidine, as prepared in the previous step, in a manner analogous to step i of Example 20 (without chromatographic purification). $^1$H NMR (300 MHz, CDCl$_3$/CD$_3$OD) δ8.34 (d, 1H, J=7.3 Hz), 8.21 (d, 1H, J=7.6 Hz), 7.94 (m, 1H), 7.83 (t, 1H, J=7.4 Hz), 7.74 (d, 2H, J=7.7 Hz), 7.50 (m, 3H), 6.64 (s, 1H), 6.57 (s, 1H), 6.53 (s, 1H), 4.03 (m, 18H), 3.67 (m, 4H), 2.26 (s, 3H), 2.12 (m, 2H). Mass spectrum (MALDI-TOF, α-cyano-4-hydroxycinnamic acid matrix) calcd. for $C_{27}H_{33}N_5O_7S_2$: 604.2 (M+H), 626.2 (M+Na). Found: 604.2, 626.3.

EXAMPLE 65

3-[5-methyl-3-(2-(4-benzylpiperazinylsulfonyl) phenylsulfonyloxy)phenoxy]propoxyguanidine hydrochloride a) N,N'-Bis-(tert-butoxycarbonyl)-3-[5-methyl-3-(2-(4-benzylpiperazinylsulfonyl)phenylsulfonyloxy)phenoxy] propoxyguanidine The title compound was prepared in 75% yield from 1-benzylpiperazine, in a manner analogous to step h of Example 20. $^1$H NMR (300 MHz, CDCl$_3$) δ9.08 (s, 1H), 8.21 (m, 1H), 8.17 (dd, 1H, J=6.6, 1.4 Hz), 7.78 (td, 1H, J=7.7, 1.5 Hz), 7.70 (s, 1H), 7.66 (td, 1H, J=7.7, 1.4 Hz), 7.28 (m, 5H), 6.57 (m, 2H), 6.51 (t, 1H, J=2.1 Hz), 4.18 (t, 2H, J=6.2 Hz), 3.94 (t, 2H, J=6.2 Hz), 3.52 br s, 2H), 3.40 (br s, 4H), 2.53 (br s, 4H), 2.23 (s, 3H), 2.08 (m, 2H), 1.49 (s, 18H).

b) 3-[5-methyl-3-(2-(4-benzylpiperazinylsulfonyl) phenylsulfonyloxy)phenoxy]propoxyguanidine hydrochloride The title compound was prepared in quantitative yield from N,N'-bis-(tert-butoxycarbony)-3-[5-methyl-3-(2-(4-benzylpiperazinylsulfonyl)phenylsulfonyloxy)phenoxy] propoxyguanidine, as prepared in the previous step, in a manner analogous to step i of Example 20 (without chromatographic purification). $^1$H NMR (300 MHz, CDCl$_3$/ CD$_3$OD) δ8.26 (d, 1H, J=7.6 Hz), 8.16 (d, 1H, J=7.7 Hz,), 7.91 (m, 1H), 7.78 (m, 1H), 7.60 (m, 2H), 7.44 (m, 4H), 6.62 (s, 1H), 6.54 (s, 1H), 6.48 (s, 1H), 4.32 (s, 2H), 4.00 (m, 2H), 3.66 (m, 2H), 3.49 (m, 2H), 3.13 (m, 2H), 2.24 (s, 3H), 2.10 (m, 2H). Mass spectrum (MALDI-TOF, α-cyano-4-hydroxycinnamic acid matrix) calcd. for $C_{28}H_{35}N_5O_7S_2$: 618.2 (M+H). Found: 618.2.

EXAMPLE 66

3-[5-methyl-3-(2-(4(2-methoxyphenyl) piperazinylsulfonyl)phenylsulfonyloxy)phenoxy] propoxyguanidine hydrochloride a) N,N'-Bis-(tert-butoxycarbony)-3-[5-methyl-3-(2-(4-(2-methoxyphenyl)piperazinylsulfonyl)phenylsulfonyloxy) phenoxy]propoxyguanidine The title compound was prepared in 79% yield from 1-(2-methoxyphenyl)piperazine, in a manner analogous to step h of Example 20. $^1$H NMR (300 MHz, CDCl$_3$) δ9.09 (s, 1H), 8.24 (dd, 1H, J=7.9, 1.3 Hz), 8.21 (dd, 1H, J=8.0, 1.4 Hz), 7.81 (td, 1H, J=7.7, 1.4 Hz), 7.69 (m, 2H), 7.02 (m, 1H), 6.90 (m, 3H), 6.59 (m, 2H), 6.53 (t, 1H, J=2.1 Hz), 4.18 (t, 2H, J=6.2 Hz), 3.95 (t, 2H, J=6.2 Hz), 3.83 (s, 3H), 3.55 (m, 4H), 3.13 (br t, 4H, J=4.8 Hz), 2.24 (s, 3H), 2.10 (pentet, 2H, J=6.2 Hz), 1.49 (s, 18H).

b) 3-[5-methyl-3-(2-(4-(2-methoxyphenyl) piperazinylsulfonyl)phenylsulfonyloxy)phenoxy] propoxyguanidine hydrochloride The title compound was prepared in 33% yield from N,N'-bis-(tert-butoxycarbony)-3-[5-methyl-3-(2-(4-(2-methoxyphenyl)piperazinylsulfonyl)phenylsulfonyloxy) phenoxy]propoxyguanidine, as prepared in the previous step, in a manner analogous to step i of Example 20 (without HCl-methanol acidification). $^1$H NMR (300 MHz, CDCl$_3$) δ8.21 (m, 2H), 7.81 (t, 1H, J=7.5 Hz), 7.69 (t, 1H, J=7.5 Hz), 7.00 (m, 1H), 6.89 (m, 3H), 6.58 (s, 2H), 6.53 (s, 1H), 3.95 (m, 4H), 3.82 (s, 3H), 3.53 (m, 4H), 3.11 (m, 4H), 2.22 (s, 3H), 2.03 (m, 2H). Mass spectrum (MALDI-TOF, α-cyano-4-hydroxycinnamic acid matrix) calcd. for $C_{28}H_{35}N_5O_8S_2$: 634.2 (M+H), 656.2 (M+Na). Found: 634.2, 656.3.

EXAMPLE 67

3-[5-methyl-3-(2-(N-(2-cyanoethyl)-N-(2-furanylmethyl)aminosulfonyl)phenylsulfonyloxy) phenylsulfonyloxy)phenoxy]propoxyguanidine a) N,N'-Bis-(tert-butoxycarbony)-3-5-methyl-3-(2-(N-(2-cyanoethyl)-N-(2-furanylmethyl)aminosulfonyl) phenylsulfonyloxy)phenoxy]proxyguanidine The title compound was prepared in 49% yield from 3-(furfurylamino)propionitrile, in a manner analogous to step h of Example 20. $^1$H NMR (300 MHz, CDCl$_3$) δ9.08 (s, 1H), 8.29 (dd, 1H, J=7.9, 1.4 Hz), 8.16 (dd, 1H, J=7.8, 1.5 Hz), 7.79 (m, 1H), 7.70 (m, 2H), 7.33 (t, 1H, J=1.3 Hz), 6.60 (m, 1H), 6.57 (m, 1H), 6.52 (t, 1H, J=2.1 Hz), 6.32 (m, 2H), 4.65 (s, 2H), 4.18 (t, 2H, J=6.2 Hz), 3.94 (t, 2H, J=6.2 Hz), 3.65 (m, 2H), 2.55 (m, 2H), 2.24 (s, 3H), 2.10 (pentet, 2H, J=6.2 Hz), 1.49 (s, 18H).

b) 3-[5-methyl-3-(2-(N-(2-cyanoethyl)-N-(2-furanylmethyl) aminosulfonyl)phenylsulfonyloxy)phenoxy] propoxyguanidine The title compound was prepared in 42% yield from N,N'-bis-(tert-butoxycarbony)-3-[5-methyl-3-(2-(N-(2-cyanoethyl)-N-(2-furanylmethyl)aminosulfonyl) phenylsulfonyloxy)phenoxy]propoxyguanidine, as prepared in the previous step, in a manner analogous to step i of Example 20 (without HCl-methanol acidification). $^1$H NMR (300 MHz, CDCl$_3$) δ8.23 (dd, 1H, J=7.9, 1.3 Hz), 8.14 (dd, 1H, J=7.9, 1.4 Hz), 7.76 (td, 1H, J=7.7, 1.4 Hz), 7.67 (td, 1H, J=7.7, 1.3 Hz), 7.29 (t, 1H, J=1.3 Hz), 6.56 (m, 2H), 6.51 (m, 1H), 6.28 (m, 2H), 4.61 (s, 2H), 3.91 (m, 4H), 3.62 (t, 2H J=7.1 Hz), 2.53 (t, 2H, J=7.1 Hz), 2.20 (s, 3H), 2.00 (pentet, 2H, J=6.1 Hz). Mass spectrum (MALDI-TOF, α-cyano-4-hydroxycinnamic acid matrix) calcd. for $C_{25}H_{29}N_5O_8S_2$: 592.2 (M+H), 614.1 (M+Na). Found: 592.2, 614.4.

EXAMPLE 68

3-[5-Methyl-3-(2-(4-methylpiperazinylsulfonyl) phenylsulfonyloxy)phenoxy]propoxyguanidine hydrochloride a) N-3-[(3-Hydroxy-5-methyl)phenoxy] propoxyphthalimide A mixture of N-3-[(3-benzyloxy-5-methyl)phenoxy] propoxyphthalimide (9.19 g, 22.0 mmol), as prepared in step c of Example 20, and 10% palladium on carbon (516 mg) in tetrahydrofuran (100 mL) and ethanol (100 mL) was stirred at room temperature under hydrogen (balloon) for 3 hours. The catalyst was removed by filtration over Celite, the filtrate was concentrated and the remaining solid was purified by trituration with cold methanol giving the title compound as a pale yellow solid (5.72 g, 79%). $^1$H NMR (300 MHz, CDCl$_3$/CD$_3$OD) δ7.83 (m, 2H), 7.77 (m, 2H), 6.26 (m, 3H), 4.40 (t, 2H, J=6.3 Hz), 4.17 (t, 2H, J=6.2 Hz), 2.23 (m, 5H).

b) 3-[5-Methyl-3-(2-chlorosulfonyl)phenylsulfonyloxy) phenoxy]propoxyphthalimide A mixture of 1,2-benzenedisulfonic anhydride (1.74 g, 7.91 mmol), as prepared in step g of Example 20, N-3-[(3-hydroxy-5-methyl)phenoxy] propoxyphthalimide (2.59 g, 7.92 mmol), as prepared in the previous step, and N,N-diisopropylethylamine (1.40 mL, 8.05 mmol) in anhydrous dichloromethane (100 mL) was stirred at room temperature under nitrogen (balloon) for 18 hours. Oxalyl chloride (1.40 ML, 16.0 mmol) and N,N-dimethylformamide (0.02 mL) were added and the reaction stirred another 4 hours at room temperature. The solution was concentrated and the residue was purified by flash chromatography (dichloromethane) giving the title compound as a white solid (3.31 g, 74%). $^1$H NMR (300 MHz, CDCl$_3$) δ8.48 (dd, 1H, J=7.6, 1.7 Hz), 8.25 (dd, 1H, J=7.5, 1.8 Hz), 7.90 (m, 4H), 7.77 (m, 2H), 6.66 (m, 1H), 6.62 (br s, 1H), 6.53 (t, 1H, J=2.2 Hz), 4.37 (t, 2H, J=6.1 Hz), 4.13 (t, 2H, J=6.1 Hz), 2.27 (s, 3H), 2.19 (pentet, 2H, J=6.1 Hz). Mass spectrum (MALDI-TOF, α-cyano-4-hydroxycinnamic acid matrix) calcd. for C$_{27}$H$_{33}$N$_5$O$_7$S$_2$: 588.0 (M+Na). Found: 588.2.

c) 3-[5-Methyl-3-(2-(4-methylpiperazinylsulfonyl) phenylsulfonyloxy)phenoxy]propoxyphthalimide A mixture of 3-[5-methyl-3-(2-chlorosulfonyl) phenylsulfonyloxy)phenoxy]propoxyphthalimide (181 mg, 0.32 mmol), as prepared in the previous step, 1-methylpiperazine (34 mg, 0.34 mmol), and N,N-diisopropylethylamine (0.06 mL, 0.35 mmol) in anhydrous CH$_2$Cl$_2$ (10 mL) was stirred at room temperature under nitrogen (balloon) for 4 hours. The solution was concentrated and the residue was purified by flash chromatography (2.5% to 5% methanol in dichloromethane) giving the title compound as a white solid (161 mg, 80%). $^1$H NMR (300 MHz, CDCl$_3$) δ8.24 (dd, 1H, J=7.9, 1.3 Hz), 8.19 (dd, 1H, J=7.9, 1.4 Hz), 7.84 (m, 2H), 7.77 (m, 3H), 7.68 (td, 1H, J=7.7, 1.3 Hz), 6.62 (br s, 1H), 6.59 (br s, 1H), 6.51 (t, 1H, J=2.2 Hz), 4.36 (t, 2H, J=6.2 Hz), 4.10 (t, 2H, J=6.1 Hz), 3.40 (m, 4H), 2.47 (br t, 4H, J=4.9 Hz), 2.28 (s, 3H), 2.25 (s, 3H), 2.18 (pentet, 2H,J=6.1 Hz).

d) 3-[5-Methyl-3-(2-(4-methylpiperazinylsulfonyl) phenylsulfonyloxy)phenoxy]propoxyamine A mixture 3-[5-methyl-3-(2-(4-methylpiperazinylsulfonyl)phenylsulfonyloxy)phenoxy] propoxyphthalimide (156 mg, 0.25 mmol), as prepared in the previous step, and 40% aqueous methylamine (1.50 mL, 21.5 mmol) in tetrahydrofuran (5 mL) and ethanol (5 mL) was stirred at room temperature for 4 hours. The solution was concentrated and the residue was purified by flash chromatography (10% methanol in dichloromethane) giving a slurry that was twice dissolved in diethyl ether, filtered, and concentrated giving the title compound as a clear oil (113 mg, 91%). $^1$H NMR (300 MHz, CDCl$_3$/CD$_3$OD) δ8.22 (dd, 1H, J=7.9, 1.3 Hz), 8.18 (dd, 1H, J=7.9, 1.4 Hz), 7.83 (td, 1H, J=7.7, 1.4 Hz), 7.70 (td, 1H, J=7.7, 1.3 Hz), 6.60 (br s, 1H), 6.56 (br s, 1H), 6.53 (t, 1H, J=2.1 Hz), 3.93 (t, 2H, J=6.3 Hz), 3.80 (t, 2H, J=6.2 Hz), 3.41 (m, 5H), 2.50 (br t, 4H, J=4.9 Hz), 2.30 (s, 3H), 2.24 (s, 3H), 2.00 (pentet, 2H, J=6.2 Hz).

e) 3-[5-Methyl-3-(2-(4-methylpiperazinylsulfonyl) phenylsulfonyloxy)phenoxy]propoxyguanidine hydrochloride A mixture of 3-[5-methyl-3-(2-(4-methylpiperazinylsulfonyl)phenylsulfonyloxy)phenoxy] propoxyamine (113 mg, 0.23 mmol), as prepared in the previous step, and 1H-pyrazole-1-carboxamidine hydrochloride (62 mg, 0.42 mmol) in anhydrous N,N-dimethylformamide (10 mL) was stirred at room temperature under nitrogen (balloon) for 18 hours. The solution was concentrated under high vacuum with heating and the residue was purified by flash chromatography (10% to 20% methanol in dichloromethane), then dissolved in dichloromethane, filtered and concentrated to give the title compound (105 mg, 80%) as a white solid. $^1$H NMR (300 MHz, CDCl$_3$) δ8.20 (m, 2H), 7.83 (td, 1H, J=7.7, 1.3 Hz), 7.70 (td, 1H, J=7.7, 1.2 Hz), 6.59 (m, 2H), 6.52 (m, 1H), 6.28 (m, 3H), 4.04 (t, 2H, J=5.8 Hz), 3.96 (t, 2H, J=5.8 Hz), 3.43 (m, 4H), 2.33 (s, 3H), 2.23 (s, 3H), 2.00 (m, 2H). Mass spectrum (MALDI-TOF, α-cyano-4-hydroxycinnamic acid matrix) calcd. for C$_{22}$H$_{31}$N$_5$O$_7$S$_2$: 542.2 (M+H), 564.2 (M+Na). Found: 542.3, 564.3.

EXAMPLE 69

{3-[5-Methyl-3-(2-(N-ethyl-N-(1-benzyl-3-pyrrolidinyl)amino sulfonyl)phenylsulfonyloxy) phenoxy]propoxy}guanidine dihydrochloride a) N-{3-[5-Methyl-3-[(2-(N-ethyl-N-(1-benzyl-3-pyrrolidinyl)aminosulfonyl)phenylsulfonyloxy]phenoxy] propoxy}phthalimide The title compound was prepared in 98% yield from 1-benzyl-3-(ethylamino)pyrrolidine in a manner analogous to step c of Example 68. $^1$H-NMR (300 MHz, CDCl$_3$) δ8.36 (br s, 1H), 8.13 (d, J=7.7 Hz, 1H), 7.75–7.86 (m, 5H), 7.68 (t, J=7.8 Hz, 1H), 7.34–7.57 (m, 5H), 6.62 (s, 1H), 6.56 (s, 1H), 6.51 (s, 1H), 4.36 (t, J=6.1 Hz, 2H), 4.10 (m, 4H), 3.50–4.16 (m, 4H), 2.31 (m 1H), 2.24 (s, 3H), 2.17 (pentet, J=6.1 Hz, 2H), 1.62 (m, 4H), 1.26 (t, J=7.1 Hz, 3H).

b) N-{3-5-Methyl-3-[(2-(N-ethyl-N-(1-benzyl-3-pyrrolidinyl)aminosulfonyl)phenylsulfonyloxy]phenoxy] propoxy}amine The title compound was prepared in 83% yield from N-{3-[5-methyl-3-[(2-(N-ethyl-N-(1-benzyl-3-pyrrolidinyl) aminosulfonyl)phenylsulfonyloxy]phenoxy] propoxy}amine, as prepared in the preceding step, in a manner analogous to step d of Example 68. $^1$H-NMR (300 MHz, CDCl$_3$) δ8.26 (d, J=7.9 Hz, 1H), 8.12 (d, J=7.9 Hz, 1H), 7.73 (t, J=7.7 Hz, 1H), 7.61 (t, J=7.7 Hz, 1H), 7.26 (m, 5H), 6.57 (s, 3H), 5.37 (br s, 2H), 4.56 (br s, 1H), 3.91 (t, J=6.3 Hz, 2H), 3.78 (t, J=6.2 Hz, 2H), 3.57 (m, 4H), 2.80 (m, 1H), 2.69 (m, 1H), 2.50 (m, 1H), 2.22 (s, 3H), 1.96 (pentet, J=6.2 Hz, 2H), 1.85 (m, 1H), 1.62 (br s, 2H), 1.22 (t, J=7.1 Hz, 3H).

c) N-{3-[5-Methyl-3-[(2-(N-ethyl-N-(1-benzyl-3-pyrrolidinyl)aminosulfonyl)phenylsulfonyloxy]phenoxy] propoxy}guanidine dihydrochloride The title compound was prepared in 83% yield from N-{3-[5-methyl-3-[(2-(N-ethyl-N-(1-benzyl-3-pyrrolidinyl) aminosulfonyl)phenylsulfonyloxy]phenoxy] propoxy}phthalimide, as prepared in the preceding step, in a manner analogous to step f of Example 1. $^1$H-NMR (300 MHz, DMSO-d$_6$) δ11.15 (br s, 2H), 8.18 (d, J=7.8 Hz, 1H), 8.14 (d, J=7.8 Hz, 1H), 8.00 (t, J=7.6 Hz, 1H), 7.88 (t, J=7.7 Hz, 1H), 7.68 (br s, 4H), 7.38 (m, 5H), 6.74 (s, 1H), 6.52 (s, 1H), 6.48 (s, 1H), 4.66 (br s, 1H), 4.04 (m, 1H), 3.97 (t, J=6.3 Hz, 2H), 3.89 (t, J=6.3 Hz, 2H), 3.50 (m, 2H), 2.75–3.20 (m, 5H), 2.21 (s, 3H), 2.13 (m, 2H), 2.01 (pentet, J=6.2 Hz, 2H), 1.10 (t, J=6.9 Hz, 3H). Mass spectrum (MALDI-TOF, α-cyano-4-hydroxycinnamic acid matrix) calcd. for C$_{30}$H$_{39}$N$_5$O$_7$S$_2$: 646.2 (M+H). Found: 646.0.

EXAMPLE 70

3-[5-Methyl-3-(2-(N-benzyl-N-(2-(N,N-dimethylamino)ethyl)aminosulfonyl) phenylsulfonyloxy)phenoxy]propoxyguanidine dihydrochloride a) N-{3-5-Methyl-3-[(2-(N-benzyl-N-(2-(N,N-dimethylamino)ethyl)aminosulfonyl)phenylsulfonyloxy] phenoxy]propoxy}phthalimide The title compound was prepared in 100% yield from N-benzyl-N,N-dimethylethylenediamine in a manner analogous to step c of Example 68. $^1$H-NMR (300 MHz, CDCl$_3$) δ8.26 (d, J=7.8 Hz, 1H), 8.18 (d, J=7.8 Hz, 1H), 7.83 (m, 2H), 7.76 (m, 3H), 7.67 (t, J=7.6 Hz, 1H), 7.32 (m, 5H), 6.62 (s, 2H), 6.55 (s, 1H), 4.63 (s, 2H), 4.35 (t, J=6.3 Hz, 2H), 4.10 (t, J=6.1 Hz, 2H), 3.65 (t, J=6.8 Hz, 2H), 2.55 (t, J=6.8 Hz, 2H), 2.33 (s, 6H), 2.25 (s, 3H), 2.17 (pentet, J=6.2 Hz, 2H).

b) N-{3-[5-Methyl-3-[(2-(N-benzyl-N-(2-(N,N-dimethylamino)ethyl)aminosulfonyl)phenylsulfonyloxy] phenoxy]propoxy}amine The title compound was prepared in 95% yield from N-{3-[5-methyl-3-[(2-(N-benzyl-N-(2-(N,N-dimethylamino)ethyl)aminosulfonyl)phenylsulfonyloxy] phenoxy]propoxy}phthalimide, as prepared in the preceding step, in a manner analogous to step d of Example 68. $^1$H-NMR (300 MHz, CDCl$_3$) δ8.36 (d, J=7.8 Hz, 1H), 8.16

(d, J=7.8 Hz, 1H), 7.73 (t, J=7.7 Hz, 1H), 7.63 (t, J=7.7 Hz, 1H), 7.31 (m, 5H), 6.62 (s, 1H), 6.59 (s, 2H), 5.37 (br s, 2H), 4.68 (s, 2H), 3.92 (t, J=6.3 Hz, 2H, 3.78 (t, J=6.2 Hz, 2H), 3.38 (t, J=7.0 Hz, 2H), 2.26 (t, J=7.1 Hz, 2H), 2.23 (s, 3H), 2.06 (s, 6H), 1.99 (pentet, J=6.2 Hz, 2H).

c) 3-[5-Methyl-3-(2-(N-benzyl-N-(2-(N,N-dimethylamino) ethyl)aminosulfonyl)phenylsulfonyloxy)phenoxy] propoxyguanidine dihydrochloride The title compound was prepared in 76% yield from N-{3-[5-methyl-3-[(2-(N-benzyl-N-(2-(N,N-dimethylamino)ethyl)aminosulfonyl)phenylsulfonyloxy] phenoxy]propoxy}amine, as prepared in the preceding step, in a manner analogous to step f of Example 1. $^1$H-NMR (300 MHz, DMSO-d$_6$) δ11.98 (br s, 2H), 8.18 (d, J=7.7 Hz, 1H), 8.16 (d, J=7.7 Hz, 1H), 7.96 (t, J=7.7 Hz, 1H), 7.89 (t, J=7.7 Hz, 1H), 7.69 (br s, 4H), 7.34 (m, 5H), 6.76 (s, 1H), 6.55 (s, 1H), 6.51 (s, 1H), 4.64 (s, 2H), 3.98 (t, J=6.2 Hz, 2H), 3.89 (t, J=6.3 Hz, 2H), 3.69 (t, J=7.1 Hz, 2H), 2.85 (br s, 2H), 2.51 (s, 6H), 2.22 (s, 3H), 2.01 (pentet, J=6.3 Hz, 2H). Mass spectrum (MALDI-TOF, α-cyano-4-hydroxycinnamic acid matrix) calcd. for $C_{28}H_{37}N_5O_7S_2$: 620.2 (M+H), 642.2 (M+Na). Found: 620.2, 642.1.

EXAMPLE 71

{3-[5-Methyl-3-(2-(N-methyl-N-(-methyl-4-piperidinyl)aminosulfonyl)phenylsulfonyloxy) phenoxy]propoxy]guanidine dihydrochloride a) N-{3-[5-Methyl-3-[(2-(N-methyl-N-(1-methyl-4-piperidinyl)aminosulfonyl)phenylsulfonyloxy)phenoxy] propoxy}phthalimide The title compound was prepared in 96% yield from 1-methyl-4-(methylamino)piperidine in a manner analogous to step c of Example 68. $^1$H-NMR (300 MHz, CDCl$_3$) δ8.33 (d, J=7.8 Hz, 1H), 8.14 (d, J=7.9 Hz, 1H), 7.83 (m, 3H), 7.78 (m, 2H), 7.69 (t, J=7.6 Hz, 1H), 6.63 (s, 1H), 6.54 (s, 1H), 6.51 (s, 1H), 4.61 (m, 1H), 4.36 (t, J=6.1 Hz, 2H), 4.10 (t, J=6.1 Hz, 2H), 4.39 (m, 2H), 2.92 (t, J=12.0 Hz, 2H), 2.79 (s, 3H), 2.74 (s, 3H), 2.55 (m, 2H), 2.24 (s, 3H), 2.17 (pentet, J=6.1 Hz, 2H), 1.99 (m, 2H).

b) N-{3-[5-Methyl-3-[(2-(N-methyl-N-(1-methyl-4-piperidinyl)aminosulfonyl)phenylsulfonyloxy]phenoxy] propoxy}amine The title compound was prepared in 88% yield from N-{3-[5-methyl-3-[(2-(N-methyl-N-(1-methyl-4-piperidinyl)aminosulfonyl)phenylsulfonyloxy]phenoxy] propoxy}amine, as prepared in the preceding step, in a manner analogous to step d of Example 68. $^1$H-NMR (300 MHz, CDCl$_3$) δ8.30 (d, J=7.9 Hz, 1H), 8.13 (d, J=7.9 Hz, 1H), 7.78 (t, J=7.6 Hz, 1H), 7.64 (t, J=7.6 Hz, 1H), 6.58 (s, 1H), 6.56 (s, 1H), 6.54 (s, 1H), 5.36 (br s, 2H), 4.06 (m, 1H), 3.91 (t, J=6.3 Hz, 2H), 3.79 (t, J=6.2 Hz, 2H), 2.90 (m, 2H), 2.83 (s, 3H), 2.28 (s, 3H), 2.23 (s, 3H), 2.11 (m, 2H), 1.99 (pentet, J=6.1 Hz, 2H), 1.84 (m, 2H), 1.68 (m, 2H).

c) N-{3-[5-Methyl-3-[(2-(N-methyl-N-(1-methyl-4-piperidinyl)aminosulfonyl)phenylsulfonyloxy]phenoxy] propoxy}guanidine dihydrochloride The title compound was prepared in 76% yield from N-{3-[5-methyl-3-[(2-(N-methyl-N-(1-methyl-4-piperidinyl)aminosulfonyl)phenylsulfonyloxy] phenoxy}phthalimide, as prepared in the preceding step, in a manner analogous to step f of Example 1. $^1$H-NMR (300 MHz, DMSO-d$_6$), δ8.25 (d, J=7.9 Hz, 1H), 8.15 (d, J=7.9 Hz, 1H), 8.02 (t, J=7.6 Hz, 1H), 7.89 (t, J=7.7 Hz, 1H), 7.37 (br s, 4H), 6.75 (s, 1H), 6.53 (s, 1H), 6.47 (s, 1H), 4.07 (m, 1H), 3.97 (t, J=6.3 Hz, 2H), 3.87 (t, J=6.3 Hz, 2H), 3.22 (m, 2H), 3.17 (s, 3H), 2.79 (s, 3H), 2.72 (t, J=12.0 Hz, 2H), 2.22 (s, 3H), 1.99 (pentet, J=6.3 Hz, 4H), 1.60 (m, 2H). Mass spectrum (MALDI-TOF, α-cyano-4-hydroxycinnamic acid matrix) calcd. for $C_{24}H_{35}N_5O_7S_2$: 570.2 (M+H), 592.2 (M+Na). Found: 570.1, 592.1.

EXAMPLE 72

3-[5-Methyl-3-(2-(N-methyl-N-(3-pyridylmethyl) amino sulfonyl)phenylsulfonyloxy)phenoxy] propoxyguanidine dihydrochloride a) N-{3-[5-Methyl-3-[(2-(N-methyl-N-(3-pyridylmethyl) aminosulfonyl)phenylsulfonyloxy]phenoxy] propoxy}phthalimide The title compound was prepared in 88% yield from 3-(methylaminomethyl)pyridine in a manner analogous to step c of Example 68. $^1$H-NMR (300 MHz, CDCl$_3$) δ8.56 (m, 2H), 8.35 (d, J=7.9 Hz, 1H), 8.21 (d, J=7.9 Hz, 1H), 7.69–7.86 (m, 7H), 7.32 (m, 1H), 6.64 (s, 1H), 6.62 (s, 1H), 6.54 (s, 1H), 4.61 (s, 2H), 4.36 (t, J=6.1 Hz, 2H), 4.11 (t, J=6.1 Hz, 2H), 2.77 (s, 3H), 2.26 (s, 3H), 2.18 (pentet, J=6.1 Hz, 2H).

b) 3-[5-Methyl-3-[(2-(N-methyl-N-(3-pyridylmethyl) aminosulfonyl)phenylsulfonyloxy]phenoxy]propoxyamine The title compound was prepared in 90% yield from N-{3-[5-methyl-3-[(2-(N-methyl-N-(3-pyridylmethyl) aminosulfonyl)phenylsulfonyloxy]phenoxy] propoxy}phthalimide, as prepared in the preceding step, in a manner analogous to step d of Example 68. $^1$H-NMR (300 MHz, CDCl$_3$) δ8.56 (m, 2H), 8.34 (d, J=7.9 Hz, 1H), 8.20 (d, J=7.9 Hz, 1H), 7.81 (t, J=7.7 Hz, 2H), 7.70 (t, J=7.7 Hz, 1H), 7.32 (m, 1H), 6.60 (s, 1H), 6.58 (s, 1H), 6.57 (s, 1H), 4.60 (s, 2H), 3.93 (t, J=6.3 Hz, 2H), 3.78 (t, J=6.1 Hz, 2H), 2.77 (s, 3H), 2.24 (s, 3H), 2.00 (pentet, J=6.2 Hz, 2H).

c) 3-[5-Methyl-3-[(2-(N-methyl-N-(3-pyridylmethyl) aminosulfonyl) phenylsulfonyloxy]phenoxy] propoxyguanidine dihydrochloride The title compound was prepared in 76% yield from 3-[5-methyl-3-[(2-(N-methyl-N-(3-pyridylmethyl) aminosulfonyl)phenylsulfonyloxy]phenoxy]propoxyamine, as prepared in the preceding step, in a manner analogous to step f of Example 1. $^1$H-NMR (300 MHz, DMSO-d$_6$) δ8.78 (t, J=5.2 Hz, 2H), 8.23 (m, 3H), 8.06 (t, J=7.7 Hz, 1H), 7.94 (t, J=7.7 Hz, 1H), 7.88 (t, J=7.9 Hz, 1H), 7.71 (br s, 4H), 6.75 (s, 1H), 6.55 (s, 1H), 6.51 (s, 1H), 4.72 (s, 2H), 3.99 (t, J=6.3 Hz, 2H), 3.90 (t, J=6.4 Hz, 2H), 2.88 (s, 3H), 2.22 (s, 3H), 2.01 (pentet, J=6.4 Hz, 2H). Mass spectrum (MALDI-TOF, α-cyano-4-hydroxycinnamic acid matrix) calcd. for $C_{24}H_{29}N_5O_7S_2$: 564.2 (M+H), 586.1 (M+Na). Found: 564.1, 586.2.

EXAMPLE 73

3-[5-Methyl-3-(2-(N-ethyl-N-(2-(N,N-dimethylamino)ethyl)amino sulfonyl) phenylsulfonyloxy)phenoxy]propoxyguanidine dihydrochloride a) 3-[5-Methyl-3-(2-(N-ethyl-N-(2-(N,N-dimethylamino) ethyl)aminosulfonyl)phenylsulfonyloxy)phenoxy]propoxy phthalimide The title compound was prepared in 100% yield from N,N-dimethyl-N'-ethylethylenediamine in a manner analogous to step c of Example 68. $^1$H-NMR (300 MHz, CDCl$_3$) δ8.27 (d, J=7.9 Hz, 1H), 8.18 (d, J=7.9 Hz, 1H), 7.75–7.86 (m, 5H), 7.69 (t, J=7.7 Hz, 1H), 6.61 (s, 1H), 6.58 (s, 1H), 6.52 (s, 1H), 4.36 (t, J=6.2 Hz, 2H), 4.10 (t, J=6.1 Hz, 2H), 3.81 (br s, 2H), 3.45 (q, J=7.1 Hz, 2H), 3.00 (br s, 2H), 2.59 (s, 6H), 2.24 (s, 3H), 2.17 (pentet, J=6.1 Hz, 2H), 1.21 (t, J=7.1 Hz, 3H).

b) 3-[5-Methyl-3-(2-(N-ethyl-N-(2-(N,N-dimethylamino) ethyl)aminosulfonyl)phenylsulfonyloxy)phenoxy] propoxyamine The title compound was prepared in 97% yield from 3-[5-methyl-3-(2-(N-ethyl-N-(2-(N,N-dimethylamino)ethyl)aminosulfonyl)phenylsulfonyloxy)phenoxy]propoxy phthalimide, as prepared in the preceding step, in a manner analogous to step d of Example 68. $^1$H-NMR (300 MHz, CDCl$_3$) δ8.32 (d, J=7.9 Hz, 1H), 8.15 (d, J=7.9 Hz, 1H), 7.76 (t, J=7.7 Hz, 1H), 7.63 (t, J=7.7 Hz, 1H), 6.60 (s, 1H), 6.58 (s, 1H), 6.57 (s, 1H), 5.39 (br s, 2H), 3.92 (t, J=6.3 Hz, 2H), 3.78 (t, J=6.1 Hz, 2H), 3.49 (m, 4H), 2.46 (t, J=7.1 Hz, 2H), 2.23 (s, 3H), 2.21 (s, 6H), 1.99 (pentet, J=6.2 Hz, 2H), 1.16(t, J=7.1 Hz, 3H).

c) 3-[5-Methyl-3-(2-(N-ethyl-N-(2-(N,N-dimethylamino)ethyl)aminosulfonyl)phenylsulfonyloxy)phenoxy]propoxyguanidine dihydrochloride The title compound was prepared in 52% yield from 3-[5-methyl-3-(2-(N-ethyl-N-(2-(N,N-dimethylamino)ethyl)aminosulfonyl)phenylsulfonyloxy)phenoxy]propoxyamine, as prepared in the preceding step, in a manner analogous to step f of Example 1. $^1$H-NMR (300 MHz, DMSO-d$_6$) δ8.19 (d, J=7.8 Hz, 1H), 8.17 (d, J=7.8 Hz, 1H), 8.03 (t, J=7.7 Hz, 1H), 7.90 (t, J=7.7 Hz, 1H), 7.69 (br s, 4H), 6.75 (s, 1H), 6.53 (s, 1H), 6.50 (s, 1H), 3.98 (t, J=6.2 Hz, 2H), 3.90 (t, J=6.3 Hz, 2H), 3.78 (t, J=7.0 Hz, 2H), 3.44 (q, J=7.1 Hz, 2H), 3.30 (t, J=7.3 Hz, 2H), 2.79 (s, 6H), 2.22 (s, 3H), 2.02 (pentet, J=6.3 Hz, 2H), 1.09 (t, J=7.1 Hz, 3H). Mass spectrum (MALDI-TOF, α-cyano-4-hydroxycinnamic acid matrix) calcd. for C$_{23}$H$_{35}$N$_5$O$_7$S$_2$: 558.2 (M+H), 580.2 (M+Na). Found: 558.3, 580.3.

EXAMPLE 74

3-[5-Methyl-3-(2-(2-(4-morpholinyl)ethylaminosulfonyl)phenylsulfonyloxy)phenoxy]propoxyguanidine dihydrochloride a) 3-[5-Methyl-3-(2-(2-(4-morpholinyl)ethylaminosulfonyl)phenylsulfonyloxy)phenoxy]propoxy phthalimide The title compound was prepared in 96% yield from 4-(2-aminoethyl)morpholine in a manner analogous to step c of Example 68. $^1$H-NMR (300 MHz, CDCl$_3$) δ8.37 (d, J=7.8 Hz, 1H), 8.08 (d, J=7.8 Hz, 1H), 7.75–7.86 (m, 5H), 7.70 (t, J=7.7 Hz, 1H), 6.68 (s, 1H), 6.63 (s, 1H), 6.58 (s, 1H), 6.53 (s, 1H), 4.36 (t, J=6.1 Hz, 2H), 4.11 (t, J=6.1 Hz, 2H), 3.89 (m, 6H), 3.48 (m, 6H), 2.24 (s, 3H), 2.18 (pentet, J=6.1 Hz, 2H).

b) 3-[5-Methyl-3-(2-(2-(4-morpholinyl)ethylaminosulfonyl)phenylsulfonyloxy)phenoxy]propoxyamine The title compound was prepared in 96% yield from 3-[5-methyl-3-(2-(2-(4-morpholinyl)ethylaminosulfonyl)phenylsulfonyloxy)phenoxy]propoxyphthalimide, as prepared in the preceding step, in a manner analogous to step d of Example 68. $^1$H-NMR (300 MHz, CDCl$_3$) δ8.36 (d, J=7.8 Hz, 1H), 8.06 (d, J=7.8 Hz, 1H), 7.81 (t, J=7.7 Hz, 1H), 7.66 (t, J=7.7 Hz, 1H), 6.68 (s, 1H), 6.60 (s, 1H), 6.58 (s, 1H), 6.56 (s, 1H), 3.90 (t, J=6.1 Hz, 2H), 3.79 (t, J=6.1 Hz, 2H), 3.67 (br s, 4H), 3.14 (br s, 2H), 2.36 (m, 6H), 2.23 (s, 3H), 1.99 (pentet, J=6.2 Hz, 2H).

c) 3-[5-Methyl-3-(2-(2-(4-morpholinyl)ethylaminosulfonyl)phenylsulfonyloxy)phenoxy]propoxyguanidine dihydrochloride The title compound was prepared in 60% yield from 3-[5-methyl-3-(2-(2-(4-morpholinyl)ethylaminosulfonyl)phenylsulfonyloxy)phenoxy]propoxyamine, as prepared in the preceding step, in a manner analogous to step f of Example 1. $^1$H-NMR (300 MHz, DMSO-d$_6$) δ8.28 (d, J=7.8 Hz, 1H), 8.11 (d, J=7.8 Hz, 1H), 8.05 (t, J=7.7 Hz, 1H), 7.95 (br s, 1H), 7.90 (t, J=7.7 Hz, 1H), 7.72 (br s, 4H), 6.76 (s, 1H), 6.55 (s, 1H), 6.50 (s, 1H), 3.98 (t, J=6.3 Hz, 2H), 3.91 (t, J=6.3 Hz, 2H), 3.79 (m, 4H), 3.25 (br s, 4H), 3.17 (m, 4H), 2.23 (s, 3H), 2.02 (pentet, J=6.3 Hz, 2H). Mass spectrum (MALDI-TOF, α-cyano-4-hydroxycinnamic acid matrix) calcd. for C$_{23}$H$_{33}$N$_5$O$_8$S$_2$: 572.2 (M+H), 594.2 (M+Na). Found: 572.3, 594.4.

EXAMPLE 75

3-[5-Methyl-3-(2-(N-methyl-N-(2-(N,N-dimethylamino)ethyl)aminosulfonyl)phenylsulfonyloxy)phenoxy]propoxyguanidine hydrochloride a) 3-[5-Methyl-3-(2-(N-methyl-N-(2-(N,N-dimethylamino)ethyl)aminosulfonyl)phenylsulfonyloxy)phenoxy]propoxyphthalimide The title compound was prepared in 98% yield from N,N,N'-trimethylethylenediamine, in a manner analogous to step c of Example 68 and was used without characterization.

b) 3-[5-Methyl-3-(2-(N-methyl-N-(2-(N,N-dimethylamino)ethyl)aminosulfonyl)phenylsulfonyloxy)phenoxy]propoxyamine The title compound was prepared in 66% yield from 3-[5-methyl-3-(2-(N-methyl-N-(2-(N,N-dimethylamino)ethyl)aminosulfonyl)phenylsulfonyloxy)phenoxy]propoxyphthalimide, as prepared in the previous step, in a manner analogous to step d of Example 68, and was used without characterization.

c) 3-[5-Methyl-3-(2-(N-methyl-N-(2-(N,N-dimethylamino)ethyl)aminosulfonyl)phenylsulfonyloxy)phenoxy]propoxyguanidine hydrochloride A mixture of 3-[5-methyl-3-(2-(N-methyl-N-(2-(N,N-dimethylamino)ethyl)aminosulfonyl)phenylsulfonyloxy)phenoxy]propoxyamine (94 mg, 0.19 mmol) and 1H-pyrazole-1-carboxamidine hydrochloride (57 mg, 0.39 mmol), in N,N-dimethylformamide (8 mL) was stirred at room temperature for 18 hours then concentrated in vacuo. The residue was dissolved in acetonitrile, filtered, and the filtrate concentrated to an oil. This was dissolved in dilute HCl (pH 3), washed with diethyl ether, basified with aqueous NaHCO$_3$, and extracted with CH$_2$Cl$_2$. The CH$_2$Cl$_2$ layer was washed with pH 7 buffer and brine, dried over Na$_2$SO$_4$ and filtered. The filtrate was acidified with HCl-methanol and concentrated giving the title compound as a white solid (100 mg, 92%). $^1$H NMR (300 MHz, CDCl$_3$) δ8.20 (m, 2H), 7.93 (td, 1H, J=7.7, 1.4 Hz), 7.78 (td, 1H, J=7.7, 1.2 Hz), 6.62 (m, 2H), 6.51 (t, 1H, J=2.2 Hz), 4.05 (t, 2H, J=6.1 Hz), 3.99 (t, 2H, J=6.0 Hz), 3.87 (t, 2H, J=6.9 Hz), 3.44 (t, 2H, J=6.9 Hz), 3.04 (s, 3H), 2.96 (s, 6H), 2.27 (s, 3H), 2.10 (m, 2H). Mass spectrum (MALDI-TOF, α-cyano-4-hydroxycinnamic acid matrix) calcd. for C$_{22}$H$_{33}$N$_5$O$_7$S$_2$: 544.2 (M+H). Found: 544.0.

EXAMPLE 76

3-[5-Methyl-3-(2-(4-(pyrrolidin-1-yl)piperidin-1-ylsulfonyl)phenylsulfonyloxy)phenoxy]propoxyguanidine a) 3-[5-Methyl-3-(2-(4-(pyrrolidin-1-yl)piperidin-1-ylsulfonyl)phenylsulfonyloxy)phenoxy]propoxyphthalimide The title compound was prepared in 99% yield from 4-(1-pyrrolidinyl)piperidine, in a manner analogous to step c of Example 68, and was used without characterization.

b) 3-[5-Methyl-3-(2-(4-(pyrrolidin-1-yl)piperidin-1-ylsulfonyl)phenylsulfonyloxy)phenoxy]propoxyamine The title compound was prepared in 66% yield from 3-[5-methyl-3-(2-(4-(pyrrolidin-1-yl)piperidin-1-ylsulfonyl)phenylsulfonyloxy)phenoxy]propoxyphthalimide, as prepared in the previous step, in a manner analogous to step d of Example 68, and was used without characterization.

c) 3-[5-Methyl-3-(2-(4-(pyrrolidin-1-yl)piperidin-1-ylsulfonyl)phenylsulfonyloxy)phenoxy]propoxyguanidine The title compound was prepared in 76% yield from 3-[5-methyl-3-(2-(4-(pyrrolidin-1-yl)piperidin-1-ylsulfonyl)phenylsulfonyloxy)phenoxy]propoxyamine, as prepared in the previous step, in a manner analogous to step c of Eg. 75 (without acidification with HCl—MeOH). $^1$H NMR (300 MHz, CDCl$_3$) δ8.25 (dd, 1H, J=7.9, 1.3 Hz), 8.17 (dd, 1H, J=7.9, 1.4 Hz), 7.78 (td, 1H, J=7.7, 1.4 Hz,), 7.66 (td, 1H, J=7.7, 1.4 Hz), 6.59 (m, 2H), 6.54 (t, 1H, J=2.2 Hz), 3.92 (m, 6H), 2.93 (m, 2H), 2.59 (m, 4H), 2.24 (s, 3H), 1.99 (m, 5H), 1.79 (m, 4H), 1.65 (m, 2H). Mass spectrum (MALDI-TOF, α-cyano-4-hydroxycinnamic acid matrix) calcd. for $C_{26}H_{37}N_5O_7S_2$: 596.2 (M+H). Found: 595.9.

EXAMPLE 77

3-[5-Methyl-3-(2-(4-ethoxycarbonyl-1-piperazinylsulfonyl)phenylsulfonyloxy)phenoxy]propoxyguanidine hydrochloride a) 3-[5-Methyl-3-(2-(4-ethoxycarbonyl-1-piperazinylsulfonyl)phenylsulfonyloxy)phenoxy]propoxyphthalimide The title compound was prepared in 97% yield from ethyl N-piperazinecarboxylate, in a manner analogous to step c of Example 68. $^1$H NMR (300 MHz, CDCl$_3$) δ8.29 (dd, 1H, J=7.9, 1.4 Hz), 8.18 (dd, 1H, J=7.8, 1.4 Hz), 7.81 (m, 5H), 7.70 (td, 1H, J=7.7, 1.4 Hz), 6.63 (m, 1H), 6.58 (m, 1H), 6.49 (t, 1H, J=2.2 Hz), 4.12 (m, 4H), 3.55 (m, 4H), 3.36 (br s, 4H), 2.25 (s, 3H), 2.18 (pentet, 2H, J=6.1 Hz), 1.24 (t, 3H, J=7.1 Hz).

b) 3-[5-Methyl-3-(2-(4-ethoxycarbonyl-1-piperazinylsulfonyl)phenylsulfonyloxy)phenoxy]propoxyamine The title compound was prepared in quantitative yield from 3-[5-methyl-3-(2-(4-ethoxycarbonyl-1-piperazinylsulfonyl)phenylsulfonyloxy)phenoxy]propoxyphthalimide, as prepared in the previous step, in a manner analogous to step d of Example 68, and was used without characterization.

c) 3-[5-Methyl-3-(2-(4-ethoxycarbonyl-1-piperazinylsulfonyl)phenylsulfonyloxy)phenoxy]propoxyguanidine hydrochloride The title compound was prepared in 78% yield from 3-[5-methyl-3-(2-(4-ethoxycarbonyl-1-piperazinylsulfonyl)phenylsulfonyloxy)phenoxy]propoxyamine, as prepared in the previous step, in a manner analogous to step c of Example 75. $^1$H NMR (300 MHz, CDCl$_3$) δ8.24 (d, 1H, J=7.6 Hz), 8.18 (d, 1H, J=7.6 Hz), 7.84 (t, 1H, J=7.5 Hz), 7.73 (t, 1H, J=7.5 Hz), 6.58 (br s, 2H), 6.50 (s, 1H), 4.11 (q, 2H, J=7.1 Hz), 4.07 (m, 2H), 3.96 (m, 2H), 3.55 (m, 4H), 3.34 (m, 4H), 2.23 (s, 3H), 2.08 (m, 2H), 1.23 (t, 3H, J=7.1 Hz). Mass spectrum (MALDI-TOF, α-cyano-4-hydroxycinnamic acid matrix) calcd. for $C_{24}H_{33}N_5O_9S_2$: 600.2 (M+H), 622.6 (M+Na). Found: 600.3, 622.2.

EXAMPLE 78

3-[5-Methyl-3-(2-(N-methyl-N-(3-(N,N-dimethylamino)propyl)aminosulfonyl)phenylsulfonyloxy)phenoxy]propoxyguanidine a) 3-[5-Methyl-3-(2-(N-methyl-N-(3-(N,N-dimethylamino)propyl)aminosulfonyl)phenylsulfonyloxy)phenoxy]propoxyphthalimide The title compound was prepared in 97% yield from N,N,N'-trimethyl-1,3-propanediamine, in a manner analogous to step c of Example 68. $^1$H NMR (300 MHz, CDCl$_3$) δ8.23 (dd, 1H, J=7.9, 1.3 Hz), 8.16 (dd, 1H, J=7.9, 1.4 Hz), 7.81 (m, 5H), 7.66 (td, 1H, J=7.7, 1.4 Hz), 6.61 (m, 2H), 6.53 (t, 1H, J=2.1 Hz), 4.36 (t, 2H, J=6.2 Hz), 4.10 (t, 2H, J=6.1 Hz), 3.39 (t, 2H, J=7.3 Hz), 2.95 (s, 3H), 2.32 (m, 2H), 2.24 (s, 3H), 2.21 (s, 6H), 2.16 (m, 2H), 1.80 (m, 2H).

b) 3-[5-Methyl-3-(2-(N-methyl-N-(3-(N,N-dimethylamino)propyl)aminosulfonyl)phenylsulfonyloxy)phenoxy]propoxyamine The title compound was prepared in quantitative yield from 3-[5-methyl-3-(2-(N-methyl-N-(3-(N,N-dimethylamino)propyl)aminosulfonyl)phenylsulfonyloxy)phenoxy]propoxyphthalimide, as prepared in the previous step, in a manner analogous to step d of Example 68, and was used without characterization.

c) 3-[5-Methyl-3-(2-(N-methyl-N-(3-(N,N-dimethylamino)propyl)aminosulfonyl)phenylsulfonyloxy)phenoxy]propoxyguanidine The title compound was prepared in 78% yield from 3-[5-methyl-3-(2-(N-methyl-N-(3-(N,N-dimethylamino)propyl)aminosulfonyl)phenylsulfonyloxy)phenoxy]propoxyamine, as prepared in the previous step, in a manner analogous to step c of Example 75 (without acidification with HCl-methanol). $^1$H NMR (300 MHz, CDCl$_3$/CD$_3$OD) δ8.18 (dd, 1H, J=5.2, 1.4 Hz), 8.15 (dd, 1H, J=5.2, 1.4 Hz), 7.83 (td, 1H, J=7.7, 1.4 Hz), 7.70 (td, 1H, J=7.7, 1.4 Hz), 6.60 (m, 1H), 6.57 (m, 1H), 6.52 (t, 1H, J=2.2 Hz), 3.95 (t, 2H, J=6.3 Hz), 3.92 (t, 2H, J=6.1 Hz), 3.37 (m, 2H), 2.95 (s, 3H), 2.38 (m, 2H), 2.27 (s, 6H), 2.24 (s, 3H), 2.03 (pentet, 2H, J=6.2 Hz), 1.81 (pentet, 2H, J=7.4 Hz). Mass spectrum (MALDI-TOF, α-cyano-4-hydroxycinnamic acid matrix) calcd. for $C_{23}H_{35}N_5O_7S_2$: 558.2 (M+H). Found: 558.0.

EXAMPLE 79

3-[5-Methyl-3-(2-(4-pyridylmethylaminosulfonyl)phenylsulfonyloxy)phenoxy]propoxyguanidine a) 3-[5-Methyl-3-(2-(4-pyridylmethylaminosulfonyl)phenylsulfonyloxy)phenoxy]propoxyphthalimide The title compound was prepared in 97% yield from 4-(aminomethyl)pyridine, in a manner analogous to step c of Eg. 68. $^1$H NMR (300 MHz, CDCl$_3$) δ8.46 (dd, 2H, J=4.5, 1.6 Hz), 8.23 (dd, 1H, J=7.7, 1.5 Hz), 8.04 (dd, 1H, J=7.7, 1.5 Hz), 7.84 (m, 2H), 7.75 (m, 3H), 7.65 (td, 1H, J=7.6, 1.5 Hz), 7.16 (dd, 2H, J=4.5, 1.5 Hz), 6.64 (br s, 1H), 6.62 (s, 1H), 6.59 (br s, 1H), 6.54 (t, 1H, J=2.2 Hz), 4.36 (t, 2H, J=6.1 Hz), 4.22 (d, 2H, J=6.6 Hz), 4.10 (t, 2H, J=6.1 Hz), 2.24 (s, 3H), 2.17 (pentet, 2H, J=6.1 Hz).

b) 3-[5-Methyl-3-(2-(4-pyridylmethylaminosulfonyl)phenylsulfonyloxy)phenoxy]propoxyamine The title compound was prepared in quantitative yield from 3-[5-methyl-3-(2-(4-pyridylmethylaminosulfonyl)phenylsulfonyloxy)phenoxy]propoxyphthalimide, as prepared in the previous step, in a manner analogous to step d of Example 68, and was used without characterization.

c) 3-[5-Methyl-3-(2-(4-pyridylmethylaminosulfonyl)phenylsulfonyloxy)phenoxy]propoxyguanidine The title compound was prepared in 78% yield from 3-[5-methyl-3-(2-(4-pyridylmethylaminosulfonyl)phenylsulfonyloxy)phenoxy]propoxyamine, as prepared in the previous step, in a manner analogous to step c of Example 75 (without acidification with HCl-methanol). $^1$H NMR (300 MHz, CDCl$_3$) δ8.46 (dd, 2H, J=4.5, 1.6 Hz), 8.21 (dd, 1H, J=7.8, 1.4 Hz), 8.03 (dd, 1H, J=7.7, 1.4 Hz), 7.73 (td, 1H, J=7.6, 1.5 Hz), 7.64 (td, 1H, J=7.7, 1.4 Hz), 7.15 (m, 2H), 6.60 (br s, 1H), 6.58 (br s, 1H), 6.54 (t, 1H, J=2.1 Hz), 4.22 (s, 2H), 3.95 (m, 4H), 2.23 (s, 3H), 2.02 (m, 2H). Mass spectrum (MALDI-TOF, α-cyano-4-hydroxycinnamic acid matrix) calcd. for $C_{22}H_{31}N_5O_7S_2$: 550.1 (M+H), 572.1 (M+Na). Found: 550.2, 572.1.

EXAMPLE 80

N-Methyl-N-{3-[5-methyl-3-(2-(methylsulfonyl) phenylsulfonyloxy)phenoxy]propoxy}guanidine hydrochloride a) N,N'-(Bis-tert-butyloxycarbonyl)-N"-{3-[5-methyl-3-(2-(methylsulfonyl)phenylsulfonyloxy)phenoxy]propoxy}guanidine The title compound was prepared in 70% yield from 2-methylsulfonylbenzenesulfonyl chloride in a manner analogous to step b of Example 19. $^1$H-NMR (300 MHz, CDCl$_3$) δ9.08 (s, 1H), 8.45 (d, J=7.8 Hz, 1H), 8.10 (d, J=7.8 Hz, 1H), 7.88 (t, J=7.7 Hz, 1H), 7.74 (t, J=7.7 Hz, 1H), 7.70 (s, 1H), 6.59 (s, 2H), 6.54 (s, 1H), 4.18 (t, J=6.2 Hz, 2H), 3.94 (t, J=6.1 Hz, 2H), 3.45 (s, 3H), 2.23 (s, 3H), 2.10 (pentet, J=6.2 Hz, 2H), 1.49 (s, 18H).

b) N,N'-(Bis-tert-butyloxycarbonyl)-N"-methyl-N"-{3-[5-methyl-3-(2-(methylsulfonyl)phenylsulfonyloxy)phenoxy]propoxy}guanidine To a solution of N,N'-(bis-tert-butyloxycarbonyl)-N"-{3-[5-methyl-3-(2-(methylsulfonyl)phenylsulfonyloxy)phenoxy]propoxy}guanidine (220 mg, 0.334 mmol), as prepared in the preceding step, triphenylphosphine (105 mg, 0.4 mmol) and anhydrous methanol (13 mg, 17 (L, 0.4 mmol) in tetrahydrofuran (5 mL) was added diethyl azodicarboxylate (70 mg, 0.4 mmol). The mixture was stirred at ambient for 4 h. After evaporated the solvent in vacuo, the residue was purified on a Waters Sep-Pak (10 g silica, dichloromethane to 2% ethyl acetate in dichloromethane) to give the title compound as a colorless oil (100 mg, 45%). $^1$H-NMR (300 MHz, CDCl$_3$) δ8.45 (d, J=7.8 Hz, 1H), 8.13 (d, J=7.8 Hz, 1H), 7.88 (t, J=7.7 Hz, 1H), 7.75 (t, J=7.7 Hz, 1H), 7.30 (s, 1H), 6.60 (s, 1H), 6.59 (s, 1H), 6.58 (s, 1H), 4.17 (t, J=6.1 Hz, 2H), 3.94 (t, J=6.1 Hz, 2H), 3.45 (s, 3H), 3.09 (s, 3H), 2.24 (s, 3H), 2.10 (pentet, J=6.2 Hz, 2H), 1.48 (s, 9H), 1.44 (s, 9H).

c) N-Methyl-N-{3-[5-methyl-3-(2-(methylsulfonyl) phenylsulfonyloxy)phenoxy]propoxy}guanidine hydrochloride The title compound was prepared in 89% yield from N,N'-(bis-tert-butyloxycarbonyl)-N"-methyl-N"-{3-[5-methyl-3-(2-(methylsulfonyl)phenylsulfonyloxy)phenoxy]propoxy}guanidine, as prepared in the preceding step, in a manner analogous to step i of Example 20. $^1$H-NMR (300 MHz, DMSO-d$_6$) δ11.00 (s, 1H), 8.37 (d, J=7.8 Hz, 1H), 8.13 (d, J=7.9 Hz, 1H), 8.11 (t, J=7.7 Hz, 1H), 7.96 (t, J=7.7 Hz, 1H), 7.53 (br s, 3H), 6.75 (s, 1H), 6.54 (s, 1H), 6.50 (s, 1H), 3.98 (t, J=6.2 Hz, 2H), 3.87 (t, J=6.2 Hz, 2H), 3.47 (s, 3H), 2.72 (s, 3H), 2.22 (s, 1H), 2.00 (pentet, J=6.3 Hz, 2H). Mass spectrum (MALDI-TOF, α-cyano-4-hydroxycinnamic acid matrix) calcd. for $C_{19}H_{25}N_3O_7S_2$: 472.1 (M+H), 494.1 (M+Na). Found: 472.1, 494.0.

EXAMPLE 81

3-[3-Methyl-5-(N-methyl-2-(methylsulfonyl) phenylsulfonylamino)phenoxy]propoxyguanidine hydrochloride a) 2-Bromo-2-methylpropanamide To a vigorously stirred solution of 2-bromo-2-methylpropanoyl bromide (11 mL) in light petroleum ether (250 mL) at 0° C. was added in portions aqueous ammonia (50 mL). Stirring was continued for a further 30 min., and the resulting precipitate was collected and washed with water (2×50 mL) to give the title compound as a white solid (14.1 g, 96%) which was directly used for next step without further purification.

b) (3-Benzyloxy-5-methyl)phenoxy-2-methylpropanamide

3-Benzyloxy-5-methylphenol (2.14 g, 10 mmol), as prepared in step a of Example 20, was stirred in dry 1,4-dioxane (50 mL) with sodium hydride (265 mg, 11 mmol) for 1 h. 2-Bromo-2-methylpropanamide (1.66 g, 10 mmol), as prepared in step b, was added and the reaction mixture was heated to 80° C. for 6 h. After cooling, the precipitated sodium bromide was filtered off, the filtrate was evaporated in vacuo. The residue was purified by flash column chromatography (7% ethyl acetate in dichloromethane) to give the title compound as a pale yellow solid (2.50 g, 83%). $^1$H-NMR (300 MHz, CDCl$_3$) δ7.40 (m, 5H), 6.61 (br s, 1H), 6.54 (s, 1H), 6.38 (s, 2H), 5.69 (br s, 1H), 5.29 (s, 2H), 2.28 (s, 3H), 1.97 (s, 3H), 1.52 (s, 3H).

c) N-1-(3-Benzyloxy-5-methylphenyl)-2-hydroxy-2-methylpropanamide

To a solution of 2-(3-benzyloxy-5-methyl)phenoxy-2-methylpropanamide (1.50 g, 5.0 mmol), as prepared in the preceding step, in 1,3-dimethyl-3,4,5,6-tetrahydro-2(1H)-pyrimidinone (DMPU) (2 mL) and N,N-dimethylformamide (18 mL) was added sodium hydride (360 mg, 15 mmol), the mixture was heated to 100° C. for 3 h. The solution was poured into water (200 mL) and extracted with ethyl acetate (3×100 mL). The organic phase was washed with water (3×100 mL), dried over Na$_2$SO$_4$, and concentrated in vacuo. The residue was purified by flash column chromatography (5% ethyl acetate in dichloromethane) to give the title compound as a white solid (870 mg, 58%). $^1$H-NMR (300 MHz, CDCl$_3$) δ8.61 (s, 1H), 7.42 (m, 5H), 7.28 (s, 1H), 6.93 (s, 1H), 6.59 (s, 1H), 5.05 (s, 2H), 2.30 (s, 3H), 2.18 (s, 1H), 1.58 (s, 3H), 1.56 (s, 3H).

d) Benzyloxy-5-methylaniline

N-1-(3-Benzyloxy-5-methylphenyl)-2-hydroxy-2-methylpropanamide (600 mg, 2.0 mmol), as prepared in the preceding step, was mixed with 10N NaOH (25 mL) and ethanol (10 mL), the mixture was heated to reflux for 2 days. After cooling to ambient temperature, the mixture was diluted with water (60 mL) and extracted with dichloromethane (3×60 mL). The dichloromethane solution was washed with brine (2×50 mL) and dried over Na$_2$SO$_4$. After the solvent was evaporated in vacuo, the residue was purified by flash column chromatography (dichloromethane) to give the title compound as a yellow oil (265 mg, 61%). $^1$H-NMR (300 MHz, CDCl$_3$) δ7.37 (m, 5H), 6.24 (s, 1H), 6.14 (s, 2H), 5.00 (s, 2H), 3.59 (br s, 2H), 2.23 (s, 3H).

e) 3-Benzyloxy-5-methyl-1-(2-(methylsulfonyl) phenylsulfonylaminobenzene

2-Methylsulfonylbenzenesulfonyl chloride (765 mg, 3.0 mmol) was added to a solution of 3-benzyloxy-5-methylaniline (640 mg, 3.0 mmol), as prepared in the preceding step, N-methylmorpholine (0.7 mL) in dichloromethane (20 mL). The mixture was stirred at ambient temperature overnight. After adding additional dichloromethane (100 mL), the dichloromethane solution was washed with saturated NaHCO$_3$ (2×50 mL), 10% HCl (2×50 mL), brine (2×50 mL), and dried over Na$_2$SO$_4$. After the solvent was evaporated in vacuo, the residue was purified by flash column chromatography (3:1 dichloromethane:hexane) to give the title compound as white solid (700 mg, 83%). $^1$H-NMR (300 MHz, CDCl$_3$) δ8.28 (d, J=7.8 Hz, 1H), 8.03 (s, 1H), 7.90 (d, J=7.8 Hz, 1H), 7.72 (t, J=7.6 Hz, 1H), 7.61 (t, J=7.6 Hz, 1H), 7.38 (m, 5H), 6.69 (s, 1H), 6.65 (s, 1H), 6.48 (s, 1H), 4.98 (s, 2H), 3.48 (s, 3H), 2.18 (s, 3H).

f) N-Methyl-3-benzyloxy-5-methyl-1-(2-(methylsulfonyl) phenylsulfonylaminobenzene 3-Benzyloxy-5-methyl-1-(2-(methylsulfonyl) phenylsulfonylaminobenzene (1.1 g, 2.5 mmol), as prepared in the preceding step, iodomethane (710 mg, 5.0 mmol), and $Cs_2CO_3$ (1.65 g, 5.0 mmol) were mixed in acetonitrile (20 mL). The mixture was stirred at ambient temperature for 4 h. The solid was removed by filtration, the filtrate was evaporated in in vacuo. The residue was dissolved in ethyl acetate (100 mL), washed with saturated $NaHCO_3$ (2×50 mL), brine (2×50 mL), and dried over $Na_2SO_4$. After the solvent was evaporated, the residue was purified by flash column chromatography (dichloromethane) to give the title compound as a yellow gum (1.08 g, 98%). $^1$H-NMR (300 MHz, $CDCl_3$) δ8.37 (d, J=7.7 Hz, 1H), 7.68 (t, J=8.1 Hz, 2H), 7.51 (t, J=8.2 Hz, 1H), 7.37 (m, 5H), 6.69 (s, 1H), 6.64 (s, 1H), 6.58 (s, 1H), 4.93 (s, 2H), 3.45 (s, 3H), 3.40 (s, 3H), 2.22 (s, 3H).

g) 3-Methyl-5-(N-methyl-2-(methylsulfonyl) phenylsulfonylamino)phenol

N-Methyl-3-benzyloxy-5-methyl-1-(2-(methylsulfonyl) phenylsulfonylaminobenzene (1.07 mg, 2.4 mmol) was mixed with 10% palladium on carbon (110 mg) in ethanol (20 mL), the mixture was stirred under hydrogen (balloon) for 2 h. the catalyst was removed by filtration through Celite, the filtrate was evaporated in vacuo to give the title compound as a pale yellow oil (680 mg, 80%) which was directly used for the next step without further purification. $^1$H-NMR (300 MHz, $CDCl_3$) δ8.38 (d, J=7.8 Hz, 1H), 7.75 (d, J=7.8 Hz, 1H), 7.72 9t, J=7.7 Hz, 1H), 7.57 (t, J=7.7 Hz, 1H), 6.55 (s, 2H), 6.51 (s, 1H), 5.16 (s, 1H), 3.46 (s, 3H), 3.39 (s, 3H), 2.20 (s, 3H).

h) 3-{5-Methyl-3-[N-methyl-2-(methylsulfonyl) phenylsulfonylamino]phenoxy}propanol The title compound was prepared in 91% yield from 3-methyl-5-(N-methyl-(2-(methylsulfonyl) phenylsulfonylamino)phenol, as prepared in the preceding step, in a manner analogous to step b of Eg. 20. $^1$H-NMR (300 MHz, $CDCl_3$), δ8.39 (d, J=7.8 Hz, 1H), 7.72 (t, J=7.7 Hz, 2H), 7.57 (t, J=7.7 Hz, 1H), 6.62 (s, 1H), 6.56 (s, 2H), 3.99 (t, J=6.0 Hz, 2H), 3.81 (t, J=6.0 Hz, 2H), 3.46 (s, 3H), 3.40 (s, 3H), 2.22 (s, 3H), 1.97 (pentet, J=6.0 Hz, 2H).

i) N-{3-[5-Methyl-[3-N'-methyl-(2-(methylsulfonyl) phenylsulfonylamino]phenoxy]propoxy}phthalimide The title compound was prepared in 86% yield from 3-{5-methyl-3-[N-methyl-(2-(methylsulfonyl) phenylsulfonylamino]phenoxy}propanol, as prepared in the preceding step, in a manner analogous to step d of Example 1. $^1$H-NMR (300 MHz, $CDCl_3$) δ8.39 (d, J=7.9 Hz, 1H), 7.85 (m, 2H), 7.77 (m, 3H), 7.72 (t, J=7.7 Hz, 2H), 7.57 (t, J=7.7 Hz, 1H), 6.62 (s, 1H), 3.99 (t, J=6.0 Hz, 2H), 3.81 (t, J=6.0 Hz, 2H), 3.46 (s, 3H), 3.40 (s, 3H), 2.22 (s, 3H), 1.97 (pentet, J=6.0 Hz, 2H).

j) 3-[5-Methyl-3-[N-methyl-(2-methylsulfonyl) phenylsulfonylamino]phenoxy]propoxyamine The title compound was prepared in 89% yield from N-{3-[5-methyl-[3 -N-methyl-2-(methylsulfonyl) phenylsulfonylamino]phenoxy]propoxy}phthalimide, as prepared in the preceding step, in a manner analogous to step e of Example 1. $^1$H-NMR (300 MHz, $CDCl_3$) δ8.39 (d, J=7.9 Hz, 1H), 7.71 (t, J=7.9 Hz, 2H), 7.56 (t, J=7.8 Hz, 1H), 6.61 (s, 1H), 6.56 (s, 1H), 6.53 (s, 1H), 5.39 (br s, 2H), 3.91 (t, J=6.3 Hz, 2H), 3.79 (t, J=6.1 Hz, 2H), 3.46 (s, 3H), 3.40 (s, 3H), 2.12 (s, 3H), 1.99 (pentet, J=6.2 Hz, 2H).

k) 3-[3-Methyl-5-(N-methyl-2-(methylsulfonyl) phenylsulfonylamino)phenoxy]propoxyguanidine hydrochloride The title compound was prepared in 85% yield from 3-[5-methyl-3-[N-methyl-2-(methylsulfonyl) phenylsulfonylamino]phenoxy]propoxyamine, as prepared in the preceding step, in a manner analogous to step f of Example 1. $^1$H-NMR (300 MHz, DMSO-$d_6$) δ8.29 (d, J=7.8 Hz, 1H), 7.95 (t, J=7.7 Hz, 1H), 7.86 (t, J=7.7 Hz, 2H), 7.82 (t, J=7.8 Hz, 1H), 7.71 (br s, 4H), 6.71 (s, 1H), 6.63 (s, 1H), 6.59 (s, 1H), 3.98 (t, J=6.3 Hz, 2H), 3.91 (t, J=6.3 Hz, 2H), 3.42 (s, 3H), 3.32 (s, 3H), 2.21 (s, 3H), 2.02 (pentet, J=6.2 Hz, 2H). Mass spectrum (MALDI-TOF, α-cyano-4-hydroxycinnamic acid matrix) calcd. for $C_{19}H_{26}N_4O_6S_2$: 471.1 (M+H), 493.1 (M+Na). Found: 471.1, 492.9.

EXAMPLE 82

3-[3-(2-Chlorophenylsulfonyloxy)-5-methylphenoxy]propylaminoguanidine diacetate a) 3-[3-(2-Chlorophenylsulfonyloxy)-5-methylphenoxy] propionaldehyde Sulfur trioxide pyridine complex (847 mg, 5.36 mmol) was added to a solution of 619 mg (1.74 mmol) 3-[3-(2-chlorophenylsulfonyloxy)-5-methylphenoxy]propanol, as prepared according to step c of Example 1, 411 μL (3.23 mmol) of N,N-diisopropylethylamine, and 230 μL (3.0 mmol) of dimethylsulfoxide in dichloromethane (10 mL). The reaction mixture was stirred at ambient temperature for 1 h and then quenched with 10% citric acid (20 mL). The reaction mixture was extracted with diethyl ether (3×30 mL), dried (MgSO$_4$), and purified by flash chromatography (diethyl ether/petroleum ether (2:1 to 4:1)) to afford 289 mg (47% yield) of the title compound as a colorless oil. $^1$H-NMR (300 MHz, CDCl$_3$) δ9.83 (t, 1H, J=1.4 Hz), 7.97 (dd, 1H), 7.56–7.65 (m, 2H), 7.35–7.42 (m, 1H), 6.60 (br s, 1H), 6.57 (br s, 1H), 6.49 (br s, 1H), 4.19 (t, 2H, J=6.1 Hz), 2.86 (dt, 2H, J=6, 1.4 Hz), and 2.25 (s, 1H).

b) 2-[2-[3-(2-Chlorophenylsulfonyloxy)-5-methylphenoxy] ethyl-1-methylene]hydrazinecarboximidamide hydrochloride A solution of 289 mg (0.82 mmol) of 3-[3-(2-chlorophenylsulfonyloxy)-5-methylphenoxy] propionaldehyde, as prepared in the preceding step, 223 mg (1.62 mmol) of aminoguanidine nitrate, and 200 μL (0.80 mmol) of 4N HCl/dioxane in 3 mL of ethanol was stirred at ambient temperature overnight. The reaction mixture was treated with 10 mL of water and stirred for 15 min. The reaction mixture was treated with 1.2 mL of 2N sodium hydroxide and then extracted into dichloromethane (3×20 mL). The organic phase was washed with water (3×20 mL), dried (K$_2$CO$_3$), and concentrated to give 321 mg of crude product as a free base. The residue was dissolved in dichloromethane (1 mL), treated with 800 μL (3.2 mmol) of 4N HCl/dioxane solution. The solvent was removed and the product was triturated from a mixture of dichloromethane/ ether/hexane to give 190 mg of the title compound as a colorless solid. $^1$H-NMR (300 MHz, DMSO-d$_6$) δ11.58 (br s, 1H), 7.95 (dd, 1H, J=7.9, 1.5 Hz), 7.90–7.80 (m, 2H), 7.52–7.61 (m, 6H), 6.77 (s, 1H), 6.49 (s, 1H), 6.46 (br t, 1H, J=2.2 Hz), 4.14 (t, 2H), 2.67 (q, 2H), and 2.21 (s, 3H). Mass spectrum (MALDI-TOF, α-cyano-4-hydroxycinnamic acid matrix) calcd. for C$_{17}$H$_{19}$ClN$_4$O$_4$S: 411.1 (M+H). Found: 411.1.

c) [3-[3-(2-Chlorophenylsulfonyloxy)-5-methylphenoxy] propylamino]guanidine diacetate To 300 mg of 2-[2-[3-(2-chlorophenylsulfonyloxy)-5-methylphenoxy]ethyl-1-methylene] hydrazinecarboximidamide hydrochloride, as prepared in the preceding step, in tetrahydrofuran (2 mL) was added 3 mL of 2N lithium borohydride in tetrahydrofuran. The reaction mixture was stirred overnight, quenched with 2N sodium hydroxide, and extracted into dichloromethane. The organic phase was dried ($K_2CO_3$) and concentrated. The residue was dissolved in dichloromethane and treated with 1 mL of glacial acetic acid. The solution was concentrated in vacuo. The residue was purified, together with the crude product obtained from another reaction using 300 mg of 2-[2-[3-(2-chlorophenylsulfonyloxy)-5-methylphenoxy]ethyl-1-methylene]hydrazinecarboximidamide hydrochloride, by flash chromatography using elutions of dichloromethane/methanol/acetic acid (85:9.5:1.5 to 78:19:3) to give 222 mg of the title compound as a gum. $^1$H-NMR (300 MHz, $CD_3OD$) δ7.92 (dd, 1H), 7.67–7.77 (m, 2H), 7.44–7.51 (ddd, 1H), 6.66–6.68 (m, 1H), 6.47–6.48 (m, 2H), 3.97 (t, 2H, J=6 Hz), 2.94 (t, 2H, J=7 Hz), 2.21 (s, 3H), 1.91 (pentet, 2H), 1.91 (s, 6H). Mass spectrum (MALDI-TOF, α-cyano-4-hydroxycinnamic acid matrix) calcd. for $C_{17}H_{21}ClN_4O_4S$: 413.1 (M+H). Found: 413.1.

EXAMPLE 83

3-[5-Methyl-3-(2-trifluoromethylphenylsulfonyloxy)phenoxy]propylaminoguanidine hydrochloride a) 5-Methyl-3-(2-trifluoromethylphenylsulfonyloxy)phenol Orcinol monohydrate (2.84 g, 20.0 mmol) and 2-trifluoromethylbenzenesulfonyl chloride (4.90 g, 20.0 mmol) were mixed in saturated $NaHCO_3$ (70 mL) and diethyl ether (70 mL). The biphasic mixture was stirred vigorously at room temperature overnight. The reaction mixture was quenched with water (100 mL) and extracted into ethyl acetate (3×80 mL). The organic phase was washed with brine (2×50 mL) and dried over $Na_2SO_4$. After removing the solvent in vacuo, the residue was purified by flash column chromatography (dichloromethane to 2% ethyl acetate in dichloromethane) to give the title compound as a white solid (3.65 g, 55%). $^1$H-NMR (300 MHz, $CDCl_3$) δ8.12 (d, J=8.0 Hz, 1H), 7.98 (d, J=7.9 Hz, 1H), 7.80 (t, J=8.2 Hz, 1H), 7.69 (t, J=7.8 Hz, 1H), 6.55 (s, 1H), 6.48 (s, 1H), 6.39 (s, 1H), 5.11 (s, 1H), 2.23 (s, 3H).

b) 3-[5-Methyl-3-(2-trifluoromethylphenylsulfonyloxy)phenoxy]propanol

To a solution of 5-methyl-3-(2-trifluoromethylphenylsulfonyloxy)phenol (665 mg, 2.0 mmol), as prepared in the preceding step, tri-N-butylphosphine (607 mg, 3.0 mmol), and 1,3-propanediol (760 mg, 10 mmol) in tetrahydrofuran (20 mL) was added 1,1'-(azodicarbonyl)dipiperidine (757 mg, 3.0 mmol). The mixture was stirred at room temperature overnight. Hexane (30 mL) was added to the mixture, and the precipitates were removed by filtration. The filtrate was evaporated in vacuo and the residue was purified by flash column chromatography (2:1 hexane/ethyl acetate) to give the title compound as a colorless oil (745 mg, 94%). $^1$H-NMR (300 MHz, $CDCl_3$) δ8.13 (d, J=7.2 Hz, 1H), 7.99 (d, J=7.2 Hz, 1H), 7.80 (t, J=7.6 Hz, 1H), 7.70 (t, J=7.3 Hz, 1H), 6.63 (s, 1H), 6.48 (s, 1H), 6.46 (s, 1H), 4.02 (t, J=6.0 Hz, 2H), 3.81 (m, 2H), 2.25 (s, 3H), 1.99 (m, 2H), 1.61 (s, 1H).

c) 3-[5-Methyl-3-(2-trifluoromethylphenylsulfonyloxy)phenoxy]propionaldehyde

Sulfur trioxide pyridine complex (1.12 mg, 7.0 mmol) was added to a solution of 3-[5-methyl-3-(2-trifluoromethylphenylsulfonyloxy)phenoxy]propanol (700 mg, 1.8 mmol), as prepared in the preceding step, N,N-diisopropylethylamine (0.7 mL, 5.5 mmol), and dimethylsulfoxide (0.4 mL, 5.6 mmol) in $CH_2Cl_2$ (20 mL). The reaction mixture was stirred at a ambient temperature for 1 hour and then quenched with 10% citric acid (50 mL). The mixture was extracted into dichloromethane (3×50 mL), then the dichloromethane solution was washed with 10% citric acid (40 mL) and dried over $Na_2SO_4$. After removing the solvent in vacuo, the residue was purified by flash column chromatography ($CH_2Cl_2$) to give the title compound as a colorless oil (595 mg, 85%). $^1$H-NMR (300 MHz, $CDCl_3$) δ9.84 (s, 1H), 8.13 (d, J=7.5 Hz, 1H), 7.99 (d, J=7.5 Hz, 1H), 7.80 (t, J=7.6 Hz, 1H), 7.70 (t, J=7.3 Hz, 1H), 6.62 (s, 1H), 6.51 (s, 1H), 6.45 (s, 1H), 4.21 (t, J=6.0 Hz, 2H), 2.87 (t, J=6.0 Hz, 2H), 2.25 (s, 3H).

d) 2-[2-[5-Methyl-3-(2-trifluoromethylphenylsulfonyloxy)phenoxy]ethyl-1-methylene]hydrazinecarboximidamide nitrate A solution of 3-[5-methyl-3-(2-trifluoromethylphenylsulfonyloxy)phenoxy]propionaldehyde (583 mg, 1.5 mmol), as prepared in the preceding step, and aminoguanidine nitrate (412 mg, 3.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a colorless solid (465 mg, 61%). $^1$H-NMR (300 MHz, DMSO-$d_6$) δ8.19 (d, J=7.7 Hz, 1H), 8.11 (d, J=7.8 Hz, 1H), 8.06 (t, J=7.6 Hz, 1H), 7.94 (t, J=7.6 Hz, 1H), 7.74 (br s, 1H), 7.55 (br s, 4H), 4.14 (t, J=6.3 Hz, 2H), 2.68 (t, J=9.0 Hz, 2H), 2.21 (s, 3H). Mass spectrum (MALDI-TOF, α-cyano-4-hydroxycinnamic acid matrix) calcd. for $C_{18}H_{19}F_3N_4O_4S$: 445.1 (M+H), 467.1 (M+Na). Found: 445.0, 466.8.

e) [3-[5-Methyl-3-(2-trifluoromethylphenylsulfonyloxy)phenoxy]propylamino]guanidine hydrochloride A mixture of 2-[2-[5-methyl-3-(2-trifluoromethylphenylsulfonyloxy)phenoxy]ethyl-1-methylene]hydrazinecarboximidamide nitrate (76 mg, 0.15 mmol) and 10% palladium on carbon (10 mg) in ethanol (5 mL) was stirred under hydrogen (balloon) overnight. The catalyst was removed by filtration through Celite. After evaporating the solvent, the residue was dissolved in dichloromethane (50 mL), washed with 2 N NaOH (10 mL) and brine (10 mL), and dried over $K_2CO_3$. After removing the dichloromethane, the residue was dissolved in HCl-methanol (10 mL) and concentrated. The residue was purified by flash column chromatography (10% methanol in dichloromethane) to give the title product as a colorless foam (38 mg, 47%). $^1$H-NMR (300 MHz, DMSO-$d_6$) δ8.90 (s, 1H), 8.19 (d, J=7.7 Hz, 1H), 8.11 (d, J=7.8 Hz, 1H), 8.06 (t, J=7.6 Hz, 1H), 7.94 (t, J=7.6 Hz, 1H), 6.90–7.70 (m, 4H), 6.76 (s, 1H), 6.41 (s, 2H), 5.29 (br s, 1H), 3.99 (t, J=9.0 Hz, 2H), 2.82 (m, 2H), 2.20 (s, 3H), 1.78 (m, 2H). Mass spectrum (MALDI-TOF, α-cyano-4-hydroxycinnamic acid matrix) calcd. for $C_{18}H_{21}F_3N_4O_4S$: 447.1 (M+H). Found: 446.9.

EXAMPLE 84

[3-[3-(5-Chlorothiophenyl-2-sulfonyloxy)-5-methylphenoxy]propylamino]guanidine acetate a) 3-[3-(5-Chlorothiophenyl-2-sulfonyloxy)-5-methylphenoxy]propionaldehyde To 3-[3-(5-chlorothiophenyl-2-sulfonyloxy)-5-methylphenoxy]propanol (1.77 g, 4.88 mmol), as prepared in step b of Example 5, in dichloromethane (30 mL) containing dimethylsulfoxide (760 μL, 9.08 mmol) and N,N-diisopropylethylamine (4 mL, 23 mmol) at 0° C. was added slowly sulfur trioxide pyridine complex (1.55 g, 9.8 mmol). The reaction mixture was stirred for 20 min, quenched with excess 5% citric acid (acidic to pH paper), and extracted into diethyl ether. The organic phase was washed with additional 5% citric acid, dried ($MgSO_4$), and purified by flash chromatography (dichloromethane to 3% diethyl ether in dichloromethane) to give 1.13 g of the title compound as an oil. $^1$H-NMR (300 MHz, CDCl$_3$) δ9.84 (t, 1H, J=1 Hz), 7.40 (d, 1H, J=4 Hz), 6.95 (d, 1H, J=4 Hz), 6.65 (br s, 1H), 6.51 (br s, 1H), 6.44 (t, 1H, J=2 Hz), 4.22 (t, 2H, J=6 Hz), 2.89 (dt, 2H, J=6, 1 Hz), 2.28 (s, 3H). Mass spectrum (MALDI-TOF, α-cyano-4-hydroxycinnamic acid matrix) calcd. for C$_{14}$H$_{13}$ClO$_5$S$_2$: 383.0 (M+Na). Found: 382.9 b) 2-[2-[3-(5-Chlorothiophenyl-2-sulfonyloxy)-5-methylphenoxy]ethyl-1-methylene]hydrazinecarboximidamide nitrate A mixture of 3-[3-(5-chlorothiophenyl-2-sulfonyloxy)-5-methylphenoxy]propionaldehyde (1.60 g, 4.4 mmol) and aminoguanidine nitrate (0.73 g, 0.53 mmol) in ethanol (15 mL) was stirred overnight at ambient temperature. Water (25 mL) was added dropwise over 15 min. The mixture was stirred for 30 min then filtered to give the title compound (1.75 g, 87%) as a white solid. $^1$H-NMR (300 MHz, DMSO-d$_6$) δ7.76 (d, 1H, J=4.2 Hz), 7.55 (t, 1H, J=5.0 Hz), 7.40 (d, 1H, J=4.2 Hz), 6.81 (br s, 1H), 6.55 (br s, 1H), 6.52 (t, 1H, J=2.2 Hz), 4.17 (t, 2H, J=6.4 Hz), 2.70 (dt, 2H, J=6.4, 5.0 Hz), 2.26 (s, 3H). Mass spectrum (MALDI-TOF, α-cyano-4-hydroxycinnamic acid matrix) calcd. for C$_{15}$H$_{17}$ClN$_4$O$_4$S$_2$: 417.0 (M+H). Found: 416.5.

c) [3-[3-(5-Chlorothiophenyl-2-sulfonyloxy)-5-methylphenoxy]propylamino]guanidine acetate To 2-[2-[3-(5-chlorothiophenyl-2-sulfonyloxy)-5-methylphenoxy]ethyl-1-methylene]hydrazinecarboximidamide nitrate (137.5 mg, 0.29 mmol), as prepared in the preceding step, in tetrahydrofuran (1 mL) was added 1 mL of 2M lithium borohydride in tetrahydrofuran. The reaction mixture was stirred for 5 min, basified with 10% potassium carbonate, extracted into dichloromethane, dried (K$_2$CO$_3$), and concentrated. The residue was treated with acetic acid (0.4 mL) and concentrated. The residue was chromatographed using a 10 g Waters Sep-Pak silica gel column eluting with dichloromethane/methanol/acetic acid (89:9.8:1.2 to 78:19:3) to give 106 mg of recovered 2-[2-[3-(5-chlorothiophenyl-2-sulfonyloxy)-5-methylphenoxy]ethyl-1-methylene]hydrazinecarboximidamide acetate and 27 mg of the title compound. Mass spectrum (MALDI-TOF, α-cyano-4-hydroxycinnamic acid matrix) calcd. for C$_{15}$H$_{19}$ClN$_4$O$_4$S$_2$: 419.1 (M+H). Found: 418.8.

EXAMPLE 85

[3-[3-(2-Methoxyphenylsulfonyloxy)-5-methylphenoxy]propylamino]guanidine diacetate a) 3-[3-(2-Methoxyphenylsulfonyloxy)-5-methylphenoxy]propionaldehyde Sulfur trioxide pyridine complex (1.87 g, 11.7 mmol) was added in portions over 15 min to a solution of 3-[3-(2-methoxyphenylsulfonyloxy)-5-methylphenoxy]propanol (2.07 g, 5.9 mmol, prepared in step c of Example 2). N,N-diisopropylethylamine (2.15 mL, 12.3 mmol), and anhydrous dimethylsulfoxide (1.25 mL, 17.6 mmol) in anhydrous dichloromethane (14 mL) at 0° C. under a nitrogen atmosphere. The solution was stirred at 0° C. for 1 h, then the reaction was quenched with 5% aqueous citric acid (50 mL). The layers were separated, and the aqueous layer was extracted with dichloromethane (15 mL). The combined organic extracts were washed with 5% aqueous citric acid (50 mL), pH 7 buffer (40 mL) and brine (50 mL), dried over Na$_2$SO$_4$, filtered, and evaporated. The residual gold oil was purified by flash column chromatography (3:2 diethyl ether/hexane) to give the title compound (1.28 g, 62%) as a colorless oil. $^1$H-NMR (300 MHz, CDCl$_3$) δ9.82 (t, 1H, J=1.5 Hz), 7.82 (dd, 1H, J=7.9, 1.7 Hz), 7.62 (ddd, 1H, J=8.4, 7.4, 1.8 Hz), 7.09 (dd, 1H, J=8.4, 0.8 Hz), 7.02 (m, 1H), 6.58 (br s, 1H), 6.54 (br s, 1H), 6.45 (t, 1H, J=2 Hz), 4.18 (t, 2H, J=6.1 Hz), 4.02 (s, 3H), 2.85 (dt, 2H, J=6.1, 1.5 Hz), 2.24 (s, 3H). Mass spectrum (MALDI-TOF, α-cyano-4-hydroxycinnamic acid matrix) calcd. for C$_{17}$H$_{18}$O$_6$S: 373.1 (M+Na). Found: 373.0.

b) 2-[2-[3-(2-Methoxyphenylsulfonyloxy)-5-methylphenoxy]ethyl-1-methylene]hydrazinecarboximidamide acetate A mixture of aminoguanidine hydrochloride (0.811 g, 7.33 mmol) and 3-[3-(2-methoxyphenylsulfonyloxy)-5-methylphenoxy]propionaldehyde (1.28 g, 3.66 mmol, prepared in the preceding step) in ethanol (30 mL) was stirred overnight at ambient temperature. The mixture was concentrated in vacuo to approximately 15 mL, then dichloromethane (60 mL) was added to precipitate excess aminoguanidine hydrochloride. The mixture was filtered and the filtrate was concentrated. The residue was dissolved in dichloromethane (30 mL) and extracted with aqueous NaOH (1.85 mL of 2N NaOH in 90 mL water). The aqueous layer was extracted with CH$_2$Cl$_2$ (2×30 mL). The combined organic extracts were washed with water (50 mL) and brine (2×50 mL), dried over K$_2$CO$_3$, filtered, and evaporated to give the free base of the title compound (1.38 g, 93%) as a gold foam.

The acetate salt of the title compound was made by adding glacial acetic acid (0.75 mL, 30 mmol) dropwise to the free base, 2-[2-[3-(2-methoxyphenylsulfonyloxy)-5-methylphenoxy]-ethyl-1-methylene]hydrazinecarboximidamide, (1.03 g, 2.53 mmol, prepared above) in dichloromethane (10 mL). Solvent was removed in vacuo at ambient temperature. Crude acetate salt was purified by flash column chromatography (20% to 100% of 1:10:40 acetic acid/methanol/dichloromethane in dichloromethane) to give the title compound (0.91 g, 77%) as a white foam. $^1$H-NMR (300 MHz, CDCl$_3$) δ7.81 (dd, 1H, J=7.9, 1.7 Hz), 7.62 (ddd, 1H, J=8.4, 7.5, 1.7 Hz), 7.54 (t, 1H, J=5 Hz), 7.09 (d, 1H, J=8.4 Hz), 7.02 (dt, 1H, J=7.9, 0.9 Hz), 6.57 (br s, 1H), 6.50 (br s, 1H), 6.46 (br s, 1H), 4.05 (t, 2H, J=6 Hz), 4.01 (s, 3H), 2.68 (q, 2H, J=6 Hz), 2.23 (s, 3H). Mass spectrum (MALDI-TOF, α-cyano-4-hydroxycinnamic acid matrix) calcd. for C$_{18}$H$_{22}$N$_4$O$_5$S: 407.1 (M+H). Found: 407.0.

c) [3-[3-(2-Methoxyphenylsulfonyloxy)-5-methylphenoxy]propylamino]guanidine diacetate A solution of 2-[2-[3-(2-methoxyphenylsulfonyloxy)-5-methylphenoxy]ethyl-1-methylene]hydrazinecarboximidamide acetate (239 mg, 0.522 mmol), as prepared in the preceding step, in 1 mL of THF was treated with 1.5 mL of 2M lithium borohydride in THF. The reaction mixture was stirred overnight and quenched carefully with 10% hydrochloric acid. The reaction mixture was basified with 10% potassium carbonate solution, extracted into dichloromethane, dried (K$_2$CO$_3$), and concentrated. The residue (174 mg) was treated with 500 μL of acetic acid and concentrated. Chromatography through a 10 g Waters Sep-Pak silica gel column eluting with dichloromethane/methanol/acetic acid (89:9.8:1.2) gave 102 mg of the title compound as a gum. $^1$H-NMR (300 MHz, DMSO-d$_6$) δ7.67–7.74 (m, 2H), 7.28 (d, 1H, J=8 Hz), 7.05 (dt, 1H, J=7, 1 Hz), 6.65 (br s, 1H), 6.46 (t, 1H, J=2 Hz), 6.43 (br s, 1H), 4.01 (s, 3H), 3.97 (t, 2H, J=6 Hz), 2.95 (t, 2H, J=7 Hz), (s, 3H), 1.92 (s, 6H), 1.90 (pentet, 2H, J=6 Hz). Mass spectrum (MALDI-TOF, α-cyano-4-hydroxycinnamic acid matrix) calcd. for C$_{18}$H$_{24}$N$_4$O$_5$S: 409.2 (M+H). Found: 408.8.

EXAMPLE 86

[3-[3-(2-Cyanophenylsulfonyloxy)-5-methylphenoxy]propylamino]guanidine acetate a) [3-(2-Cyanophenylsulfonyloxy)-5-methylphenoxy]propionaldehyde Sulfur trioxide pyridine complex (480 mg, 3.0 mmol) was added to a solution of 3-[3-(2-cyanophenylsulfonyloxy)-5- methylphenoxy]propanol (315 mg, 0.9 mmol), as prepared in step b of Example 6, N,N-diisopropylethylamine (0.5 mL, 3.9 mmol) and dimethylsulfoxide (0.2 mL. 2.8 mmol) in dichloromethane (10 mL). The reaction mixture was stirred at ambient temperature for 1 hour and then quenched with 10% citric acid (30 mL). The mixture was extracted into dichloromethane (3×40 mL), and the dichloromethane solution was washed with 10% citric acid (30 mL) and dried over $Na_2SO_4$. After removing the solvent in vacuo, the residue was purified by flash column chromatography (dichloromethane) to give the title compound as a colorless oil (260 mg, 83%). $^1$H-NMR (300 MHz, $CDCl_3$) δ9.84 (s, 1H), 8.11 (m, 1H), 7.94 (m, 1H), 7.78–7.81 (m, 2H), 6.65 (s, 1H), 6.61 (s, 1H), 6.57 (s, 1H), 4.24 (t, J=6.0 Hz, 2H), 2.88 (t, J=6.0 Hz, 2H), 2.27 (s, 3H).

b) [2-[3-(2-Cyanophenylsulfonyloxy)-5-methylphenoxy] ethyl-1-methylene]hydrazinecarboximidamide hydrochloride A solution of 3-[3-(2-cyanophenylsulfonyloxy)-5-methylphenoxy]propionaldehyde (240 mg, 0.7 mmol), as prepared in the preceding step, and aminoguanidine nitrate (200 mg, 1.5 mmol) in ethanol (8 mL) was stirred at ambient temperature overnight. Water (20 mL was added to the reaction mixture. The precipitates were collected, washed with water (2×15 mL) and diethyl ether (2×20 mL), and dried under high vacuum. The solid was suspended in water (40 mL), treated with 2N sodium hydroxide (1.0 mL), and extracted into dichloromethane (3×50 mL). The organic phase was dried over $K_2CO_3$. After removing the solvent, the residue was dissolved in dichloromethane (1 mL), and the dichloromethane solution was added to the solution of 1.5 mL of 0.6M HCl methanol in diethyl ether (50 mL) to give the title compound as a colorless solid (245 mg, 80%). $^1$H-NMR (300 MHz, DMSO-$d_6$) δ8.28 (m, 1H), 8.09 (m, 1H), 7.97–8.04 (m, 2H), 7.55 (br s, 5H), 6.80 (s, 1H), 6.50 (s, 2H), 4.15 (t, J=6.3 Hz, 2H), 2.68 (m, 2H), 2.22 (s, 3H). Mass spectrum (MALDI-TOF, α-cyano-4-hydroxycinnamic acid matrix) calcd. for $C_{18}H_{19}N_5O_4S$: 402.1 (M+H), 424.1 (M+Na), 440.1 (M+K). Found: 402.1, 424.1, 440.1.

c) -[3-(2-Cyanophenylsulfonyloxy)-5-methylphenoxy] propylamino]guanidine acetate To a suspension of 2-[2-[3-(2-cyanophenylsulfonyloxy)-5-methylphenoxy]ethyl-1-methylene] hydrazinecarboximidamide hydrochloride (190 mg, 0.4 mmol), prepared in the preceding step, in tetrahydrofuran (5 mL) was added lithium borohydride (2M, 3.0 mL. 6.0 mmol). The reaction mixture was stirred at ambient temperature for two days under nitrogen. The solution was acidified (pH 2) with 10% HCl solution, and the mixture was stirred for 10 minutes. The solution was basified (pH 8–9) with 2N NaOH, and the mixture was extracted with dichloromethane (3×50 mL). The dichloromethane extracts were washed with brine (50 mL) and dried over $K_2CO_3$. After removing the solvent, the residue was purified by flash column chromatography (90:9:1 dichloromethane/ methanol/acetic acid) to give the title compound as a colorless gum (65 mg, 35%). $^1$H-NMR (300 MHz, $CDCl_3$) δ8.30 (br s, 2H), 7.94–8.11 (m, 4H), 6.78 (s, 1H), 6.49 (s, 1H), 6.43 (s, 1H), 4.09 (t, J=8.0 Hz, 2H), 2.75 (t, J=6.7 Hz, 2H), 2.22 (s, 3H), 1.78 (m, 2H). Mass spectrum (MALDI-TOF, α-cyano-4-hydroxycinnamic acid matrix) calcd. for $C_{18}H_{21}N_5O_4S$: 404.1 (M+H). Found: 404.5.

EXAMPLE 87

In vitro Inhibition of Purified Enzymes

Reagents

All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations

All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 μL of substrate solution, 10 μL of test compound solution, and the plate allowed to thermally equilibrate at 37° C. in a Molecular Devices plate reader for >15 minutes. Reactions were initiated by the addition of a 10 μL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin

Thrombin activity was assessed as the ability to hydrolyze the substrate N-succinyl-Ala-Ala-Pro-Arg-p-nitroanilide. Substrate solutions were prepared at a concentration of 32 μM (32 μM<<Km=180 μM) in assay buffer. Final DMSO concentration was 4.3%. Purified human α-thrombin was diluted into assay buffer to a concentration of 15 nM. Final reagent concentrations were: [thrombin]=0.5 nM, [substrate N-succinyl-Ala-Ala-Pro-Arg-p-nitroanilide]=32 μM.

Factor X [FXa]

FXa activity was assessed as the ability to hydrolyze the substrate N-benzoyl-Ile-Glu-Gly-Arg-p-nitroanilide hydrochloride. Substrate solutions were prepared at a concentration of 51 μM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]= 51 μM.

Plasmin

Plasmin activity was assessed as the ability to hydrolyze the N-p-Tosyl-Gly-Pro-Lys-p-nitroanilide. Substrate solutions were prepared at a concentration of 37 µM (37 µM<<$K_m$=243 µM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 µM.

Chymotrypsin

Chymotrypsin activity was assessed as the ability to hydrolyze N-succinyl-Ala-Ala-Pro-Phe-p-nitroanilide. Substrate solutions were prepared at a concentration of 14 µM (14 µM<<$K_m$=62 µM) in assay buffer. Final DMSO concentration was 4.3%. Purified bovine chymotrypsin was diluted into assay buffer to a concentration of 81 nM. Final reagent concentrations were: [Chymotrypsin]=2.7 nM, [N-succinyl-Ala-Ala-Pro-Phe-p-nitroanilide]=14 µM.

Trypsin

Trypsin activity was assessed as the ability to hydrolyze N-benzoyl-Phe-Val-Arg-p-nitroanilide. Substrate solutions were prepared at a concentration of 13 µM (13 µM<<$K_m$=291 µM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe-Val-Arg-p-nitroanilide]=13 µM.

Elastase

Elastase activity was assessed as the ability to hydrolyze N-succinyl-Ala-Ala-Pro-Val-p-nitroanilide. Substrate solutions were prepared at a concentration of 19 µM (19 µM<<$K_m$=89 µM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 µM.

Urokinase

Urokinase activity was assessed as the ability to hydrolyze N-CBZ-Val-Gly-Arg-p-nitroanilide. Substrate solutions were prepared at a concentration of 100 µM (100 µM<$K_m$=1.2 mM) in assay buffer. Final DMSO concentration was 4.3%. Purified human kidney urokinase was diluted into assay buffer to a concentration of 1.2 µM. Final reagent concentrations were: [Urokinase]=40 nM, and N-CBZ-Val-Gly-Arg-p-nitroanilide]=100 mM.

The results of the compounds of Examples 1, 2, 3, 8, 11, 82 and 83 are shown in the following table.

The results indicate that the compounds of the present invention are inhibitors of proteases, including thrombin. In addition, the compounds of Examples 1, 2, 3, 8, 11, 82 and 83 are potent and highly selective inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

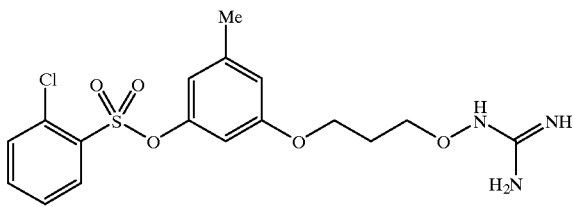

3-[3-(2-Chlorophenylsulfonyloxy)-5-methylphenoxy]propoxyguanidine

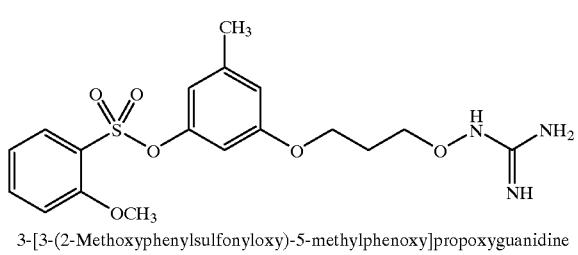

3-[3-(2-Methoxyphenylsulfonyloxy)-5-methylphenoxy]propoxyguanidine

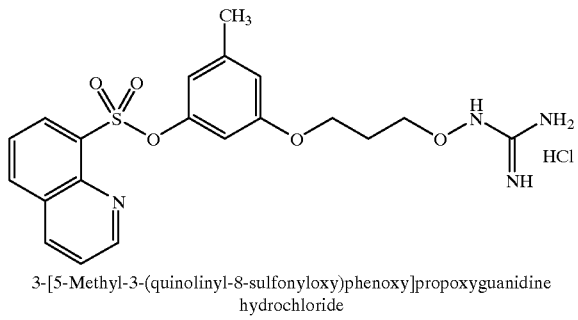

3-[5-Methyl-3-(quinolinyl-8-sulfonyloxy)phenoxy]propoxyguanidine hydrochloride

TABLE 1

| Compound (Eg. No.) | Thrombin | FXa | Chymotrypsin | Elastase | Plasmin | Trypsin |
|---|---|---|---|---|---|---|
| | | Assay, $K_i$(nM) or (% inhibition at [nM]) | | | | |
| 82 | 2.6 | 45000 | (0% at 12500) | (0% at 12500) | (0% at 12500) | 36000 |
| 83 | 7.2 | (0% at 1400) | (0% at 1400) | (0% at 1400) | (0% at 1400) | (0% at 1400) |
| 1 | 7.5 | (0% at 13300) | (0% at 13300) | (0% at 13300) | (0% at 13300) | 37000 |
| 2 | 10 | (0% at 2600) | (0% at 2600) | (0% at 2600) | (0% at 2600) | (0% at 2600) |
| 3 | 7 | (0% at 21870) | (0% at 21870) | (0% at 21870) | (0% at 21870) | 21000 |
| 8 | 10 | (0% at 22490) | (0% at 22490) | (0% at 22490) | (0% at 22490) | 25000 |
| 11 | 11 | (0% at 21360) | (0% at 21360) | (0% at 21360) | (0% at 21360) | (0% at 21360) |

-continued

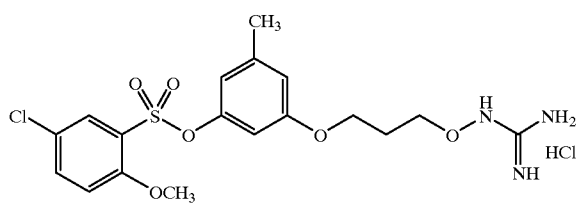
3-[3-(5-Chloro-2-methoxyphenylsulfonyloxy)-5-methylphenoxy]propoxyguanidine hydrochloride

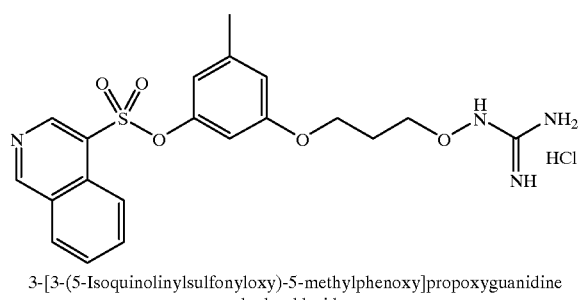
3-[3-(5-Isoquinolinylsulfonyloxy)-5-methylphenoxy]propoxyguanidine hydrochloride

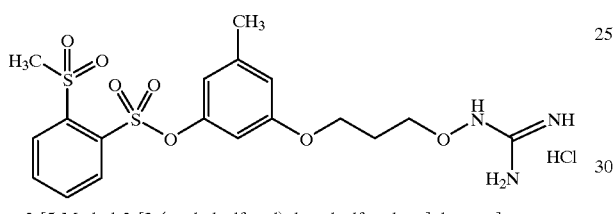
3-[5-Methyl-3-[2-(methylsulfonyl)phenylsulfonyloxy]phenoxy]propoxyguanidine hydrochloride

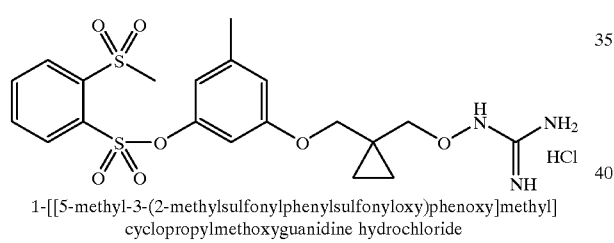
1-[[5-methyl-3-(2-methylsulfonylphenylsulfonyloxy)phenoxy]methyl]cyclopropylmethoxyguanidine hydrochloride

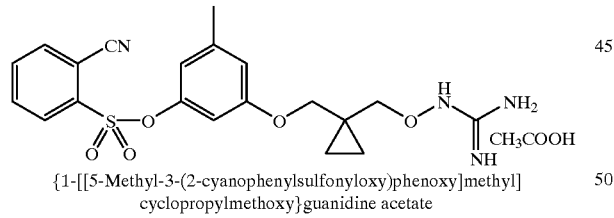
{1-[[5-Methyl-3-(2-cyanophenylsulfonyloxy)phenoxy]methyl]cyclopropylmethoxy}guanidine acetate

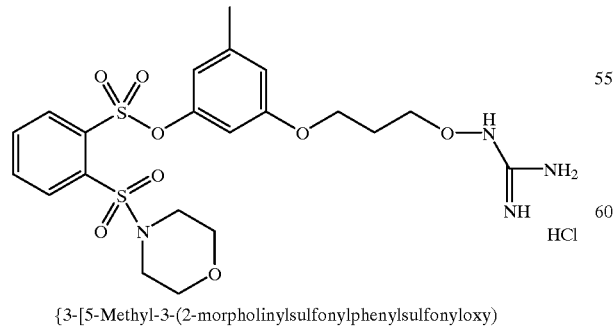
{3-[5-Methyl-3-(2-morpholinylsulfonylphenylsulfonyloxy)phenoxy]propoxy}guanidine hydrochloride -continued

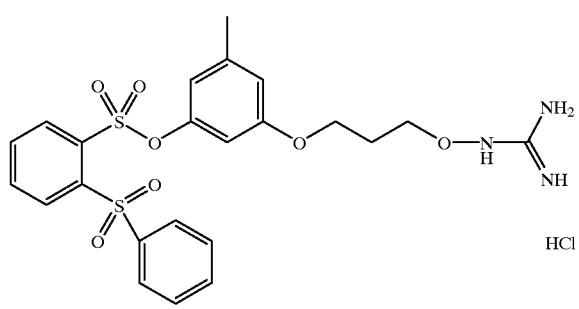
{3-[5-Methyl-3-(2-(phenylsulfonyl)phenylsulfonyloxy)phenoxy]propoxy}guanidine hydrochloride

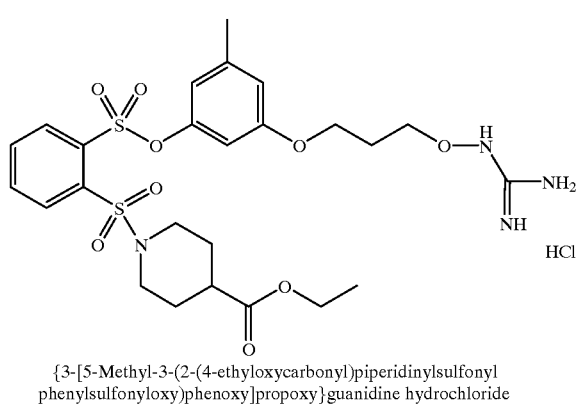
{3-[5-Methyl-3-(2-(4-ethyloxycarbonyl)piperidinylsulfonyl phenylsulfonyloxy)phenoxy]propoxy}guanidine hydrochloride

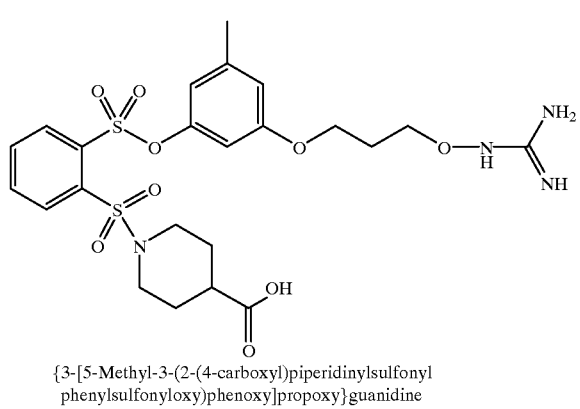
{3-[5-Methyl-3-(2-(4-carboxyl)piperidinylsulfonyl phenylsulfonyloxy)phenoxy]propoxy}guanidine

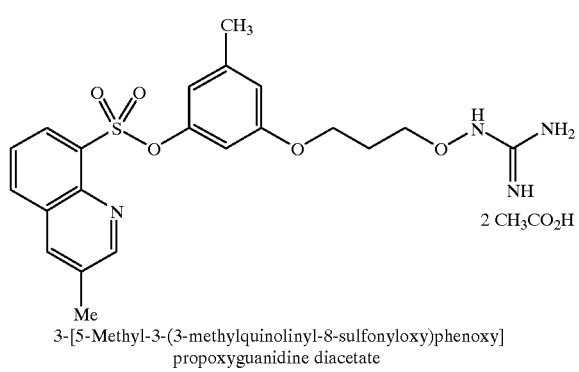
3-[5-Methyl-3-(3-methylquinolinyl-8-sulfonyloxy)phenoxy]propoxyguanidine diacetate 127
-continued

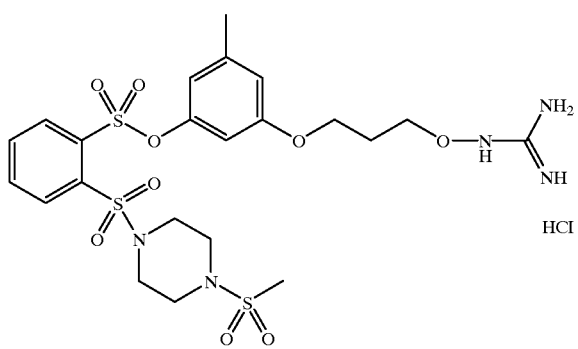

3-[5-Methyl-3-(2-(4-methylsulfonylpiperazin-1-ylsulfonyl)phenyl
sulfonyloxy)phenoxy]propoxy}guanidine hydrochloride

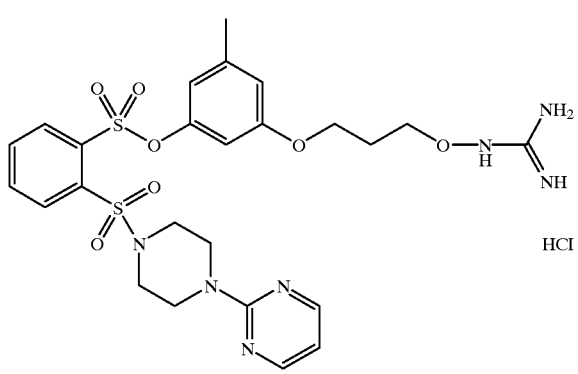

{3-[5-Methyl-3-(2-(4-(2-pyrimidinyl)piperazin-1-ylsulfonyl)phenyl
sulfonyloxy)phenoxy]propoxyguanidine hydrochloride

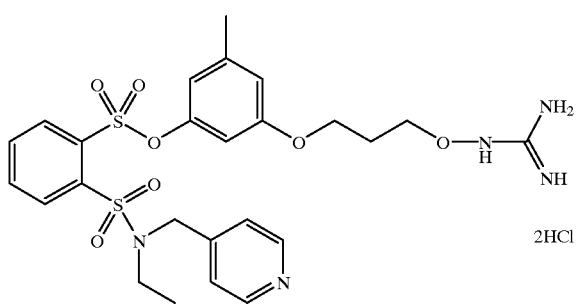

3-[5-Methyl-3-(2-(N-ethyl-N-(4-pyridylmethyl)aminosulfonyl)
phenylsulfonyloxy)phenoxy]propoxyguanidine dihydrochloride

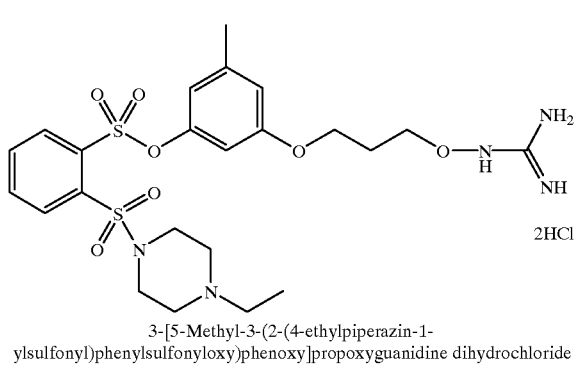

3-[5-Methyl-3-(2-(4-ethylpiperazin-1-
ylsulfonyl)phenylsulfonyloxy)phenoxy]propoxyguanidine dihydrochloride 128
-continued

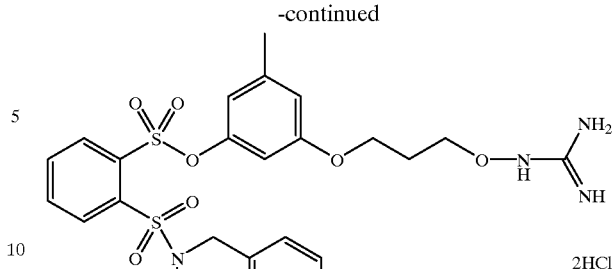

3-[5-Methyl-3-(2-(N-(2-cyanoethyl)-N-(3-pyridylmethyl)amino
sulfonyl)phenylsulfonyloxy)phenoxy]propoxyguanidine dihydrochloride

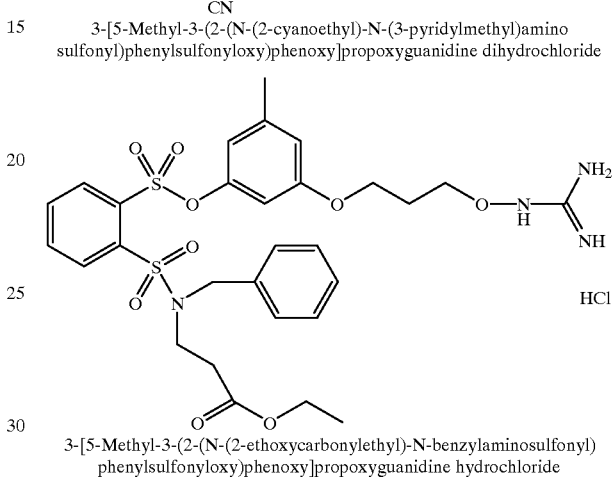

3-[5-Methyl-3-(2-(N-(2-ethoxycarbonylethyl)-N-benzylaminosulfonyl)
phenylsulfonyloxy)phenoxy]propoxyguanidine hydrochloride

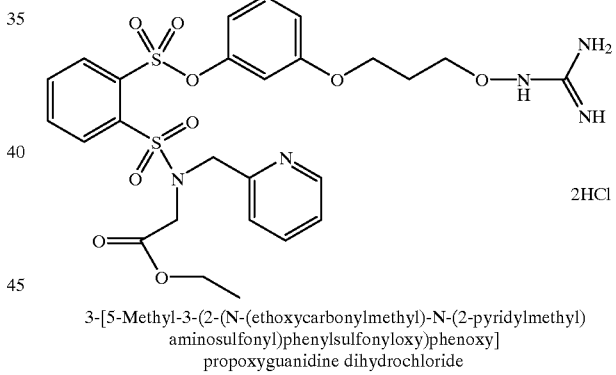

3-[5-Methyl-3-(2-(N-(ethoxycarbonylmethyl)-N-(2-pyridylmethyl)
aminosulfonyl)phenylsulfonyloxy)phenoxy]
propoxyguanidine dihydrochloride

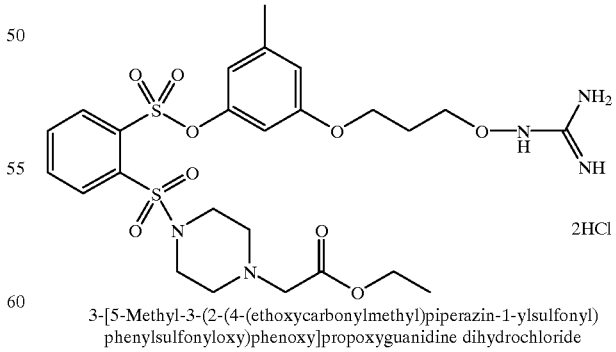

3-[5-Methyl-3-(2-(4-(ethoxycarbonylmethyl)piperazin-1-ylsulfonyl)
phenylsulfonyloxy)phenoxy]propoxyguanidine dihydrochloride -continued

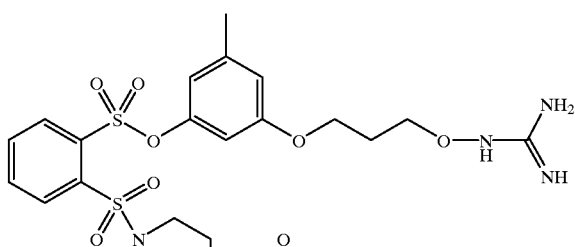

{3-[5-Methyl-3-(2-(4-(carboxymethyl)piperazin-1-ylsulfonyl)phenylsulfonyloxy)phenoxy]propoxy}guanidine

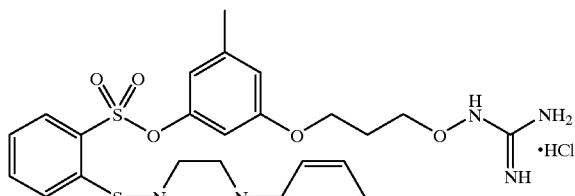

3-[5-methyl-3-(2-(4-(2-pyridyl)piperazinylsulfonyl)phenylsulfonyloxy)phenoxy]propoxyguanidine hydrochloride

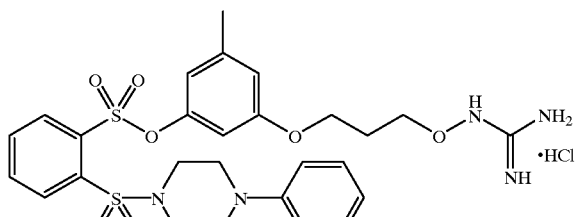

3-[5-methyl-3-(2-(4-phenylpiperazinylsulfonyl)phenylsulfonyloxy)phenoxy]propoxyguanidine hydrochloride

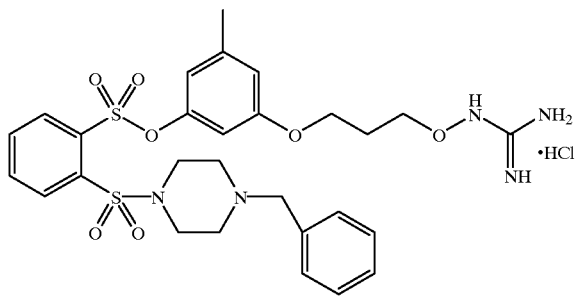

3-[5-methyl-3-(2-(4-benzylpiperazinylsulfonyl)phenylsulfonyloxy)phenoxy]propoxyguanidine hydrochloride

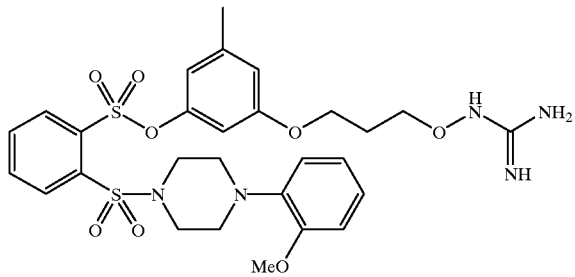

3-[5-methyl-3-(2-(4-(2-methoxyphenyl)piperazinylsulfonyl)phenylsulfonyloxy)phenoxy]propoxyguanidine hydrochloride -continued

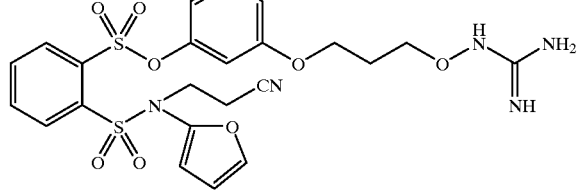

3-[5-methyl-3-(2-(N-(2-cyanoethyl)-N-(2-furanylmethyl)aminosulfonyl)phenylsulfonyloxy)phenoxy]propoxyguanidine

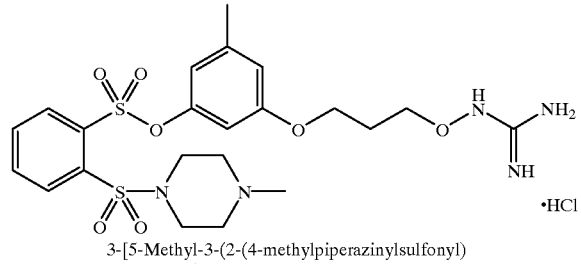

3-[5-Methyl-3-(2-(4-methylpiperazinylsulfonyl)phenylsulfonyloxy)phenoxy]propoxyguanidine hydrochloride

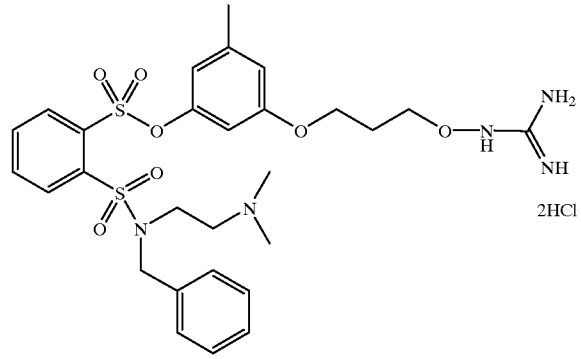

3-[5-Methyl-3-(2-(N-benzyl-N-(2-(N,N-dimethylamino)ethyl)aminosulfonyl)phenylsulfonyloxy)phenoxy]propoxyguanidine dihydrochloride

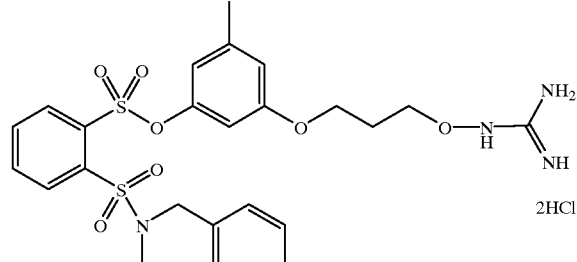

3-[5-Methyl-3-(2-(N-methyl-N-(3-pyridylmethyl)aminosulfonyl)phenylsulfonyloxy)phenoxy]propoxyguanidine dihydrochloride

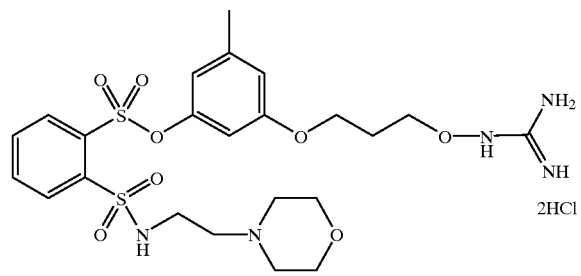

3-[5-Methyl-3-(2-(2-(4-morpholinyl)ethylaminosulfonyl)phenylsulfonyloxy)phenoxy]propoxyguanidine dihydrochloride

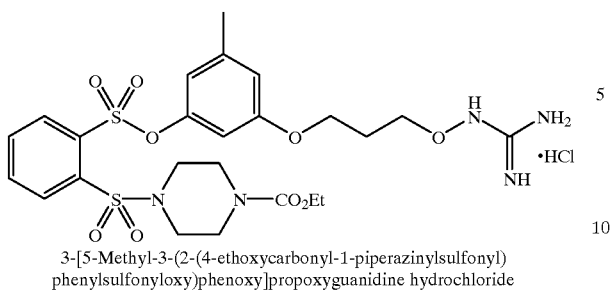

3-[5-Methyl-3-(2-(4-ethoxycarbonyl-1-piperazinylsulfonyl)
phenylsulfonyloxy)phenoxy]propoxyguanidine hydrochloride

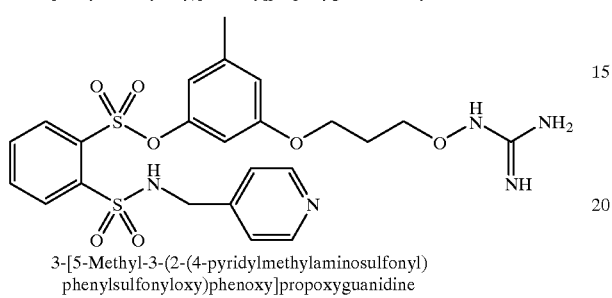

3-[5-Methyl-3-(2-(4-pyridylmethylaminosulfonyl)
phenylsulfonyloxy)phenoxy]propoxyguanidine

What is claimed is:

1. A compound having the Formula I:

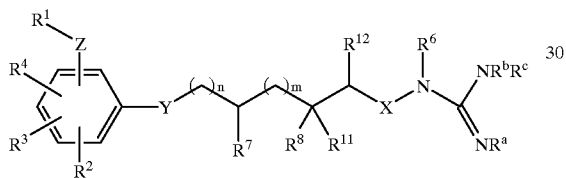

or a solvate, hydrate or pharmaceutically acceptable salt thereof; wherein:

$R^1$ is one of $C_{3-8}$ alkyl, cycloalkyl, alkenyl, alkynyl, aryl, aralkyl, any of which may be optionally substituted;

Z is —OSO$_2$— or —SO$_2$O—;

$R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^2$, $R^3$ and $R^4$ are each independently one of hydrogen, alkyl, cycloalkyl, alkenyl, alkynyl, aryl, aralkyl, trifluoromethyl, halogen, hydroxyalkyl, cyano, nitro, carboxamido, —CO$_2$R$^x$, —CH$_2$OR$^x$ or —OR$^x$, or when present on adjacent carbon atoms, $R^2$ and $R^3$ may also be taken together to form one of —CH=CH—CH=CH— or —(CH$_2$)$_q$—, where q is from 2 to 6, and $R^4$ is defined as above;

$R^x$, in each instance, is independently one of hydrogen, alkyl or cycloalkyl wherein said alkyl or cycloalkyl groups may optionally have one or more unsaturations;

Y is one of —O—, —NR$^{10}$—, —S—, —CHR$^{10}$— or a covalent bond;

X is oxygen or NR$^9$;

$R^9$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, acylamino, cyano or trifluoromethyl;

$R^6$ is one of hydrogen, alkyl, aralkyl, aryl, hydroxyalkyl, aminoalkyl, monoalkylamino($C_{2-10}$)alkyl, dialkylamino($C_{2-10}$)alkyl or carboxyalkyl; or $R^6$ and $R^{12}$ are taken together to form —(CH$_2$)$_w$—, where w is 1–5;

$R^7$ is one of hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, or mono- or di-alkylamino, provided that n is other than zero when $R^7$ is hydroxy, alkoxy, aralkoxy, aryloxy, or mono- or di-alkylamino; $R^8$, $R^{11}$ and $R^{12}$ are each independently one of hydrogen, alkyl, aralkyl, aryl, hydroxyalkyl, aminoalkyl, monoalkylaminoalkyl, dialkylaminoalkyl or carboxyalkyl; or $R^7$ and $R^8$ are taken together to form —(CH$_2$)$_y$—, where y is zero (a bond), 1 or 2, while $R^{11}$ and $R^{12}$ are defined as above; or $R^7$ and $R^{12}$ are taken together to form —(CH$_2$)$_q$—, where q is zero (a bond), or 1 to 8, while $R^8$ and $R^{11}$ are defined as above; or $R^8$ and $R^{11}$ are taken together to form —(CH$_2$)$_r$—, where r is 2–8, while $R^7$ and $R^{12}$ are defined as above;

$R^{10}$, in each instance, is independently one of hydrogen, alkyl, aralkyl, aryl, hydroxyalkyl, aminoalkyl, monoalkylamino($C_{2-10}$)alkyl, dialkylamino($C_{2-10}$)alkyl or carboxyalkyl;

$R^a$, $R^b$ and $R^c$ are independently hydrogen, alkyl, hydroxy, alkoxy, aryloxy, aralkoxy, alkoxycarbonyloxy, cyano or —CO$_2$R$^w$;

$R^w$ is alkyl, cycloalkyl, phenyl, benzyl,

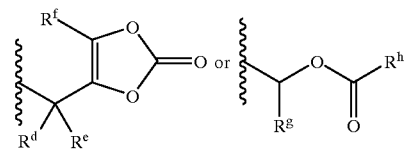

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; and m is from zero to 4.

2. A compound of claim 1, wherein $R^1$ is one of $C_{3-8}$ alkyl, $C_{4-7}$ cycloalkyl, $C_{2-8}$ alkenyl, $C_{2-8}$ alkynyl or $C_{6-4}$ aryl, any of which is optionally substituted.

3. A compound of claim 1, wherein $R^1$ is one of $C_{3-8}$ alkyl, $C_{4-7}$ cycloalkyl, $C_{2-8}$ alkenyl, $C_{2-8}$ alkynyl or $C_{6-14}$ aryl, any of which is optionally substituted by one or two moieties independently selected from the group consisting of alkyl, hydroxy, nitro, trifluoromethyl, halogen, alkoxy, aminoalkoxy, aminoalkyl, hydroxyalkyl, hydroxyalkoxy, cyano, aryl, amino, monoalkylamino, dialkylamino, carboxy, carboxyalkyl, carboxyalkoxy, mono(hydroxyalkyl)amino, bis(hydroxyalkyl)amino, mono(carboxyalkyl)amino, bis(carboxyalkyl)amino, alkoxycarbonylamino, alkoxycarbonyl, aralkoxycarbonyl, alkenylcarbonyl, alkynylcarbonyl, alkylsulfonyl, alkenylsulfonyl, alkynylsulfonyl, arylsulfonyl, aralkylsulfonyl, alkylsulfinyl, alkylsulfonamido, arylsulfonamido, aralkylsulfonamido, amidino, guanidino, alkyliminoamino, formyliminoamino, trifluoromethoxy, perfluoroethoxy and $R^{13}R^{14}$NSO$_2$—, where $R^{13}$ and $R^{14}$ are independently selected from the group consisting of hydrogen, alkyl, cycloalkyl, alkenyl, alkynyl, aryl, aralkyl, carboxyalkyl, alkoxycarbonylalkyl, cyanoalkyl, hydroxyalkyl, alkoxyalkyl, mono- and di-alkylaminoalkyl.

4. A compound of claim 1, wherein Y is one of —O—, —NR$^{10}$— or a covalent bond, and $R^{10}$ in each instance is one of hydrogen, $C_{1-6}$alkyl, benzyl, phenethyl, $C_{2-10}$hydroxyalkyl or $C_{2-7}$carboxyalkyl.

5. A compound of claim 4, wherein Y is —O—.
6. A compound of claim 1, wherein Z is —SO$_2$O—.
7. A compound of claim 1, wherein $R^a$, $R^b$ and $R^c$ are hydrogen.
8. A compound of claim 1, wherein $R^7$ and $R^8$ and $R^{11}$ and $R^{12}$ are independently hydrogen, $C_{1-6}$alkyl, $C_{6-10}$ar($C_{1-6}$)alkyl, $C_{6-10}$aryl, $C_{2-10}$hydroxyalkyl or $C_{2-10}$ carboxyalkyl.
9. A compound of claim 1, wherein $R^7$ and $R^8$ are taken together to form —(CH$_2$)$_y$—, and y is 0, 1 or 2.
10. A compound of claim 1, wherein n is from 1 to 4.
11. A compound of claim 1, wherein m is zero, 1, 2 or 3.
12. A compound of claim 1, wherein m and n are each zero and $R^7$, $R^8$, $R^{11}$ and $R^{12}$ are each hydrogen.
13. A compound of claim 1, wherein $R^2$ and $R^4$ are hydrogen and $R^3$ is methyl.
14. A compound of claim 1, wherein:

$R^1$ is $C_{6-10}$ aryl which is optionally substituted by one or two of hydroxy, nitro, trifluoromethyl, halogen, $C_{1-6}$ alkyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono ($C_{1-4}$) alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy ($C_{2-6}$)alkoxy, mono- and di-$C_{1-4}$ alkylamino($C_{2-6}$) alkoxy, $C_{2-10}$ mono(carboxyalkyl)amino, bis($C_{2-10}$ carboxyalkyl)amino, $C_{6-14}$ ar($C_{1-6}$)alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, perfluoroethoxy and $R^{13}R^{14}NSO_2$—;

$R^{13}$ and $R^{14}$ are independently selected from the group consisting of hydrogen, alkyl, cycloalkyl, alkenyl, alkynyl, aryl, aralkyl, carboxyalkyl, alkoxycarbonylalkyl, cyano($C_{2-10}$)alkyl, hydroxy ($C_{2-10}$) alkyl, alkoxy($C_{2-10}$)alkyl, mono- and di-alkylamino($C_{2-10}$)alkyl;

Z is —SO$_2$O—;

$R^2$, $R^3$ and $R^4$ are independently one of hydrogen, $C_{1-4}$ alkyl, $C_{3-8}$ cycloalkyl, phenyl, benzyl, trifluoromethyl, halogen, hydroxy($C_{1-4}$)alkyl, cyano, nitro, carboxamido, carboxy, $C_{1-4}$ alkoxycarbonyl, $C_{1-4}$ alkoxymethyl or $C_{1-4}$ alkoxy; or alternatively, $R^2$ and $R^3$, when present on adjacent carbon atoms, may also be taken together to form one of—CH=CH—CH=CH— or —(CH$_2$)$_q$—, where q is from 2 to 6, and $R^4$ is as defined above;

Y is one of —O—, —S—, —NR$^{10}$—, or a covalent bond;

$R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

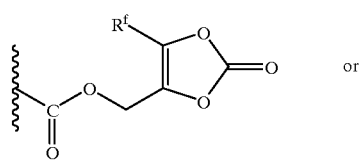

or

-continued

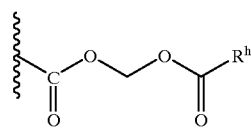

where
$R^h$ is benzyl, methyl, ethyl, isopropyl, sec-butyl or t-butyl, and where $R^f$ is hydrogen or $C_{1-6}$ alkyl;

$R^6$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, mono ($C_{1-4}$)alkylamino($C_{2-8}$)alkyl, di($C_{1-4}$)alkylamino($C_{2-8}$) alkyl or $C_{2-10}$ carboxyalkyl;

$R^7$, $R^8$, $R^{11}$ and $R^{12}$ are independently one of hydrogen, $C_{1-6}$ alkyl, $C_{2-10}$ carboxyalkyl or $C_{2-10}$ hydroxyalkyl, or $R^7$ and $R^8$ are taken together to form —(CH$_2$)$_y$— where y is zero, 1 or 2, while $R^{11}$ and $R^{12}$ are defined as above; or $R^7$ and $R^{12}$ are taken together to form —(CH$_2$)$_q$—, where q is zero (a bond), or 1, 2 or 3, while $R^8$ and $R^{11}$ are defined as above; or $R^8$ and $R^{11}$ are taken together to form —(CH$_2$)$_r$—, where r is 2, 3, or 4, while $R^7$ and $R^{12}$ are defined as above;

$R^9$ is hydrogen, or $C_{1-10}$ alkyl, optionally substituted with amino, mono($C_{1-4}$)alkylamino, $C_{1-6}$ alkoxy, hydroxy, carboxy, phenyl, $C_{1-4}$ alkyloxycarbonyl, $C_{6-10}$ ar($C_{1-4}$) alkoxycarbonyl, $C_{1-6}$ acylamino, cyano or trifluoromethyl;

$R^{10}$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxyalkyl;

n is from zero to 8; and m is from zero to 4.

15. A compound of claim 1, wherein:

$R^1$ is phenyl or naphthyl, optionally substituted by one or two of chloro, methoxy, methyl, trifluoromethyl, cyano, nitro, amino or dimethylamino;

Z is —SO$_2$O—;

$R^2$ and $R^3$ are hydrogen or $C_{1-4}$ alkyl, or $R^2$ and $R^3$ may also be taken together to form —CH=CH—CH=CH—;

$R^4$ is one hydrogen, methyl, methoxy or trifluoromethyl;

Y is one of O, NR$^{10}$ or a covalent bond;

$R^a$, $R^b$ and $R^c$ are hydrogen, hydroxy,

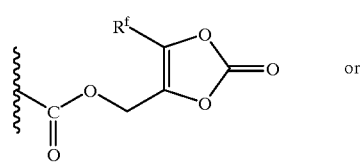

or

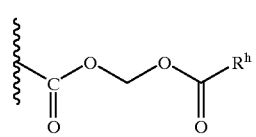

where
$R^h$ is benzyl or t-butyl, and where $R^f$ is hydrogen or methyl;

$R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl;

$R^7$, $R^8$, $R^{11}$ and $R^{12}$ are independently one of hydrogen, $C_{1-6}$ alkyl, $C_{2-10}$ hydroxyalkyl or $C_{2-10}$ carboxyalkyl, or $R^7$ and $R^8$ are taken together to form —(CH$_2$)$_y$— where y is zero, 1 or 2, while $R^{11}$ and $R^{12}$ are defined as above; or $R^7$ and $R^{12}$ are taken together to form —(CH$_2$)$_q$—, where q is zero (a bond), or 1, 2 or 3, while $R^8$ and $R^{11}$ are defined as above; or $R^8$ and $R^{11}$ are taken together to form —(CH$_2$)$_r$—, where r is 2, 3 or 4, while $R^7$ and $R^{12}$ are defined as above;

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino ($C_{2-8}$)alkyl;

n is from zero to 4; and m is zero, 1, 2 or 3.

16. A compound of claim 1, wherein:

$R^1$ is phenyl, substituted by $C_{1-6}$ alkylsulfonyl, $C_{6-10}$ arylsulfonyl, $C_{6-10}$ ar($C_{1-6}$)alkylsulfonyl, $C_{6-10}$ arylsulfonamido, $C_{6-10}$ ar($C_{1-6}$)alkylsulfonamido, or $R^{13}R^{14}NSO_2$—, where $R^{13}$ and $R^{14}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$) alkyl, carboxy($C_{1-6}$)alkyl, $C_{1-4}$ alkoxycarbonyl($C_{1-4}$) alkyl, cyano($C_{2-6}$)alkyl, hydroxy($C_{2-6}$)alkyl, $C_{1-4}$alkoxy($C_{2-6}$)alkyl, mono- and di-($C_{1-4}$)alkylamino ($C_{2-6}$)alkyl;

Z is one of —SO$_2$O—, —SO$_2$NR$^{10}$—, —CH$_2$O— or —OCH$_2$—;

$R^2$ and $R^3$ are hydrogen of $C_{1-4}$ alkyl, or $R^2$ and $R^3$ may also be taken together to form —CH=CH—CH=CH—, $R^4$ is one of hydrogen, methyl, methoxy or trifluoromethyl;

Y is one of O, NR$^{10}$ or a covalent bond;

$R^1$, $R^b$ and $R^c$ are hydrogen, hydroxy,

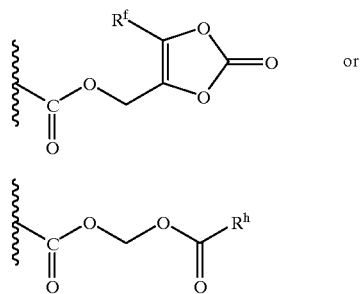

where $R^h$ is benzyl or t-butyl, and where $R^f$ is hydrogen or methyl;

$R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl;

$R^7$, $R^8$, $R^{11}$ and $R^{12}$ are independently one of hydrogen, $C_{1-6}$ alkyl, $C_{2-10}$ hydroxyalkyl or $C_{2-10}$ carboxyalkyl, or $R^7$ and $R^8$ are taken together to form —(CH$_2$)$_y$— where y is zero, 1 or 2, while $R^{11}$ and $R^{12}$ are defined as above; or $R^7$ and $R^{12}$ are taken together to form —(CH$_2$)$_q$—, where q is zero (a bond), or 1, 2 or 3, while $R^8$ and $R^{11}$ are defined as above; or $R^8$ and $R^{11}$ are taken together to form —(CH$_2$)$_r$—, where r is 2, 3 or 4, while $R^7$ and $R^{12}$ are defined as above;

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino ($C_{2-8}$)alkyl;

n is from zero to 4; and m is zero, 1, 2 or 3.

17. A compound of claim 1, wherein the moiety —Z—R$^1$ is attached to the benzene ring in a position meta- to Y.

18. A compound of claim 1, wherein:

$R^1$ is phenyl, substituted by $C_{1-6}$ alkylsulfonyl, $C_{6-10}$ arylsulfonyl, $C_{6-10}$ ar($C_{1-6}$)alkylsulfonyl, $C_{6-10}$ arylsulfonamido, $C_{6-10}$ ar($C_{1-6}$)alkylsulfonamido, or $R^{13}R^{14}NSO_2$—, where $R^{13}$ and $R^{14}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$) alkyl, carboxy($C_{1-6}$)alkyl, $C_{1-4}$ alkoxycarbonyl($C_{1-4}$) alkyl, cyano($C_{2-6}$)alkyl, hydroxy($C_{2-6}$)alkyl, $C_{1-4}$alkoxy($C_{2-6}$)alkyl, mono- and di-($C_{1-4}$)alkylamino ($C_{2-6}$)alkyl;

Z is —SO$_2$O—;

$R^2$ and $R^3$ are hydrogen or $C_{1-4}$ alkyl, or $R^2$ and $R^3$ may also be taken together to form —CH=CH—CH=CH—;

$R^4$ is one of hydrogen, methyl, methoxy or trifluoromethyl;

Y is one of O, NR$^{10}$ or a covalent bond;

$R^a$, $R^b$ and $R^c$ are hydrogen, hydroxy,

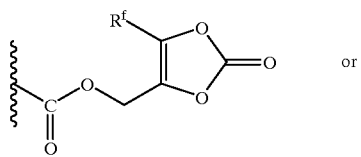

where $R^h$ is benzyl or t-butyl, and where $R^f$ is hydrogen or methyl;

$R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl;

$R^7$, $R^8$, $R^{11}$ and $R^{12}$ are independently one of hydrogen, $C_{1-6}$ alkyl, $C_{2-10}$ hydroxyalkyl or $C_{2-10}$ carboxyalkyl, or $R^7$ and $R^8$ are taken together to form —(CH$_2$)$_y$— where y is zero, 1 or 2, while $R^{11}$ and $R^{12}$ are defined as above; or $R^7$ and $R^{12}$ are taken together to form —(CH$_2$)$_q$—, where q is zero (a bond), or 1, 2 or 3, while $R^8$ and $R^{11}$ are defined as above; or $R^8$ and $R^{11}$ are taken together to form —(CH$_2$)$_r$—, where r is 2, 3 or 4, while $R^7$ and $R^{12}$ are defined as above;

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino ($C_{2-8}$)alkyl;

n is from zero to 4; and m is zero, 1, 2 or 3.

19. A compound of claim 18, wherein:

$R^{24}$ is methyl; Y' is O; a is one; and X' is O or NH.

20. A compound having the formula:

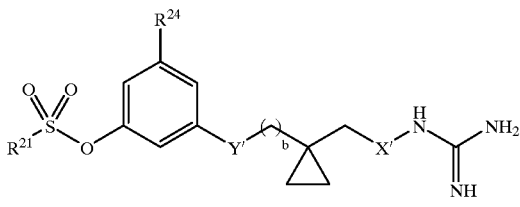

or a solvate, hydrate, pharmaceutically acceptable salt or prodrug thereof, wherein $R^{21}$ is phenyl or naphthyl, optionally substituted by one or two substituents independently selected from the group consisting of halogen, $C_{1-4}$ alkyl, $C_{1-4}$ alkoxy, methoxy, trifluoromethyl, cyano, nitro, amino or dimethylamino; and when $R^{21}$ is phenyl, said phenyl can be optionally substituted by $C_{1-6}$ alkylsulfonyl, $C_{6-10}$ arylsulfonyl, $C_{6-10}$ ar($C_{1-6}$)alkylsulfonyl, $C_{6-10}$ arylsulfonamido, $C_{6-10}$ ar($C_{1-6}$) alkylsulfonamido, or $R^{22}R^{23}NSO_2$—, where $R^{22}$ and $R^{23}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$)alkyl, carboxy($C_{1-6}$)alkyl, $C_{1-4}$ alkoxycarbonyl ($C_{1-4}$)alkyl, cyano($C_{2-6}$)alkyl, hydroxy($C_{2-6}$)alkyl, $C_{1-4}$ alkoxy($C_{2-6}$)alkyl, mono- and di-($C_{1-4}$)alkylamino ($C_{2-6}$)alkyl;

$R^{24}$ is hydrogen or $C_{1-4}$ alkyl;

X' is O or $NR^{29}$; and $R^{29}$ is hydrogen or $C_{1-4}$ alkyl;

Y' is one of O, $NR^{10}$ or a covalent bond, wherein $R^{10}$ is hydrogen, $C_{1-6}$ alkyl, $C_{6-10}$ ar($C_{1-6}$)alkyl, $C_{6-10}$ aryl, $C_{2-10}$ hydroxyalkyl $C_{2-10}$ aminoalkyl, $C_{2-7}$ carboxyalkyl, mono($C_{1-4}$ alkyl)amino($C_{1-8}$)alkyl, and di($C_{1-4}$ alkyl)amino($C_{1-8}$)alkyl; and b is 0, 1 or 2.

21. A compound of claim 1, which is one of

3-[3-(2-chlorophenylsulfonyloxy)-5-methylphenoxy] propoxyguanidine;

3-[3-(2-methoxyphenylsulfonyloxy)-5-methylphenoxy] propoxyguanidine;

3-[3-(5-chloro-2-methoxyphenylsulfonyloxy)-5-methylphenoxy]propoxyguanidine hydrochloride;

3-[5-methyl-3-[2-(methylsulfonyl)phenylsulfonyloxy] phenoxy]propoxyguanidine hydrochloride;

1-[[5-methyl-3-(2-methylsulfonylphenylsulfonyloxy) phenoxy]methyl]cyclopropylmethoxyguanidine hydrochloride;

3-[5-methyl-3-(2-phenylsulfonyl)phenoxy] propoxyguanidine hydrochloride;

3-[5-methyl-3-(2-(N-(2-ethoxycarbonylethyl)-N-benzylaminosulfonyl)phenylsulfonyloxy)phenoxy] propoxyguanidine hydrochloride;

3-[5-methyl-3-(-2-(N-benzyl-N-(2-(N,N-dimethylamino) ethyl)aminosulfonyl)phenylsulfonyloxy)phenoxy] propoxyguanidine dihydrochloride;

or a hydrochloride or acetate salt thereof.

22. A compound having the Formula I:

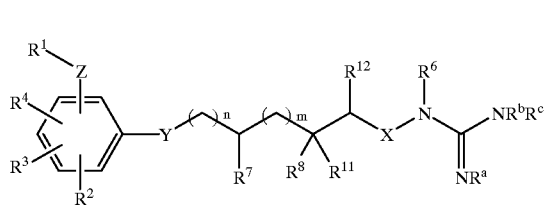

I or a solvate, hydrate or pharmaceutically acceptable salt thereof; wherein:

$R^1$ is one of alkyl, cycloalkyl, alkenyl, alkynyl, aryl, or aralkyl, any of which may be optionally substituted;

Z is —$OSO_2$— or —$SO_2O$—;

$R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^2$, $R^3$ and $R^4$ are each independently one of hydrogen, alkyl, cycloalkyl, alkenyl, alkynyl, aryl, aralkyl, trifluoromethyl, halogen, hydroxyalkyl, cyano, nitro, carboxamido, —$CO_2R^x$, —$CH_2OR^x$ or —$OR^x$, or when present on adjacent carbon atoms, $R^2$ and $R^3$ may also be taken together to form one of —CH=CH—CH=CH— or —$(CH_2)_q$—, where q is from 2 to 6, and $R^4$ is defined as above;

$R^x$, in each instance, is independently one of hydrogen, alkyl or cycloalkyl wherein said alkyl or cycloalkyl groups may optionally have one or more unsaturations;

Y is one of —O—, —$NR^{10}$—, —S—, —$CHR^{10}$— or a covalent bond;

$R^{10}$, in each instance, is independently one of hydrogen, alkyl, aralkyl, aryl, hydroxyalkyl, aminoalkyl, monoalkylamino($C_{2-10}$)alkyl, dialkylamino($C_{2-10}$) alkyl or carboxyalkyl;

$R^w$ is alkyl, cycloalkyl, phenyl, benzyl,

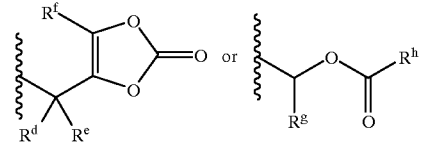

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl; and:

A. $R^7$ and $R^{12}$ are taken together to form —$(CH_2)_o$—, where o is 1, 2 or 3; $R^{11}$ is hydrogen, alkyl, aralkyl, aryl, hydroxyalkyl or carboxyalkyl; $R^8$ is hydrogen; $R^a$, $R^b$ and $R^c$ are hydrogen, hydroxy,

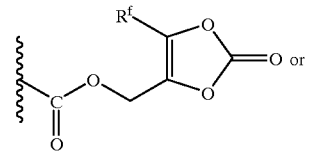

-continued

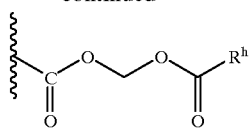

where $R^h$ is benzyl or t-butyl, and where $R^f$ is hydrogen or methyl; and $R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl; or B. $R^{11}$ is hydrogen, alkyl, aralkyl, aryl, hydroxyalkyl or carboxyalkyl; $R^8$ and $R^{12}$ are taken together to form —$CH_2$—$CH_2$—$(CH_2)_p$—, where p is 1, 2 or 3; $R^7$ is hydrogen; and $R^a$, $R^b$ and $R^c$ are hydrogen, hydroxy,

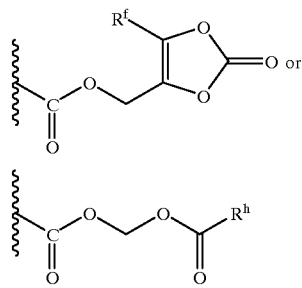

where $R^h$ is benzyl or t-butyl, and where $R^f$ is hydrogen or methyl; and $R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl.

23. A pharmaceutical composition for inhibiting proteolysis in a mammal, comprising an amount of a compound of any one of claims 1, 14, 15, 16, 18, 20 or 21 effective to inhibit proteolysis, and a pharmaceutically acceptable carrier or diluent.

24. The pharmaceutical composition of claim 23, comprising an amount of said compound effective to inhibit a trypsin-like protease.

25. A method of inhibiting proteolysis in mammal, comprising administering to the mammal a composition of claim 23.

26. The method of claim 25, wherein a trypsin-like protease is inhibited.

27. A method of treating pancreatitis, thrombosis, ischemia, stroke, restenosis, emphysema or inflammation in a mammal, comprising administering to the mammal a composition of claim 23.

28. A method of inhibiting thrombin-induced platelet aggregation and clotting of fibrinogen in plasma, comprising administering to the mammal a composition of claim 23.

29. A method for inhibiting thrombin in blood comprising adding to the blood a compound of claim 1.

30. A method for inhibiting formation of blood platelet aggregates in blood comprising adding to the blood a compound of claim 1.

31. A method for inhibiting thrombus formation in blood comprising adding to the blood a compound of claim 1.

32. In a device used in blood collection, blood circulation, and blood storage wherein said device includes an effective amount of a thrombin inhibiting compound or macromolecule as an anticoagulant, either embedded in, or physically linked to, one or more materials that form the structure of said device, the improvement comprising employing as said thrombin inhibitor one or more compounds as claimed in claim 1.

33. The device of claim 32, wherein said device is a catheter, blood dialysis machine, blood collection syringe, blood collection tube, blood line or extracorporeal blood circuit.

34. The device of claim 32, wherein said device is a stent that can be surgically inserted into a mammal.

35. A process for preparing an aminoguanidine compound of claim 1, comprising reacting an aminoguanidine of the formula

VII

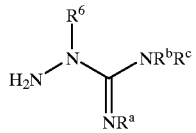

wherein $R^9$, $R^a$, $R^b$ and $R^c$ are defined in claim 1, with a carbonyl-containing compound of the formula

VIII

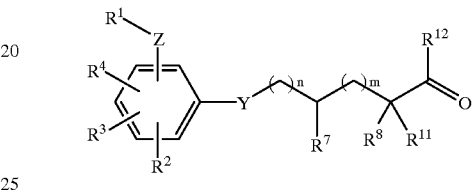

wherein $R^1$–$R^4$, Z, Y, n, m, $R^7$, $R^8$, $R^{11}$ and $R^{12}$ are defined in claim 1 to form an amidinohydrazone, and thereafter selectively reducing the hydrazone carbon to nitrogen double bond of the amidinohydrazone.

36. The process of claim 35, wherein the aminoguanidine of Formula VII is provided as a hydrochloride, acetate or nitrate salt.

37. The process of claim 35, wherein the reaction is conducted at ambient temperature using an alcohol as a solvent.

38. The process of claim 35, wherein an acid is added to the reaction mixture.

39. A process for preparing an alkoxyguanidine compound of claim 1, comprising reacting an alkoxyamine compound of the formula

IX

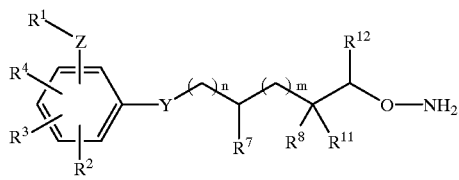

wherein $R^1$–$R^4$, Z, Y, n, m, $R^7$, $R^8$, $R^{11}$ and $R^{12}$ are defined in claim 1, with a guanidinylating reagent.

40. The process of claim 39, wherein said guanidinylating reagent is aminoiminosulfonic acid, optionally substituted 1H-pyrazole-1-carboxamidines, or N,N'-bis(tert-butoxycarbonyl)S-methyl isothiourea.

41. A compound of claim 1, which is 1-[[5-methyl-3-(2-methylsulfonylphenylsulfonyloxy)phenoxy]methyl] cyclopropylmethoxyguanidine hydrochloride.

42. A compound of claim 1, which is 1-[[5-methyl-3-(2-methylsulfonylphenylsulfonyloxy)phenoxy]methyl] cyclopropylmethoxyguanidine of a solvate, a hydrate, or a pharmaceutically acceptable salt thereof.

* * * * *

UNITED STATES PATENT AND TRADEMARK OFFICE
CERTIFICATE OF CORRECTION

PATENT NO. : 6,235,778 B1
DATED : May 22, 2001
INVENTOR(S) : Tomczuk et al.

It is certified that error appears in the above-identified patent and that said Letters Patent is hereby corrected as shown below:

Column 134,
Line 44, after "one" please insert -- of --.

Column 135,
Line 28, please delete "one of".
Lines 28-29, please delete ",—$SO_2NR^{10}$—, —$CH_2O$— or —$OCH_2$—".
Line 36, please delete "$R^1$" and insert therein -- $R^n$ --.

Column 136,
Please delete claim 18 in its entirety and insert the following:
-- 18. A compound having the formula:

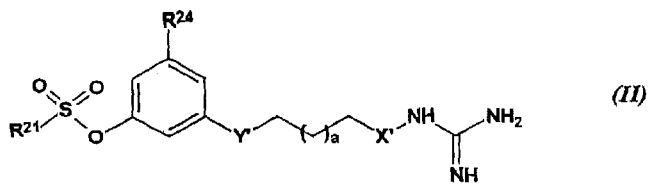

(II)

or a solvate, hydrate, pharmaceutically acceptable salt or prodrug thereof: wherein $R^{21}$ is phenyl or naphthyl, optionally substituted by one or two substituents independently selected from the group consisting of halogen, $C_{1-4}$ alkyl, $C_{1-4}$ alkoxy, methoxy, trifluoromethyl, cyano, nitro, amino or dimethylamino; and when $R^{21}$ is phenyl, said phenyl can be optionally substituted by $C_{1-6}$ alkylsulfonyl, $C_{6-10}$ arylsulfonyl, $C_{6-10}$ ar($C_{1-6}$) alkylsulfonyl, $C_{6-10}$ arylsulfonamido, $C_{6-10}$ ar($C_{1-6}$) alkylsulfonamido, or $R^{22}R^{23}NSO_2$–, where $R^{22}$ and $R^{23}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$)alkyl, carboxy($C_{1-6}$)alkyl, $C_{1-4}$ alkoxycarbonyl($C_{1-4}$)alkyl, cyano($C_{2-6}$)alkyl, hydroxy($C_{2-6}$)alkyl, $C_{1-4}$alkoxy($C_{2-6}$)alkyl, mono- and di-($C_{1-4}$)alkylamino($C_{2-6}$)alkyl;

$R^{24}$ is hydrogen or $C_{1-4}$ alkyl,

Y' is one of O, $NR^{10}$ or a covalent bond, wherein $R^{10}$ is hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, mono($C_{1-4}$ alkyl)amino($C_{1-8}$)alkyl, and di($C_{1-4}$ alkyl)amino($C_{1-8}$)alkyl; and a is 0, 1 or 2;

X' is O or $NR^{29}$; and $R^{29}$ is hydrogen or $C_{1-4}$ alkyl.--

UNITED STATES PATENT AND TRADEMARK OFFICE
CERTIFICATE OF CORRECTION

PATENT NO. : 6,235,778 B1
DATED : May 28, 2001
INVENTOR(S) : Tomczuk et al.

It is certified that error appears in the above-identified patent and that said Letters Patent is hereby corrected as shown below:

Column 137,
Line 57, please delete "3-[5-methyl-3-(2-phenylsulfonyl)phenoxy]propoxyguanidine" and insert therein -- 3-[5-methyl-3-(2-(phenylsulfonyl)phenylsulfonyloxy)phenoxy] propoxyguanidine --.

Column 140,
Line 64, please delete "of" and insert therein -- or --.

Signed and Sealed this

Fifteenth Day of July, 2003

JAMES E. ROGAN
*Director of the United States Patent and Trademark Office*